US008003612B2

(12) United States Patent
Lake et al.

(10) Patent No.: US 8,003,612 B2
(45) Date of Patent: *Aug. 23, 2011

(54) SMALL PEPTIDES FOR THE TREATMENT OF ALZHEIMER'S DISEASE AND OTHER BETA-AMYLOID PROTEIN DISORDERS

(75) Inventors: Thomas Lake, Snohomish, WA (US); Alan D. Snow, Lynnwood, WA (US); Gerardo Castillo, Bothell, WA (US); Beth Nguyen, Gurnee, IL (US); Virginia Sanders, San Francisco, CA (US); Qubai Hu, Kirkland, WA (US); Judy A. Cam, Bellevue, WA (US)

(73) Assignee: Proteotech Inc., Kirkland, WA (US)

( * ) Notice: Subject to any disclaimer, the term of this patent is extended or adjusted under 35 U.S.C. 154(b) by 307 days.

This patent is subject to a terminal disclaimer.

(21) Appl. No.: 12/323,944

(22) Filed: Nov. 26, 2008

(65) Prior Publication Data

US 2009/0253637 A1 Oct. 8, 2009

Related U.S. Application Data

(60) Continuation-in-part of application No. 11/732,226, filed on Apr. 2, 2007, now Pat. No. 7,759,311, which is a division of application No. 11/016,706, filed on Dec. 16, 2004, now Pat. No. 7,384,910, which is a continuation-in-part of application No. 09/962,955, filed on Sep. 24, 2001, now Pat. No. 6,933,280, which is a continuation-in-part of application No. 09/938,275, filed on Aug. 22, 2001, now Pat. No. 7,314,724, which is a continuation of application No. 08/947,057, filed on Oct. 8, 1997, now abandoned.

(60) Provisional application No. 60/531,406, filed on Dec. 18, 2003, provisional application No. 60/554,342, filed on Mar. 17, 2004, provisional application No. 60/615,614, filed on Sep. 30, 2004.

(51) Int. Cl.
*A61K 38/08* (2006.01)
(52) U.S. Cl. ...................................... 514/17.8; 514/21.7
(58) Field of Classification Search ........................ None
See application file for complete search history.

(56) References Cited

U.S. PATENT DOCUMENTS 5,948,763 A 9/1999 Soto-Jara et al.

FOREIGN PATENT DOCUMENTS

WO WO 01/34631 A2 5/2001

OTHER PUBLICATIONS

Castillo et al., "Perlecan Binds to the β-Amyloid Proteins (Aβ) of Alzheimer's Disease, Accelerates Aβ Fibril Formation, and Maintains . . . ", J. Neurochem. 69:2452-2465 (1997).

Chen et al., "A learning deficit related to age and beta-amyloid plaques in a mouse model of Alzheimer's disease", Nature 408(6815):975-979 (2000).
Fields, G.B. and Noble, R.L, "Solid phase peptide synthesis utilizing 9-fluorenylmethoxycarbonyl amino acids", Int. J. Polypeptide Prot. Res. 35:161-214 (1990).
Flood et al., "Amnestic effects in mice of four synthetic peptides homologous to amyloid β protein from patients with . . . ", Procl. Natl. Acad. Sci. 88:3363-3366 (1991).
Flood et al., "An amyloid β-protein fragment, Aβ[12-28], equipotently impairs post-training memory, processing when injected . . . ", Brain Research 663:271-276 (1994).
Fukuchi et al., "Increased expression of beta-amyloid protein precursor and microtubule-associated protein tau during . . . ", J. Neurochem. 8(5):1863-1873 (1992).
Games et al., "Alzheimer-type neuropathology in transgenic mice overexpressing V717F β-amyloid precursor protein", Nature 373:523-527 (1995).
Ghilardi et al., "Intra-arterial infusion of [125I]A beta 1-40 labels amyloid deposits in the aged primate brain in vivo", Neuroreport. 7(15-17):2607-11 (1996).
Glenner, G.G. and Wong, C.W., "Alzheimer's Disease: Initial Report of the Purification and Characterisation . . . ", Biochem Biophys Res Comm 120(3): 885-890 (1984).
Grundke-Iqbal et al., "Abnormal phosphorylation of the microtubule—associated protein τ (tau) in Alzheimer . . . ", Procl. Natl. Acad. Sci. USA 83:4913-4917 (1986).
Haass et al., "The Swedish mutation causes early-onset Alzheimer's Disease by β-secretase cleavage within the secretory pathway", Nature Medicine 1(12):1291-1296 (1995).
Haass, C. and De Strooper, B., "The presenilins in Alzheimer's disease—proteolysis holds the key", Science 286(5441):916-9 (1999).
Hardy J., "Framing β-amyloid", Nature Genetics 1:233-234 (1992).
Harrigan et al., "Beta Amyloid is Neurotoxic in Hippocampal Slice Cultures", Neurobiology of Aging 16(5):779-789 (1995).
Hsiao et al., "Correlative memory Deficits, Aβ Elevation, and Amyloid Plaques in Transgenic Mice", Science 274:99-102 (1996).
Hu et al., "Endoproteolytic Cleavage of FE65 Converts the Adaptor Protein to a Potent Suppressor of the sAPPα Pathway in Primates", J Biol Chem. 280:12548-12558 (2005).
Husby et al., "Nomenclature of Amyloid and Amyloidosis", Bull. WHO 71 (1):105-108 (1993).
Janus, et al., "Aβ peptide immunization reduces behavioral impairment and plaques in a model of Alzheimer's disease", Nature 408:979-982 (2000).
Kitaguchi et al., "Novel precursor of Alzheimer's disease amyloid protein shows protease inhibitory activity", Nature 331:530-532 (1988).
Klafki et al., "Electrophoretic separation of betaA4 peptides (1-40) and (1-42)", Anal Biochem. 237(1):24-9 (1996).
Kosik et al., "Microtubule-associated protein tau (τ) is a major antigenic component of paired helical filaments . . . ", Procl. Natl. Acad. Sci. USA 83:4044-4048 (1986).

(Continued)

*Primary Examiner* — Christina Bradley
(74) *Attorney, Agent, or Firm* — Rebecca Eagen

(57) ABSTRACT

Use of a peptide or pharmaceutical composition comprising Leu-Ala-Phe-Val-Leu-Arg-Lys-amide having at least one D amino acid for the reduction of beta-amyloid protein, modulating APP processing, modulating activity of APP secretases, treatment of beta-amyloid protein diseases and the treatment of Alzheimer's disease.

19 Claims, 87 Drawing Sheets

OTHER PUBLICATIONS

Kukar et al., "Substrate-targeting gamma-secretase modulators", Nature 453 (7197):925-9 (2008).

Lee et al., "A-68: A Major Subunit of Paired Helical Filaments and Derivatized Forms of Normal Tau", Science 251:675-678 (1991).

LeVine III H, "Thioflavine T interaction with synthetic Alzheimer's disease β-amyloid peptides: Detection of amyloid aggregation in solution", Protein Science 2:404-410 (1993).

LeVine III H., "Thioflavine T interacton with amyloid β-sheet structures", Amyloid: Int. J. Exp. Clin. Invest. 2:1-6 (1995).

Mandybur T., "Cerebral Amyloid Angiopathy: The Vascular Pathology and Complications", Journal of Neuropathology and Experimental Neurology 45(1):79-90 (1986).

Masters et al., "Amyloid plaque core protein in Alzheimer's disease and Down syndrome", Proc. Natl. Sci. USA 82:4245-4249 (1985).

Merrifield, B., "Solid Phase Synthesis", Science 232:341-347 (1986).

Morgan, et al., "Aβ peptide vaccination prevents memory loss in an animal model of Alzheimer's disease", Nature 408:982-985 (2000).

Murrell et al., "A mutation in the Amyloid Precursor Protein Associated with Hereditary Alzheimer's Disease", Science 254: 97-99 (1991).

Naiki, H. and Nakauki, K. "First-order kinetic model of Alzheimer's beta-amyloid fibril extension in vitro", Lab Invest 74(2):374-83 (1996).

Pardridge et al., "Amyloid Angiopathy of Alzheimer's Disease: Amino Acid Composition and Partial Sequence of a 4,200-Dalton . . . ", J. Neurochem. 49(5):1394-1401 (1987).

Pardridge, W.M., "Recent developments in peptide drug delivery to the brain", Pharmacol Toxicol. 71(1):3-10 (1992).

Pardridge, W.M., "New approaches to drug delivery through the blood-brain barrier",Trends Biotechnol. 12(6):239-45 (1994).

Permanne et al., "Reduction of amyloid load and cerebral damage in a transgenic mouse model of Alzheimer's disease . . . ", The FASEB Journal Express Article pub Apr. 10, 2002.

Pike et al., "In vitro aging of β-amyloid protein causes peptide aggregation and neurotoxicity", Brain Research 563:311-314 (1991).

Pike et al., "Structure-Activity Analyses of β-Amyloid Peptides: Contributions of the β25-35 Region to Aggregation and Neurotoxicity", J. Neurochem. 64(1):253-265 (1995).

Pluta et al., "Evidence of blood-brain barrier permeability/leakage for circulating human Alzheimer's beta-amyloid-(1-42)-peptide", Neuroreport.7(7):1261-5 (1996).

Poduslo et al., "Permeability and residual plasma volume of human, Dutch variant, and rat amyloid beta-protein 1-40 at the blood-brain barrier", Neurobiol. Dis. 4:27-34 (1997).

Ponte et al. ,"A new A4 amyloid mRNA contains a domain homologous to serine proteinase inhibitors", Nature 311:525-527 (1988).

Postina, R., "A closer look at alpha-secretase", Curr Alzheimer Res. 5 (2):179-86 (2008).

Selkoe, D.J., "Alzheimer's disease: genes, proteins, and therapy", Physiol Rev. 81(2):741-766 (2001).

Tanzi et al., "Protease inhibitor domain encoded by an amyloid protein precursor mRNA associated with Alzheimer's disease", Nature 331:528-532 (1988).

Van Broeckhoven et al., "Amyloid β Protein Precursor Gene and Hereditary Cerebral Hemorrhage with Amyloidosis (Dutch)", Science 248:1120-1122 (1990).

Van Bree et al., "Drug transport across the blood-brain barrier. III. Mechanisms and methods to improve drug delivery to the central . . . ", Pharm. World Sci. 15(1):2-9 (1993).

Yang et al., "A Dominant Role for FE65 (APBB1) in Nuclear Signaling", J Biol Chem. 281:4207-4214 (2006).

Zlokovic , B., "Can blood-brain barrier play a role in the development of cerebral amyloidosis and Alzheimer's disease pathology", Neurobiol. Dis. 4:23-6 (1997).

Peptide DP-074

Sequence: Leu-Ala-Phe-Val-Leu-Arg-Lys-amide
Formula: $C_{41}H_{72}N_{12}O_7$
Mol. Wt.: 845.10
Structure:

Ranking Order of Peptides to Abeta based on Thio T % Inhibition

| | Thio T | |
|---|---|---|
| | 1:2 w/w | 1:1 w/w |
| DP-072 (WHLAFVLR) | 32.6 | 32.2 |
| DP-071 (TLFLAR) | 15.3 | 14.6 |
| DP-070 (HGRLVFM-amide) | 18.7 | 0.0 |
| DP-067 (RVAVIM-amide) | 19.2 | 12.2 |
| DP-069 (LAFVLR-amide) | 18.2 | 11.1 |
| DP-066 (WHRVAVI-amide) | 13.5 | 13.0 |
| DP-068 (RVAVIMG-amide) | 11.5 | 12.8 |
| DP-065 (WHRVAVIM-amide) | 9.6 | 14.0 |

SEQUENCE LISTING

```
<160> NUMBER OF SEQ ID NOS: 8

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Arg Lys Arg Leu Gln Val Gln Leu Ser Ile Arg Thr
 1               5                   10

<210> SEQ ID NO 2
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Arg Gln Val Phe Gln Val Ala Tyr Ile Ile Ile Lys Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Tyr Leu Ser Lys Gly Arg Leu Val Phe Ala Leu Gly
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Thr Leu Phe Phe Met Arg Leu Val His Ala Leu Gly
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ala Gly Gln Trp His Arg Val Ser Val Arg Trp Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Asp Gly Arg Trp His Arg Val Ala Val Ile Met Gly
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Leu Pro Phe Phe Asp
```

```
                          -continued
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<223> OTHER INFORMATION: N-term acetylated and C-term amidated

<400> SEQUENCE: 8

Leu Pro Phe Phe Asp
 1               5
```

SMALL PEPTIDES FOR THE TREATMENT OF ALZHEIMER'S DISEASE AND OTHER BETA-AMYLOID PROTEIN DISORDERS

RELATED APPLICATIONS

This application is a continuation-in-part of U.S. application Ser. No. 11/732,226 filed Apr. 2, 2007 now U.S. Pat. No. 7,759,311 which is a divisional of U.S. application Ser. No. 11/016,706 filed Dec. 16, 2004 now U.S. Pat. No. 7,384,910 which is a continuation-in-part of U.S. patent application Ser. No. 09/962,955 filed Sep. 24, 2001 now U.S. Pat. No. 6,933,280 which is a continuation-in-part of U.S. patent application Ser. No. 09/938,275 filed Aug. 22, 2001, now U.S. Pat. No. 7,314,724 which is a continuation of U.S. patent application Ser. No. 08/947,057 filed Oct. 8, 1997 now abandoned; This application also claims priority to U.S. Provisional Application 60/531,406 filed Dec. 18, 2003 and to U.S. Provisional Application 60/554,342 filed Mar. 17, 2004 and to U.S. Provisional Application 60/615,614 filed Sep. 30, 2004. The text and drawings of each application set out above are hereby incorporated by reference into the present application as if fully set forth herein.

TECHNICAL FIELD

This invention relates to the use of 5 to 13 mer peptides and peptide derivatives for the treatment of Alzheimer's disease and other beta-amyloid protein fibrillogenesis disorders.

BACKGROUND OF THE INVENTION

Additional background for therapeutic use of peptide fragments in the treatment of Alzheimer's disease and other amyloidoses can be found in U.S. patent application Ser. No. 09/938,275 filed Aug. 22, 2001, and in U.S. patent application Ser. No. 09/962,955 filed Sep. 24, 2001, the text and drawings of each of which are hereby incorporated by reference into the present application as if fully set forth herein.

Beta-Amyloid Protein as a Therapeutic Target for Alzheimer's Disease

Alzheimer's disease AD) is characterized by the deposition and accumulation of a 39-43 amino acid peptide termed the beta-amyloid protein, $A\beta$ or $\beta/A4$ Glenner and Wong, Biochem. Biophys. Res. Comm. 120:885-890. 1984; Masters et al, Proc. Nat. Acad. Sci. U.S.A. 82:4245-4249, 1985; Husby et al, Bull. WHO 71:105-108, 1993). $A\beta$ is derived from larger precursor proteins termed beta amyloid precursor proteins or APPs) of which there are several alternatively spliced variants. The most abundant forms of the APPs include proteins consisting of 695, 751 and 770 amino acids Kitaguchi et al, Nature 331:530-532, 1988; Ponte et al, Nature 331:525-527, 1988; Tanzi et al, Nature 331:528-530, 1988). The small $A\beta$ peptide is a major component that makes up the core of amyloid deposits called "plaques" in the brains of patients with AD. In addition, AD is characterized by the presence of numerous neurofibrillary "tangles", consisting of paired helical filaments which abnormally accumulate in the neuronal cytoplasm Grundke-lqbal et al Proc. Natl. Acad. Sci. U.S.A. 83:4913-4917, 1986; Kosik et al, Proc. Natl. Acad. Sci. U.S.A. 83:4044-4048, 1986; Lee et al, Science 251:675-678, 1991). The other major type of lesion found in AD brain is the accumulation of amyloid in the walls of blood vessels, both within the brain parenchyma and meningeal vessels that lie outside the brain. The amyloid deposits localized to the walls of blood vessels are referred to as cerebrovascular amyloid or congophilic angiopathy Mandybur, J. Neuropath. Exp. Neurol. 45:79-90, 1986; Pardridge et al, J. Neurochem. 49:1394-1401, 1987). The pathological hallmarks of AD therefore are the presence of "plaques", "tangles", and cerebrovascular amyloid deposits.

For many years there has been an ongoing scientific debate as to the importance of "amyloid" in AD and whether the "plaques" and "tangles" characteristic of this disease, were a cause or merely the consequences of the disease. Recent studies indicate that amyloid is indeed a causative factor for AD and should not be regarded merely as a consequence. The Alzheimer's $A\beta$ protein in cell culture has been shown to cause degeneration of nerve cells within a short time period Pike et al, Br. Res. 563:311-314, 1991; J. Neurochem. 64:253-265, 1995). Studies suggest that it is the fibrillar structure, characteristic of all amyloids, that is mainly responsible for the neurologic effects. $A\beta$ has also been found to be neurologic in slice cultures of hippocampus Hadrian et al, Neurobiol. Aging 16:779-789, 1995) and induces nerve cell death in transgenic mice Games et al, Nature 373:523-527, 1995; Hsiao et al, Science 274:99-102, 1996). Injection of $A\beta$ into rat brain also causes memory impairment and neuronal dysfunction Flood et al, Proc. Natl. Acad. Sci. U.S.A. 88:3363-3366, 1991; Br. Res. 663:271-276, 1994). Convincing evidence that $A\beta$ amyloid is directly involved in the pathogenesis of AD comes from genetic studies. It was discovered that the increased production of $A\beta$ could result from mutations in the gene encoding, its precursor, APP Van Broeckhoven et al, Science 248:1120-1122, 1990; Murrell et al, Science 254:97-99, 1991; Haass et al, Nature Med. 1:1291-1296, 1995). The identification of mutations in the APP gene which causes early onset familial AD is a strong argument that $A\beta$ and amyloid are central to the pathogenetic process underlying this disease. Four reported disease-causing mutations have now been discovered which demonstrate the importance of $A\beta$ in causing familial AD reviewed in Hardy, Nature Gen. 1:233-234, 1992). Lastly, recent studies suggest that a reduction in amyloid plaque load in APP transgenic mice lead to improvements in behavioral impairment and memory loss Chen et al, Nature 408:978-982, 2000; Janus et al, Nature 408:979-982, 2000; Morgan et al, Nature 408:982-985, 2000). This is the strongest argument to date that implicates that reduction of $A\beta$ amyloid load in brain should be a central target for the development of new and effective treatments of AD and related disorders.

In addition, besides Alzheimer's disease, a number of other beta-amyloid protein diseases involve formation, deposition, accumulation and persistence of $A\beta$ fibrils, including Down's syndrome, disorders involving congophilic angiopathy, such as but not limited to, hereditary cerebral hemorrhage of the Dutch type, inclusion body myositosis, dementia pugilistica, cerebral $\beta$-amyloid angiopathy, dementia associated with progressive supranuclear palsy, dementia associated with cortical basal degeneration and mild cognitive impairment.

Modulators of APP Secretases as Therapeutic Targets for Alzheimer's Disease

Elucidating APP metabolism and its role in the formation of $A\beta$ plaques in AD is becoming increasingly important as therapeutics for AD and other beta-amyloid protein diseases are sought. Intracellular trafficking and proteolytic processing of APP directly influences the amount and type of $A\beta$ peptide and can thus have a profound impact on amyloid plaque load.

Processing of APP in vivo and in cultured cells occurs by two major pathways Haass and De Strooper, Science 2865441):916-9 1999) and; Selkoe, Physiol Rev. 81 2):741-66, 2001)). Cleavage of APP at the N-terminus of the $A\beta$ region by $\beta$-secretase and at the C-terminus by $\gamma$-secretases represents the amyloidogenic pathway for processing of APP. β-secretase cleaves APP between residues Met$^{595}$ and Asp$^{596}$ codon numbering refers to the APP695 isoform), and yields Aβ peptide plus the β-C-terminal fragment βCTF or C99). Following β-secretase cleavage, a second cleavage by γ-secretase occurs at the C-terminus of Aβ peptide that releases Aβ from CTF. This cleavage occurs in the vicinity of residue 636 of the C-terminus. γ-secretase can cleave the C-terminal region at either Val$^{636}$ or Ile$^{638}$ to produce a shorter Aβ peptide Aβ1-40) or the longer Aβ peptide Aβ1-42). The predominant form of Aβ found in the cerebrospinal fluid and conditioned media of cultured cells is the shorter Aβ40 peptide. Despite its lower abundance, Aβ42 is the peptide that is initially deposited within the extracellular plaques of AD patients. In addition, Aβ42 is shown to aggregate at a much lower concentration than the Aβ40 form. Alternatively, APP can also be processed via the non-amyloidogenic pathway whereby α-secretase cleaves within the Aβ domain between Lys$^{611}$ and Leu$^{612}$, and produces a large soluble APP domain sAPPα) and the αC-terminal fragment αCTF or C83). The latter can then be cleaved by γ-secretase at residue 636 or 638 to release a P3 peptide and the APP intracellular domain AICD). The α-cleavage pathway is the major pathway used to process APP in vivo; it does not yield Aβ peptide Selkoe, Physiol Rev. 812):741-66, 2001). The characterization of APP cleavage and the related secretases has provided significant advancement in therapeutic strategies that may lead to limiting the deposition of Aβ peptide in the brain and eliminate or delay the associated pathological effects in AD.

Alzheimer's Disease and the Aging Population

Alzheimer's disease is a leading cause of dementia in the elderly, affecting 5-10% of the population over the age of 65 years Jorm, A Guide to Understanding of Alzheimer's Disease and Related Disorders, New York University Press, New York, 1987). In AD, the parts of the brain essential for cognitive processes such as memory, attention, language, and reasoning degenerate. In some inherited forms of AD, onset is in middle age, but more commonly, symptoms appear from the mid-60's onward. AD today affects 4-5 million Americans, with slightly more than half of these people receiving care in many different health care institutions. The prevalence of AD and other dementias doubles every 5 years beyond the age of 65, and recent studies indicate that nearly 50% of all people age 85 and older have symptoms of AD NIH Progress Report on AD, National Institute on Aging, 2000). Thirty-three million people of the total population of the United States are age 65 and older, and this will climb to 51 million people by the year 2025 NIH Progress Report on AD, National Institute on Aging, 2000). The annual economic toll of AD in the United States in terms of health care expenses and lost wages of both patients and their caregivers is estimated at $80 to $100 billion NIH Progress Report on AD, National Institute on Aging, 2000).

DISCLOSURE OF THE INVENTION

Small peptides are disclosed which demonstrate great efficacy in inhibiting and/or disrupting amyloid fibrils. Also disclosed is the use of the same peptides for imaging the location of Aβ in the body for the purpose of diagnosis of Alzheimer's disease and other beta-amyloid protein Aβ) fibrillogenesis disorders, as well as the use of the same peptides for detecting Aβ in biological samples for the purpose of diagnosis of Alzheimer's disease and other beta-amyloid protein Aβ) fibrillogenesis disorders. "Fibrillogenesis" as used herein means the clinical or pathological binding of beta-amyloid to itself to form fibrils, and sometimes beta sheets, as known to those skilled in the art.

This disclosure pertains to compounds and pharmaceutical compositions thereof, that can bind to beta-amyloid protein Aβ) and modulate or moderate the aggregation and/or fibrillogenisis of Aβ, for the treatment and diagnosis of Aβ diseases such as Alzheimer's disease and other disorders that involve the accumulation and persistence of Aβ. These Aβ diseases include, but are not limited to, the amyloid associated with Alzheimer's disease and Down's syndrome, and various forms of cerebral amyloidosis, such as will be familiar to those knowledgeable in the art.

The disclosure relates to the novel and surprising discovery that certain peptides are binders and disruptors of Aβ amyloid fibrils, and are therefore useful for the therapeutic intervention of Alzheimer's disease and related Aβ disorders. Selected peptides are binders of Alzheimer's disease Aβ amyloid, and are therefore useful for the imaging and diagnosis of Alzheimer's disease and related Aβ disorders. Methods are disclosed for treating Alzheimer's disease and other Aβ disorders, comprising administering to a subject or patient a therapeutically effective dose of a selected 6-9mer peptide.

In one embodiment, in which preferably all amino acids indicated are D-amino acids, except where otherwise indicated such as by designating L-form peptides with "LP" number codes, or prefixing selected amino acid codes with "L-"), pharmaceutical compositions preferably contain at least one I peptide selected from the group of peptides comprising Ala-Gly-Gln-Trp-His-Arg-Val DP-026), Gly-Gln-Trp-His-Arg-Val-Ser DP-027), Gln-Trp-His-Arg-Val-Ser-Val DP-028), Trp-His-Arg-Val-Ser-Val-Arg DP-029), His-Arg-Val-Ser-Val-Arg-Trp DP-030), Arg-Val-Ser-Val-Arg-Trp-Gly DP-031), Asp-Gly-Arg-Trp-His-Arg-Val DP-032), Gly-Arg-Trp-His-Arg-Val-Ala DP-033), Arg-Trp-His-Arg-Val-Ala-Val DP-034), Trp-His-Arg-Val-Ala-Val-Ile DP-035), His-Arg-Val-Ala-Val-Ile-Met DP-036), Arg-Val-Ala-Val-Ile-Met-Gly DP-037), Thr-Leu-Phe-Leu-Ala-His-Gly DP-038), Leu-Phe-Leu-Ala-His-Gly-Arg DP-039), Phe-Leu-Ala-His-Gly-Arg-Leu DP-040), Leu-Ala-His-Gly-Arg-Leu-Val DP-041), Ala-His-Gly-Arg-Leu-Val-Phe DP-042), His-Gly-Arg-Leu-Val-Phe-Met DP-043), Gly-Leu-Ala-Phe-Val-Leu-Arg DP-044), Leu-Ala-Phe-Val-Leu-Arg-Gly DP-045), Ala-Phe-Val-Leu-Arg-Gly-Lys DP-046), Phe-Val-Leu-Arg-Gly-Lys-Ser DP-047), Val-Leu-Arg-Gly-Lys-Ser-Leu DP-048), Leu-Arg-Gly-Lys-Ser-Leu-Tyr DP-049), Arg-Val-Ala-Val-Ille-Met-Pro-Arg-Val-Ala-Val-Ile-Met DP-050), Trp-His-Arg-Val-Ala-Val-Ile-Met DP-051), Arg-Val-Ala-Val-Ile-Met DP-052), His-Arg-Pro-Ala-Val-Ile-Met DP-053), His-Arg-Val-Pro-Val-Ile-Met DP-054), His-Arg-Val-Ala-Val-Pro-Met DP-055), Leu-Ala-Phe-Val-Leu-Arg DP-056), Leu-Pro-Phe-Val-Leu-Arg DP-057), Arg-Arg-Pro-Ala-Phe-Val-Leu-Arg DP-058), Thr-Arg-Ile-Ser-Leu-Gln-Val DP-059), Ser-Leu-Gln-Val-Gln-Leu-Arg DP-060), Gln-Val-Gln-Leu-Arg-Lys-Arg DP-061), Arg-Val-Ser-Val-Arg-Trp DP-062), Arg-Val-Ser-Val-Arg DP-063), His-Pro-Arg-Leu-Val-Phe-Met DP-064), Trp-His-Arg-Val-Ala-Val-Ile-Met-amide DP-065), Trp-His-Arg-Val-Ala-Val-Ile-amide DP-066), Arg-Val-Ala-Val-Ile-Met-amide DP-067), Arg-Val-Ala-Val-Ile-Met-Gly-amide DP-068), Leu-Ala-Phe-Val-Leu-Arg-amide DP-069), His-Gly-Arg-Leu-Val-Phe-Met-amide DP-070), Thr-Leu-Phe-Leu-Ala-Arg DP-071), Trp-His-Leu-Ala-Phe-Val-Leu-Arg DP-072), Acetyl-Leu-Ala-Phe-Val-Leu-Arg-amide DP-073), Leu-Ala-Phe-Val-Leu-Arg-Lys-amide DP-074), Thr-Leu-Phe-Leu-Ala-Arg-amide DP-075), Acetyl-Thr-Leu-Phe-Leu-Ala-Arg-amide DP-076), Thr-Leu-Phe-Leu-Ala-Arg-Lys DP-077), Thr-Leu- Phe-Leu-Ala-Arg-Lys-amide DP-078), Trp-His-Leu-Ala-Phe-Val-Leu-Arg-amide DP-079), Trp-His-Leu-Ala-Phe-Val-Leu-Arg-Lys-amide DP-080). The group also includes certain analogs, derivatives, enantiomers, or fragments of the disclosed sequences herein as further discussed herein, and all hereafter referred to for easy reference as Sequence Group A.

In certain preferred embodiments, a compound has the general formula, or structure: Y—X-aa)-Z wherein X-aa) is essentially a peptide selected from the group consisting of -Arg-Val-Ser-Val-Arg-Trp-, -Arg-Val-Ala-Val-Ile, -His-Gly-Arg-Leu-Val-Phe-, -Leu-Ala-Phe-Val-Leu-Arg-, or -Thr-Leu-Phe-Leu-Ala-Arg-; and wherein Y— is an amino terminal N-terminal) modifying group which can be another an amino acid, a N-acylated amino acid, a peptide, a N-acylated peptide, or hydrogen, or other known N-terminus modifying compounds, and wherein Z is carboxyl-terminal C-terminal) modifying group selected from the group consisting of hydrogen, an amino acid, a C-amidated amino acid, a peptide, a C-amidated peptide, or other known C-terminal modifying groups.

Examples of peptides from Sequence Group A that work in the Y—X-aa)-Z model, hereafter referred to as Sequence Group B, include, His-Arg-Val-Ser-Val-Arg-Trp DP-030) Arg-Val-Ser-Val-Arg-Trp-Gly DP-031), Trp-His-Arg-Val-Ala-Val-Ile DP-035), His-Arg-Val-Ala-Val-Ile-Met DP-036), Arg-Val-Ala-Val-Ile-Met-Gly DP-037), Ala-His-Gly-Arg-Leu-Val-Phe DP-042), His-Gly-Arg-Leu-Val-Phe-Met DP-043), Trp-His-Arg-Val-Ala-Val-Ile-Met DP-051), Leu-Ala-Phe-Val-Leu-Arg DP-056), Trp-His-Arg-Val-Ala-Val-Ile-amide DP-066), Arg-Val-Ala-Val-Ile-Met-Gly-amide DP-068), Leu-Ala-Phe-Val-Leu-Arg-amide DP-069), His-Gly-Arg-Leu-Val-Phe-Met-amide DP-070), Thr-Leu-Phe-Leu-Ala-Arg DP-071), Trp-His-Leu-Ala-Phe-Val-Leu-Arg DP-072), Acetyl-Leu-Ala-Phe-Val-Leu-Arg-amide DP-073), Leu-Ala-Phe-Val-Leu-Arg-Lys-amide DP-074), Acetyl-Thr-Leu-Phe-Leu-Ala-Arg-amide DP-076), Trp-His-Leu-Ala-Phe-Val-Leu-Arg-amide DP-079), Trp-His-Leu-Ala-Phe-Val-Leu-Arg-Lys-amide DP-080).

It is preferable to select a peptide Y—X-aa)-Z as defined above but containing X-aa) peptides selected from -Arg-Val-Ala-Val-Ile-, -Leu-Ala-Phe-Val-Leu-Arg-, Thr-Leu-Phe-Leu-Ala-Arg-. Examples of these preferred structures hereafter referred to as Sequence Group C include Trp-His-Arg-Val-Ala-Val-Ile DP-035), His-Arg-Val-Ala-Val-Ile-Met DP-036), Arg-Val-Ala-Val-Ile-Met-Gly DP-037), Trp-His-Arg-Val-Ala-Val-Ile-Met DP-051), Trp-His-Arg-Val-Ala-Val-Ile-amide DP-066), Arg-Val-Ala-Val-Ile-Met-Gly-amide DP-068), Leu-Ala-Phe-Val-Leu-Arg DP-056), Leu-Ala-Phe-Val-Leu-Arg-amide DP-069), Trp-His-Leu-Ala-Phe-Val-Leu-Arg DP-072), Acetyl-Leu-Ala-Phe-Val-Leu-Arg-amide DP-073), Leu-Ala-Phe-Val-Leu-Arg-Lys-amide DP-074), Trp-His-Leu-Ala-Phe-Val-Leu-Arg-amide DP-079), Trp-His-Leu-Ala-Phe-Val-Leu-Arg-Lys-amide DP-080), Thr-Leu-Phe-Leu-Ala-Arg DP-071), Acetyl-Thr-Leu-Phe-Leu-Ala-Arg-amide DP-076).

Preferred efficacious peptide fragments in this disclosure are -Arg-Val-Ser-Val-Arg-Trp-, -Arg-Val-Ala-Val-Ile-, -His-Gly-Arg-Leu-Val-Phe-, -Leu-Ala-Phe-Val-Leu-Arg-, and -Thr-Leu-Phe-Leu-Ala-Arg-. These preferred fragments may be therapeutically employed either alone, in combination with each other, as foundations for further synthesis, or as otherwise disclosed herein.

Also disclosed is the use of N-methylated analogs of Sequence Group A, B, or C, including the use of αN-methylation or L-amino acids preferably methylated amino acids) exclusively or partially during synthesis such that the resulting peptides will have purely αN-methylated amide bonds or partially αN-methylated or alternating αN-methylated and non-αN-methylated amide bonds. Preferred compounds are selected from Sequence Group A, B, or C with modified amide bonds such that at least one of the amide bonds in the peptide back-bone is N-methylated, preventing the peptide itself from beta-sheet formation.

Mimetic peptidomimetic) compounds are also disclosed as modeled from other peptides disclosed herein, including the peptides of Sequence Group A, B, or C. The term "mimetic" generally includes "isosteres", such as modifications of the peptide backbones i.e. amide bond mimetics) with amide nitrogen, amide carbonyl, or complete replacement of the amide bond. The amide bond can advantageously be replaced by similar length bridges known to those skilled in the art, such as: —$CH_2S$—, —CH=CH—, —$CH_2NH$—, —$CSNH_2$—, or $COCH_2$.

Mimetics can be generated using software that can derive a virtual peptide model from several of the peptide structures disclosed herein. This can be done using the software derived from SLATE algorithm. See, Perkin, Mills and Dean, 1995 Journal of Computer Aided Molecular Design 96) p 479-490; Mills et al. 2001 Journal of Computer Aided Molecular Design 151) p 81-96; De Esch, I J, et al 2001 Journal of Med. Chem. 4411) p 1666-74; Mills Perkins and Dean 1997 Journal of Computer Aided Molecular Design 11 2) p 175-92). One example of the program derived from SLATE algorithm is Quasi by De Novo Pharmaceutical. This program superimposes several active but apparently dissimilar peptide molecules that are active to arrive at the most probable structures essential for activity with minimum energy constraint). This can be used to generate a mold or target binding site with predicted position of hydrogen binding atoms in three dimensional space. This can then be used to generate a non-peptide mimic of the original ligand peptides. These molecule generator softwares are now commercially available example Skelgen and Skelgen II).

A "mimetic" of a compound also refers to a compound in which chemical structures of the compound that are necessary for functional activity have been replaced with other chemical structures which mimic the conformation of the compound or peptides thereof. The term "mimetic" as used herein is also intended to include molecules which mimic the chemical structure of a L or D-peptidic structure, and retain the functional properties of a L- or D-peptidic structure. Other approaches to designing peptide analogs, derivatives and mimetics are also well known in the art. For example, see P. S. Farmer, in Drug Design, E. J. Ariens, ed., Academic Press, New York, 1980, v. 10, pp. 119-143; Ball and Alewood, J. Mol. Recognition. 3:55, 1990; Morgan and Gainor, Ann. Rep. Med. Chem. 24:243, 1989; and Freidinger, Trends Pharmacol. Sci. 10:270, 1989. See also Sawyer, "Peptidomimetic design and chemical approaches to peptide metabolism", in M D Taylor and G L Amidon, eds., in Peptide-Based Drug Design: Controlling Transport and Metabolism, Ch. 17, 1995; Smith et al, J. Am. Chem. Soc. 117:11113-11123, 1995; Smith et al, J. Am. Chem. Soc. 116:9947-9962, 1994; and Hirschman et al, J. Am. Chem. Soc. 115:12550-12568, 1993.

The term "analogs" includes variants of the peptide molecule brought about by, for example, homologous substitution of one or more amino acid residues as will be appreciated by those skilled in the art, reversal of the sequence, or partial or complete replacement of component amino acids with compositionally identical enantiomers D-vs L-amino acids). Analogs also include "conservative amino acid substitutions" in which one amino acid is substituted with an amino acid having a similar side chain. Examples of similar side chain amino acids, are basic side chain amino acids e.g., lysine, arginine, histidine), acidic side chain amino acids e.g., aspartic acid, glutamic acid), non polar side chain amino acids e.g., glycine, alanine, valine, leucine, isoleucine, proline, phenylalanine, methionine, tryptophan), uncharged polar side chain amino acids e.g., aspargine, glutamine, serine, threonine, tyrosine, cystine), branched side chain amino acids e.g., threonine, leucine, valine, isoleucine) and aromatic side chain amino acids e.g., tyrosine, phenylalanine, tryptophan, histidine). Analogs also include "homolougous amino acid substitutions" in which an amino acid is substituted with homologous amino acids, such as replacement of phenyalanine with tyrosine, pyridylalanine, or homophenylalanine, and replacement of leucine with valine, or vice versa.

The term "derivative" includes minor chemical changes familiar to those skilled in the art in which one or more reactive groups on Sequence Group A, B, or C peptides have been "peptide derivatized" such that there are peptides in which an amino acid side chain, peptide backbone, or amino- or carboxy-terminus has been derivatized as further discussed herein.

In any of the above structures or sequences, the nomenclature or symbolic representation of any or all of the individual amino acids are given by the standard 3-letter abbreviation for the amino acids preceded optionally by either D- or L-representing the 2 enantiomeric forms mirror images of each other) of individual amino acids making up the sequence. Acetyl- and -amide at the N- and C-terminal respectively are optionally included when present or indicated as preferred.

Also disclosed are compounds that include Sequence Group A, B, or C peptides, portions of Sequence Group A, B, or C peptides and their novel analogs and derivatives thereof, the administration of which comprises a method for treating Alzheimer's disease and other Aβ amyloidoses. A method is thus provided for treating Alzheimer's disease and other disorders involving the formation and persistence of Aβ, comprising the administration to the subject a therapeutically effective amount of a compound such that the subject is treated for disorder associated with Aβ amyloidosis. Preferably, the disorders are Alzheimer's disease, Down's syndrome and other Aβ amyloidoses. Typically, the pharmaceutical composition includes a therapeutically effective amount of a disclosed compound or pharmaceutically acceptable salts of a compound, with optional pharmaceutically acceptable carrier, diluent or excipient.

Also disclosed is the use of pills, tablets, caplets, soft and hard gelatin capsules, lozenges, sachets, cachets, vegicaps, liquid drops, elixers, suspensions, emulsions, solutions, syrups, tea bags, aerosols as a solid or in a liquid medium), suppositories, sterile injectable solutions, and sterile packaged powders, which contain a disclosed compound to treat patients with Alzheimer's disease and other Aβ amyloidoses. Therefore, the use of a disclosed compound for therapy or for the manufacture of a medicament for the treatment of a disorder associated with Aβ amyloidoses is also contemplated.

Compositions and methods involving administering to a subject a therapeutic dose of a selected disclosed compound that inhibits Aβ amyloid deposition, or Aβ amyloidosis in disorders in which Aβ amyloid deposition occurs are provided. Disclosed compounds can be used therapeutically to treat amyloidosis or can be used prophylactically in a subject susceptible to Aβ amyloidosis. The methods are based, at least in part, on directly binding Aβ amyloid either in the brain or in peripheral circulation, inhibiting Aβ amyloid fibril formation, and/or causing dissolution of pre-formed Aβ amyloid fibrils. Peripheral sequestration of Aβ by Sequence Group A, B, or C compounds is believed to result in movement of Aβ from the brain to the peripheral circulation, thereby inhibiting brain Aβ amyloid fibril formation, and/or causing dissolution of pre-formed brain Aβ amyloid fibrils.

Methods for detecting the presence or absence of Aβ peptides in a biological sample are provided. These methods include contacting a biological sample with a selected compound, wherein the compound is labeled with a detectable substance, for example, with a radionucleotide, phosphorescent compound, fluorescent compound, fluorescent protein, paramagnetic compound, metal chelators, or enzyme, all of which are readily detectable in various assays and diagnostics know to those skilled in the art, and then detecting the detectable substance bound to Aβ peptides in the biological sample.

Methods for imaging the presence or absence of Aβ peptides in the body or biological tissues are provided. These methods include contacting Aβ peptides in the body with a compound, wherein the compound is labeled with detectable substance, for example, with a radionucleotide, phosphorescent compound, fluorescent compound, fluorescent protein, paramagnetic compound, metal chelator, or enzyme, and detecting the detectable substance bound to Aβ peptides in the body or biological tissues.

Use of anti-idiotypic antibodies to Sequence Group A, B, or C peptides, analogs, derivatives or fragments thereof, as potent binders of Aβ, and inhibitors of Aβ amyloid formation, deposition, accumulation and/or persistence in Alzheimer's disease and other Aβ amyloidosis is presented. The term "anti-idiotypic antibodies" refers to the antibodies A) raised against or that specifically recognize the Fab regions of other antibodies B), and the Fab regions of antibodies B, recognize one of the peptides in Sequence Group A, B, or C. The result is that the anti-idiotypic antibodies A to Sequence Group A, B, or C peptides have Fab regions mimicking a Sequence Group A, B, or C peptide, in terms of reactivity, amyloid binding and amyloid disrupting properties.

Use of antibodies recognizing compounds for in vivo labeling is presented; for example, with a radionucleotide, for radioimaging to be utilized for in vivo diagnosis, and/or for in vitro diagnosis.

An important Aβ amyloidosis to which the disclosed therapeutics is addressed is Alzheimer's disease. A preferred therapeutically effective amount of disclosed compound is a dosage in the range of from about 10 μg to about 50 mg/kg body weight/per day, and more preferably in the range of from about 100 μg to about 10 mg/kg body weight per day.

A pharmaceutical agent containing a selected disclosed compound may advantageously be given by injection or infusion or nasal drop or nasal spray or oral administration. In any of the above structures or sequences, the nomenclature or symbolic representation of any or all of the individual amino acids may be given by either the standard 3-letter abbreviation for the amino acid, or the standard single letter code for the amino acid, and sometimes both in appropriate cases.

In one embodiment, there is disclosed the use of a peptide comprising Leu-Ala-Phe-Val-Leu-Arg-Lys-amide having at least one D amino acid either for the reduction of beta-amyloid protein Aβ) in vivo or for the treatment of beta-amyloid protein diseases such as Alzheimer's disease, Down's syndrome, congophilic angiopathy, hereditary cerebral hemorrhage of the Dutch type, inclusion body myositosis, dementia pugilistica, cerebral β-amyloid angiopathy, dementia associated with progressive supranuclear palsy, dementia associated with cortical basal degeneration and mild cognitive impairment. Additionally, the amino acids in the peptide can be N-methylated.

In another embodiment, there is disclosed the use of a pharmaceutical composition comprising the peptide Leu-Ala-Phe-Val-Leu-Arg-Lys-amide having at least one D amino acid for the treatment of beta-amyloid protein diseases wherein the pharmaceutical composition further comprises a pharmaceutically acceptable carrier, diluent or excipient.

In another embodiment, there is disclosed the use of a pharmaceutical composition comprising the peptide Leu-Ala-Phe-Val-Leu-Arg-Lys-amide having at least one D amino acid for modulating APP processing or for modulating activity of APP secretases wherein the secretase can be gamma or beta secretase. The pharmaceutical composition can be used in a dosage in the range of from about 10 μg to about 100 mg/kg body weight/day or from about 100 μg to about 50 mg/kg body weight/day and can be administered in a subcutaneous, interperitoneal, intramuscular, parenteral injectable form, or in infusible form or either orally or by nasal spray.

BRIEF DESCRIPTION OF THE DRAWINGS

The following drawings are illustrative of embodiments of the invention and are not meant to limit the scope of the invention.

FIG. 52 is a summary of Thio T ranking 65-72.

BEST MODE OF CARRYING OUT THE INVENTION

Example 1

Preparation of Peptides

Figure 1:
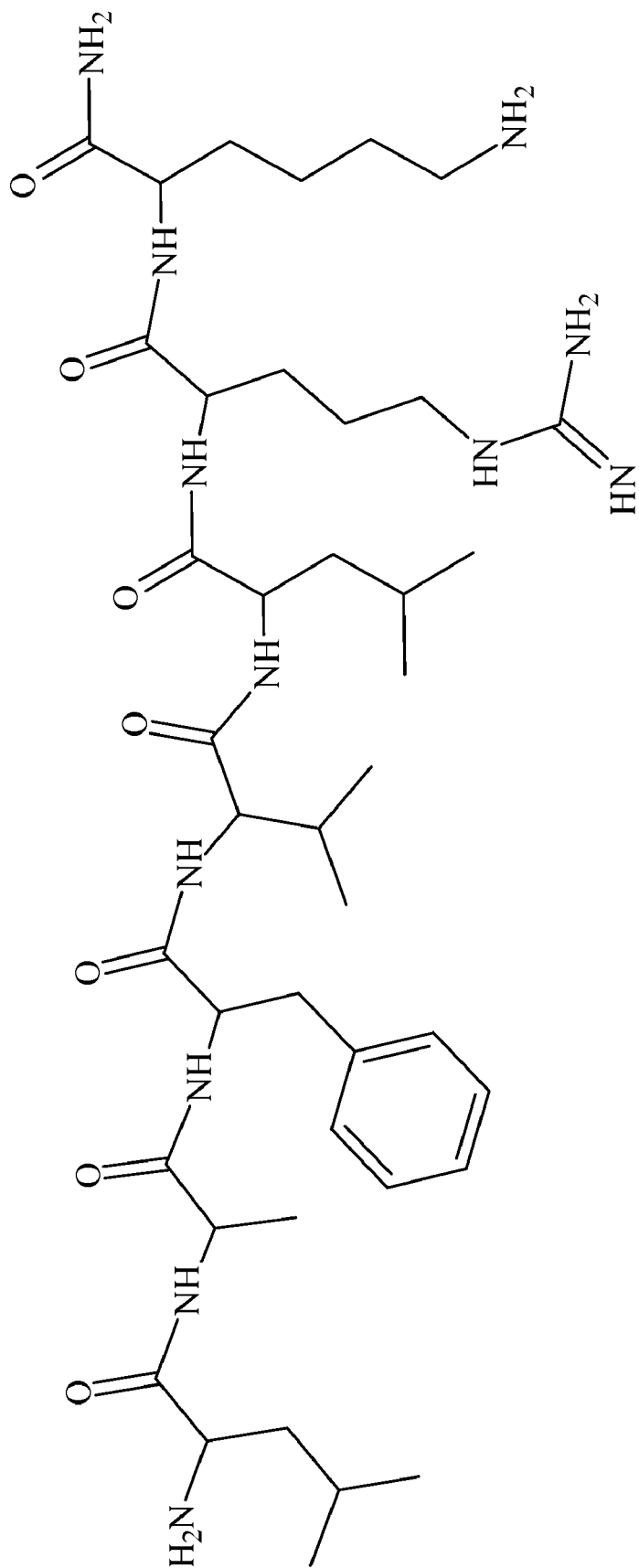
FIG. 1 shows the structure of DP-074.

The peptides disclosed herein were produced in both the L- and D-amino acid forms. In addition, truncated peptides and peptide analogs were assembled for use as potential therapeutic peptides for the treatment of Aβ fibrillogenesis in Alzheimer's disease and related disorders. These peptides are preferably conventionally synthesized. For example, L- and D-peptides were synthesized on peptide synthesizers known to those skilled in the art, such as the Advanced ChemTech Model 396 multiple peptide synthesizer Louisville, Ky.), using an automated protocol established by the manufacturer for 0.025 mmole scale synthesis. Double couplings were performed on all cycles using 2-1H-benzotriazol-1-yl)-1,1,3,3-tetramethyluronium hexafluorophosphate HBTU)/N,N-diisopropylethylamine DIEA)/HOBt/FMOC-AA in four-fold excess for 30 minutes, followed by DIC/HOBt/FMOC-AA in fourfold excess for 45 minutes.

The peptide was then de-protected and removed from the resin by treatment with TFA/water 95%/5%) for 3 hours and then precipitated with cold ether. The resulting solid was then pelleted by centrifugation 2400 rpm×10 min), and the ether was discarded. The solid was then be re-suspended in ether and re-centrifuged for the second time after which the ether was decanted for the second time. The solid was dissolved in 10% acetic acid and lyophilized to dryness ~30 mg for 12 amino acid peptides; 18 mg for 7 amino acid peptides). The crude peptide was purified by preparative HPLC using instruments known to those skilled in the art, such as a HP 1100 series with diode array detector, with a Vydac C18 column 21×250 mm) using a 15%-40% acetonitrile gradient over 80 minutes at a flow rate of 5 ml/min). The primary fraction was then collected and re-analyzed for purity using analytical HPLC to ensure a single symmetrical peak at all wavelengths. The confirmation of structures and sequences was based on comparison of predicted molecular weights, to molecular weights obtained by ESI mass spectroscopy. These analyses were performed using instruments known to those skilled in the art, such as a Sciex API IIIE triple quadruple ion spray mass spectrometer or ESI Agilent MSD-SL. 12-13mer peptides were synthesized with the following sequences, preferably all employing D-amino acids, except where otherwise indicated:

Arg-Lys-Arg-Leu-Gln-Val-Gln-Leu-Ser-Ile-Arg-Thr DP-001), Arg-Gln-Val-Phe-Gln-Val-Ala-Tyr-Ile-Ile-Ile-Lys-

Ala DP-002), Tyr-Leu-Ser-Lys-Gly-Arg-Leu-Val-Phe-Ala-Leu-Gly DP-003), Thr-Leu-Phe-Leu-Ala-His-Gly-Arg-Leu-Val-Phe-Met DP-004), Ala-Gly-Gln-Trp-His-Arg-Val-Ser-Val-Arg-Trp-Gly DP-005), Asp-Gly-Arg-Trp-His-Arg-Val-Ala-Val-Ile-Met-Gly DP-006), His-Gln-Thr-Trp-Thr-Arg-Asn-Leu-Gln-Val-Thr-Leu DP-007), Ile-Ser-Asn-Val-Phe-Val-Gln-Arg-Leu-Ser-Leu-Ser DP-008), Arg-Gly-Leu-Val-Phe-His-Thr-Gly-Thr-Lys-Asn-Ser-Phe DP-009), Gly-Asn-Ser-Thr-Ile-Ser-Ile-Arg-Ala-Pro-Val-Tyr DP-010), Val-Arg-Trp-Gly-Met-Gln-Gln-Ile-Gln-Leu-Val-Val DP-011), Ala-Pro-Val-Asn-Val-Thr-Ala-Ser-Val-Gln-Ile-Gln DP-012), Thr-Arg-Ile-Ser-Leu-Gln-Val-Gln-Leu-Arg-Lys-Arg DP-013), Ala-Lys-Ile-Ile-Ile-Tyr-Ala-Val-Gln-Phe-Val-Gln-Arg DP-014), Gly-Leu-Ala-Phe-Val-Leu-Arg-Gly-Lys-Ser-Leu-Tyr DP-015), Met-Phe-Val-Leu-Arg-Gly-His-Ala-Leu-Phe-Leu-Thr DP-016), Gly-Trp-Arg-Val-Ser-Val-Arg-His-Trp-Gln-Gly-Ala DP-017), Gly-Met-Ile-Val-Ala-Val-Arg-His-Trp-Arg-Gly-Asp DP-018), L-Arg-L-Lys-L-Arg-L-Leu-L-Gln-L-Val-L-Gln-L-Leu-L-Ser-L-Ile-L-Arg-L-Thr DP-019), and Arg-Val-Ala-Val-Ile-Met-Pro-Arg-Val-Ala-Val-Ile-Met DP-050).

In addition 6-9mer peptides including, iAβ5 LP-025) and piAβ5 LP-081) were synthesized with the following sequences and/or modifications: L-Leu-L-Pro-L-Phe-L-Phe-L-Asp LP-025), Ala-Gly-Gln-Trp-His-Arg-Val DP-026), Gly-Gln-Trp-His-Arg-Val-Ser DP-027), Gln-Trp-His-Arg-Val-Ser-Val DP-028), Trp-His-Arg-Val-Ser-Val-Arg DP-029), His-Arg-Val-Ser-Val-Arg-Trp DP-030), Arg-Val-Ser-Val-Arg-Trp-Gly DP-031), Asp-Gly-Arg-Trp-His-Arg-Val DP-032), Gly-Arg-Trp-His-Arg-Val-Ala DP-033), Arg-Trp-His-Arg-Val-Ala-Val DP-034), Trp-His-Arg-Val-Ala-Val-Ile DP-035), His-Arg-Val-Ala-Val-Ile-Met DP-036), Arg-Val-Ala-Val-Ile-Met-Gly DP-037), Thr-Leu-Phe-Leu-Ala-His-Gly DP-038), Leu-Phe-Leu-Ala-His-Gly-Arg DP-039), Phe-Leu-Ala-His-Gly-Arg-Leu DP-040), Leu-Ala-His-Gly-Arg-Leu-Val DP-041), Ala-His-Gly-Arg-Leu-Val-Phe DP-042), His-Gly-Arg-Leu-Val-Phe-Met DP-043), Gly-Leu-Ala-Phe-Val-Leu-Arg DP-044), Leu-Ala-Phe-Val-Leu-Arg-Gly DP-045), Ala-Phe-Val-Leu-Arg-Gly-Lys DP-046), Phe-Val-Leu-Arg-Gly-Lys-Ser DP-047), Val-Leu-Arg-Gly-Lys-Ser-Leu DP-048), Leu-Arg-Gly-Lys-Ser-Leu-Tyr DP-049), Trp-His-Arg-Val-Ala-Val-Ile-Met DP-051), Arg-Val-Ala-Val-Ile-Met DP-052), His-Arg-Pro-Ala-Val-Ile-Met DP-053), His-Arg-Val-Pro-Val-Ile-Met DP-054), His-Arg-Val-Ala-Val-Pro-Met DP-055), Leu-Ala-Phe-Val-Leu-Arg DP-056), Leu-Pro-Phe-Val-Leu-Arg DP-057), Arg-Arg-Pro-Ala-Phe-Val-Leu-Arg DP-058), Thr-Arg-Ile-Ser-Leu-Gln-Val DP-059), Ser-Leu-Gln-Val-Gln-Leu-Arg DP-060), Gln-Val-Gln-Leu-Arg-Lys-Arg DP-061), Arg-Val-Ser-Val-Arg-Trp DP-062), Arg-Val-Ser-Val-Arg DP-063), His-Pro-Arg-Leu-Val-Phe-Met DP-064), Trp-His-Arg-Val-Ala-Val-Ile-Met-amide DP-065), Trp-His-Arg-Val-Ala-Val-Ile-amide DP-066), Arg-Val-Ala-Val-Ile-Met-amide DP-067), Arg-Val-Ala-Val-Ile-Met-Gly-amide DP-068), Leu-Ala-Phe-Val-Leu-Arg-amide DP-069), His-Gly-Arg-Leu-Val-Phe-Met-amide DP-070), Thr-Leu-Phe-Leu-Ala-Arg DP-071), Trp-His-Leu-Ala-Phe-Val-Leu-Arg DP-072), Acetyl-Leu-Ala-Phe-Val-Leu-Arg-amide DP-073), Leu-Ala-Phe-Val-Leu-Arg-Lys-amide DP-074), Thr-Leu-Phe-Leu-Ala-Arg-amide DP-075), Acetyl-Thr-Leu-Phe-Leu-Ala-Arg-amide DP-076), Thr-Leu-Phe-Leu-Ala-Arg-Lys DP-077), Thr-Leu-Phe-Leu-Ala-Arg-Lys-amide DP-078), Trp-His-Leu-Ala-Phe-Val-Leu-Arg-amide DP-079), Trp-His-Leu-Ala-Phe-Val-Leu-Arg-Lys-amide DP-080), and Acetyl-L-Leu-L-Pro-L-Phe-L-Asp-L-amide LP-081). D-indicates D-amino acids and L-indicates L-amino acids.

Example 2

Disruption of Alzheimer Fibrils Beta-Sheet Secondary Structure by 12-13mer Peptides as Assessed by CD Spectropolarimetry Circular dichroism CD) spectra of Aβ42 in the presence or absence of synthetic peptides outlined in Example 1 were recorded at 25° C. on a JASCO-810 Spectropolarimeter using a 0.5 mm path length quartz cuvette, and over the range of 190-260 nm. The instrument was calibrated with an aqueous solution of +)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity MRE) of Aβ42, after subtraction of the background solvent spectrum and/or test peptide spectrum. For this study, fibrillar Aβ42 0.1 mg/ml) in TPBSF 10% TFE, 150 mM NaF, 50 mM HNaPO$_4$, pH 7.4) was incubated for 3 days at 37° C. in the presence and absence of various 12-13mer peptides at an Aβ42:peptide wt/wt ratio of 1:2, before recording the CD spectra. The percent disruption of beta-sheet structure was determined by the calculating the percent loss of negative ellipticity at 218 nm compared to Aβ42 alone, after the corresponding blanks were subtracted.

Figure 2:
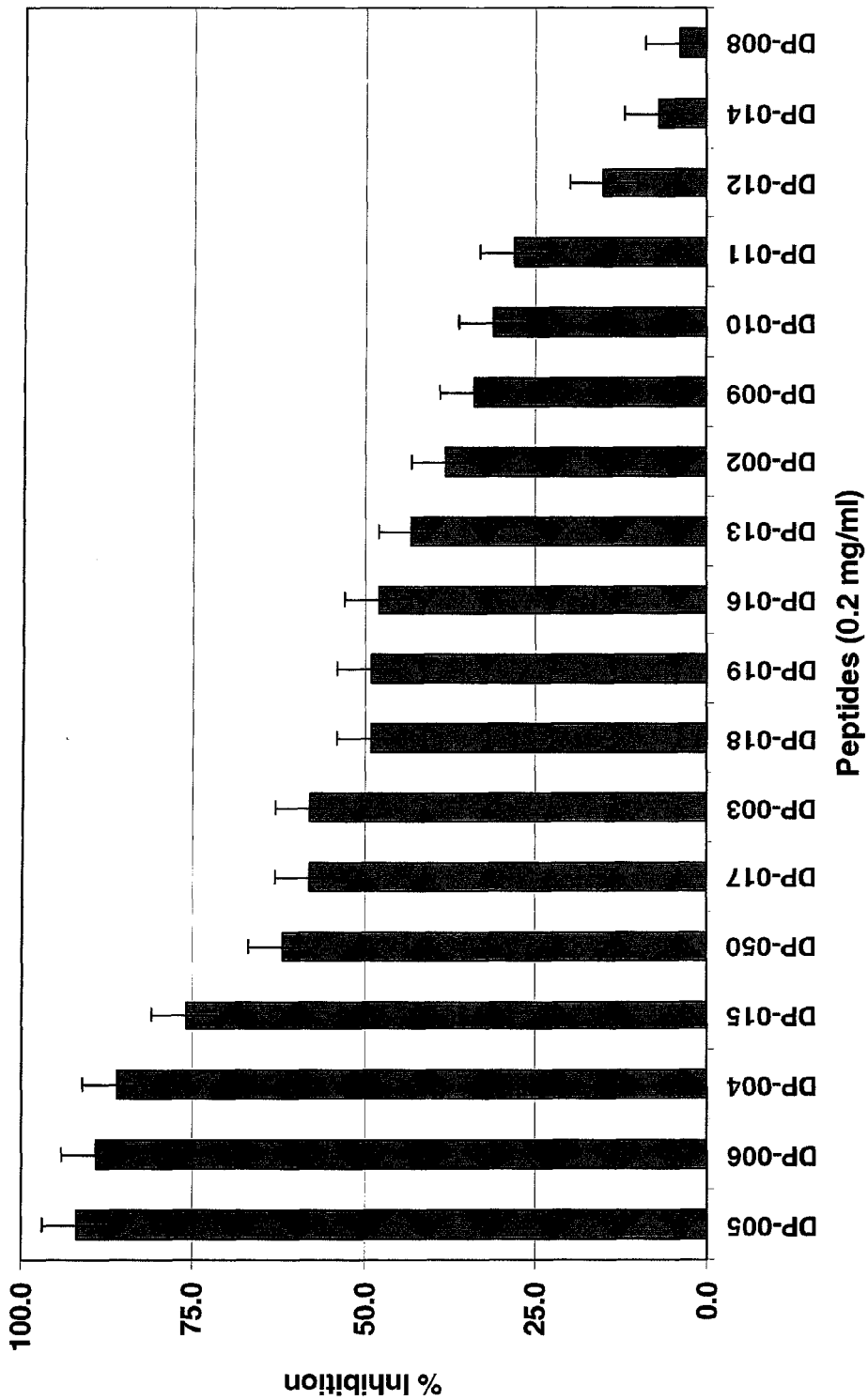
FIG. 2 is a graph showing an ordered summary comparison of the effect of various 12-13mer peptides on beta-sheet secondary structure of 25 μM Aβ42 amyloid fibrils as assessed by circular dichroism CD) spectropolarimetry. Shown is the percent disruption of Aβ42 fibrils as assessed by loss of ellipticity at 218 nm, representing the signal that is inversely related to beta-sheet secondary structure.

FIG. 2 showing the disrupters of Aβ42 beta-sheet secondary structure among 12-13 mer peptide analogs, sorted in order of effectiveness, as assessed by CD spectropolarimetry. Other peptides that are also effective are not included in this list. The preferred peptides include in order of effectiveness as shown in FIG. 2 are Ala-Gly-Gln-Trp-His-Arg-Val-Ser-Val-Arg-Trp-Gly DP-005), Asp-Gly-Arg-Trp-His-Arg-Val-Ala-Val-Ile-Met-Gly DP-006), Thr-Leu-Phe-Leu-Ala-His-Gly-Arg-Leu-Val-Phe-Met DP-004), Gly-Leu-Ala-Phe-Val-Leu-Arg-Gly-Lys-Ser-Leu-Tyr DP-015), Arg-Val-Ala-Val-Ile-Met-Pro-Arg-Val-Ala-Val-Ile-Met DP-050), Gly-Trp-Arg-Val-Ser-Val-Arg-His-Trp-Gln-Gly-Ala DP-017), Tyr-eu-Ser-Lys-Gly-Arg-Leu-Val-Phe-Ala-Leu-Gly DP-003), Gly-Met-Ile-Val-Ala-Val-Arg-His-Trp-Arg-Gly-Asp DP-018), L-Arg-L-Lys-L-Arg-L-Leu-L-Gln-L-Val-L-Gln-L-Leu-L-Ser-L-Ile-L-Arg-L-Thr DP-019), Met-Phe-Val-Leu-Arg-Gly-His-Ala-Leu-Phe-Leu-Thr DP-016), Thr-Arg-Ile-Ser-Leu-Gln-Val-Gln-Leu-Arg-Lys-Arg DP-013), Arg-Gln-Val-Phe-Gln-Val-Ala-Tyr-Ile-Ile-Ile-Lys-Ala DP-002), Arg-Gly-Leu-Val-Phe-His-Thr-Gly-Thr-Lys-Asn-Ser-Phe DP-009), Gly-Asn-Ser-Thr-Ile-Ser-Ile-Arg-Ala-Pro-Val-Tyr DP-010), Val-Arg-Trp-Gly-Met-Gln-Gln-Ile-Gln-Leu-Val-Val DP-011), Ala-Pro-Val-Asn-Val-Thr-Ala-Ser-Val-Gln-Ile-Gln DP-012), Ala-Lys-Ile-Ile-Ile-Tyr-Ala-Val-Gln-Phe-Val-Gln-Arg DP-014), and Ile-Ser-Asn-Val-Phe-Val-Gln-Arg-Leu-Ser-Leu-Ser DP-008). DP-005, DP-006, DP-004 and DP-015 show >75% disruption of fibrillar Aβ42, whereas DP-050, DP-017 and DP-003, show >50% disruption of Aβ42 fibrils FIG. 2).

Example 3

Disruption of Alzheimer's Aβ Fibrils by 12-13mer Peptides as Assessed by Thioflavin T Fluorometry Various peptides synthesized as outlined in Example 1 were tested for potential Aβ amyloid disrupting activity using a variety of in vitro assays. One such assay, Thioflavin T fluorometry, which measures the amount of amyloid fibrils LeVine III, Protein Sci. 2:404-410, 1993; Amyloid: Int. J. Exp. Clin. Invest. 2:1-6, 1995; Naiki and Nakakuki, Lab.

Invest., 74:374-383, 1996; Castillo et al, *J. Neurochem.* 69:2452-2465, 1997) was used to identify synthetic peptides capable of disrupting Aβ42 amyloid fibrils. For these studies, 0.1 mg/ml of Aβ42 Bachem Inc) was incubated in microcentrifuge tubes at 37° C. for 3 days in triplicate), either alone, or in the presence of 0.2 mg/ml peptide at an Aβ:peptide weight ratio of 1:2) in TPBSF 10% TFE, 150 mM NaF, 50 mM HNaPO$_4$, pH 7.4). Fifty μl aliquots were taken for analysis at day 3, and 200 ul aliquots of 125 μM Thioflavin T in 62 mM NaPO4 pH 6.0), were added to give a final Thioflavin T concentration of 100 μM and 62 mM of NaPO4. Fluorescence emission at 480 nm was measured on a microplate 96well-fluorometer Labsystem) at an excitation wavelength of 450 nm. For all determinations any fluorescence given off by peptides in the presence of the Thioflavin T reagent was always subtracted from all pertinent readings. Previous studies have indicated that increasing concentrations of fibrillar A42 gives a proportional increase in fluorescence in the presence of 100 μM Thioflavin T, ruling out the presence of any disproportionate inner filter effects at this Thioflavin T concentration Castillo et al *J. Neurochem.* 69:2452-2465, 1997).

Figure 3:
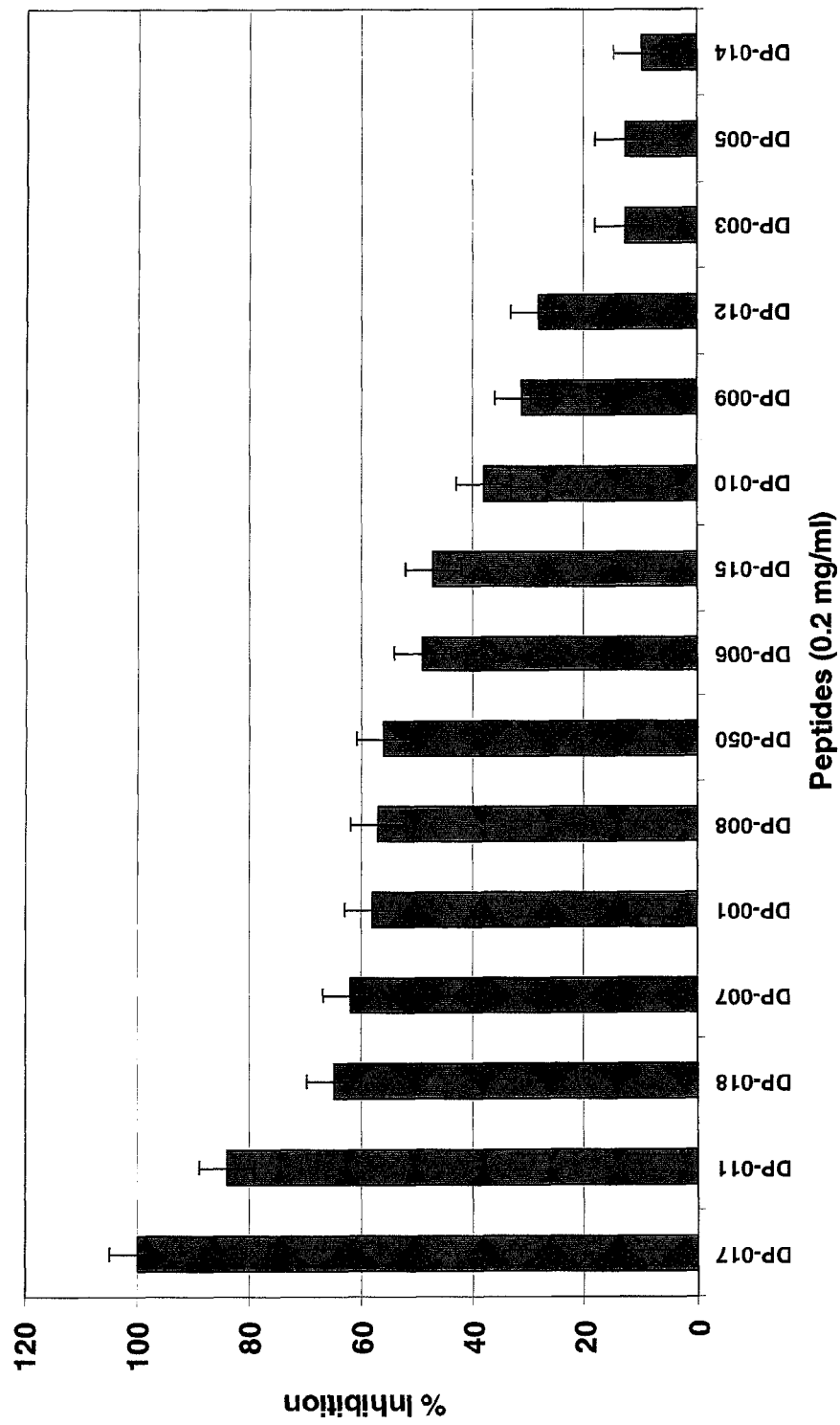
FIG. 3 is a graph showing an ordered summary comparison of the effect of 12-13mer peptides on beta-sheet secondary structure of 25 μM Aβ42 amyloid fibrils as assessed by Thioflavin T fluorometry. Shown is the percent disruption of Aβ42 fibrils by various 12-13mer peptides at an Aβ42:12-13mer peptide weight ratio of 1:2.

FIG. 3 shows preferred disrupters of Thioflavin T binding to Aβ42 from among 12-13 amino acid peptide analogs, sorted in order of effectiveness. The peptides in order of effectiveness as determined by Thioflavin T fluorometry, include but are not limited to Gly-Trp-Arg-Val-Ser-Val-Arg-His-Trp-Gln-Gly-Ala DP-017), Val-Arg-Trp-Gly-Met-Gln-Gln-Ile-Gln-Leu-Val-Val DP-011), Gly-Met-Ile-Val-Ala-Val-Arg-His-Trp-Arg-Gly-Asp DP-018), His-Gln-Thr-Trp-Thr-Arg-Asn-Leu-Gln-Val-Thr-Leu DP-007), Arg-Lys-Arg-Leu-Gln-Val-Gln-Leu-Ser-Ile-Arg-Thr DP-001), Ile-Ser-Asn-Val-Phe-Val-Gln-Arg-Leu-Ser-Leu-Ser DP-008), Arg-Val-Ala-Val-Ile-Met-Pro-Arg-Val-Ala-Val-Ile-Met DP-050), Asp-Gly-Arg-Trp-His-Arg-Val-Ala-Val-Ile-Met-Gly DP-006), Gly-Leu-Ala-Phe-Val-Leu-Arg-Gly-Lys-Ser-Leu-Tyr DP-015), Gly-Asn-Ser-Thr-Ile-Ser-Ile-Arg-Ala-Pro-Val-Tyr DP-010), Arg-Gly-Leu-Val-Phe-His-Thr-Gly-Thr-Lys-Asn-Ser-Phe DP-009), Ala-Pro-Val-Asn-Val-Thr-Ala-Ser-Val-Gln-Ile-Gln DP-012), Tyr-eu-Ser-Lys-Gly-Arg-Leu-Val-Phe-Ala-Leu-Gly DP-003), Ala-Gly-Gln-Trp-His-Arg-Val-Ser-Val-Arg-Trp-Gly DP-005), and Ala-Lys-Ile-Ile-Ile-Tyr-Ala-Val-Gln-Phe-Val-Gln-Arg DP-014). DP-017 and DP-011 demonstrate >80% disruption of Aβ42 fibrils, DP-018 and DP-007 demonstrate >60% disruption of Aβ42 fibrils, whereas DP-001, DP-008, DP-050, DP-006 and DP-015 demonstrate >40% disruption of Aβ42 fibrils FIG. 3).

Example 4

Disruption of Alzheimer Fibrils β-Sheet Secondary Structure by 6-9mer Peptides as Assessed by CD Spectropolarimetry Circular dichroism CD) spectropolarimetry is another in vitro technique used to determine a given peptide's effectiveness in disrupting the b-sheet secondary structure of Aβ-fibrils. CD spectra of Aβ42 in the presence or absence of synthetic peptides were recorded at 25° C. on a JASCO-810 Spectropolarimeter using a 0.5 mm path length quartz cuvette, and over the range of 190-260 nm. The instrument was calibrated with an aqueous solution of +)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity MRE) of Aβ42, after subtraction of the background solvent spectrum and/or test peptide spectrum. For this study, fibrillar Aβ42 0.1 mg/ml) in TPBSF 10% TFE, 150 mM NaF, 50 mM HNaPO$_4$, pH 7.4) was incubated for 3 days at 37° C. in the presence and absence of various peptides at an Aβ42:peptide wt/wt ratio of 1:2, before recording the CD spectra. The percent disruption of beta-sheet structure was determined by the calculating the percent loss of negative ellipticity at 218 nm compared to Aβ42 alone after the corresponding blanks were subtracted.

Figure 73:
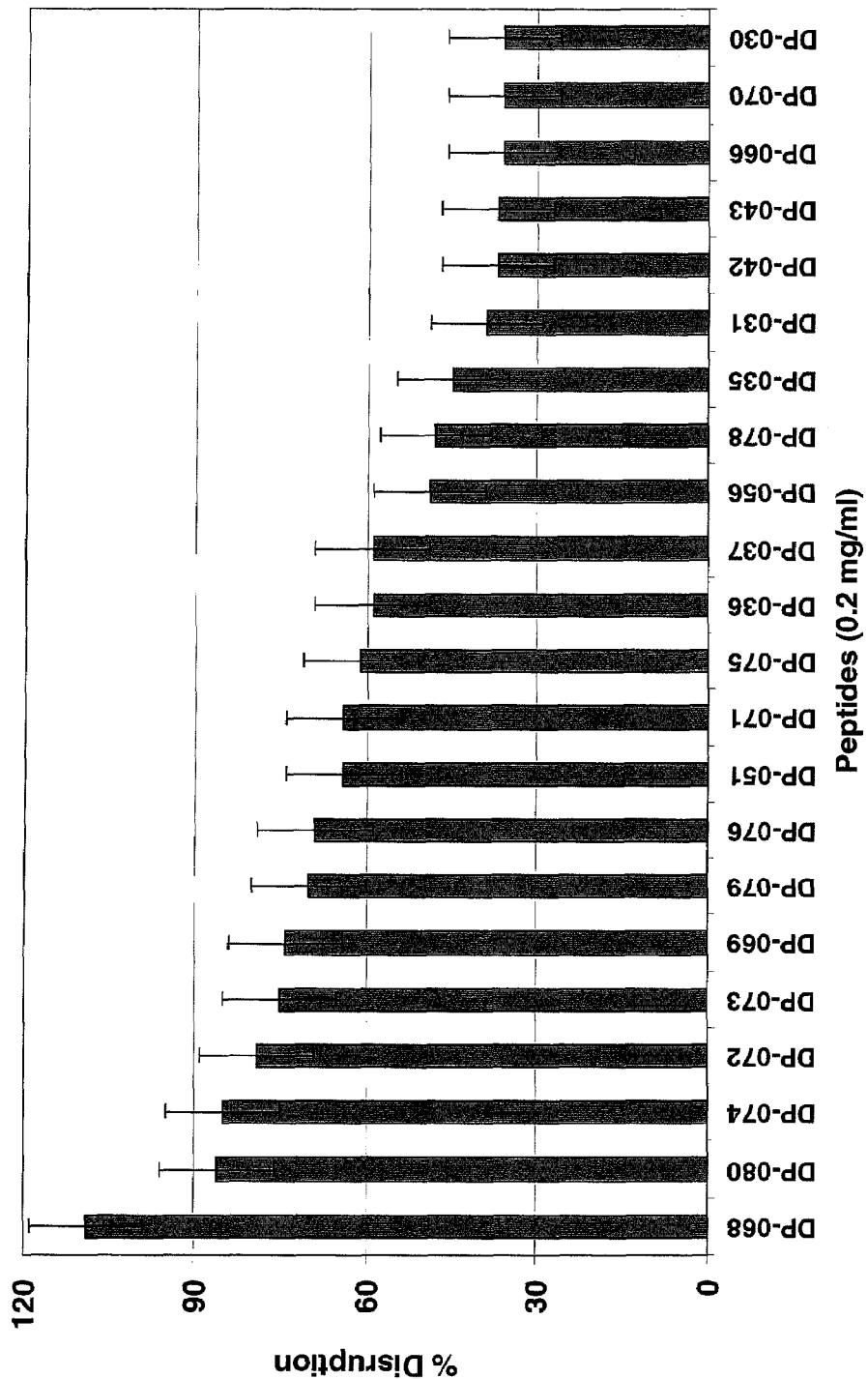
FIG. 73 is a graph showing an ordered summary comparison of the effect of 6-9mer peptides on beta-sheet secondary structure of 25 uM Aβ42 amyloid fibrils as assessed by CD spectropolarimetry. Shown is the percent disruption of Aβ42 fibrils as assessed by loss of ellipticity at 218 nm, representing the signal that is inversely related to beta-sheet secondary structure.

FIG. 73 showing the disrupters of Aβ42 beta-sheet structure among 6-9mer peptides and analogs, sorted in order of effectiveness as assessed by CD spectropolarimetry. The preferred peptides in order of effectiveness, include, but are not limited to Arg-Val-Ala-Val-Ile-Met-Gly-amide DP-068), Trp-His-Leu-Ala-Phe-Val-Leu-Arg-Lys-amide DP-080), Leu-Ala-Phe-Val-Leu-Arg-Lys-amide DP-074), Trp-His-Leu-Ala-Phe-Val-Leu-Arg DP-072), Acetyl-Leu-Ala-Phe-Val-Leu-Arg-amide DP-073), Leu-Ala-Phe-Val-Leu-Arg-amide DP-069), Trp-His-Leu-Ala-Phe-Val-Leu-Arg-amide DP-079), Acetyl-Thr-Leu-Phe-Leu-Ala-Arg-amide DP-076), Trp-His-Arg-Val-Ala-Val-Ile-Met DP-051), Thr-Leu-Phe-Leu-Ala-Arg DP-071), Thr-Leu-Phe-Leu-Ala-Arg-amide DP-075), His-Arg-Val-Ala-Val-Ile-Met DP-036), Arg-Val-Ala-Val-Ile-Met-Gly DP-037), Leu-Ala-Phe-Val-Leu-Arg DP-056), Thr-Leu-Phe-Leu-Ala-Arg-Lys-amide DP-078), Trp-His-Arg-Val-Ala-Val-Ile DP-035), Arg-Val-Ser-Val-Arg-Trp-Gly DP-031), Ala, His-Gly-Arg-Leu-Val-Phe DP-042), His-Gly-Arg-Leu-Val-Phe-Met DP-043), Trp-His-Arg-Val-Ala-Val-Ile-amide DP-066), His-Gly-Arg-Leu-Val-Phe-Met-amide DP-070), and His-Arg-Val-Ser-Val-Arg-Trp DP-030). DP-068 demonstrates >90% disruption of Aβ42 β-sheet structure, whereas DP-080, DP-074, DP-072, DP-073, DP-069, DP-079, DP-076, DP-051, DP-071 and DP-075 all demonstrate >60% disruption of Aβ42 β-sheet structure FIG. 73).

Example 5

Disruption of Alzheimer's Aβ Fibrils by 6-9mer Peptides as Assessed by Thioflavin T Fluorometry Thioflavin T fluorometry, which measures the amount of amyloid fibrils LeVine III, *Protein Sci.* 2:404-410, 1993; Amyloid: *Int. J. Exp. Clin. Invest.* 2:1-6, 1995; Naiki and Nakakuki, *Lab. Invest.*, 74:374-383, 1996; Castillo et al, *J. Neurochem.* 69:2452-2465, 1997) was also used to determine the effectiveness of 6-9mer peptides on disrupting Aβ42 amyloid fibrils. For these studies, 0.1 mg/ml of Aβ42 Bachem Inc) was incubated in microcentrifuge tubes at 37° C. for 3 days in triplicate), either alone, or in the presence of 0.2 mg/ml peptide at an Aβ:peptide weight ratio of 1:2) in TPBSF 10% TFE, 150 mM NaF, 50 mM HNaPO$_4$, pH 7.4). Fifty μl aliquots were taken for analysis at day 3 and 200 ul aliquots of 125 μM Thioflavin T in 62 mM NaPO4 pH 6.0), were added giving a final Thioflavin T concentration of 100 μM and 62 mM of NaPO4. Fluorescence emission at 480 nm was measured on a microplate 96well fluorometer Labsystem) at an excitation wavelength of 450 nm. For all determinations any fluorescence given off by peptides in the presence of the Thioflavin T reagent was always subtracted from all pertinent readings. Previous studies have indicated that increasing concentrations of fibrillar Aβ42 gives a proportional increase in fluorescence in the presence of 100 μM Thioflavin T, ruling out the presence of any disproportionate inner filter effects at this Thioflavin T concentration Castillo et al *J. Neurochem.* 69:2452-2465, 1997).

Figure 74:
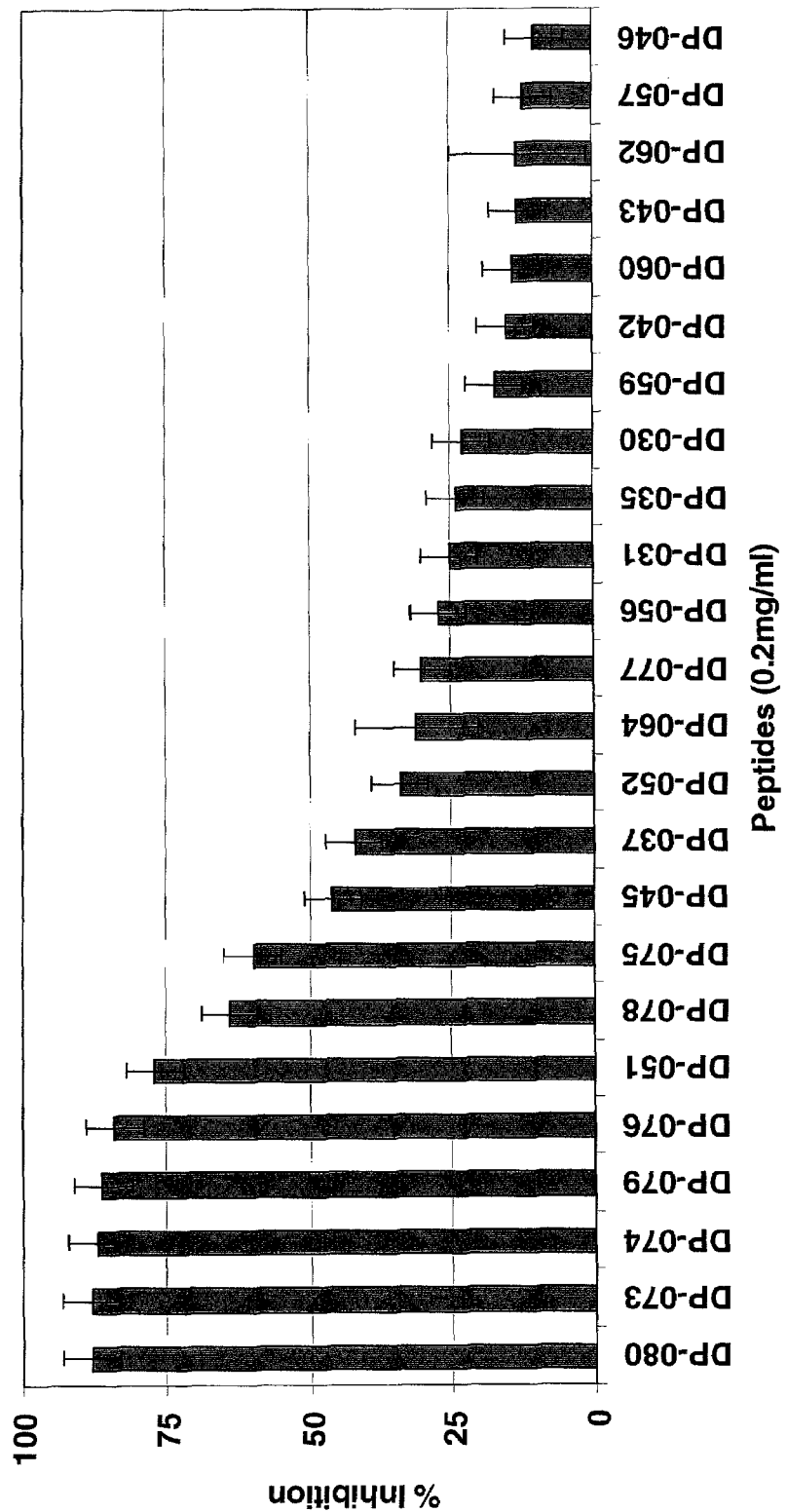
FIG. 74 is a graph showing an ordered summary comparison of the effect of the 6-9mer peptides on beta-sheet secondary structure of 25 uM Aβ42 amyloid fibrils as assessed by Thioflavin T fluorometry. Shown is the percent disruption of Aβ42 fibrils by various 6-9mer peptides at an Aβ42:6-9mer peptide weight ratio of 1:2.

FIG. 74 shows the disrupters of Thioflavin T binding to Aβ42 from among 6-9mer peptides and analogs, sorted in order of effectiveness. The preferred peptides in order of effectiveness, include but are not limited to, Trp-His-Leu-Ala-Phe-Val-Leu-Arg-Lys-amide DP-080), Acetyl-Leu-Ala-Phe-Val-Leu-Arg-amide DP-073), Leu-Ala-Phe-Val-Leu-Arg-Lys-amide DP-074), Trp-His-Leu-Ala-Phe-Val-Leu-Arg-amide DP-079), Acetyl-Thr-Leu-Phe-Leu-Ala-Arg-amide DP-076), Trp-His-Arg-Val-Ala-Val-Ile-Met DP-051), Thr-Leu-Phe-Leu-Ala-Arg-Lys-amide DP-078), Thr-Leu-Phe-Leu-Ala-Arg-amide DP-075), Leu-Ala-Phe-Val-Leu-Arg-Gly DP-045), Arg-Val-Ala-Val-Ile-Met-Gly DP-037), Arg-Val-Ala-Val-Ile-Met DP-052), His-Pro-Arg-Leu-Val-Phe-Met DP-064), Thr-Leu-Phe-Leu-Ala-Arg-Lys DP-077), Leu-Ala-Phe-Val-Leu-Arg DP-056), Arg-Val-Ser-Val-Arg-Trp-Gly DP-031), Trp-His-Arg-Val-Ala-Val-Ile DP-035), His-Arg-Val-Ser-Val-Arg-Trp DP-030), Thr-Arg-Ile-Ser-Leu-Gln-Val DP-059), Ala-His-Gly-Arg-Leu-Val-Phe DP-042), Ser-Leu-Gln-Val-Gln-Leu-Arg DP-060), His-Gly-Arg-Leu-Val-Phe-Met DP-043), Arg-Val-Ser-Val-Arg-Trp DP-062), Leu-Pro-Phe-Val-Leu-Arg DP-057), and Ala-Phe-Val-Leu-Arg-Gly-Lys DP-046). DP-080, DP-073, DP-074, DP-079, DP-076 and DP-051 all demonstrated >75% inhibition/disruption of Aβ42 fibrils, whereas DP-078 abd DP-075 demonstrated >50% inhibition/disruption of Aβ42 fibrils.

Example 6

Binding of 6-9mer Peptides to Alzheimer's Aβ42 Fibrils

The ability of various peptides to bind to substrate bound Aβ42 was determined by a solid phase binding assay along with a determination of unbound peptide fractions using high pressure liquid chromatography attached to a mass selective detector HPLC/MSD; Agilent 1100 HPLC system). The peptides were resolved in HPLC using a Synergi-Max RP 2×0.4 cm; 2 um) column from phenomenex with a flow rate of 1 ml/min and a gradient of 0-60% acetonitrile in water, containing 1% formic acid over 5.5 minutes. The peptides were detected as they come out from the column using MSD SL Agilent). The MSD had the following settings: Positive ion monitoring in scan mode from 200-1200 Da; fragmentor voltage, 150; drying gas flow, 13 L/min $N_2$; nebuliser pressure, 45 psi; drying gas temperature, 350° C.; and capillary voltage, 3500 volts.

The solid phase binding assay was performed as follows: 10 ug aliquots of Aβ42 were bound to PVDF membrane at the bottom of a 96-well microplate available from Millipore), according to the manufacturer's instructions. The plate was allowed to dry and aliquots of 150 ul of 0.1 mg/ml of 6-9mer peptides were applied in each well. Each 6-9mer peptide was applied in triplicate in the Aβ42-containing wells test wells), and in triplicate in the non-Ab42 containing wells blank wells). The plates containing 16 different 6-9mer peptides was incubated at 37° C. for 2 hrs. The unbound peptide in each well was then transferred to HPLC/MSD vials for analysis with the settings outlined above. The peptides recovered from wells without Aβ42 were taken as the total peptides, whereas the peptides recovered from wells with Aβ42, were taken as the total-bound peptides. The percentages of various peptides bound after 2 hrs of incubation were then plotted FIG. 75)

Figure 75:
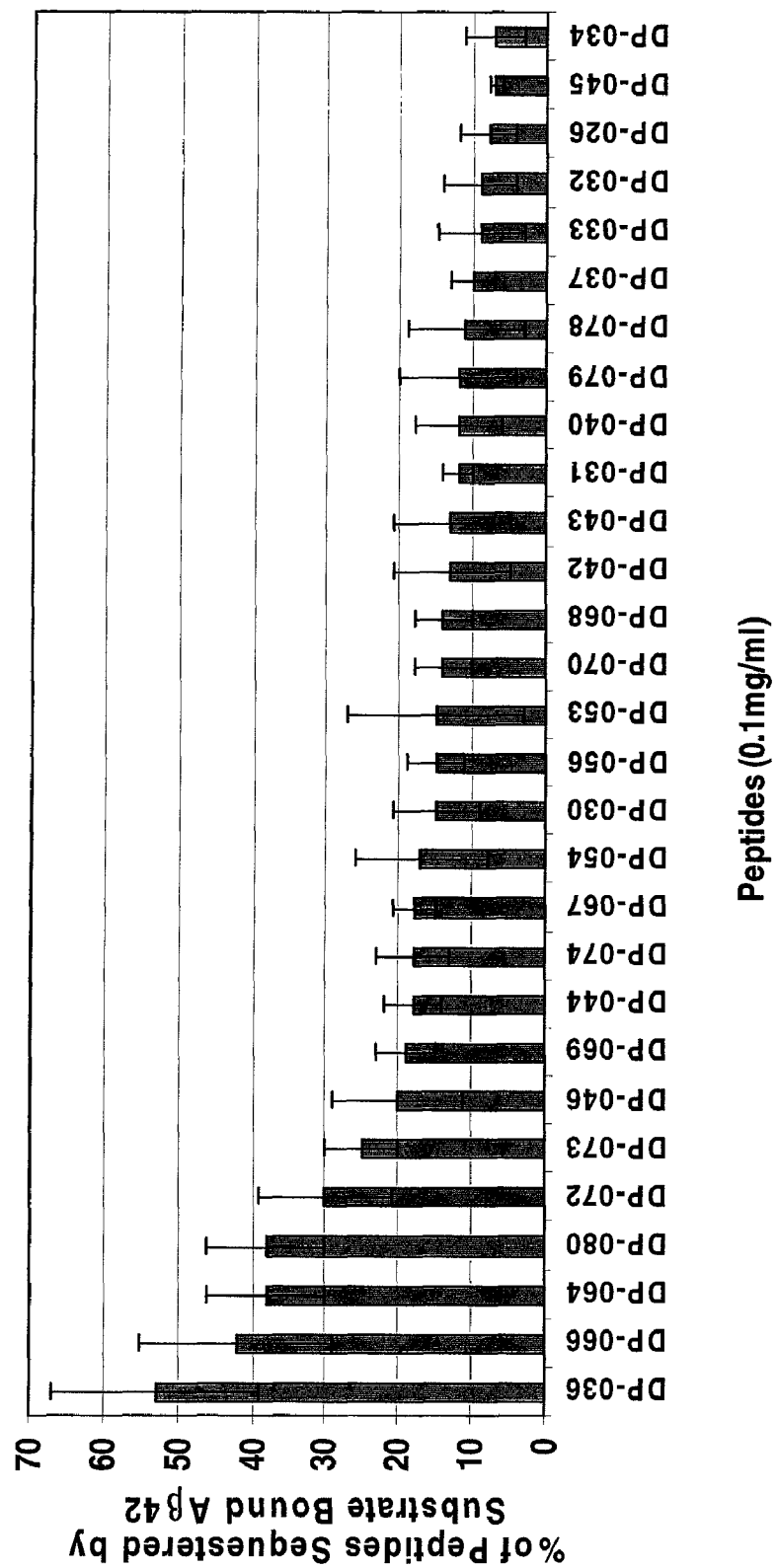
FIG. 75 is a graph showing an ordered summary comparison of the binding efficiency of 6-9mer peptides on substrate bound Aβ42 as assessed by LC/MS measurements of unbound peptides after a 2 hour equilibration period. Shown is the percent of various 6-9mer peptides unbound to Aβ42 fibrils after 2 hrs of incubation.

FIG. 75 shows the binders of Aβ42 from among the 6-9mer peptides and analogs, sorted in order of effectiveness. The preferred peptides in order of effectiveness, include, but are not limited to, His-Arg-Val-Ala-Val-Ile-Met DP-036), Trp-His-Arg-Val-Ala-Val-Ile-amide DP-066), His-Pro-Arg-Leu-Val-Phe-Met DP-064), Trp-His-Leu-Ala-Phe-Val-Leu-Arg-Lys-amide DP-080), Trp-His-Leu-Ala-Phe-Val-Leu-Arg DP-072), Acetyl-Leu-Ala-Phe-Val-Leu-Arg-amide DP-073), Ala-Phe-Val-Leu-Arg-Gly-Lys DP-046), Leu-Ala-Phe-Val-Leu-Arg-amide DP-069), Gly-Leu-Ala-Phe-Val-Leu-Arg DP-044), Leu-Ala-Phe-Val-Leu-Arg-Lys-amide DP-074), Arg-Val-Ala-Val-Ile-Met-amide DP-067), His-Arg-Val-Pro-Val-Ile-Met DP-054), His-Arg-Val-Ser-Val-Arg-Trp DP-030), Leu-Ala-Phe-Val-Leu-Arg DP-056), His-Arg-Pro-Ala-Val-Ile-Met DP-053), His-Gly-Arg-Leu-Val-Phe-Met-amide DP-070), Arg-Val-Ala-Val-Ile-Met-Gly-amide DP-068), Ala-His-Gly-Arg-Leu-Val-Phe DP-042), His-Gly-Arg-Leu-Val-Phe-Met DP-043), Arg-Val-Ser-Val-Arg-Trp-Gly DP-031), Phe-Leu-Ala-His-Gly-Arg-Leu DP-040), Trp-His-Leu-Ala-Phe-Val-Leu-Arg-amide DP-079), Thr-Leu-Phe-Leu-Ala-Arg-Lys-amide DP-078), Arg-Val-Ala-Val-Ile-Met-Gly DP-037), Gly-Arg-Trp-His-Arg-Val-Ala DP-033), Asp-Gly-Arg-Trp-His-Arg-Val DP-032), Ala-Gly-Gln-Trp-His-Arg-Val DP-026), Leu-Ala-Phe-Val-Leu-Arg-Gly DP-045), and Arg-Trp-His-Arg-Val-Ala-Val DP-034). DP-036 and DP-066 demonstrated >40% binding to substrate bound A142, whereas DP-064 and DP-080 demonstrated >30% binding, and DP-0072 and DP-073 demonstrated >20% binding FIG. 75).

Example 7

Disruption of Alzheimer Fibrils ε-Sheet Secondary Structure by 6-9mer Peptides as Assessed by CD Spectropolarimetry Circular dichroism CD) spectropolarimetry is another in vitro technique used to determine a given peptide's effectiveness in disrupting the b-sheet secondary structure of Aβ-fibrils. CD spectra of Aβ42 in the presence or absence of synthetic 6-9mer peptides were recorded at 25° C. on a JASCO-810 Spectropolarimeter using a 0.5 mm path length quartz cuvette, and over the range of 190-260 nm. The instrument was calibrated with an aqueous solution of +)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity MRE) of Aβ42, after subtraction of the background solvent spectrum and/or test peptide spectrum. For this study, fibrillar Aβ42 0.1 mg/ml) in TPBSF 10% TFE, 150 mM NaF, 50 mM $HNaPO_4$, pH 7.4) was incubated for 3 days at 37° C. in the presence and absence of various 6-9mer peptides at an Aβ42:peptide wt/wt ratio of 1:2, before recording the CD spectra.

Figure 62:
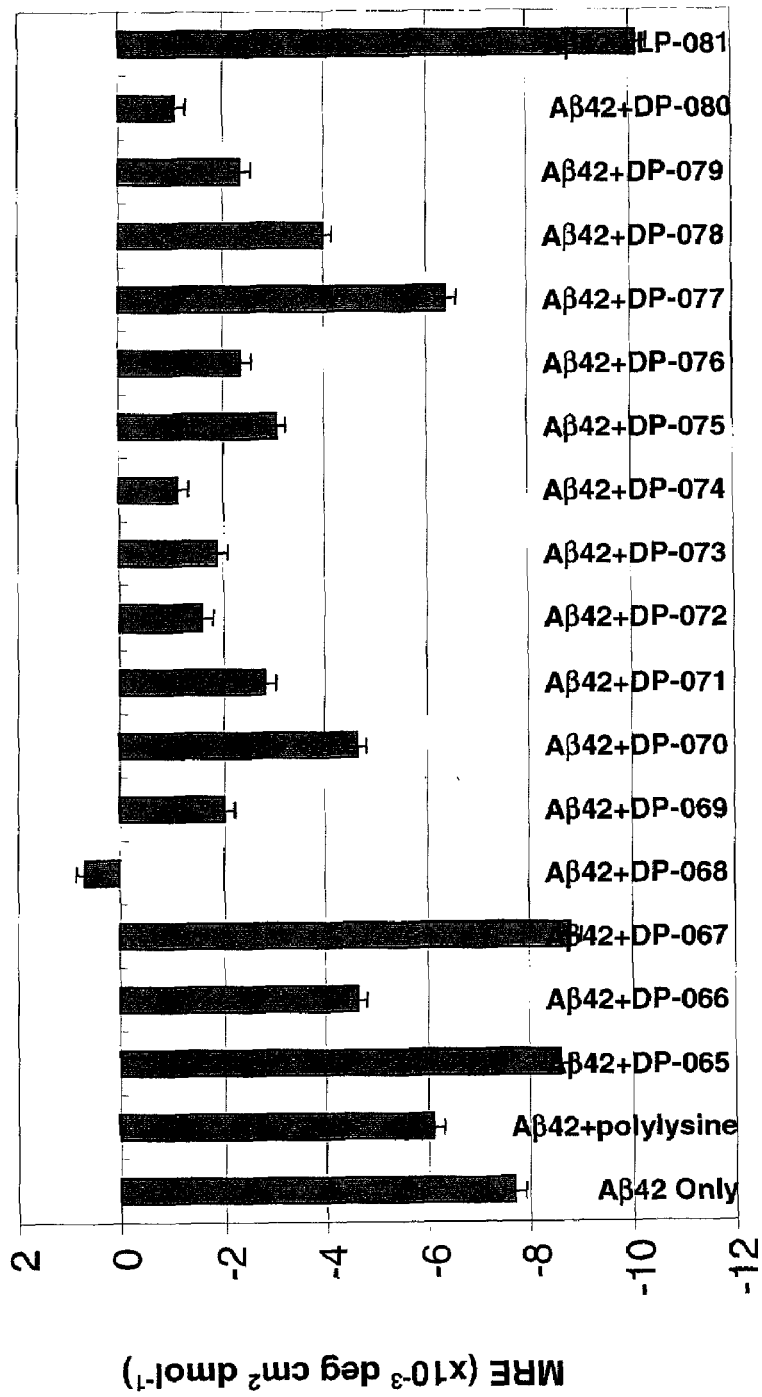
FIG. 62 is a graph showing a summary comparison of the effect of 0.2 mg/ml peptides DP-065 to LP-081, and polylysine, on beta-sheet secondary structure of 25 uM Aβ42 amyloid fibrils as assessed by CD. Shown is the molar residue ellipticity of Aβ42 at 218 nm in the y-axis, representing the signal associated with beta-sheet secondary structure. Loss of ellipticity at 218 nm compared to the signal of Aβ42 fibrils only, indicates the peptides ability to reduce beta-sheet secondary structure.
Figure 63:
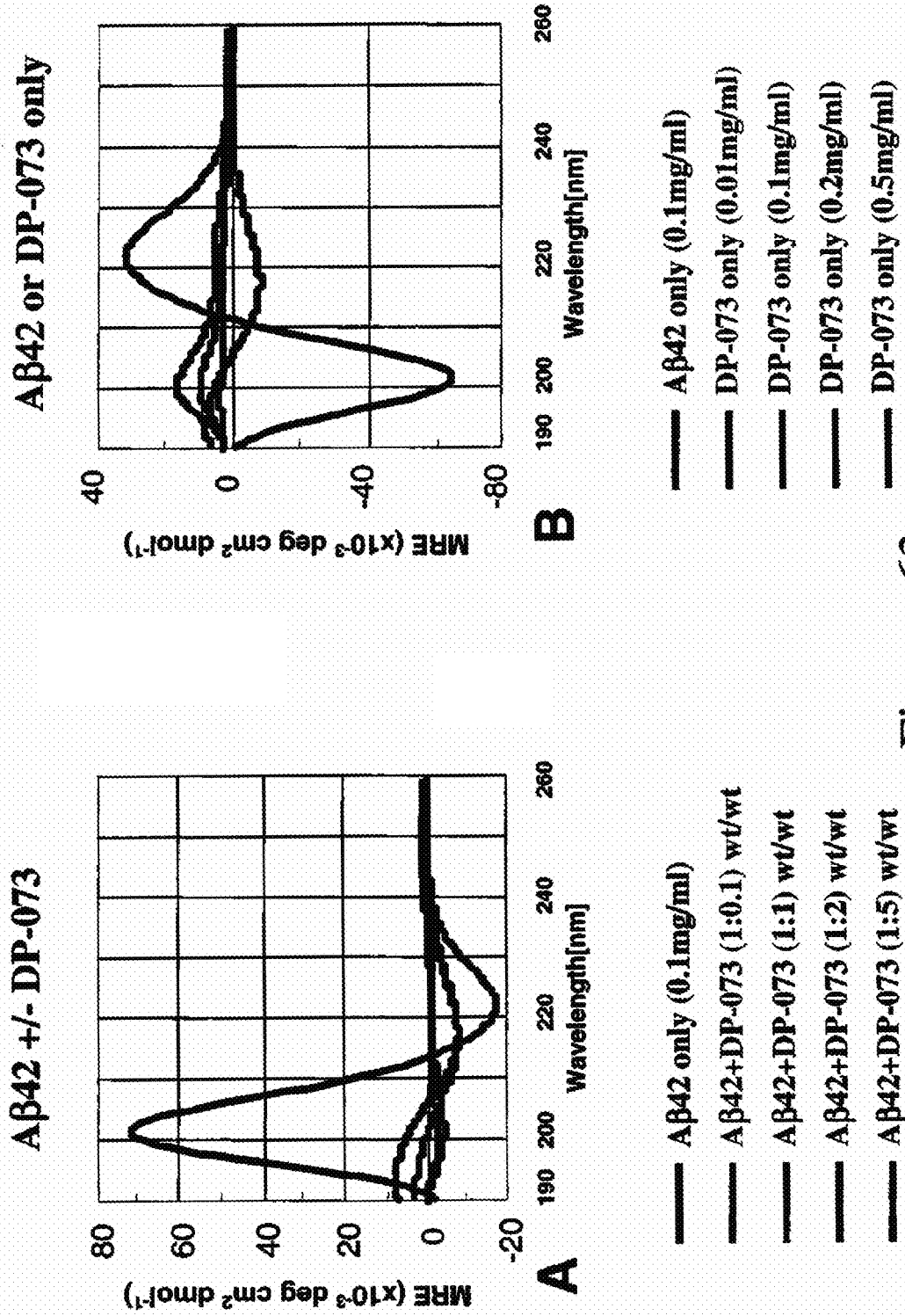
FIG. 63A are CD spectra showing the dose-dependent effects of peptide DP-073 on beta-sheet secondary structure of Aβ42 amyloid fibrils i.e. Aβ 42+/−DP-073).
FIG. 63B shows the CD spectra of Aβ 42 or DP-073 only.
Figure 64:
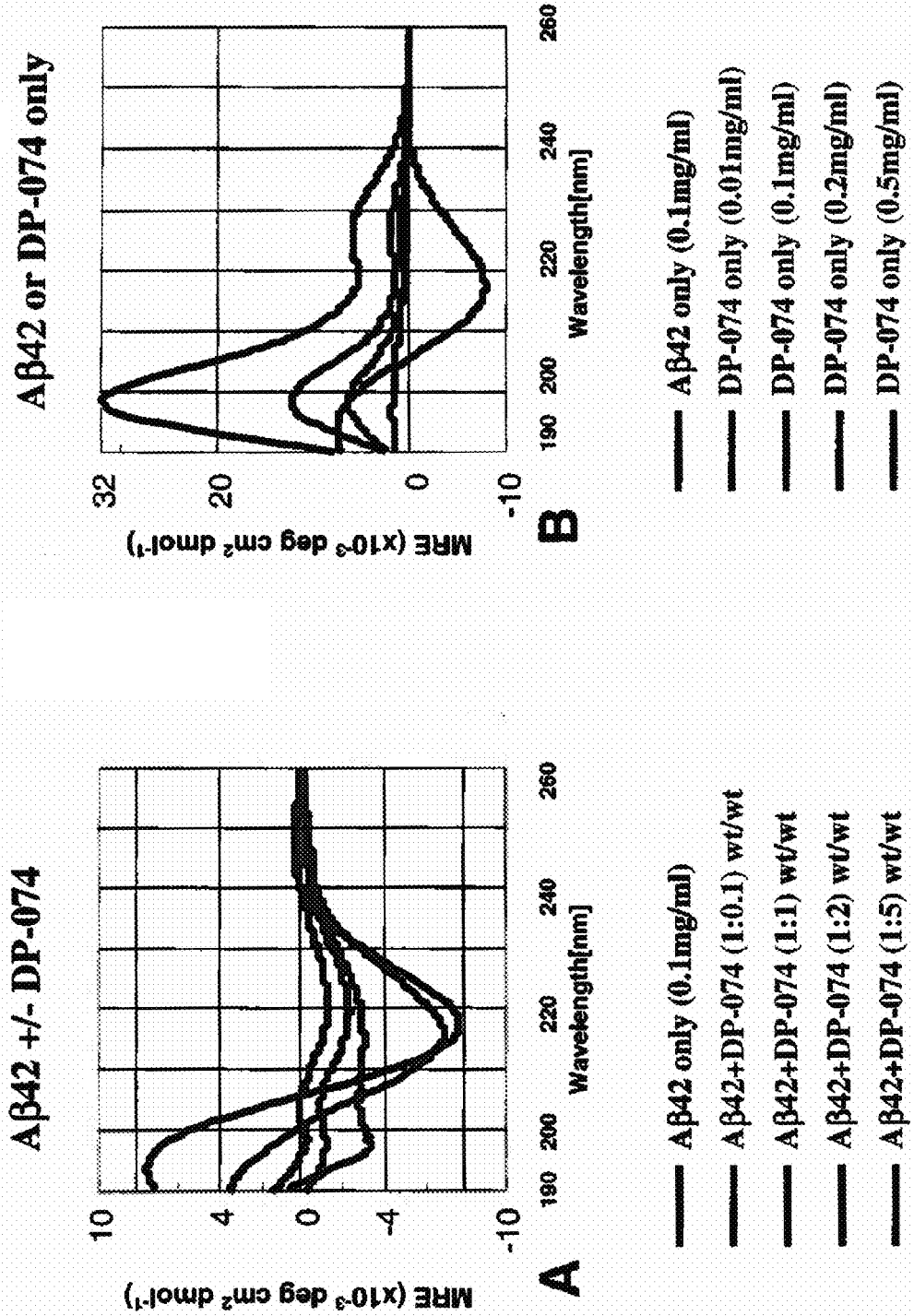
FIG. 64A are CD spectra showing the dose-dependent effects of peptide DP-074 on beta-sheet secondary structure of Aβ42 amyloid fibrils i.e. Aβ 42+/−DP-074).
FIG. 64B shows the CD spectra of Aβ 42 or DP-074 only.
Figure 65:
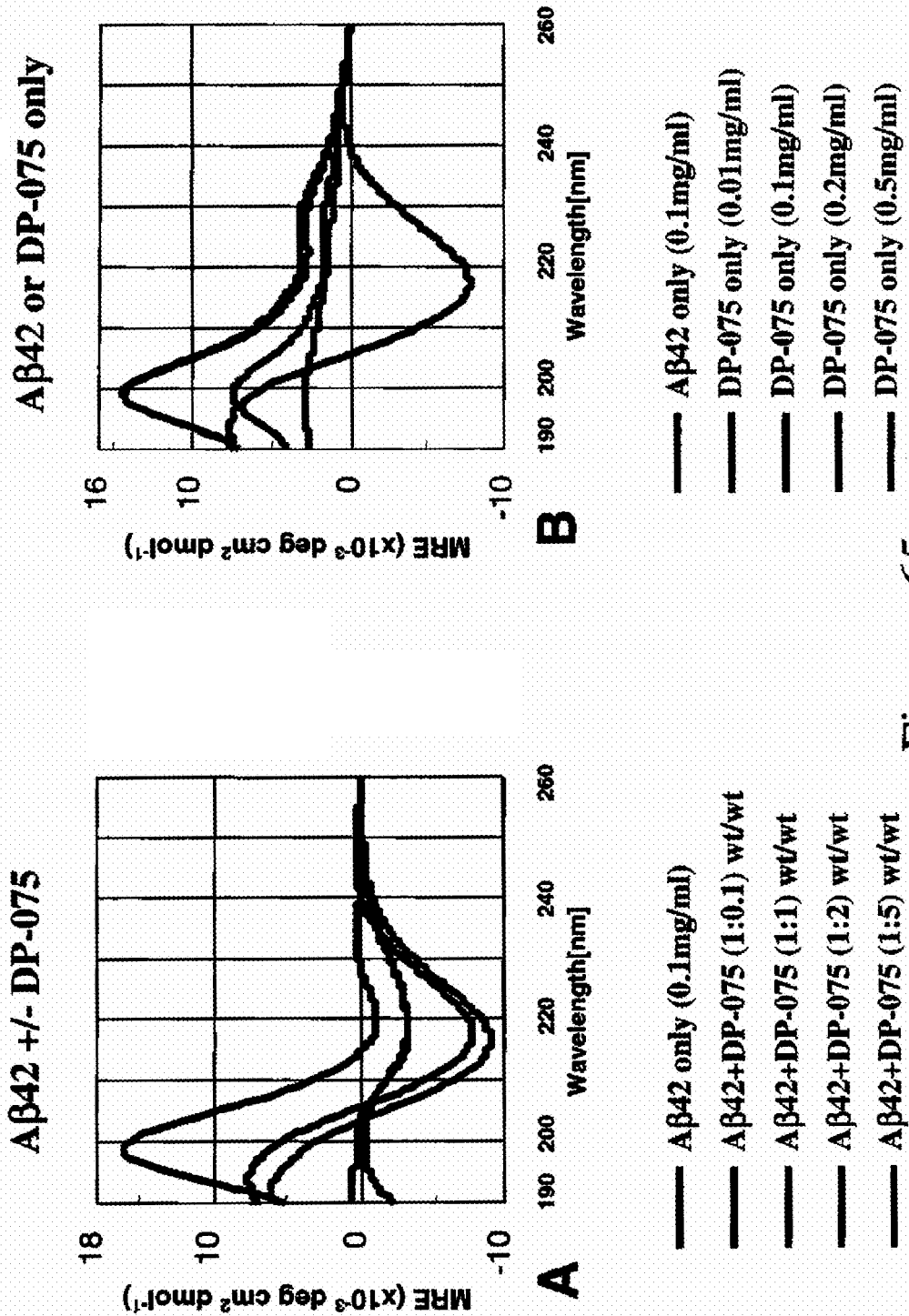
FIG. 65A are CD spectra showing the dose-dependent effects of peptide DP-075 on beta-sheet secondary structure of Aβ42 amyloid fibrils i.e. Aβ 42+/−DP-075).
FIG. 65B shows the CD spectra of Aβ 42 or DP-075 only.
Figure 66:
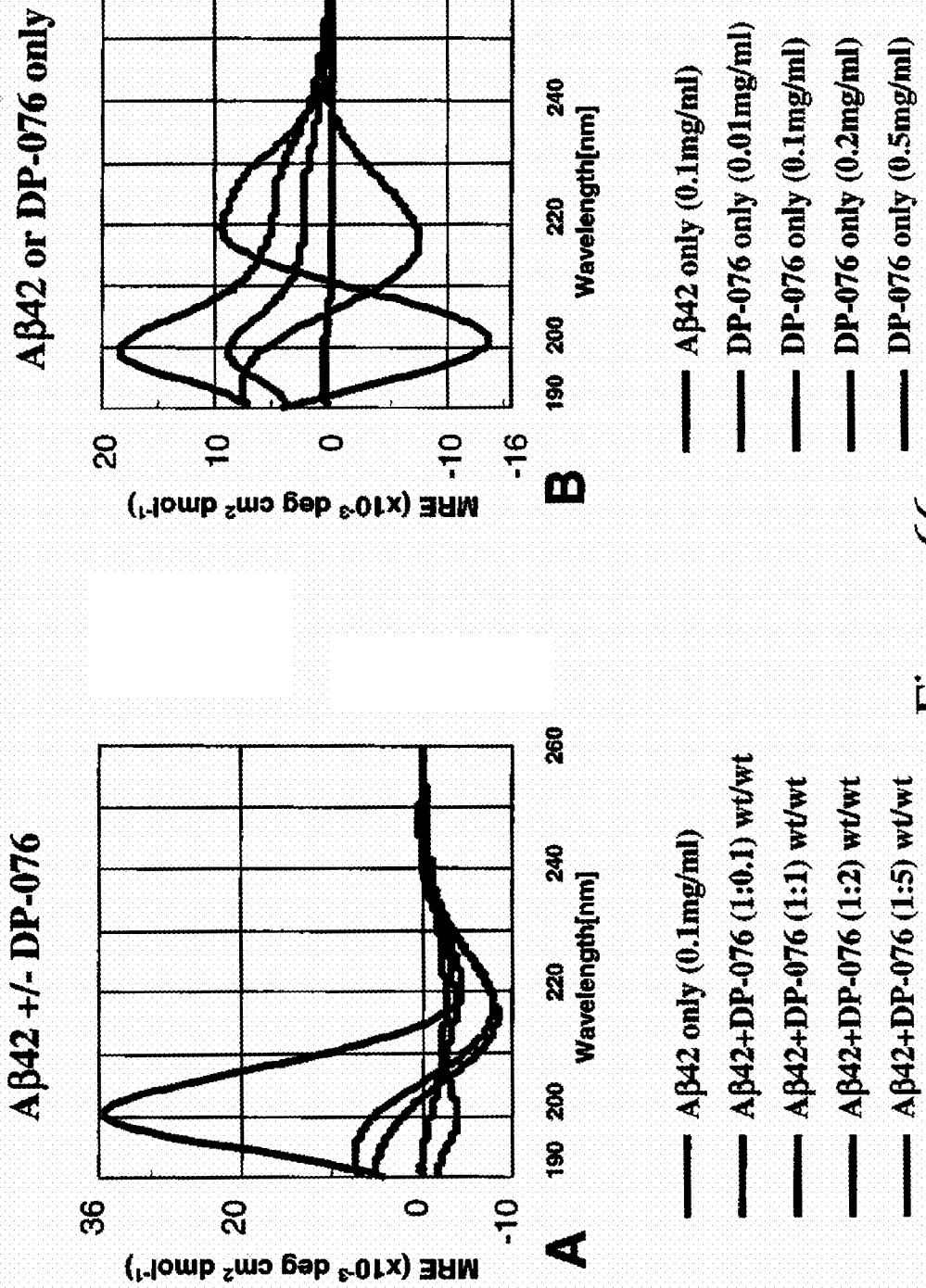
FIG. 66A are CD spectra showing the dose-dependent effects of peptide DP-076 on beta-sheet secondary structure of Aβ42 amyloid fibrils i.e. Aβ 42+/−DP-076).
FIG. 66B shows the CD spectra of Aβ42 or DP-076 only.
Figure 67:
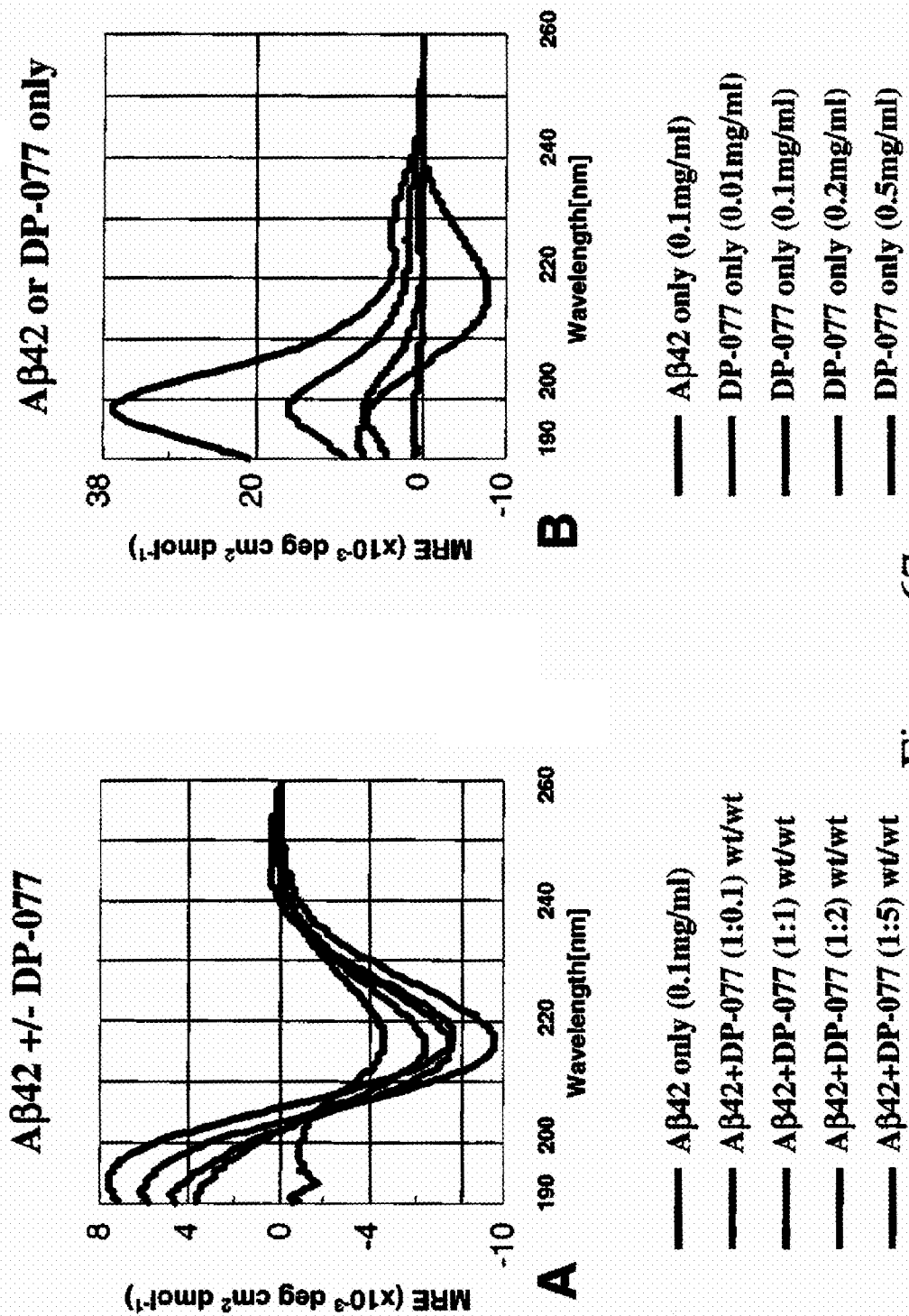
FIG. 67A are CD spectra showing the dose-dependent effects of peptide DP-077 on beta-sheet secondary structure of Aβ42 amyloid fibrils i.e. Aβ 42+/−DP-077).
FIG. 67B shows the CD spectra of Aβ 42 or DP-077 only.
Figure 68:
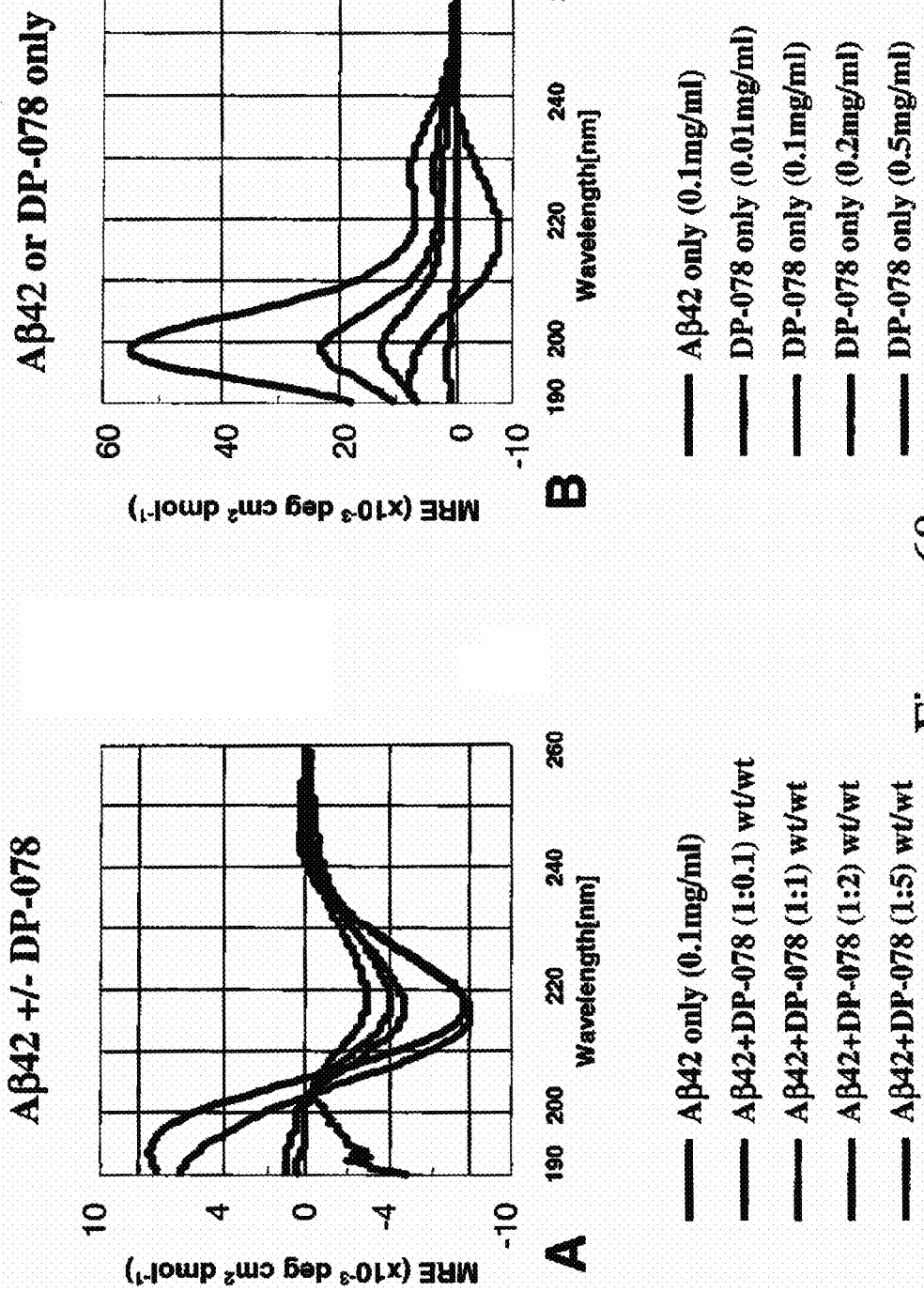
FIG. 68A are CD spectra showing the dose-dependent effects of peptide DP-078 on beta-sheet secondary structure of Aβ42 amyloid fibrils i.e. Aβ 42+/−DP-078).
FIG. 68B shows the CD spectra of Aβ 42 or DP-078 only.
Figure 69:
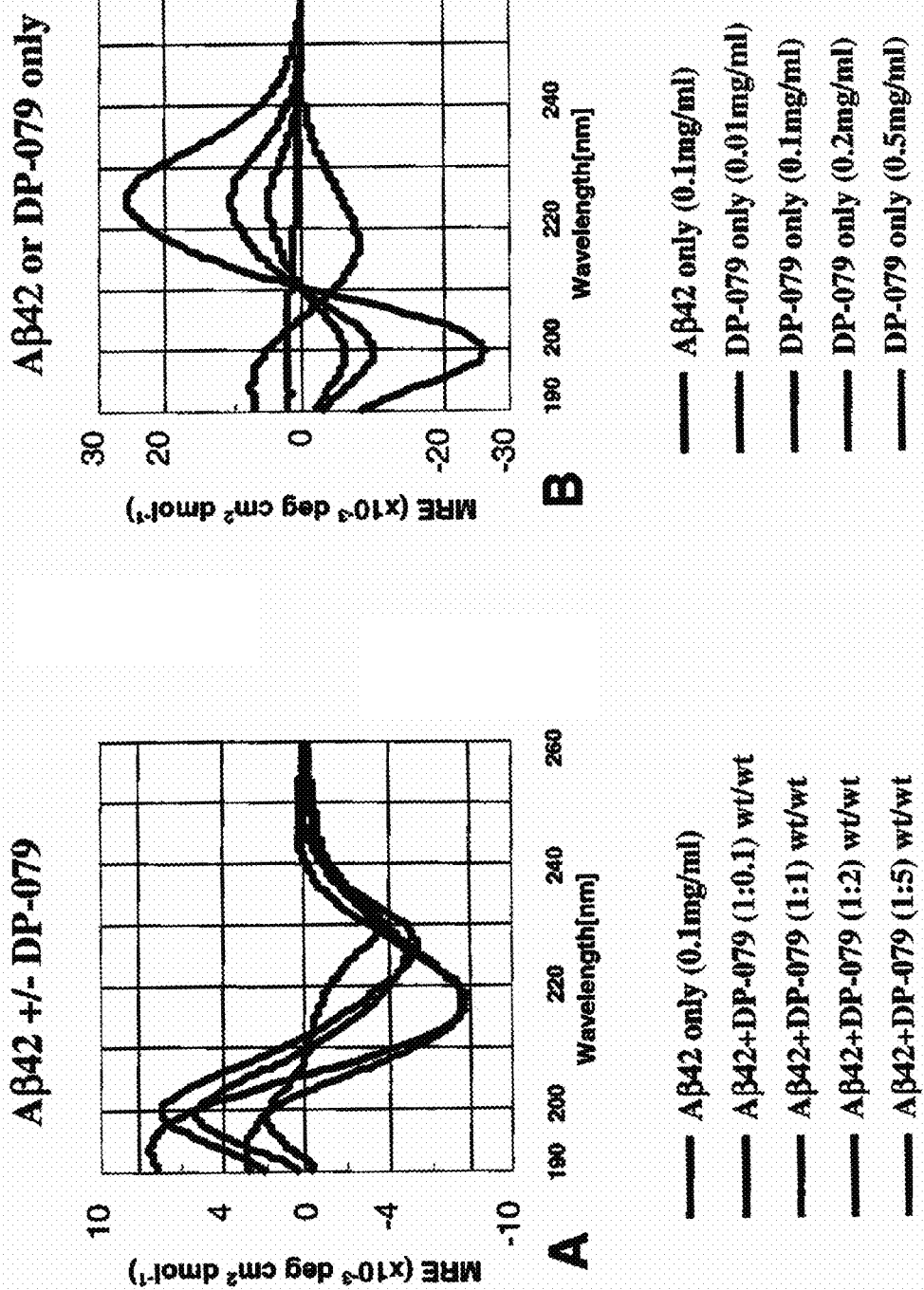
FIG. 69A are CD spectra showing the dose-dependent effects of peptide DP-079 on beta-sheet secondary structure of Aβ42 amyloid fibrils i.e. Aβ 42+/−DP-079).
FIG. 69B shows the CD spectra of Aβ 42 or DP-079 only.
Figure 70:
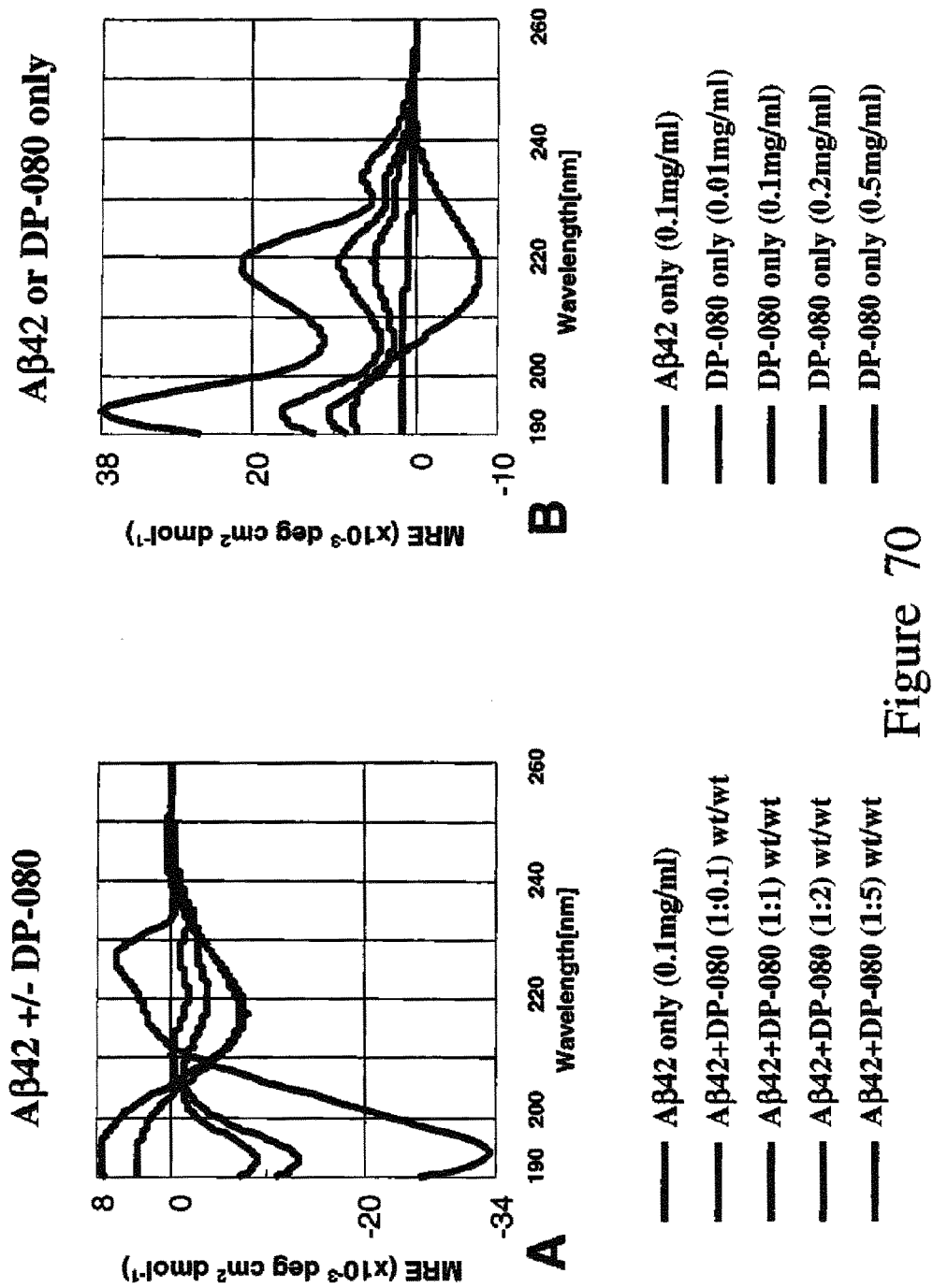
FIG. 70A are CD spectra showing the dose-dependent effects of peptide DP-080 on beta-sheet secondary structure of Aβ42 amyloid fibrils i.e. Aβ 42+/−DP-080).
FIG. 70B shows the CD spectra of Aβ 42 or DP-080 only.
Figure 71:
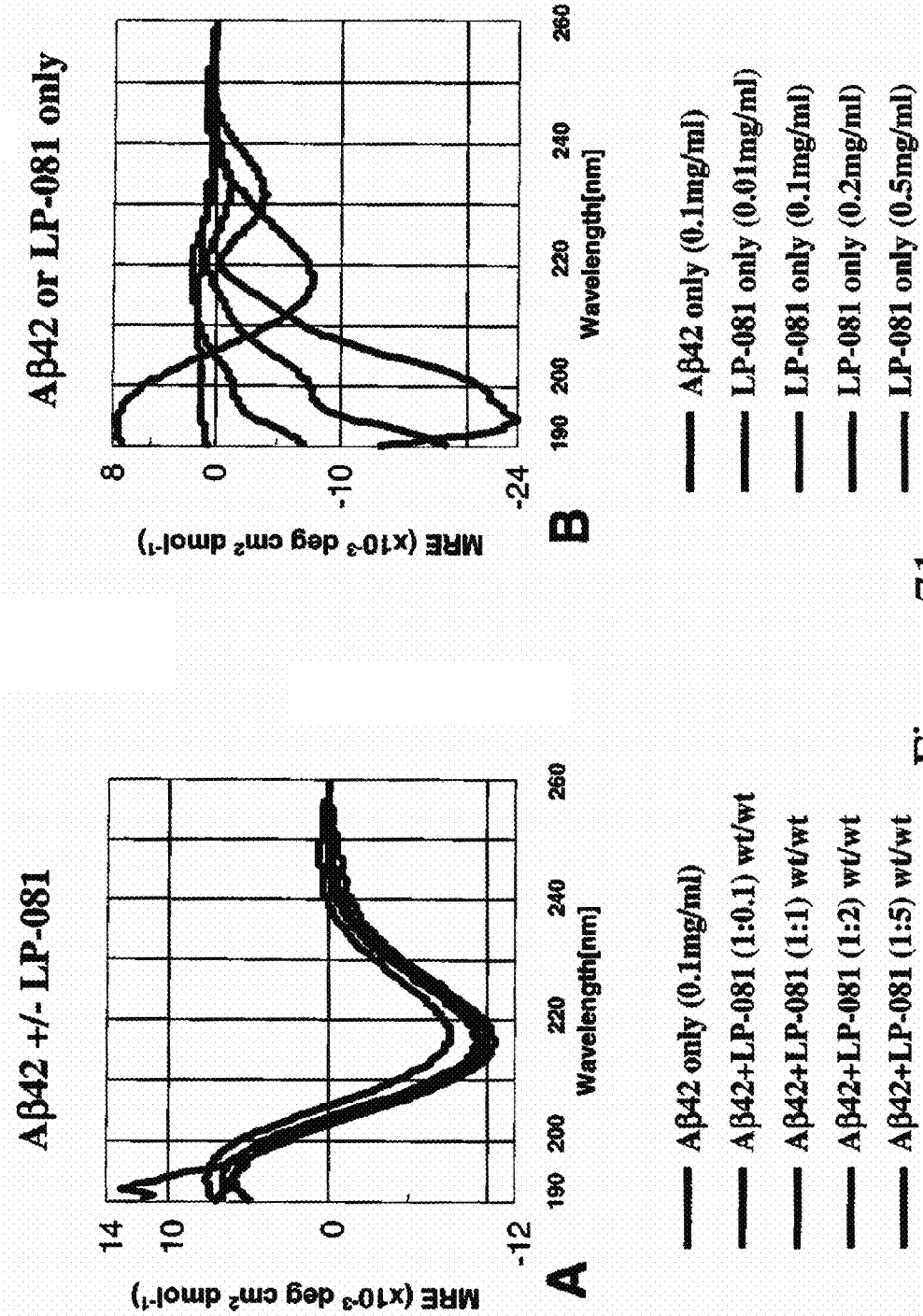
FIG. 71A are CD spectra showing the dose-dependent effects of peptide LP-081 on beta-sheet secondary structure of Aβ42 amyloid fibrils i.e. Aβ 42+/−LP-081).
FIG. 71B shows the CD spectra of Aβ 42 or LP-081 only.

The CD spectra of Aβ42 alone, Aβ42 plus 6-9mer peptide, and 6-9mer peptide alone, are presented in FIGS. 53 to 61, with an overall summary in FIG. 62.

FIG. 53A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure. Also in FIG. 53A is the CD spectrum of 0.1 mg/ml of Aβ42 in the presence of 0.2 mg/ml of DP-073 after 3 days of incubation dotted line), with correction for the spectrum of peptide DP-073. The significant loss of negative ellipticity at 218 nm in the presence of DP-073 indicates a loss of beta-sheet structure in Aβ42. FIG. 53B shows the CD spectrum of 0.2 mg/ml of DP-073 alone dotted line) with positive ellipticities and maxima at 200 nm indicating an inverted random coil consistent with a amino acid peptide, containing very little beta sheet structure. Also shown in FIG. 53B for comparison is the CD spectrum of 0.1 mg/ml of Aβ42 after 3 days of incubation solid line)

FIG. 54A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure. Also in FIG. 54A is the CD spectrum of 0.1 mg/ml of Aβ42 in the presence of 0.2 mg/ml of DP-074 after 3 days of incubation dotted line), with correction for the spectrum of peptide DP-074. The significant loss of negative ellipticity at 218 nm in the presence of DP-074 indicates a loss of beta-sheet structure in Aβ42. FIG. 54B shows the CD spectrum of 0.2 mg/ml of DP-074 alone dotted line) with positive ellipticities and maxima at around 200 nm indicating an inverted random coil consistent with a amino acid peptide, with very little beta-sheet structure. Also shown in FIG. 53B for comparison is the CD spectrum of 0.1 mg/ml of Aβ42 after 3 days of incubation solid line)

FIG. 55A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure. Also in FIG. 55A is the CD spectrum of 0.1 mg/ml of Aβ42 in the presence of 0.2 mg/ml of DP-075 after 3 days of incubation dotted line). The significant loss of negative ellipticity at 218 nm in Aβ42 in the presence of DP-075, indicates a loss of beta-sheet structure in Aβ42. FIG. 55B shows the CD spectrum of 0.2 mg/ml of DP-075 alone dotted line) with positive ellipticities and maxima at 200 nm indicating an inverted random coil consistent with a amino acid peptide, containing very little beta sheet structure. Also shown in FIG. 55B for comparison is the CD spectrum of 0.1 mg/ml of Aβ42 after 3 days of incubation solid line).

FIG. 56A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure in Aβ42. Also in FIG. 56A is the CD spectrum of 0.1 mg/ml of Aβ42 in the presence of 0.2 mg/ml of DP-076 after 3 days of incubation dotted line). The significant loss of negative ellipticity at 218 nm in the presence of DP-076 indicates a loss of beta-sheet structure in Aβ42. FIG. 56B shows the CD spectrum of 0.2 mg/ml of DP-076 alone dotted line) with positive ellipticities and maxima at 200 nm indicating an inverted random coil consistent with a amino acid peptide, containing very little beta sheet structure. Also shown in FIG. 56B for comparison is the CD spectrum of 0.1 mg/ml of Aβ42 after 3 days of incubation solid line).

FIG. 57A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure in Aβ42. Also in FIG. 57A is the CD spectrum of 0.1 mg/ml of Aβ42 in the presence of 0.2 mg/ml of DP-077 after 3 days of incubation dotted line). The slight loss of negative ellipticity at 218 nm in the presence of DP-077 indicates only a slight loss of beta-sheet structure in Aβ42. FIG. 57B shows the CD spectrum of 0.2 mg/ml of DP-077 alone dotted line) with positive ellipticities and maxima at 200 nm indicating an inverted random coil consistent with a amino acid peptide, containing very little beta sheet structure. Also shown in FIG. 57B for comparison is the CD spectrum of 0.1 mg/ml of Aβ42 after 3 days of incubation solid line).

FIG. 58A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure in Aβ42. Also in FIG. 58A is the CD spectrum of 0.1 mg/ml of Aβ42 in the presence of 0.2 mg/ml of DP-078 after 3 days of incubation dotted line). The significant loss of negative ellipticity at 218 nm in the presence of DP-078 indicates a loss of beta-sheet structure in Aβ42. FIG. 58B shows the CD spectrum of 0.2 mg/ml of DP-078 alone dotted line) with positive ellipticities and maxima at about 200 nm indicating an inverted random coil consistent with a amino acid peptide, containing very little beta sheet structure. Also shown in FIG. 58B for comparison is the CD spectrum of 0.1 mg/ml of Aβ42 after 3 days of incubation solid line).

FIG. 59A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure in Aβ42. Also in FIG. 59A is the CD spectrum of 0.1 mg/ml of Aβ42 in the presence of 0.2 mg/ml of DP-079 after 3 days of incubation dotted line). The significant loss of negative ellipticity at 218 nm in the presence of DP-079 indicates a loss of beta-sheet structure in Aβ42. However, the shift of minima from 218 nm to 225 nm is unexpected, and thus any loss of ellipticity at 218 nm, may not be due to loss of beta-sheet structure alone. FIG. 59B shows the CD spectrum of 0.2 mg/ml of DP-079 alone dotted line) with positive ellipticities and maxima at 225 nm and a minima at 200 nm indicating an inverted beta sheet consistent with amino acid peptide with beta sheet structure. However, the maximum at 225 nm indicates a structure reminiscent of cross-linking or disulfide binding protein. Also shown in FIG. 59B for comparison is the CD spectrum of 0.1 mg/ml of Aβ42 after 3 days of incubation solid line).

FIG. 60A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure in Aβ42. Also in FIG. 60A is the CD spectrum of 0.1 mg/ml of Aβ42 in the presence of 0.2 mg/ml of DP-080 after 3 days of incubation dotted line). The significant loss of negative ellipticity at 218 nm in the presence of DP-080 indicates a loss of beta-sheet structure in Aβ42. FIG. 60B shows the CD spectrum of 0.2 mg/ml of DP-080 alone dotted line) with positive ellipticities and maxima at about 195 nm indicating an inverted random coil consistent with a amino acid peptide, containing very little beta sheet structure. Also shown in FIG. 60B for comparison is the CD spectrum of 0.1 mg/ml of Aβ42 after 3 days of incubation solid line).

FIG. 61A shows the CD spectrum of 0.1 mg/ml of Aβ42 after 3 days of incubation solid line). Both the negative ellipticity at 218 nm and the positive ellipticity at 195 nm indicate the presence of beta-sheet secondary structure in Aβ42. Also in FIG. 61A is the CD spectrum of 0.1 mg/ml of Aβ42 in the presence of 0.2 mg/ml of LP-081 after 3 days of incubation dotted line). The significant gain of negative ellipticity at 218 nm in the presence of LP-081 indicates a gain of beta-sheet structure in Aβ42. FIG. 61B shows the CD spectrum of 0.2 mg/ml of LP-081 alone dotted line) with negative ellipticities and maxima at about 200 nm indicating an random coil structure of L-peptide. Also shown in FIG. 61B for comparison is the CD spectrum of 0.1 mg/ml of Aβ42 after 3 days of incubation solid line). It should be noted that LP-081 is the beta-sheet breaker peptide previously reported in the literature Permanne et al, *FASEB J*. Published online Apr. 10, 2002; Soto-Jara et al, U.S. Pat. No. 5,948,763 Sep. 7, 1999; Soto-Jara, PCT WO 01/34631 A2 May 17, 2001).

FIG. 62 shows the CD ellipticites of 0.1 mg/ml of Aβ42 at 218 nm in the presence of 0.2 mg/ml of various 6-9mer peptides after 3 days of incubation, and after correction for the CD ellipticites of various peptides. The peptides tested here are DP-065 to LP-081, and polylysine. It should be noted that peptides DP-065, DP-067, and LP-081 caused an increase in negative ellipticity at 218 nm, indicating that these peptides surprisingly promote formation of beta-sheet structure of Aβ42. Refer to FIG. 73 for the ranking of effectiveness of various 6-9mer peptides.

Example 8

Dose-Dependent Disruption of Alzheimer Fibrils β-Sheet Secondary Structure by 6-9mer Peptides as Assessed by CD Spectropolarimetry Circular dichroism CD) spectropolarimetry is another in vitro technique used to determine a given peptide's effectiveness in disrupting the b-sheet secondary structure of Aβ-fibrils. CD spectra of Aβ42 in the presence or absence of synthetic 6-9mer peptides were recorded at 25° C. on a JASCO-810 Spectropolarimeter using a 0.5 mm path length quartz cuvette, and over the range of 190-260 nm. The instrument was calibrated with an aqueous solution of +)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity MRE) of Aβ42, after subtraction of the background solvent spectrum and/or test peptide spectrum. For this study, fibrillar Aβ42 0.1 mg/ml) in TPBSF 10% TFE, 150 mM NaF, 50 mM HNaPO$_4$, pH 7.4) was incubated for 3 days at 37° C. in the presence and absence of various peptides at Aβ42:peptide wt/wt ratios of 1:0.1, 1:1, 1:2, and 1:10 before recording the CD spectra.

Figure 72:
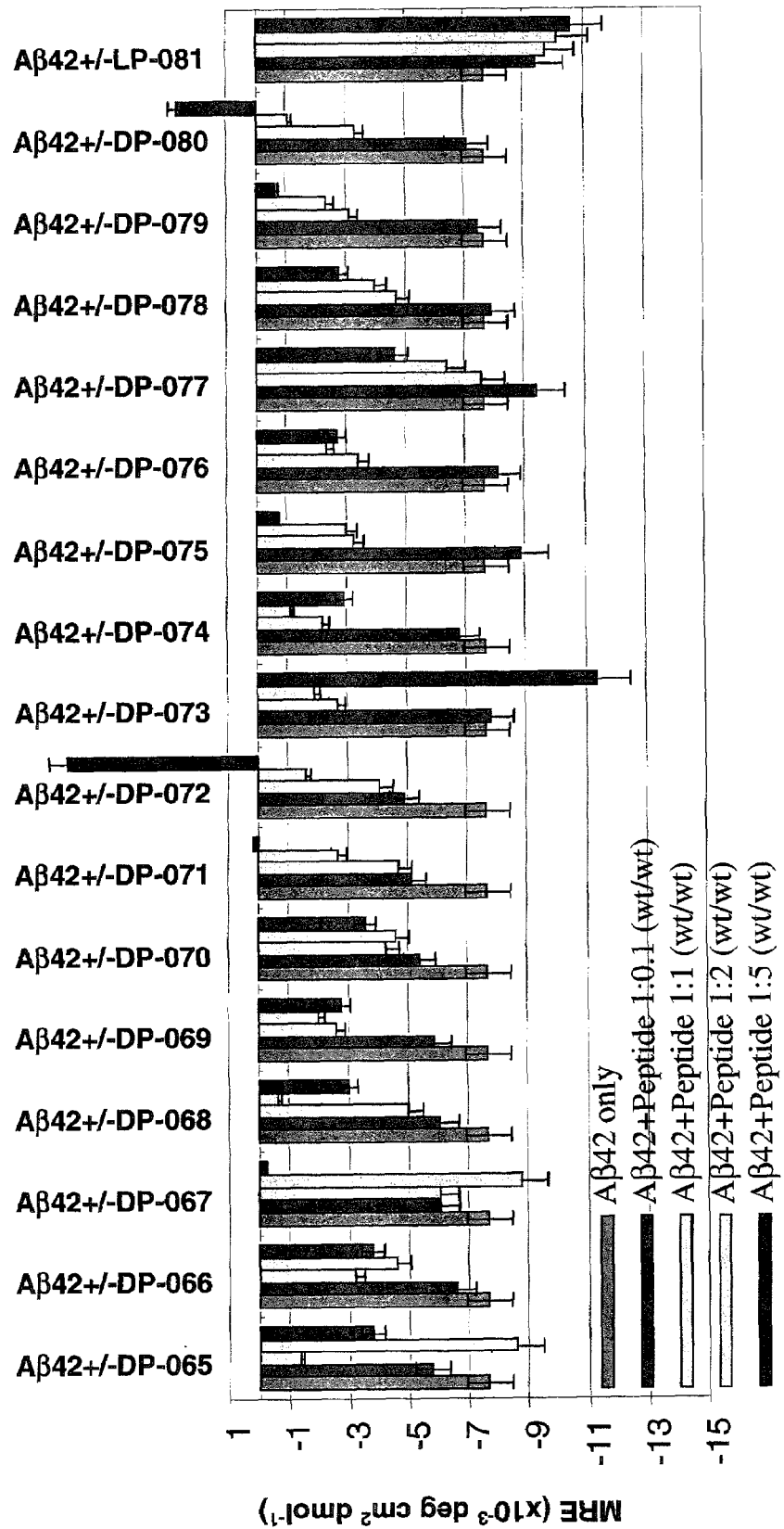
FIG. 72 is a graph showing a summary comparison of the dose-dependent effect of peptides DP-065 to LP-081 on beta-sheet secondary structure of 25 uM Aβ42 amyloid fibrils as assessed by CD. Shown is the molar residue ellipticity of Aβ42 at 218 nm in the y-axis, 45 representing the signal inversely related to the beta-sheet secondary structure.

The CD spectra of Aβ42 alone, Aβ42 plus 6-9mer peptide, and peptide alone were presented in FIGS. 63 to 71, with an overall summary in FIG. 72.

FIG. 63A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 63A is the CD spectrum of 0.1 mg/ml of Aβ42 in the presence of 0.01, 0.1, 0.2, and 0.5 mg/ml of peptide DP-073 after 3 days of incubation with correction for the spectrum of peptide DP-073). The significant loss of negative ellipticity at 218 nm indicates a loss of beta-sheet structure in Aβ42. The dose-dependent effect is only observed at 0.2 mg/ml and lower. At 0.5 mg/ml of peptide DP-074 the trend stops and reverses course. This is perhaps due to the very high concentration of test peptide causing a significant absorption of the incoming light. FIG. 63B shows the CD spectrum of 0.01, 0.1, 0.2, and 0.5 mg/ml of peptide DP-073 alone with positive ellipticities and maxima at 200 nm, indicating an inverted random coil consistent with a D-amino acid peptide with very little beta-sheet structure. However at a high concentration 0.5 mg/ml) an inverted beta-sheet structure is observed. Also shown in FIG. 63B for comparison is the CD spectrum of 0.1 mg/ml of Aβ42 after 3 days of incubation blue).

FIG. 64A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 63A is the CD spectrum of 0.1 mg/ml of Aβ42 in the presence of 0.01, 0.1, 0.2, and 0.5 mg/ml of peptide DP-074 after 3 days of incubation with correction for the spectrum of peptide DP-074). The significant loss of negative ellipticity at 218 nm indicates a loss of beta-sheet structure in Aβ42. The dose-dependent effect is only observed at 0.2 mg/ml and lower. At 0.5 mg/ml of peptide DP-074 the trend stops and reverses course. This is perhaps due to the very high concentration of test peptide causing a significant absorption of the incoming light. FIG. 63B shows the CD spectrum of 0.01, 0.1, 0.2, and 0.5 mg/ml of peptide DP-074 alone with positive ellipticities and maxima at approximately 200 nm, indicating an inverted random coil consistent with a D-amino acid peptide with very little beta-sheet structure. Also shown in FIG. 64B for comparison is the CD spectrum of 0.1 mg/ml of Aβ42 after 3 days of incubation blue).

FIG. 65A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 65A is the CD spectrum of 0.1 mg/ml of Aβ42 in the presence of 0.01, 0.1, 0.2, and 0.5 mg/ml of peptide DP-075 after 3 days of incubation with correction for the spectrum of peptide DP-075). The significant loss of negative ellipticity at 218 nm indicates a loss of beta-sheet structure in Aβ42. The dose-dependent effect is only observed at 0.1 mg/ml and lower. At 0.01 mg/ml of peptide DP-075 the Aβ42 beta-sheet structure is enhanced. FIG. 65B shows the CD spectrum of 0.01, 0.1, 0.2, and 0.5 mg/ml of peptide DP-075 alone with positive ellipticities and maxima at approximately 200 nm, indicating an inverted random coil consistent with a D-amino acid peptide with very little beta-sheet structure. Also shown in FIG. 64B for comparison is the CD spectrum of 0.1 mg/ml of Aβ42 after 3 days of incubation blue).

FIG. 66A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 66A is the CD spectrum of 0.1 mg/ml of Aβ42 in the presence of 0.01, 0.1, 0.2, and 0.5 mg/ml of peptide DP-076 after 3 days of incubation with correction for the spectrum of peptide DP-076). The significant loss of negative ellipticity at 218 nm indicates a loss of beta-sheet structure in Aβ42. The dose-dependent effect is only observed at 0.1 mg/ml and lower. At 0.01 mg/ml of peptide DP-076 the Aβ42 beta-sheet structure is enhanced. FIG. 66B shows the CD spectrum of 0.01, 0.1, 0.2, and 0.5 mg/ml of peptide DP-076 alone with positive ellipticities and maxima at approximately 200 nm, indicating an inverted random coil consistent with a D-amino acid peptide with very little beta-sheet structure. However at a concentration of 0.5 mg/ml significant formation of inverted beta-sheet structure is observed Also shown in FIG. 66B for comparison is the CD spectrum of 0.1 mg/ml of Aβ42 after 3 days of incubation blue).

FIG. 67A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 67A is the CD spectrum of 0.1 mg/ml of Aβ42 in the presence of 0.01, 0.1, 0.2, and 0.5 mg/ml of peptide DP-077 after 3 days of incubation with correction for the spectrum of peptide DP-077). The loss of negative ellipticity at 218 nm indicates a loss of beta-sheet structure in Aβ42. The dose-dependent effect is only observed at 0.1 mg/ml and higher. FIG. 67B shows the CD spectrum of 0.01, 0.1, 0.2, and 0.5 mg/ml of peptide DP-077 alone with positive ellipticities and maxima at approximately 200 nm, indicating an inverted random coil consistent with a D-amino acid peptide with very little beta-sheet structure. Also shown in FIG. 67B for comparison is the CD spectrum of 0.1 mg/ml of Aβ42 after 3 days of incubation blue).

FIG. 68A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 68A is the CD spectrum of 0.1 mg/ml of Aβ42 in the presence of 0.01, 0.1, 0.2, and 0.5 mg/ml of peptide DP-078 after 3 days of incubation with correction for the spectrum of peptide DP-078). The significant loss of negative ellipticity at 218 nm indicates a loss of beta-sheet structure in Aβ42. The dose-dependent effect is observed. FIG. 68B shows the CD spectrum of 0.01, 0.1, 0.2, and 0.5 mg/ml of peptide DP-078 alone with positive ellipticities and maxima at approximately 200 nm, indicating an inverted random coil consistent with a D-amino acid peptide with very little beta-sheet structure. Also shown in FIG. 68B for comparison is the CD spectrum of 0.1 mg/ml of Aβ42 after 3 days of incubation blue).

FIG. 69A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 69A is the CD spectrum of 0.1 mg/ml of Aβ42 in the presence of 0.01, 0.1, 0.2, and 0.5 mg/ml of peptide DP-079 after 3 days of incubation with correction for the spectrum of peptide DP-079). The significant loss of negative ellipticity at 218 nm indicates a loss of beta-sheet structure in Aβ42. However, the shift of minima from 218 nm to 225 nm is unexpected, and thus any loss of ellipticity at 218 nm may not be due to loss of beta-sheet structure alone. The loss of ellipticities at 218 nm is however, dose dependent. FIG. 69B shows the CD spectrum of 0.01, 0.1, 0.2, and 0.5 mg/ml of peptide DP-079 alone with positive ellipticities and maxima at approximately 225 nm and a minima at 200 nm indicating an inverted beta-sheet consistent with D-amino acid peptide, with beta-sheet structure. However, the maximum at 225 nm indicates a structure reminiscent of cross-linking or disulfide bonding protein, despite the lack of methionine or cystine. Also shown in FIG. 69B for comparison is the CD spectrum of 0.1 mg/ml of Aβ42 after 3 days of incubation blue).

FIG. 70A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 70A is the CD spectrum of 0.1 mg/ml of Aβ42 in the presence of 0.01, 0.1, 0.2, and 0.5 mg/ml of peptide DP-080 after 3 days of incubation with correction for the spectrum of peptide DP-080). There is a dose-dependent loss of negative ellipticity at 218 nm indicating a dose-dependent loss of beta-sheet structure in Aβ42. FIG. 70B shows the CD spectrum of 0.01, 0.1, 0.2, and 0.5 mg/ml of peptide DP-080 alone with positive ellipticities and maxima at approximately 195 nm, indicating an inverted random coil consistent with a D-amino acid peptide with little beta-sheet structure. Also shown in FIG. 70B for comparison is the CD spectrum of 0.1 mg/ml of Aβ42 after 3 days of incubation blue).

FIG. 71A shows the CD spectrum of 0.1 mg/ml of Aβ42 after 3 days of incubation blue). Both the negative ellipticity at 218 nm and the positive ellipticity at 195 nm indicate the presence of beta-sheet structure in Aβ42. Also in FIG. 71A is the CD spectrum of 0.1 mg/ml of Aβ42 in the presence of 0.01, 0.1, 0.2, and 0.5 mg/ml of peptide LP-081 after 3 days of incubation with correction for the spectrum of peptide LP-081). The significant gain of negative ellipticity at 218 nm indicates a gain of beta-sheet structure. However, no dose dependent effect is observed. FIG. 71A shows the CD spectrum of 0.01, 0.1, 0.2, and 0.5 mg/ml of peptide LP-081 alone with positive ellipticities and maxima at approximately 200 nm, indicating a random coil structure of L-peptide. Also shown in FIG. 71B for comparison is the CD spectrum of 0.1 mg/ml of Aβ42 after 3 days of incubation blue). It should be noted that LP-081 is the beta-sheet breaker peptide previously reported Permanne et al, *FASEB J. Published online Apr.* 10, 2002; Soto-Jara et al, U.S. Pat. No. 5,948,763 Sep. 7, 1999; Soto-Jara, PCT WO 01/34631 A2 May 17, 2001). FIG. 72 shows the CD spectra and represents a summary of the data of Aβ42 in the presence of increasing amounts of DP-065 to DP-080, and LP-081, as discussed in detail above.

Example 9

Stability of Peptides in Human Serum

A desirable characteristic of any potential therapeutic or drug candidate is the ability to resist degradation by enzymes in the blood, to have enough time reach its target. One of the in vitro assays used to determine the stability of peptides in Sequence Group A, B, or C is by incubating these peptides in human serum, and determining the level of the intact peptides and possible degradation) at various time points. Fifty ul aliquots of various peptides were added to 700 ul of human serum in triplicate samples). One hundred ul aliquots were then taken at 0, 2, 4, 6, 24, and 32 hrs, followed immediately with the addition of 200 ul of ethanol or 20 ul of trifluoroacetic acid or 300 ul methanol) and centrifuged at 14,000×g Eppendorf) for 10 minutes. The level of intact peptides in the supernatant was then determined using LC/MS Agilent HPLC/MS SL 1100 Series). MS monitored each peptide as it came out of the HPLC using SIM mode positive ion monitoring at masses corresponding to single, double and triple charge peptide ions. The peak in the resulting ion chromatograms were integrated to obtain total ion abundance in each sample. The average of triplicate determinations of total ion abundance for each serum incubation time-point was then plotted as a function of serum incubation time. Most of the peptide degrading enzymes in the body recognizes natural peptides made up of all L-amino acids. As the peptides consist of D-amino acids, their degradation in biological fluids will likely be retarded, as demonstrated in this Example and the following figures.

Figure 76:
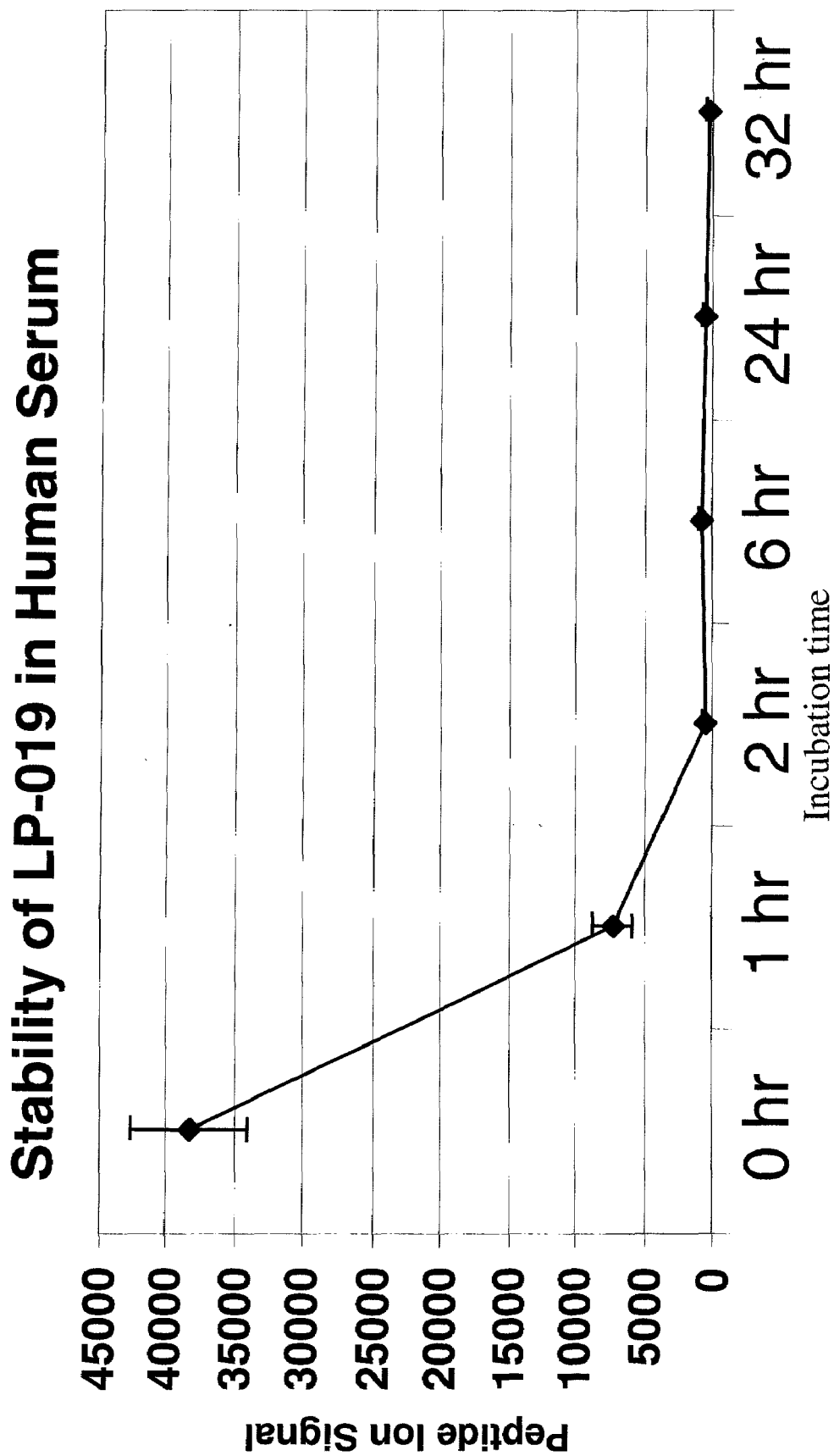
FIG. 76 is a graph demonstrating the lack of stability of peptide LP-019 negative control) in human serum within a 32-hour incubation period, as assessed by LC/MS.

FIG. 76 shows the level of peptide LP-019 in human serum as a function of time over a 32 hour incubation period. The peptide LP-019 consists of all L-amino acids, and as shown in FIG. 76, it is rapidly degraded in serum in less than 1 hr.

Figure 77:
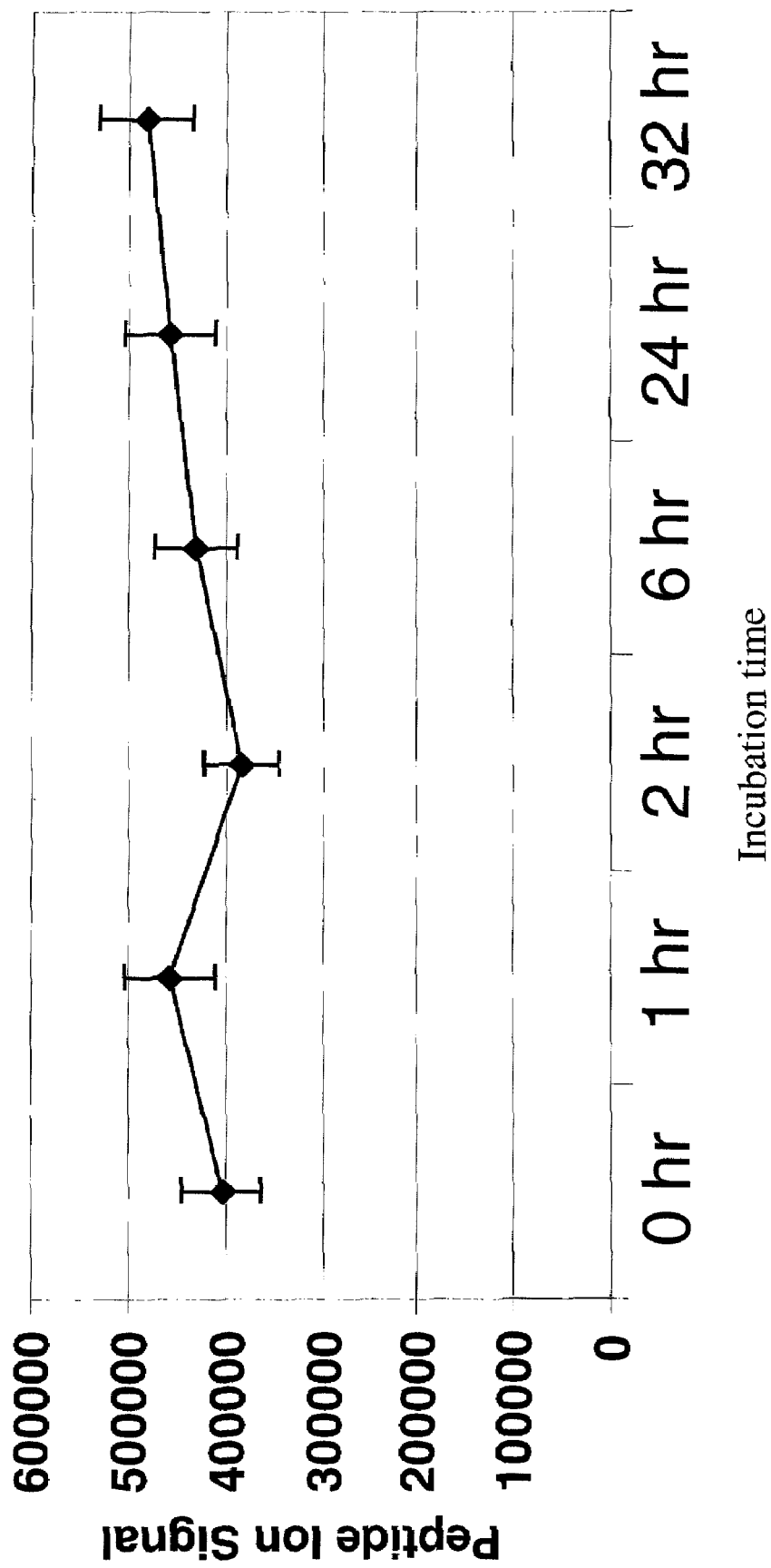
FIG. 77 is a graph demonstrating the stability of peptide DP-068 in human serum within a 32-hour incubation period, as assessed by LC/MS.

FIG. 77 shows the level of peptide DP-068 in human serum as a function of time over a 32 hour incubation period. The peptide DP-068 consists of all D-amino acids, and as shown in FIG. 77, it is resistant to degradation in the serum up to and including, 32 hrs.

Figure 78:
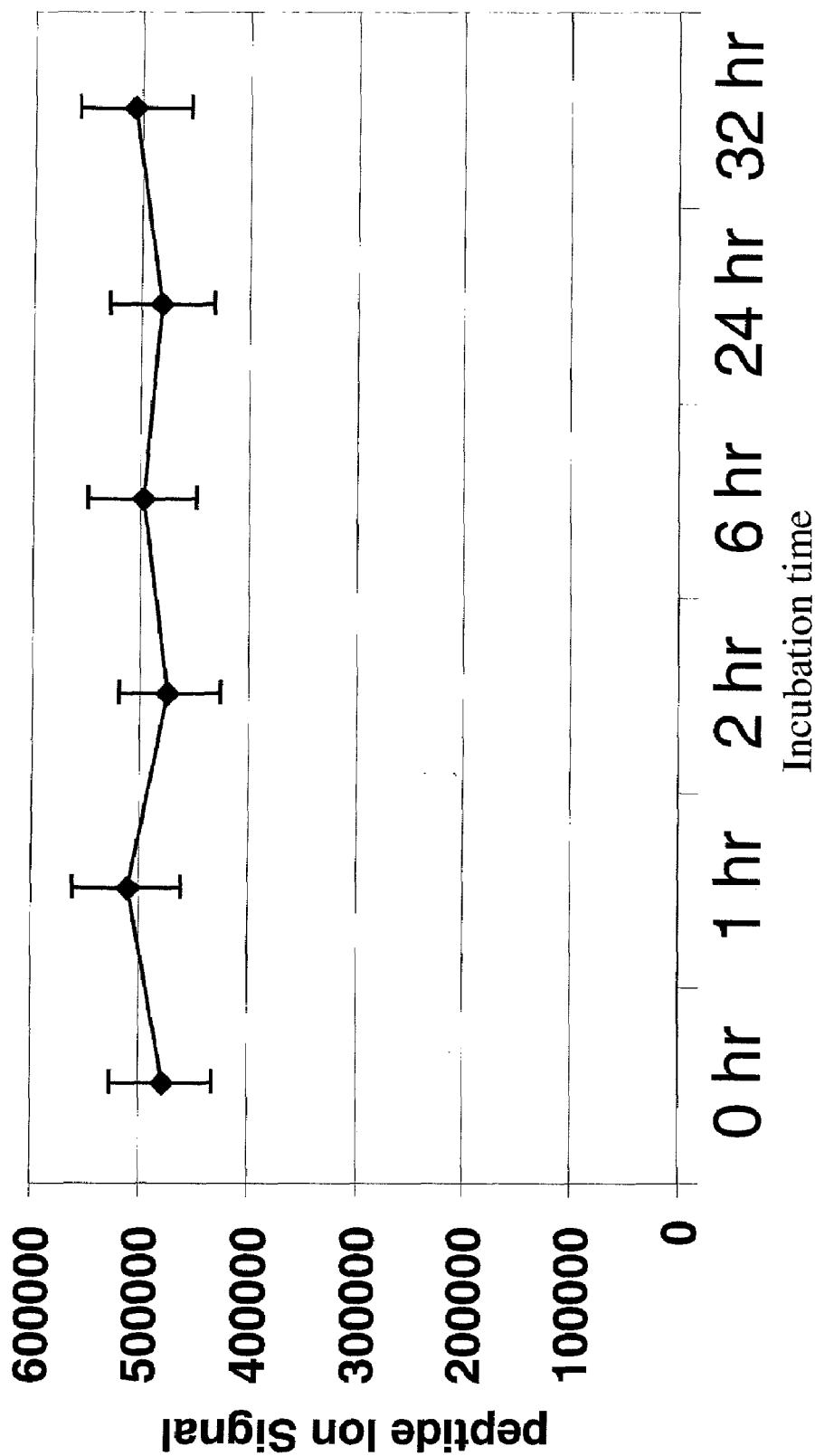
FIG. 78 is a graph demonstrating the stability of peptide DP-069 in human serum within a 32-hour incubation period, as assessed by LC/MS.

FIG. 78 shows the level of peptide DP-069 in human serum as a function of time over a 32 hour incubation period. The peptide DP-069 consists of all D-amino acids, and as shown in FIG. 78, it is resistant to degradation in the serum up to and including, 32 hrs.

Figure 79:
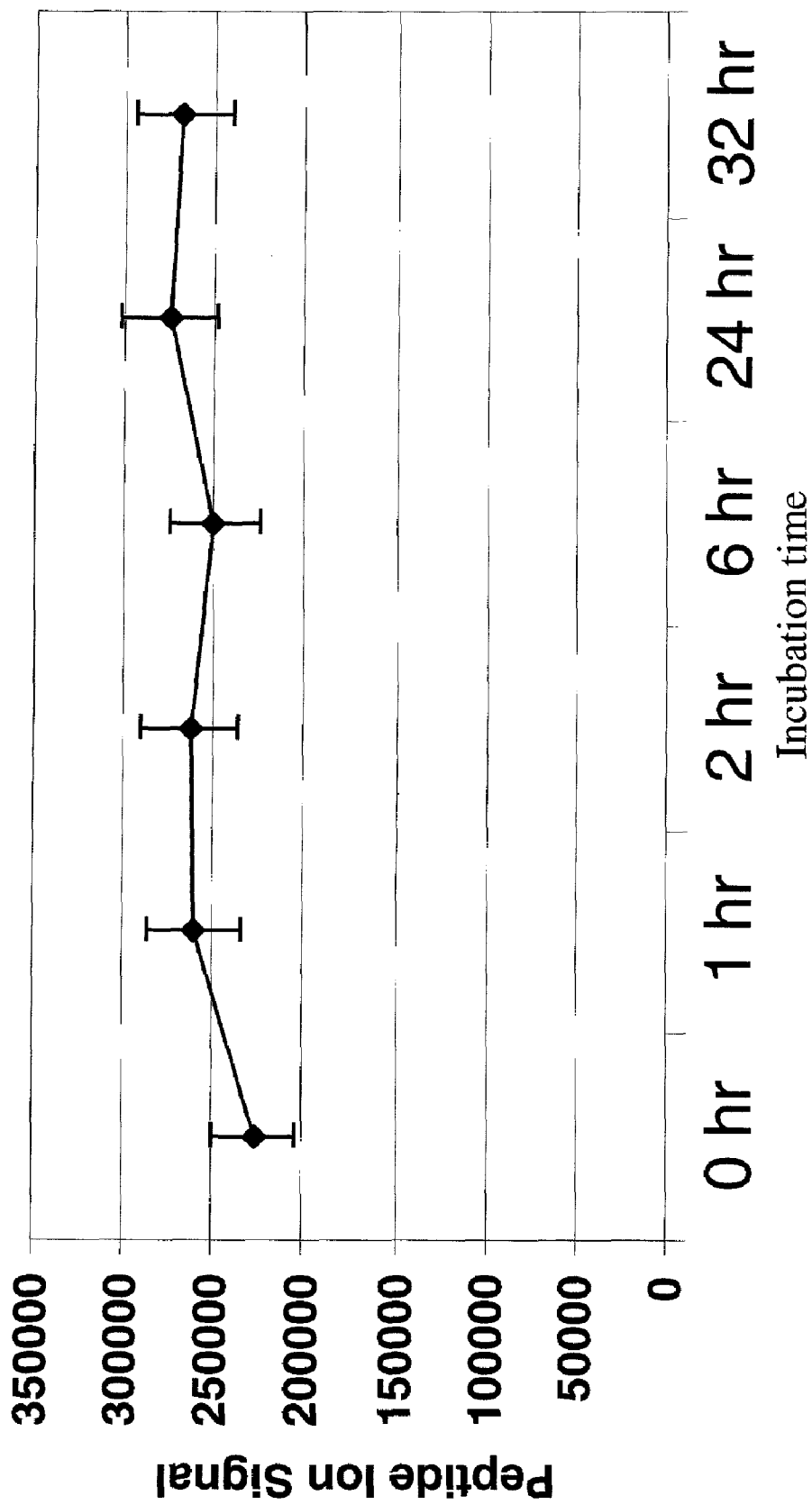
FIG. 79 is a graph demonstrating the stability of peptide DP-074 in human serum within a 32-hour incubation period, as assessed by LC/MS.

FIG. 79 shows the level of peptide DP-074 in human serum as a function of time over a 32 hour incubation period. The peptide DP-074 consists of all D-amino acids, and as shown in FIG. 79, it is resistant to degradation in the serum up to and including, 32 hrs.

Figure 80:
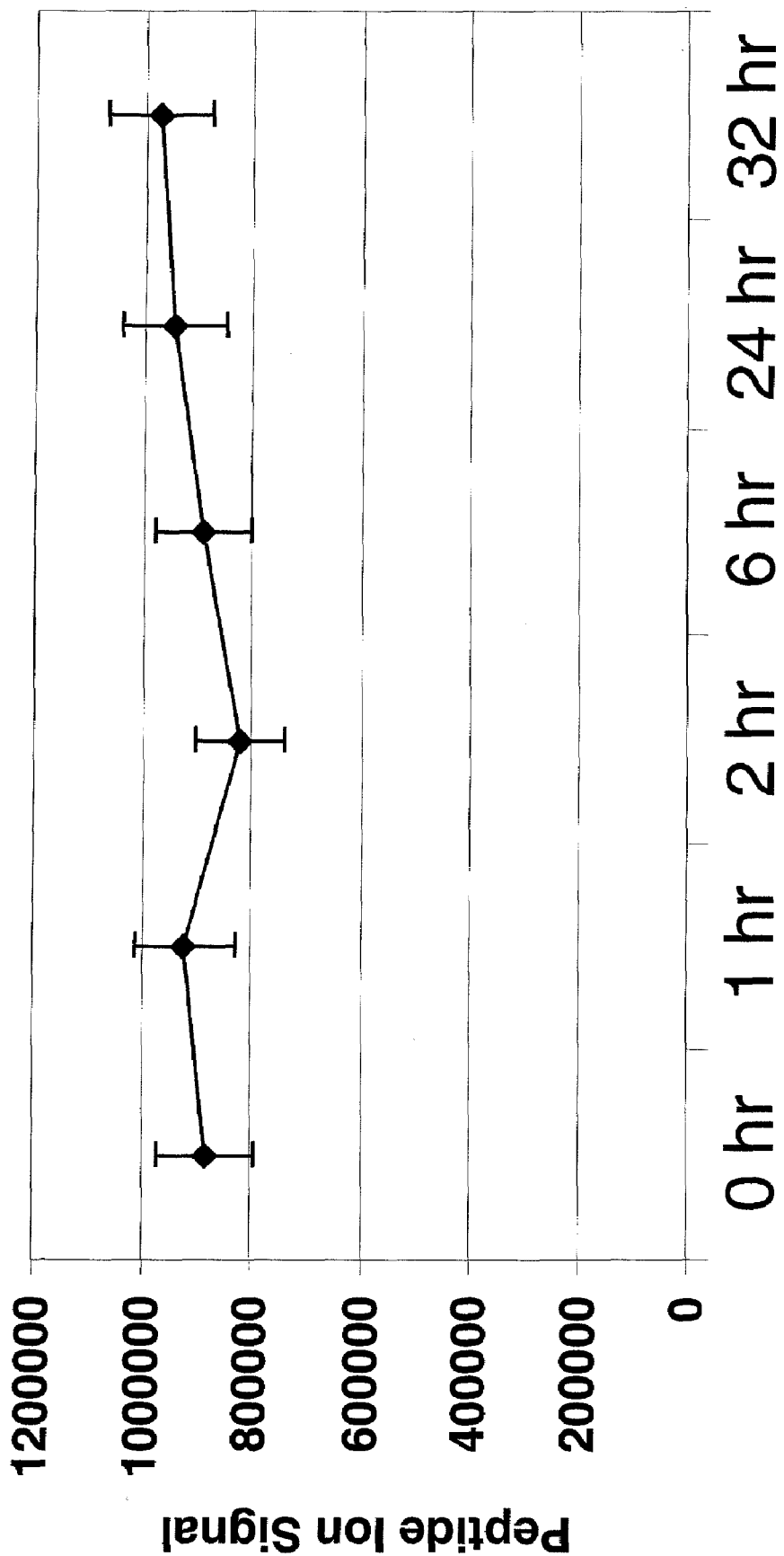
FIG. 80 is a graph demonstrating the stability of peptide DP-076 in human serum within a 32-hour incubation period, as assessed by LC/MS.

FIG. 80 shows the level of peptide DP-076 in human serum as a function of time over a 32 hour incubation period. The peptide DP-076 consists of all D-amino acids, and as shown in FIG. 80, it is resistant to degradation in the serum up to and including, 32 hrs.

Figure 81:
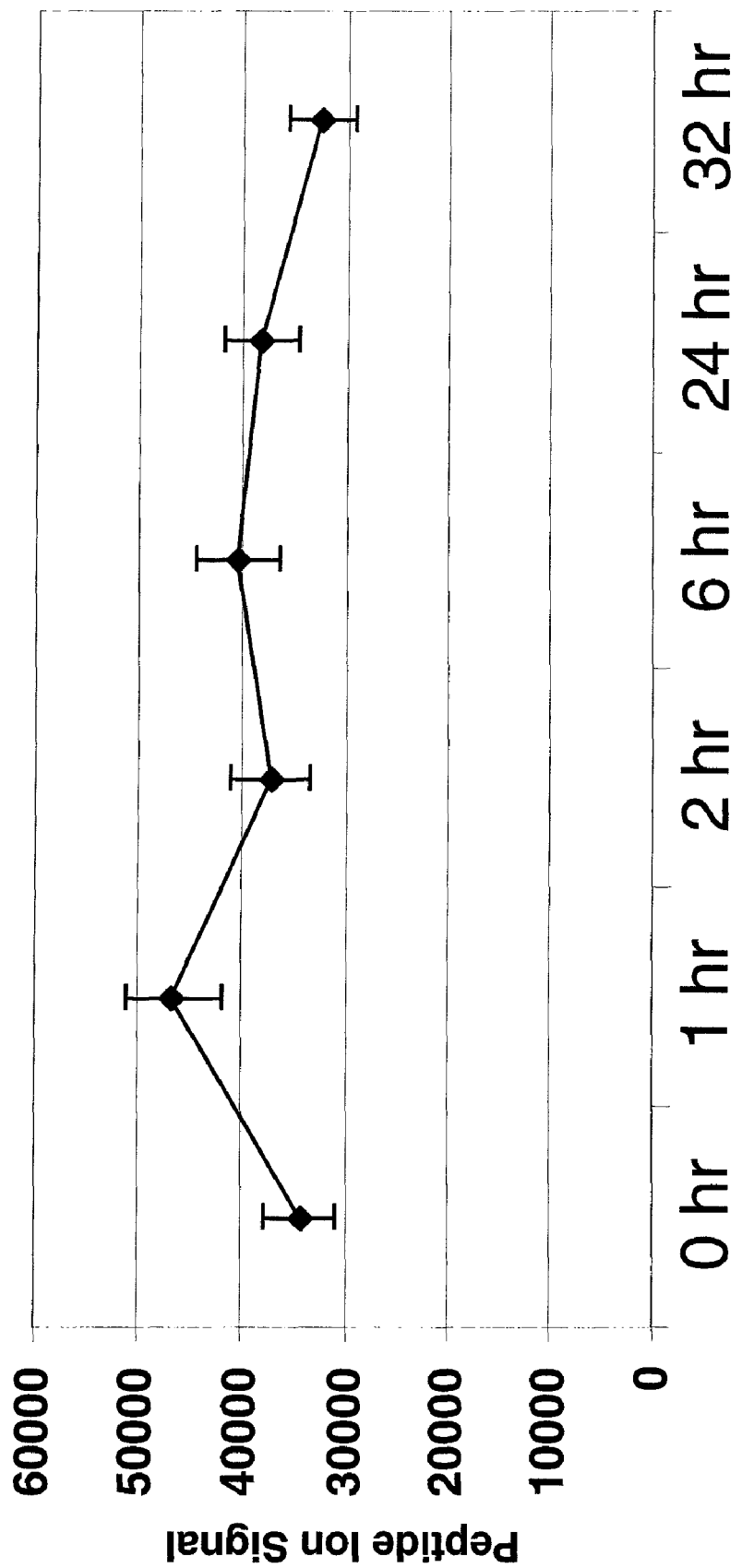
FIG. 81 is a graph demonstrating the stability of peptide DP-080 in human serum within a 32-hour incubation period, as assessed by LC/MS.

FIG. 81 shows the level of peptide DP-080 in human serum as a function of time over a 32 hour incubation period. The peptide DP-080 consists of all D-amino acids, and as shown in FIG. 81, it is resistant to degradation in the serum up to and including, 32 hours.

Further data are illustrated as follows:

FIG. 1 shows the structure of DP-074.

FIG. 2 is a graph showing an ordered summary comparison of the effect of various 12-13mer peptides on beta-sheet secondary structure of 25 µM Aβ42 amyloid fibrils as assessed by circular dichroism CD) spectropolarimetry. Shown is the percent disruption of Aβ42 fibrils as assessed by loss of ellipticity at 218 nm, representing the signal that is inversely related to beta-sheet secondary structure.

FIG. 3 is a graph showing an ordered summary comparison of the effect of 12-13mer peptides on beta-sheet secondary structure of 25 uM Aβ42 amyloid fibrils as assessed by Thioflavin T fluorometry. Shown is the percent disruption of Aβ42 fibrils by various 12-13mer peptides at an Aβ42:12-13mer peptide weight ratio of 1:2.

Figure 4:
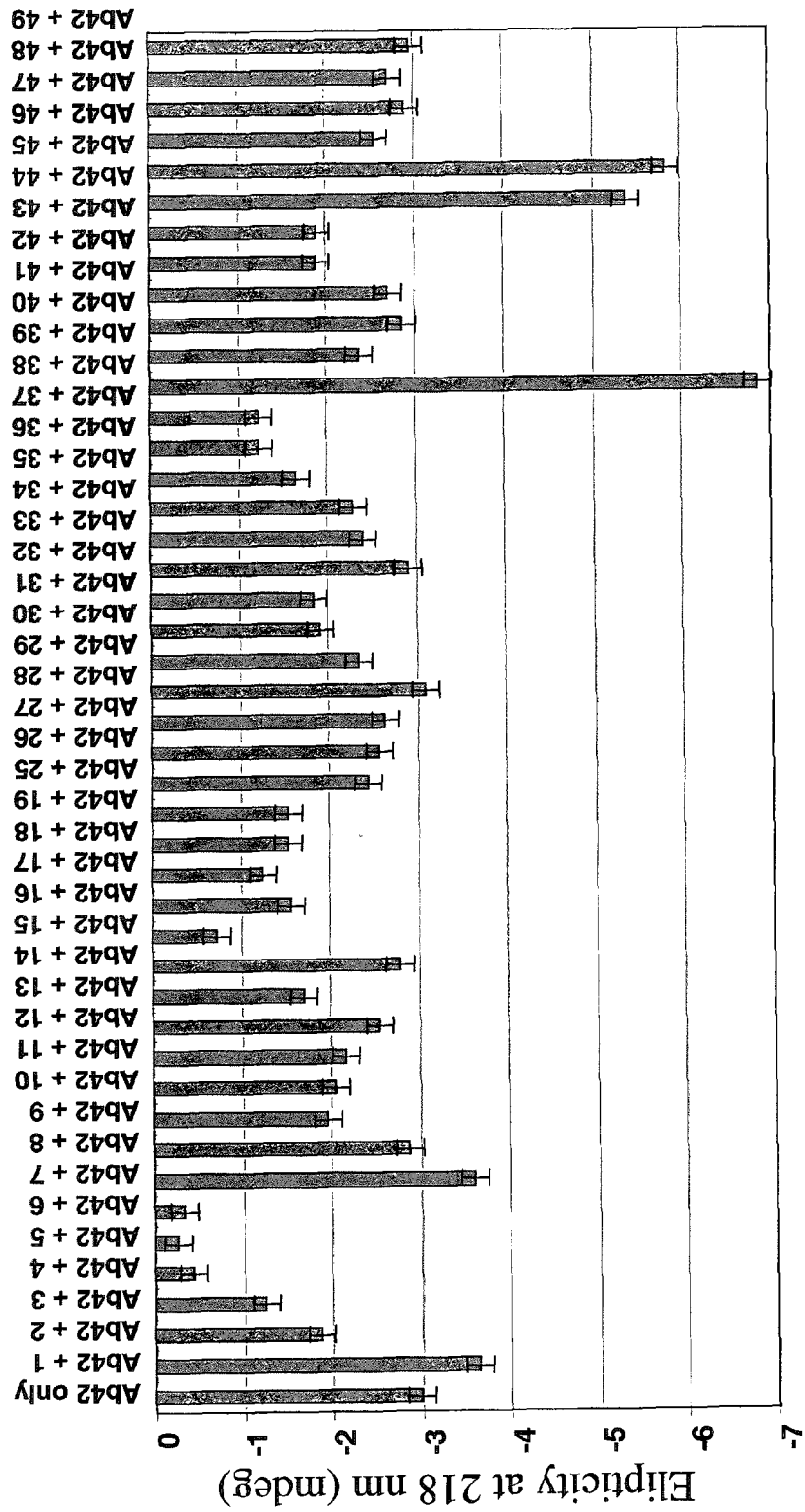
FIG. 4 is a summary of CD spectroscopy results of all peptides up to DP-049.

FIG. 4 is a summary of CD spectroscopy results of all peptides up to DP-049.

Figure 5:
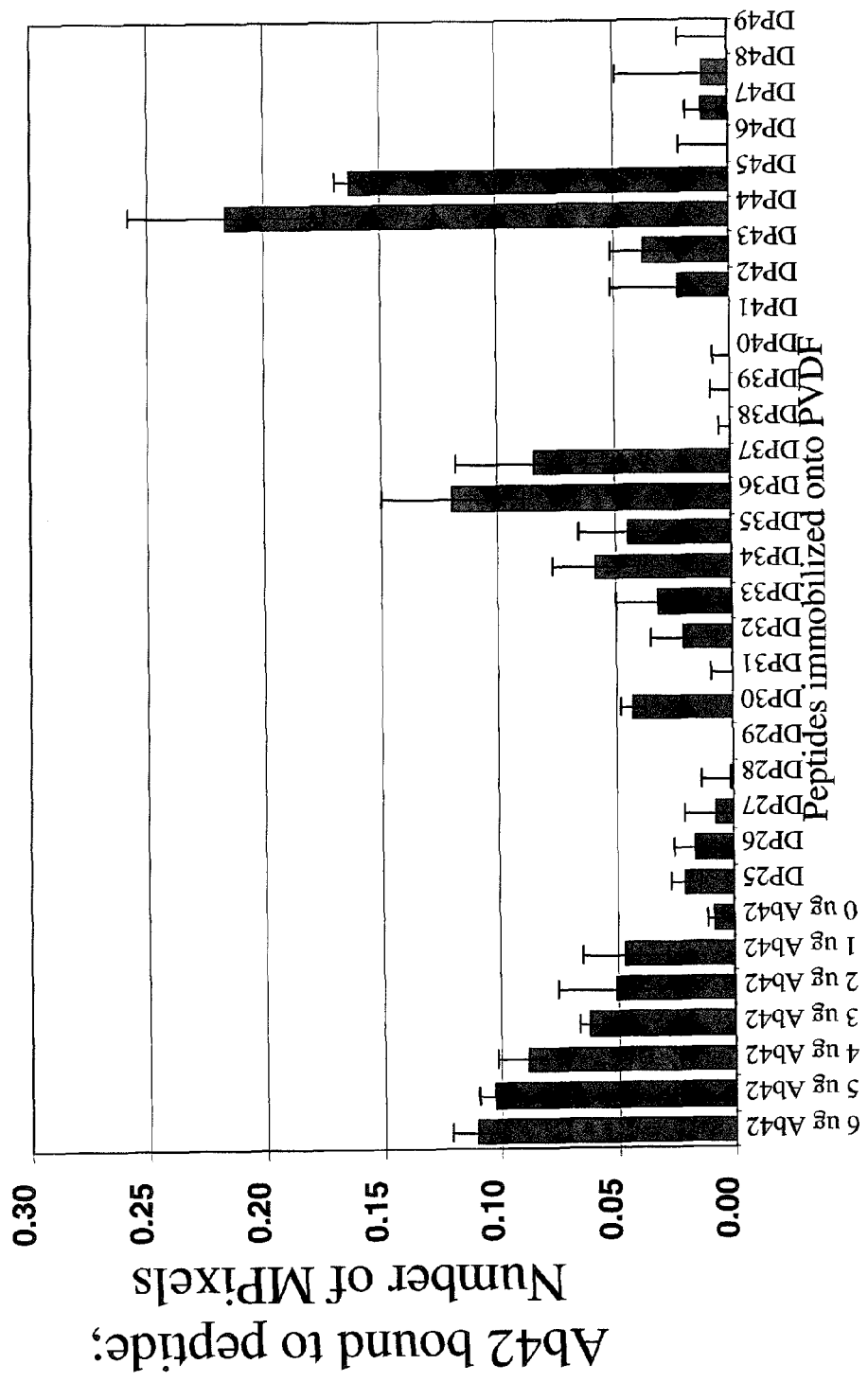
FIG. 5 is a summary of Aβ42 binding for peptides LP-025 and DP-026-049.
Figure 6:
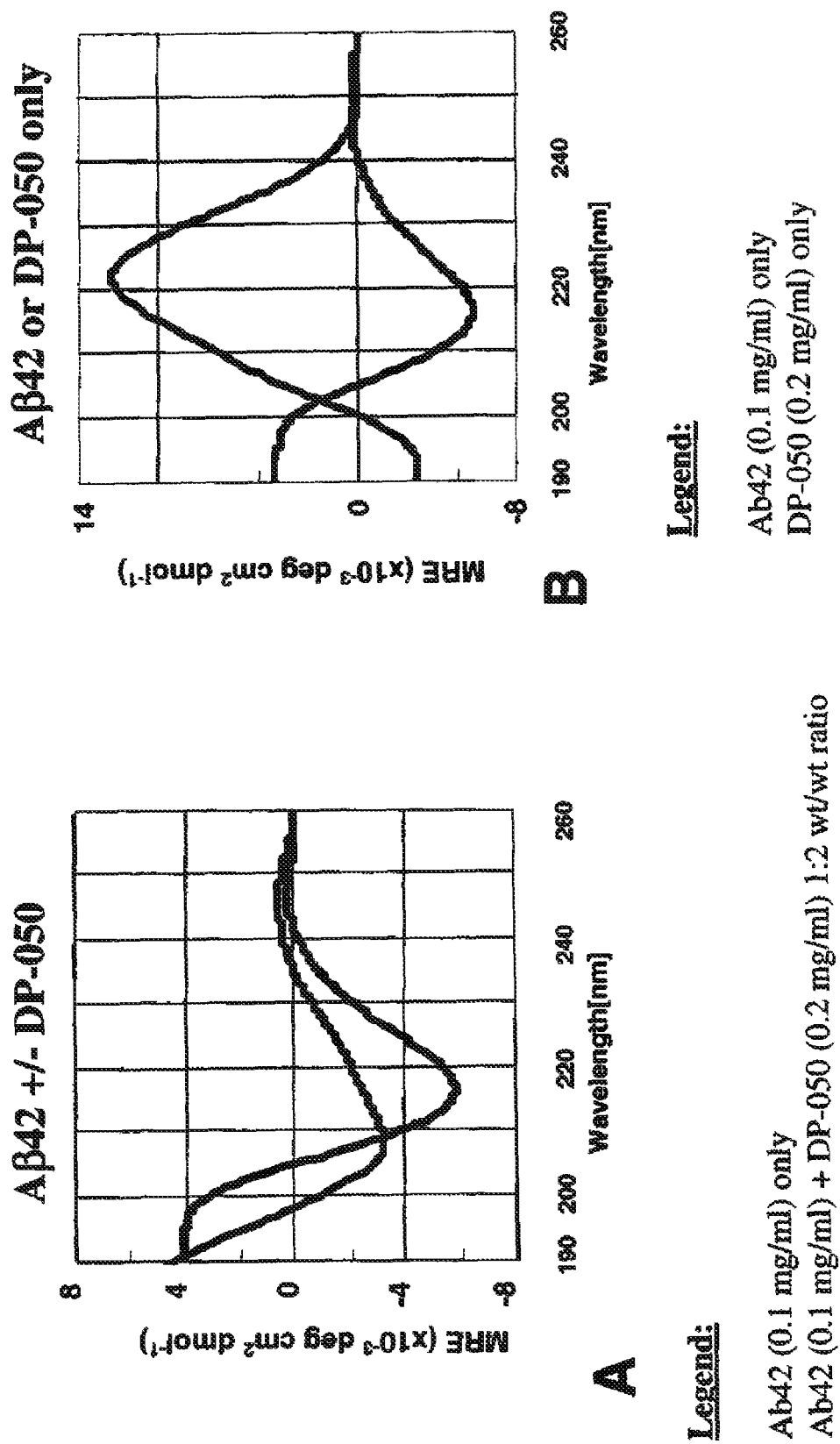
FIGS. 6-20 are CD spectra of Aβ42 plus DP-50 through DP-064, respectively, at 1:2).
Figure 7:
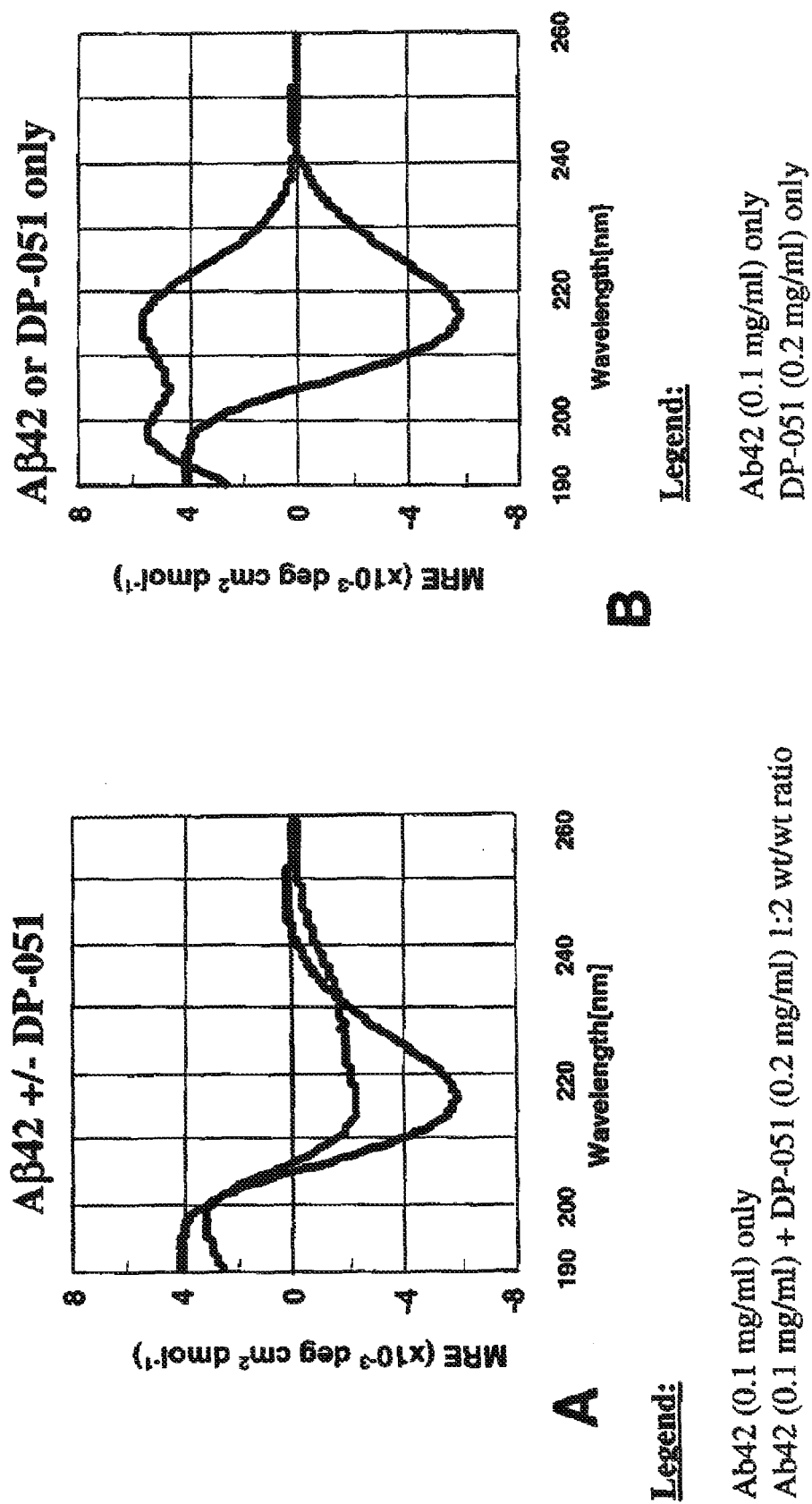
Figure 8:
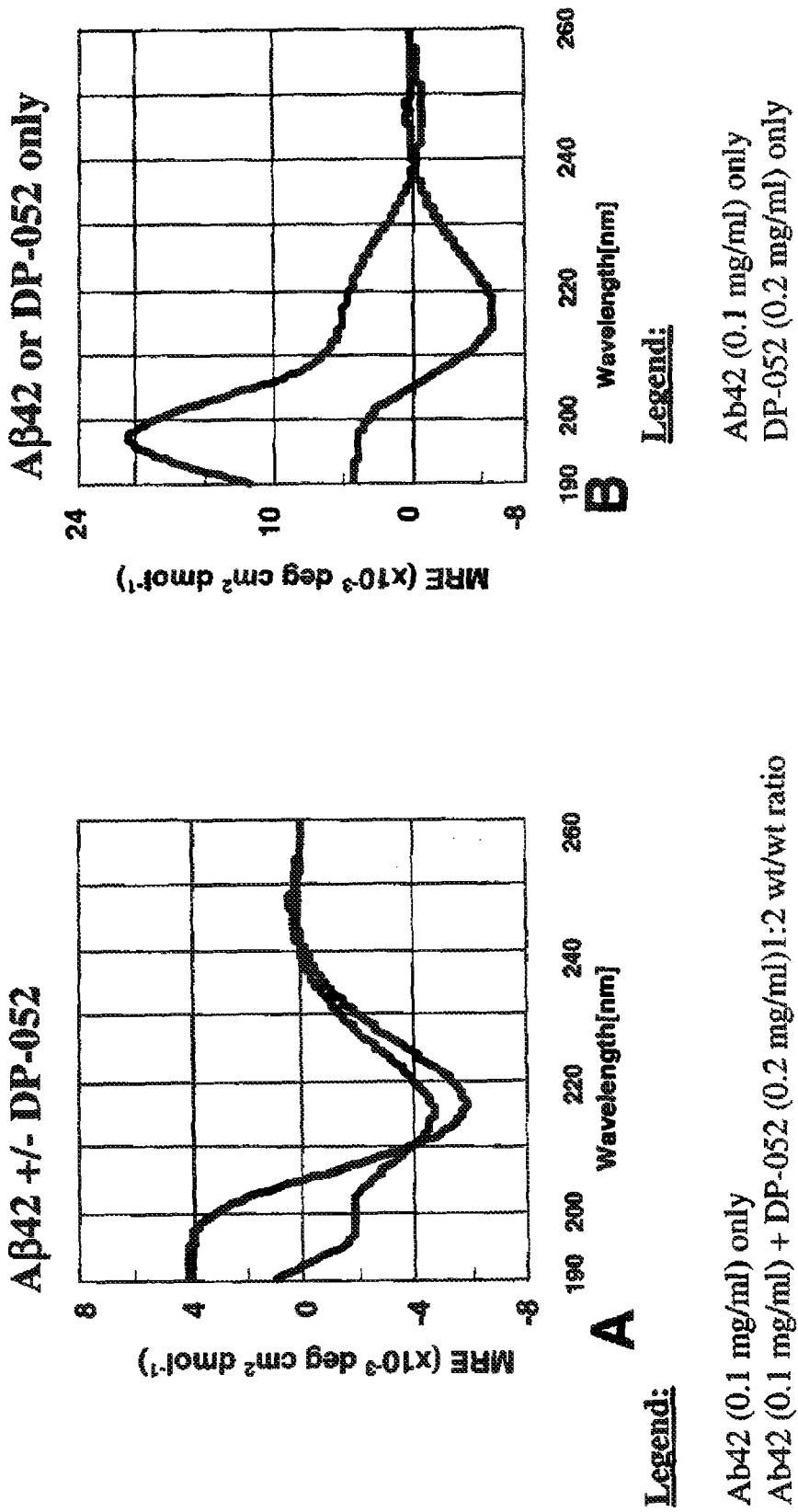
Figure 9:
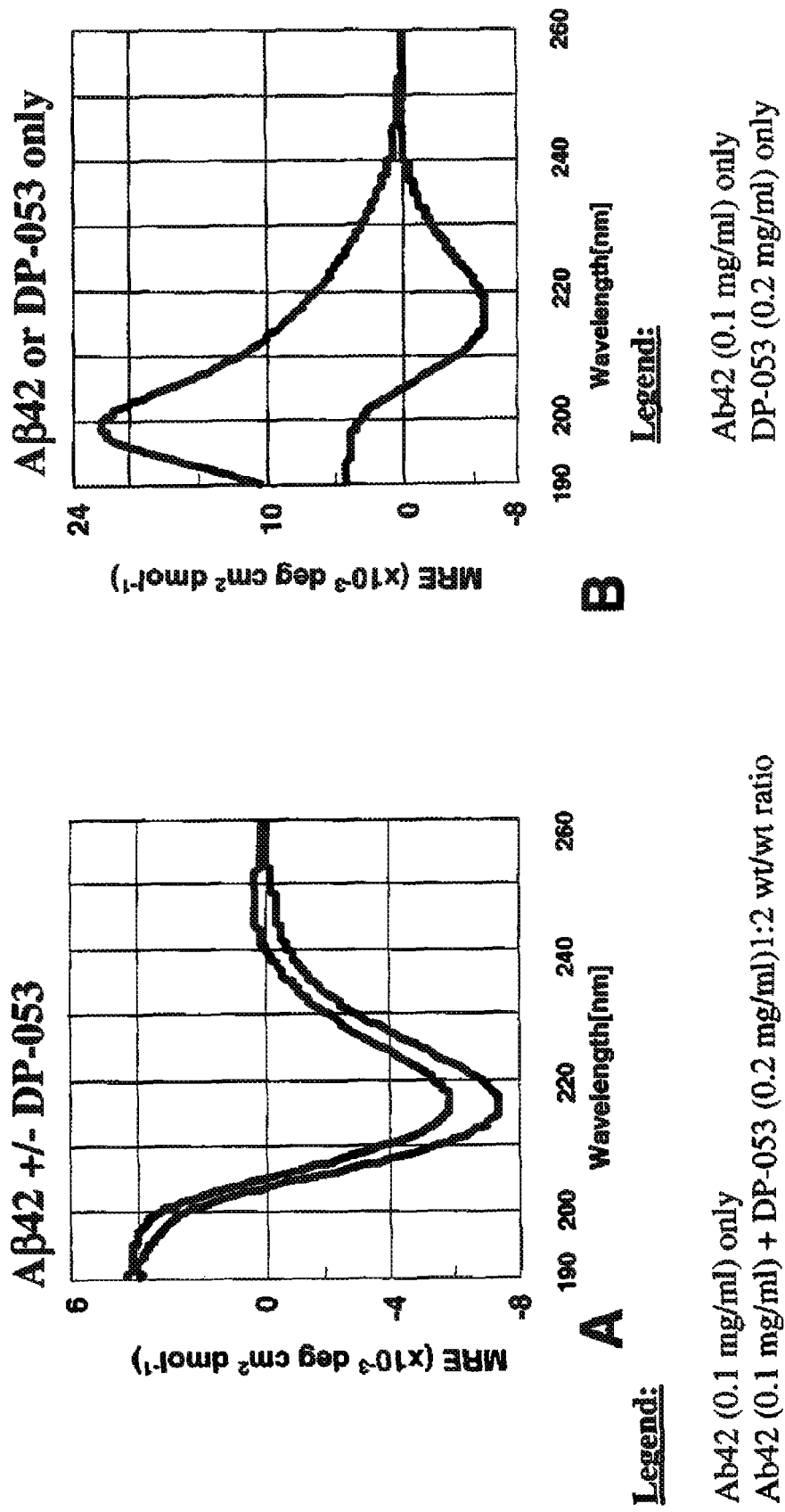
Figure 10:
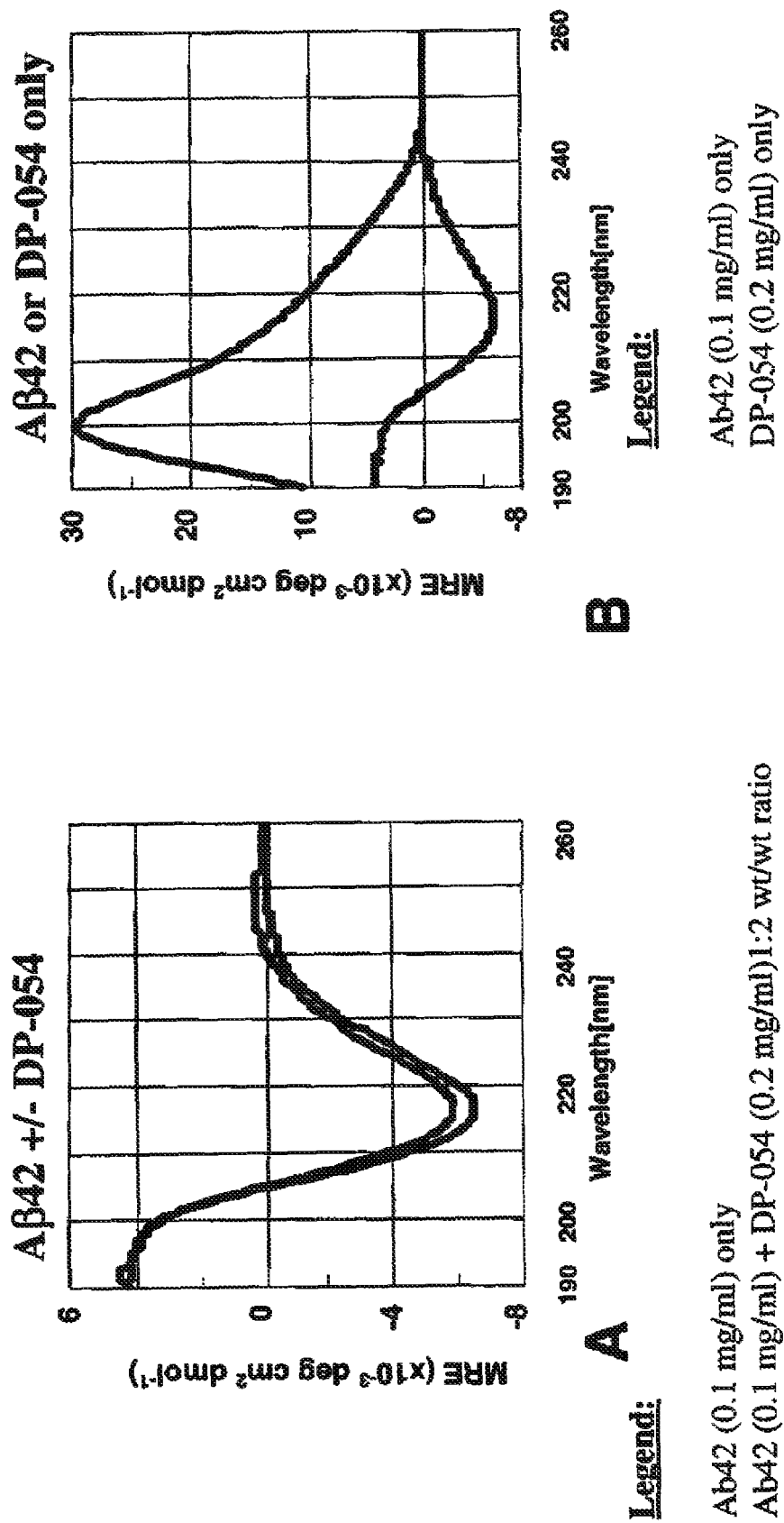
Figure 11:
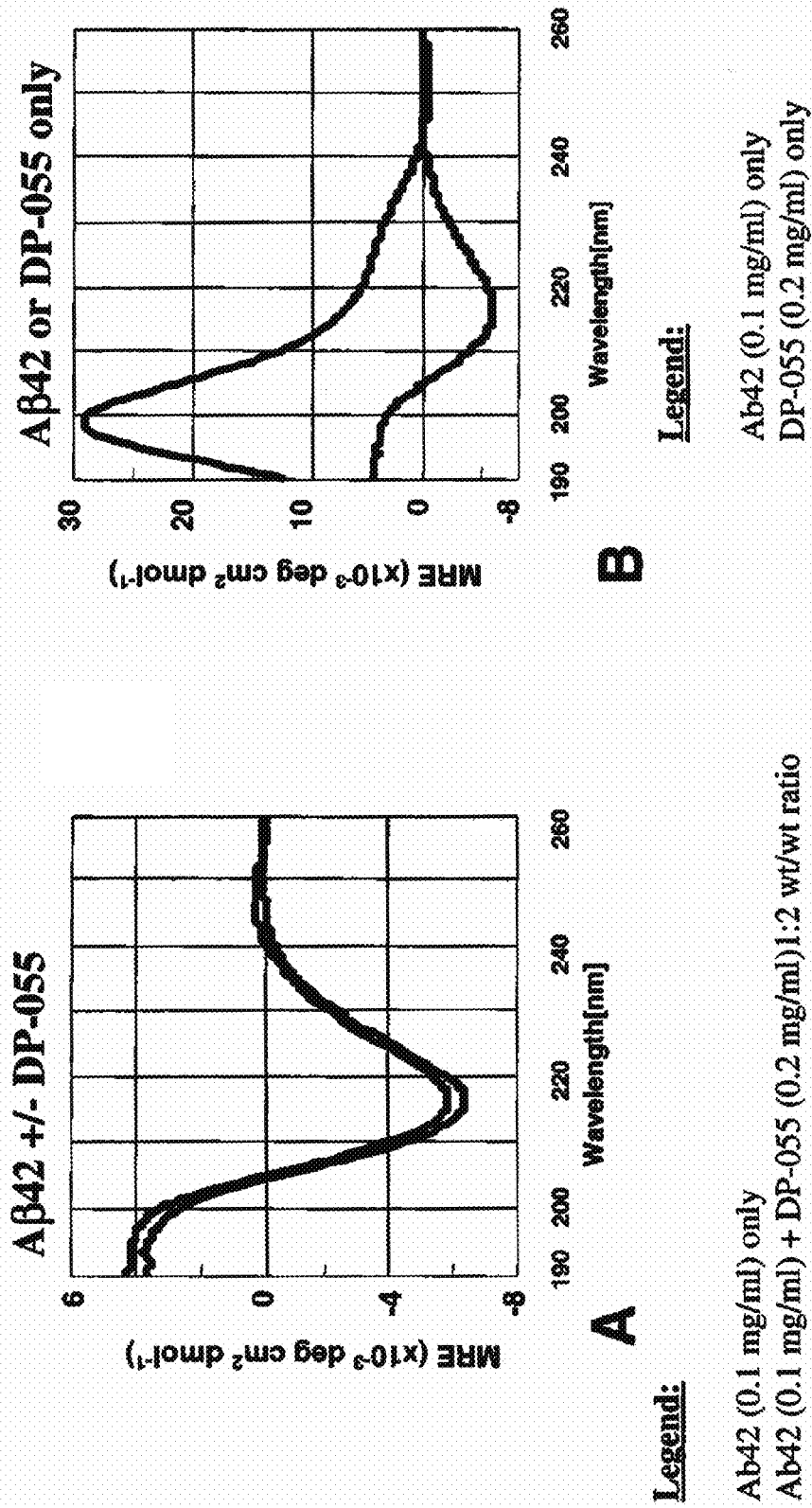
Figure 12:
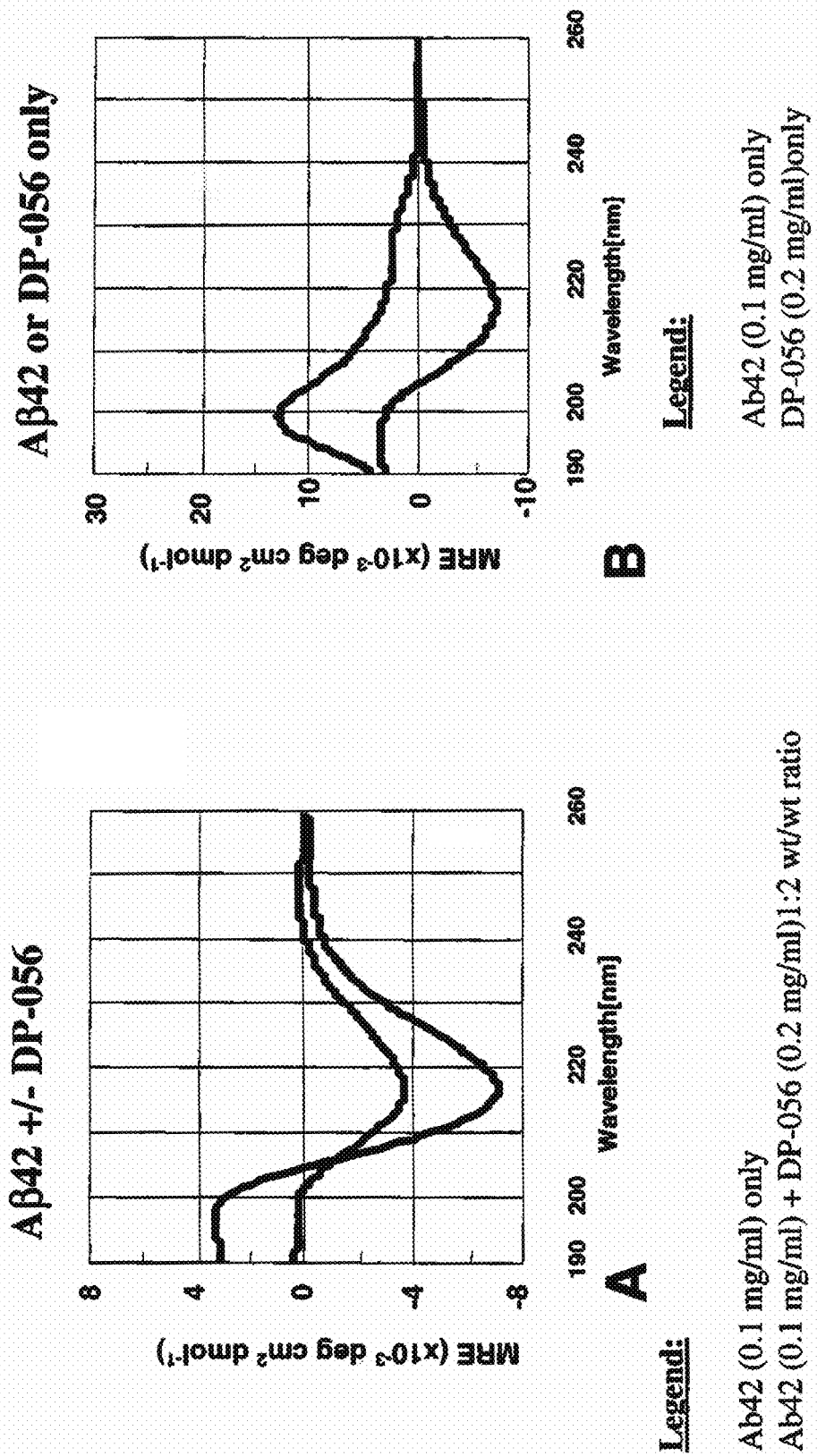
Figure 13:
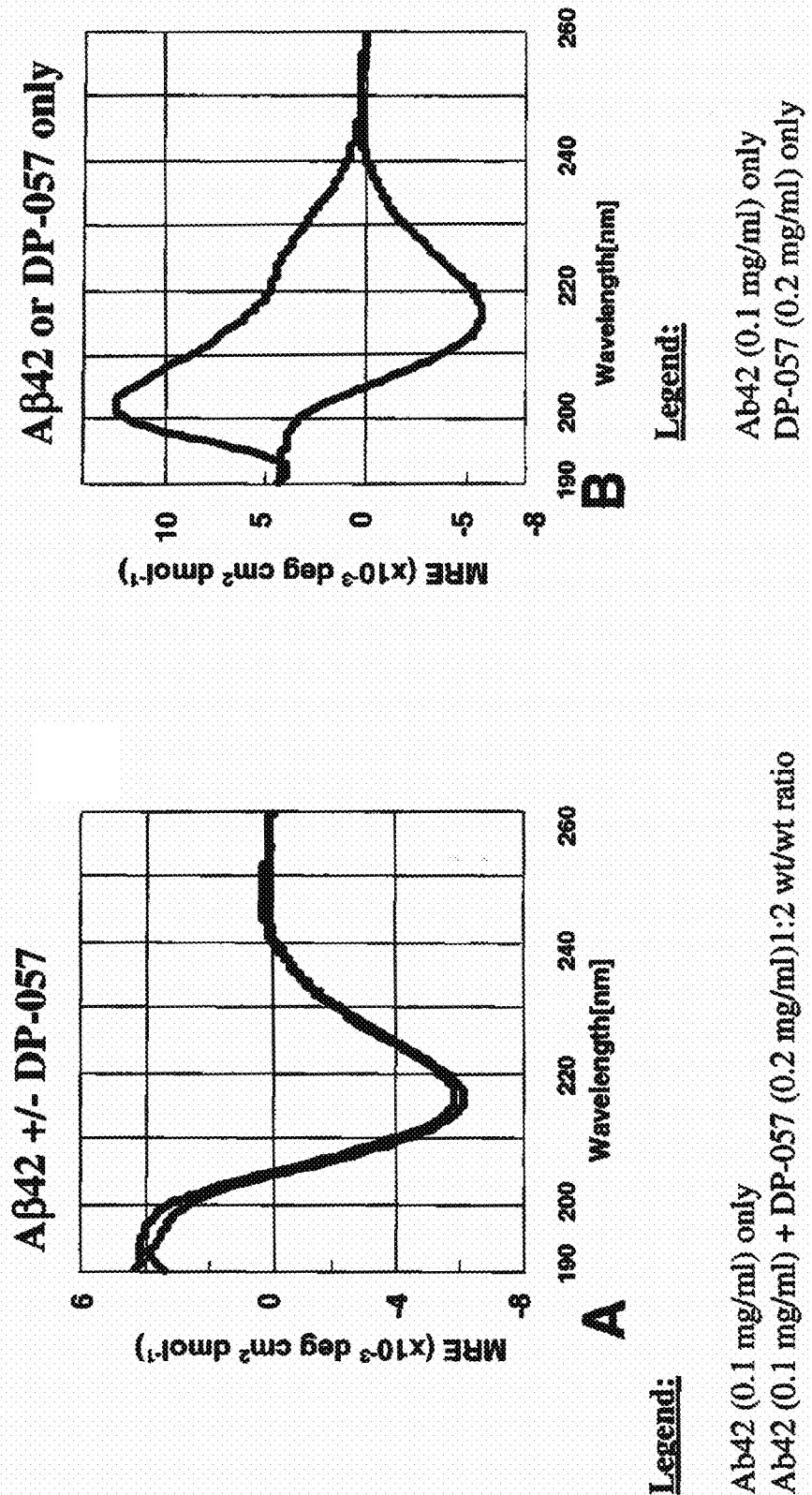
Figure 14:
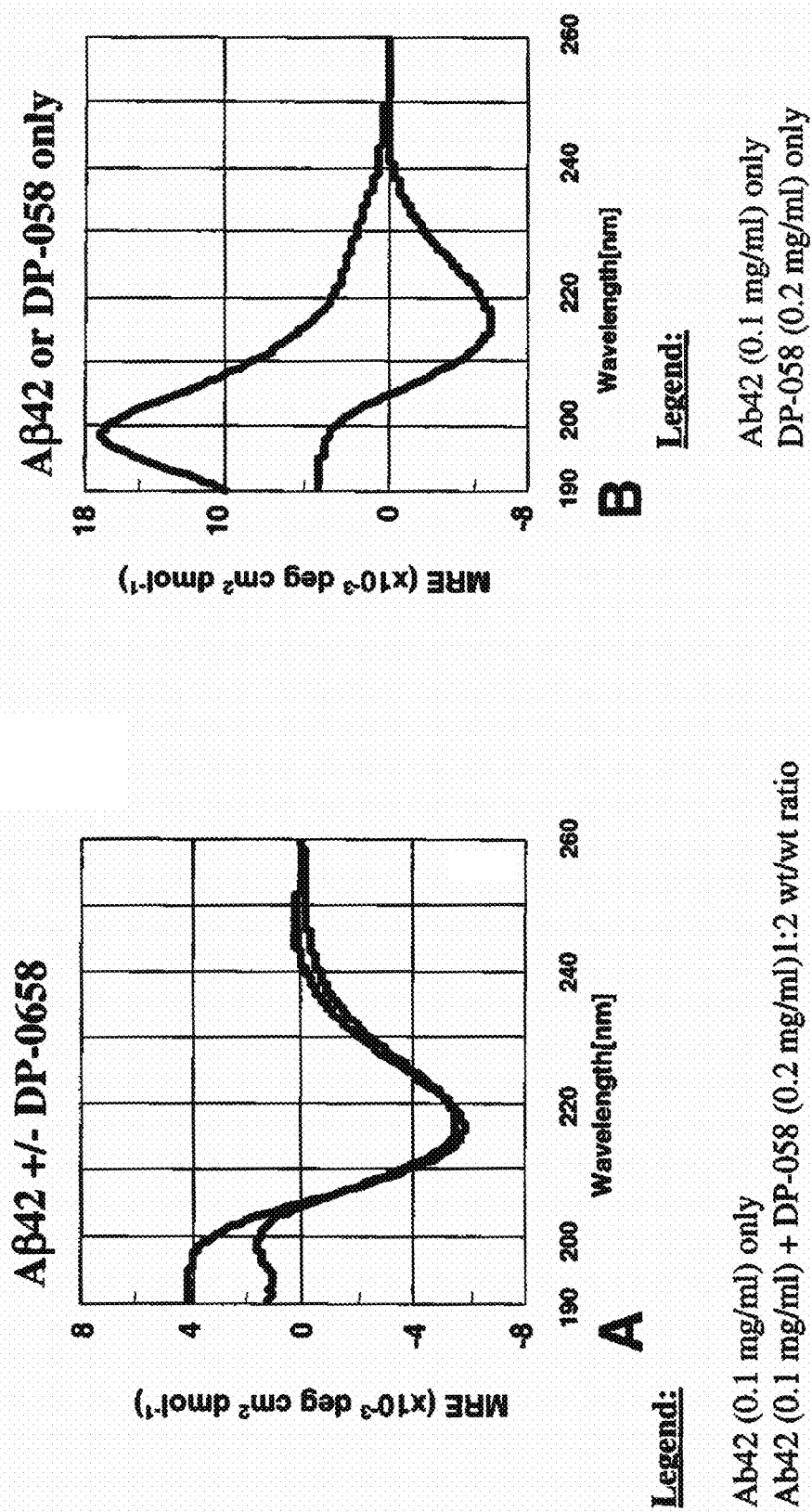
Figure 15:
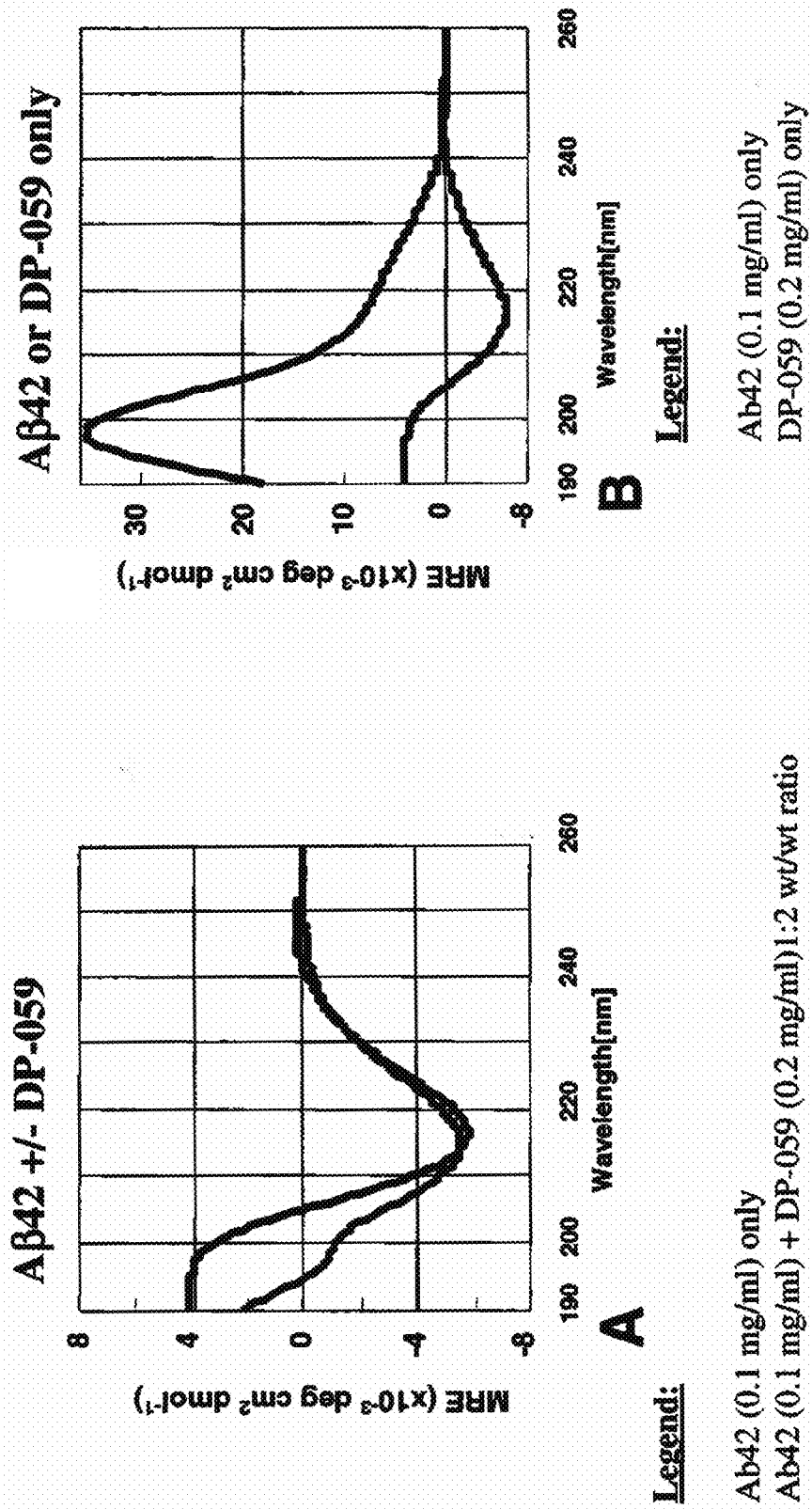
Figure 16:
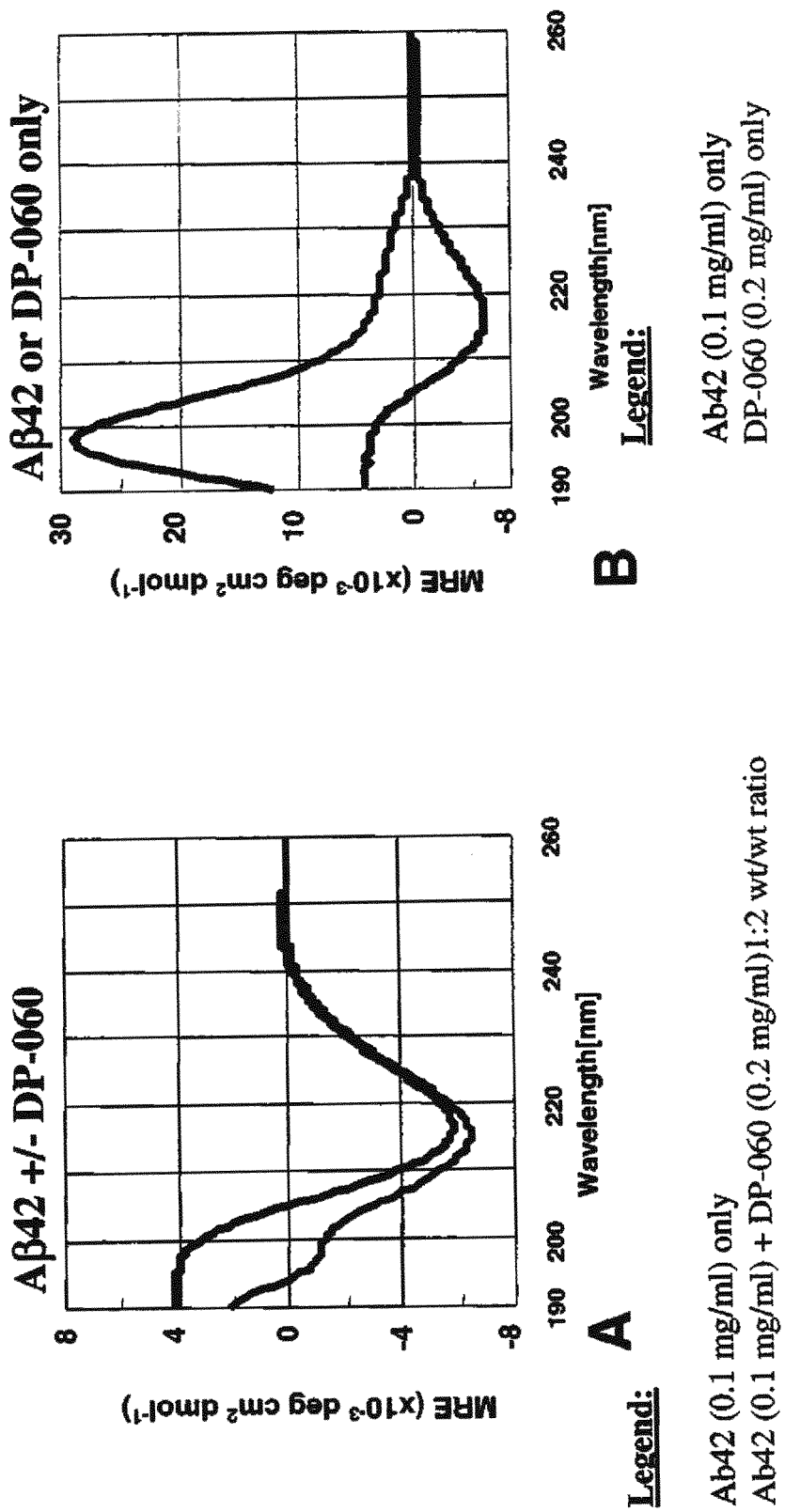
Figure 17:
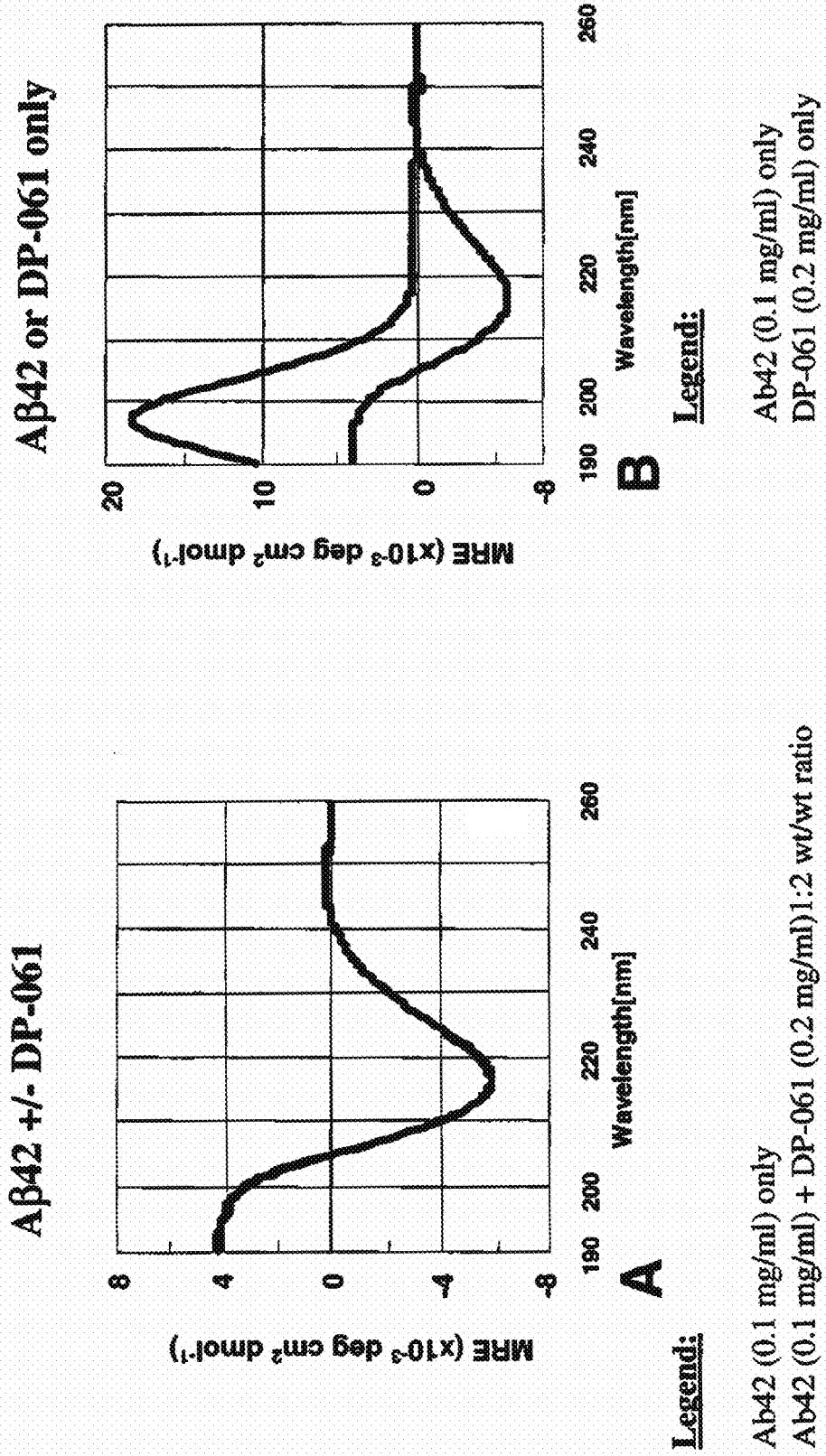
Figure 18:
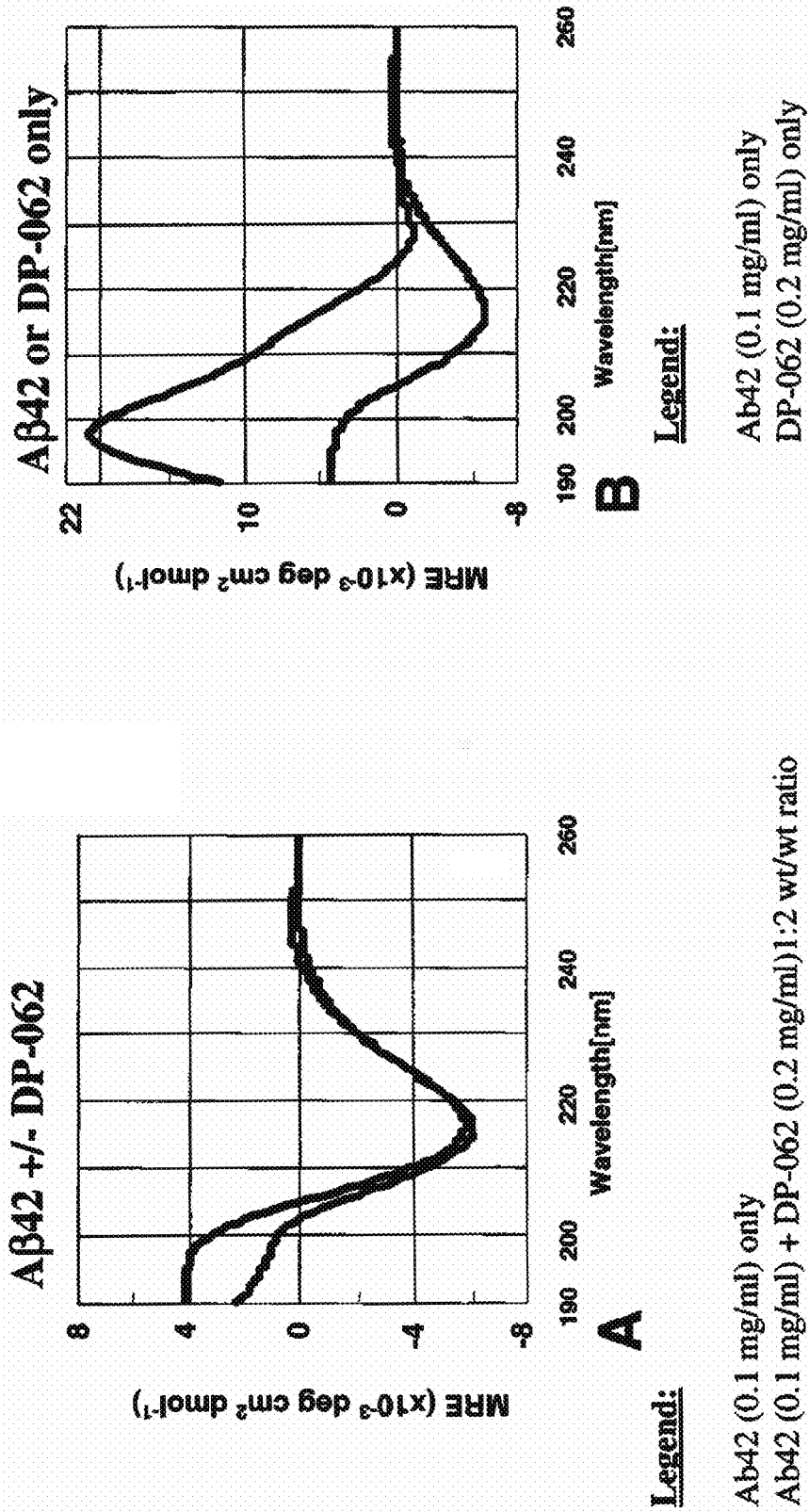
Figure 19:
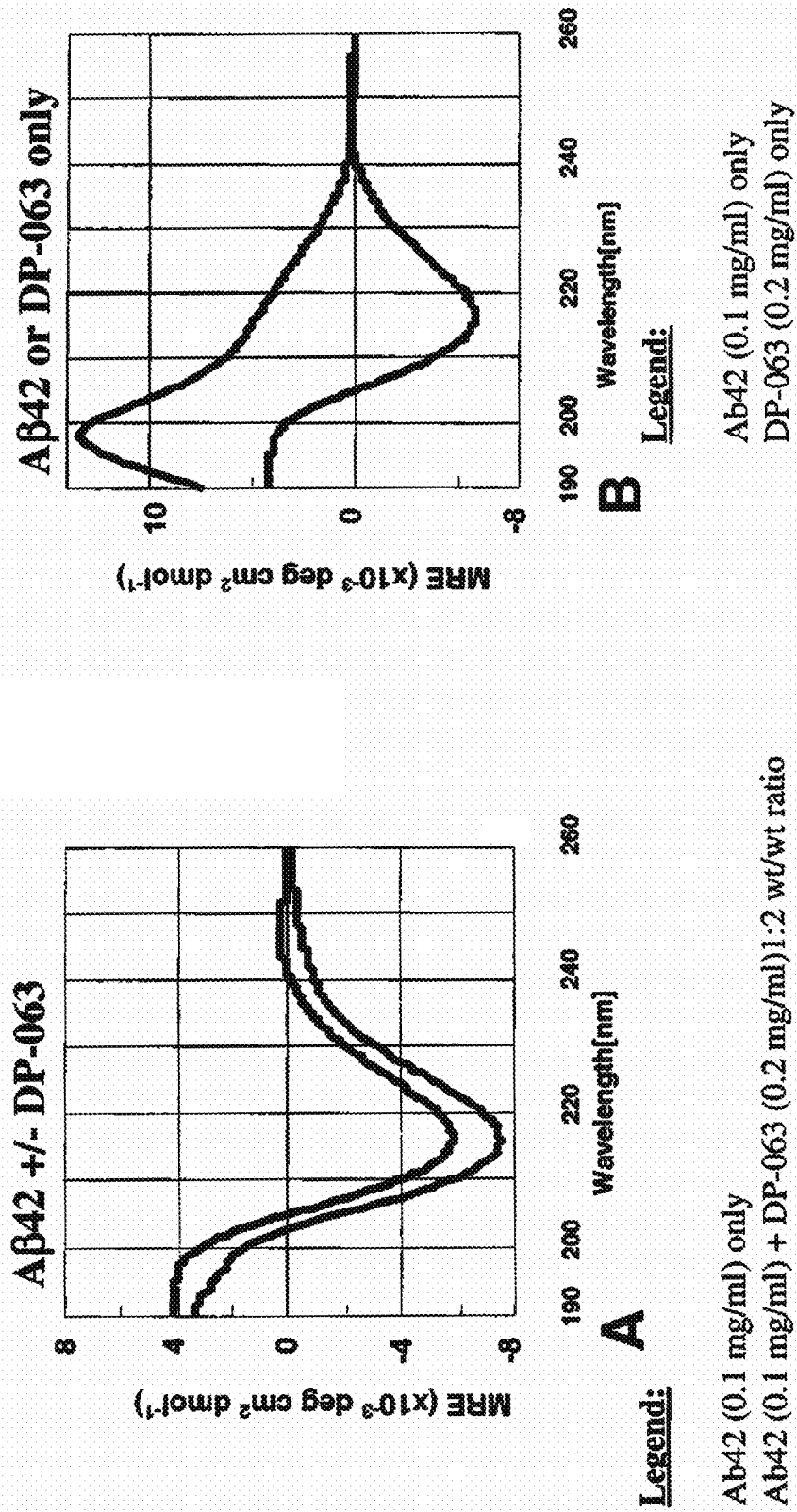
Figure 20:
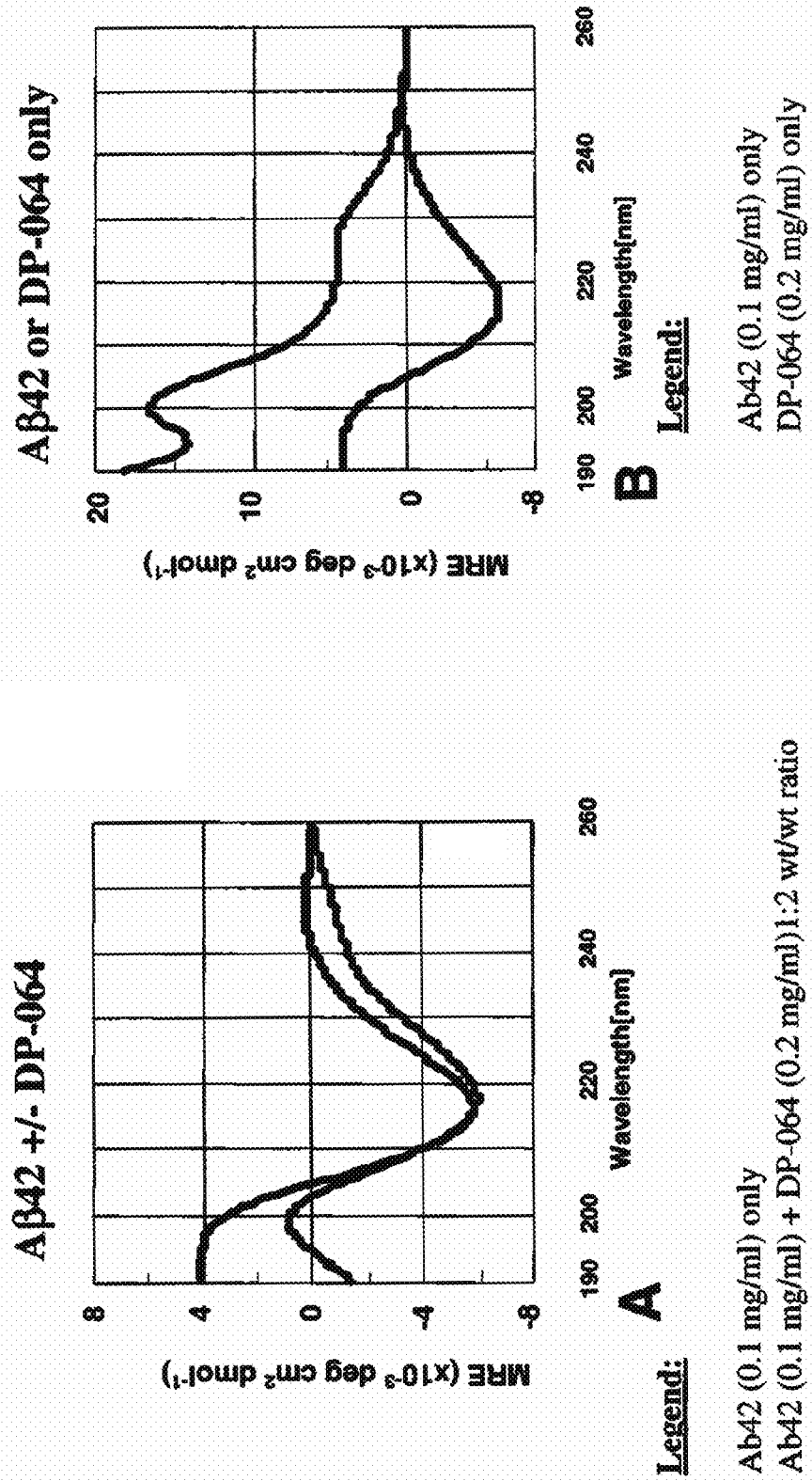
Figure 21:
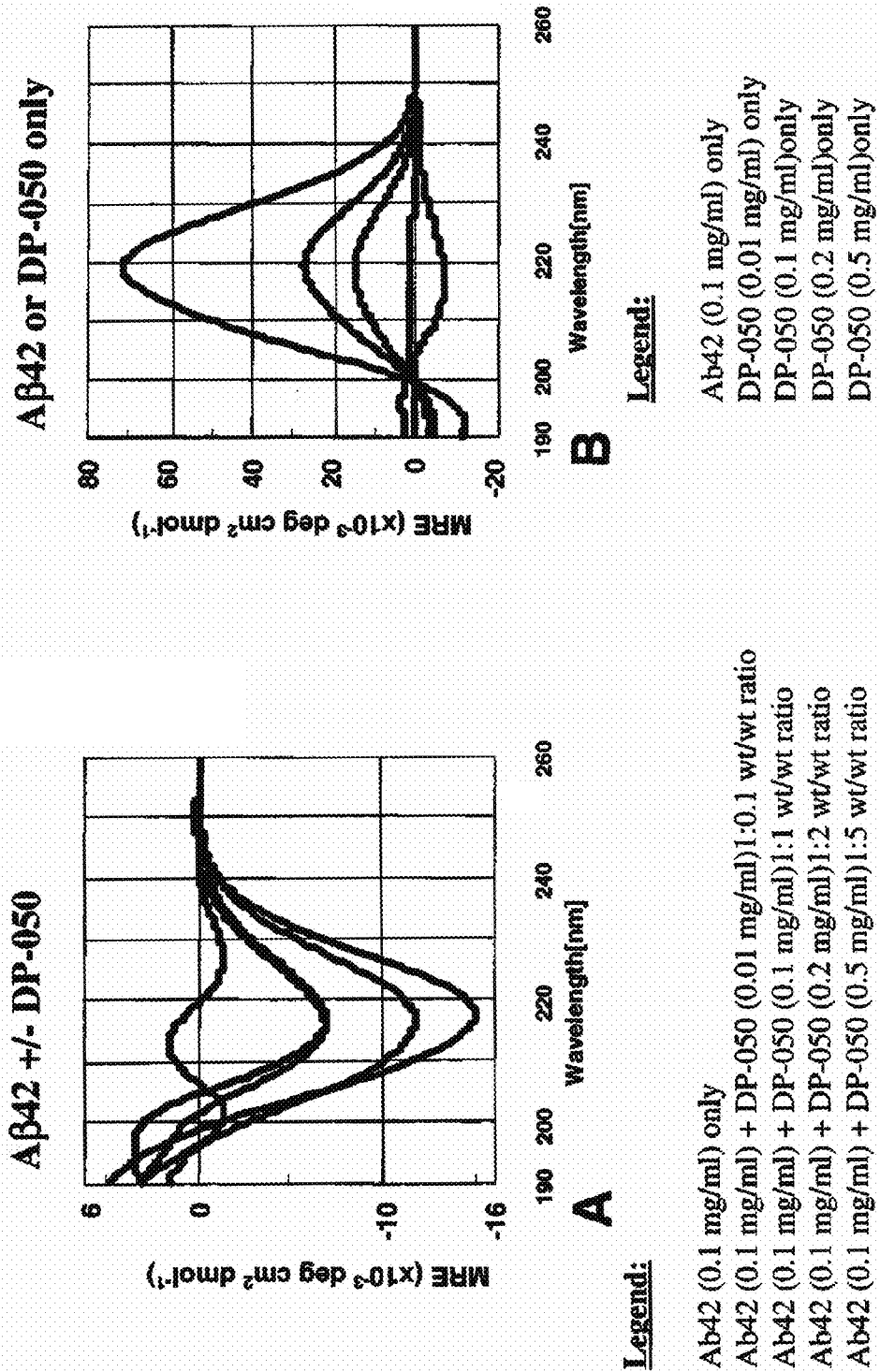
FIGS. 21-30 are CD spectra of Aβ42 plus DP-50, 51, 52, 56-61 and DP-064, respectively, at 1:0.1, 1:1, 1:2, 1:5).
Figure 22:
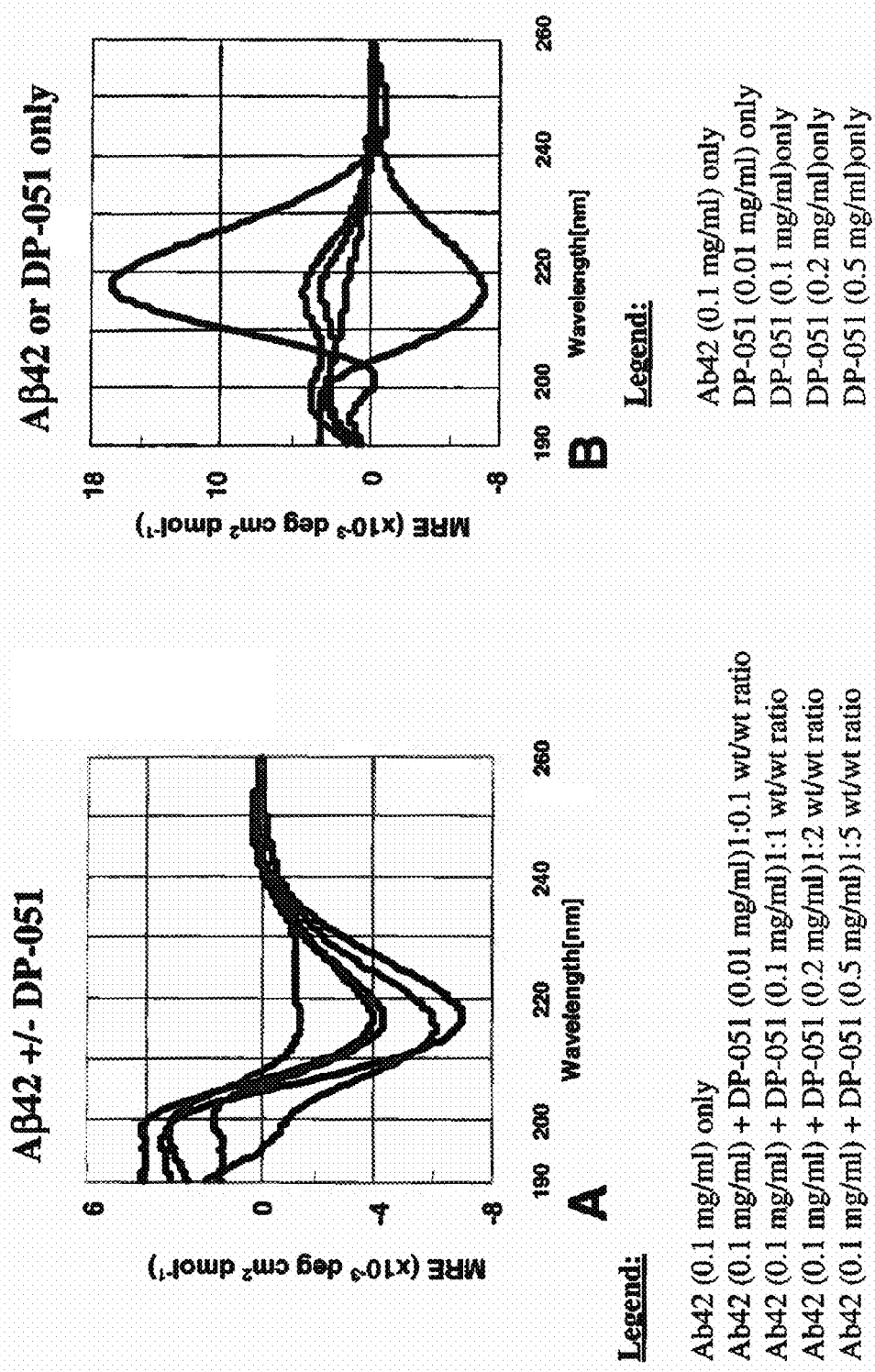
Figure 23:
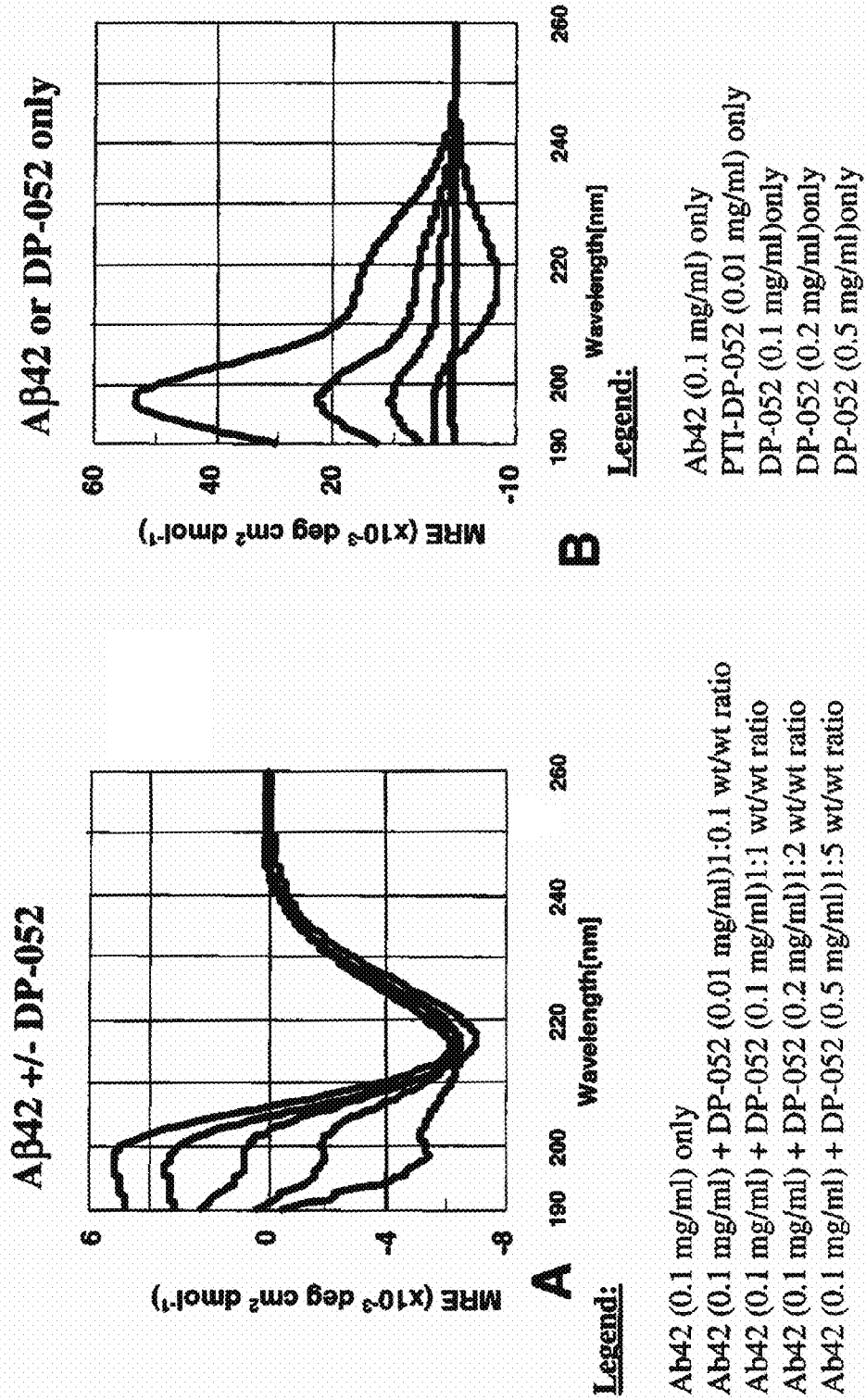
Figure 24:
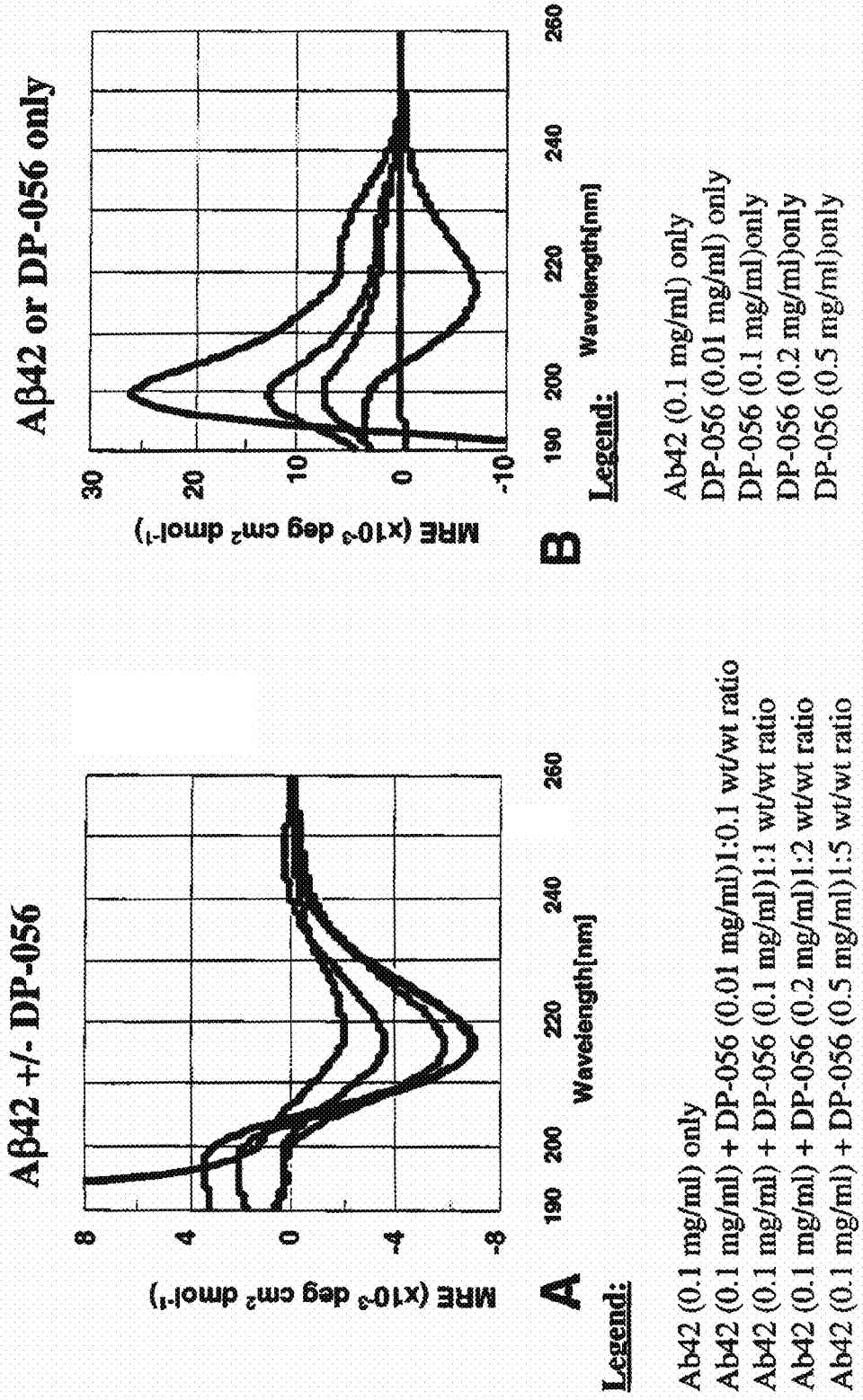
Figure 25:
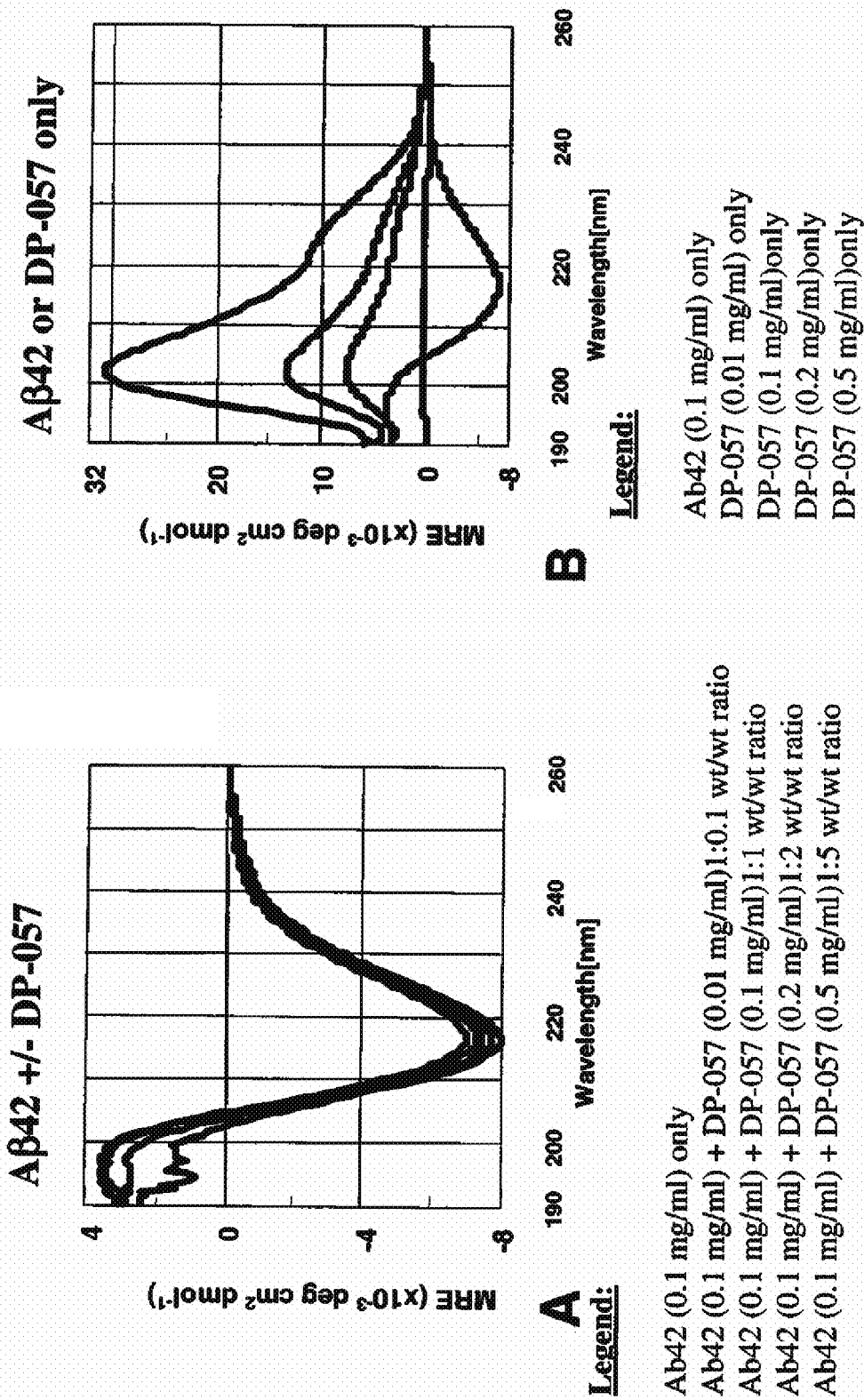
Figure 26:
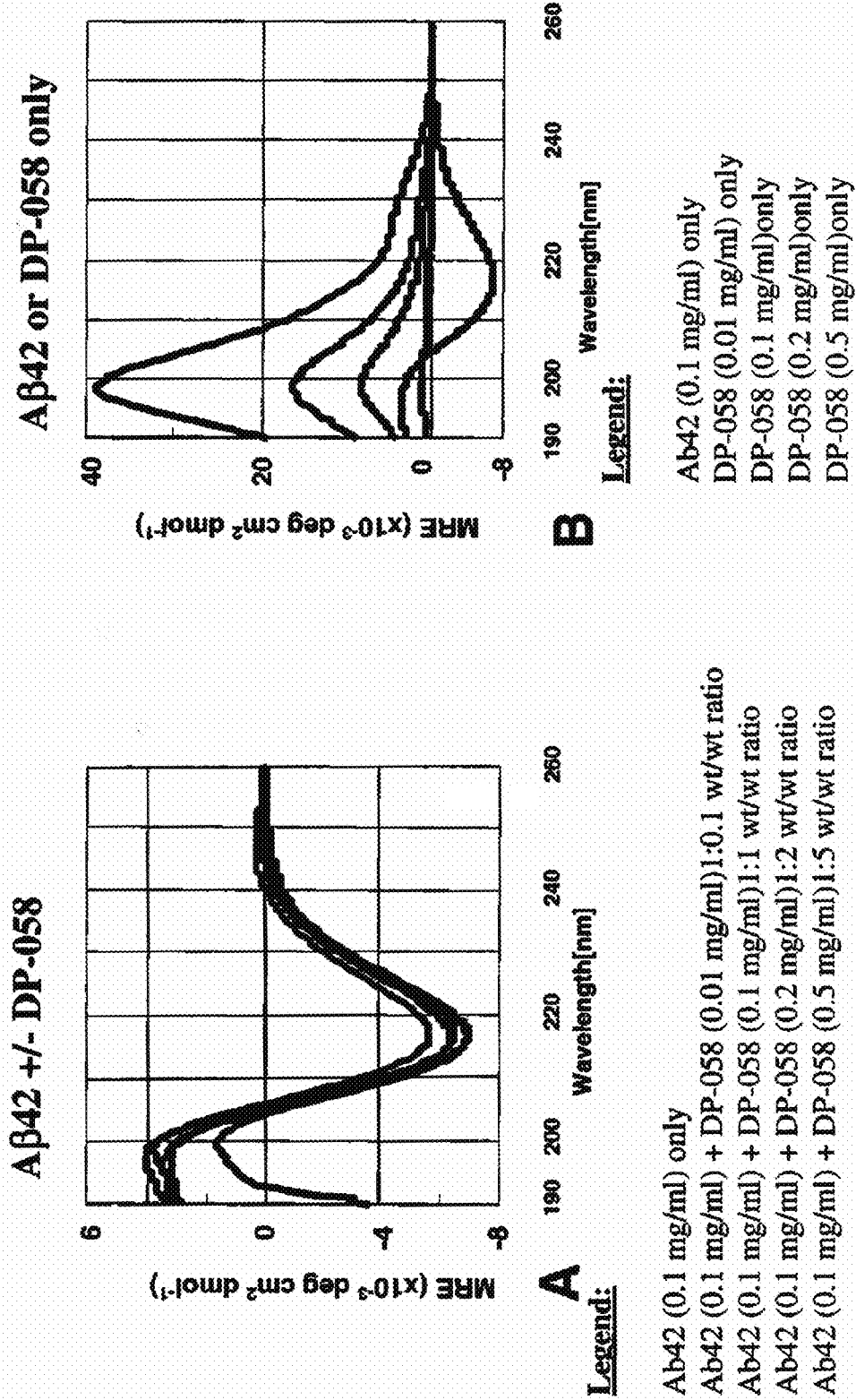
Figure 27:
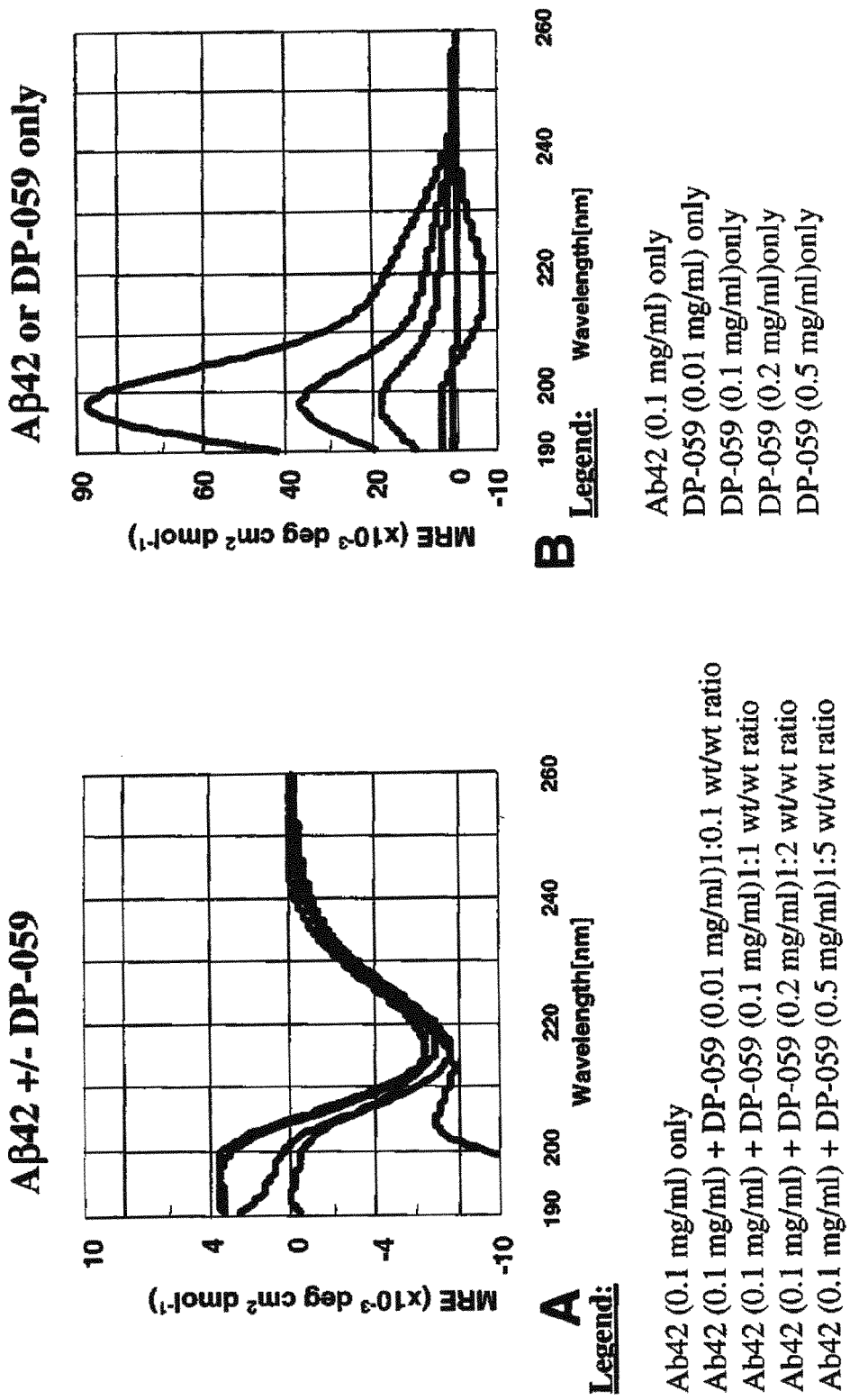
Figure 28:
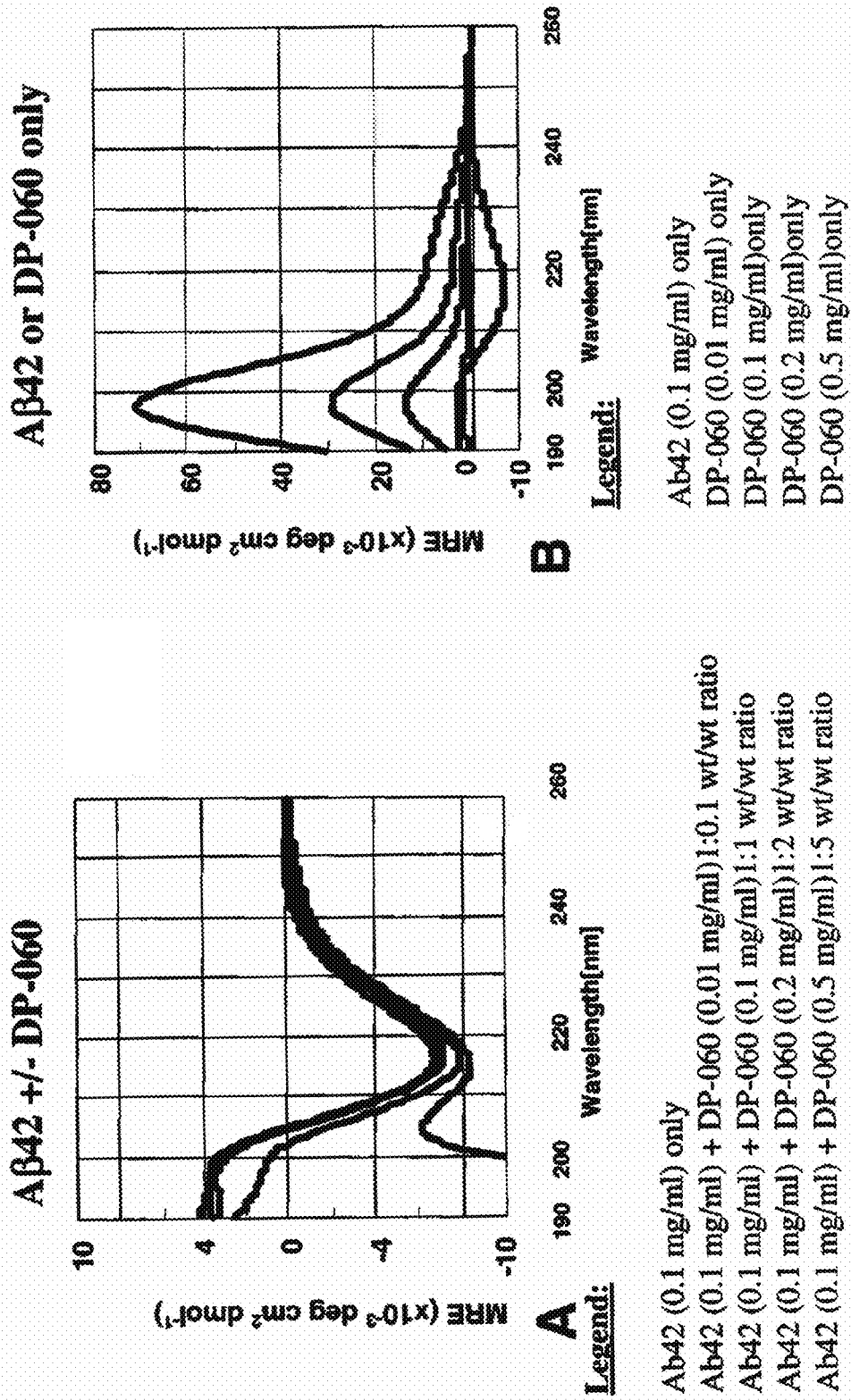
Figure 29:
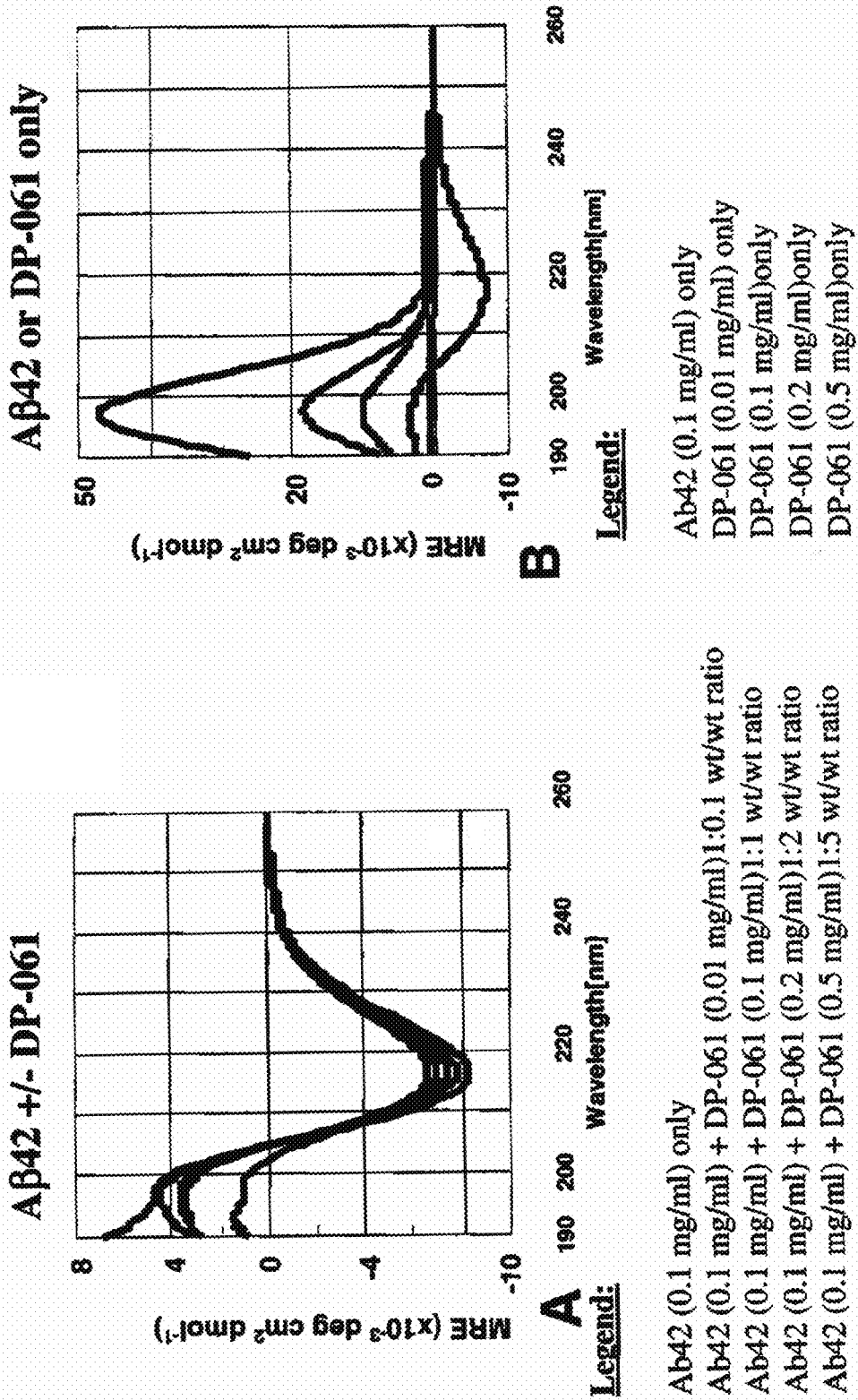
Figure 30:
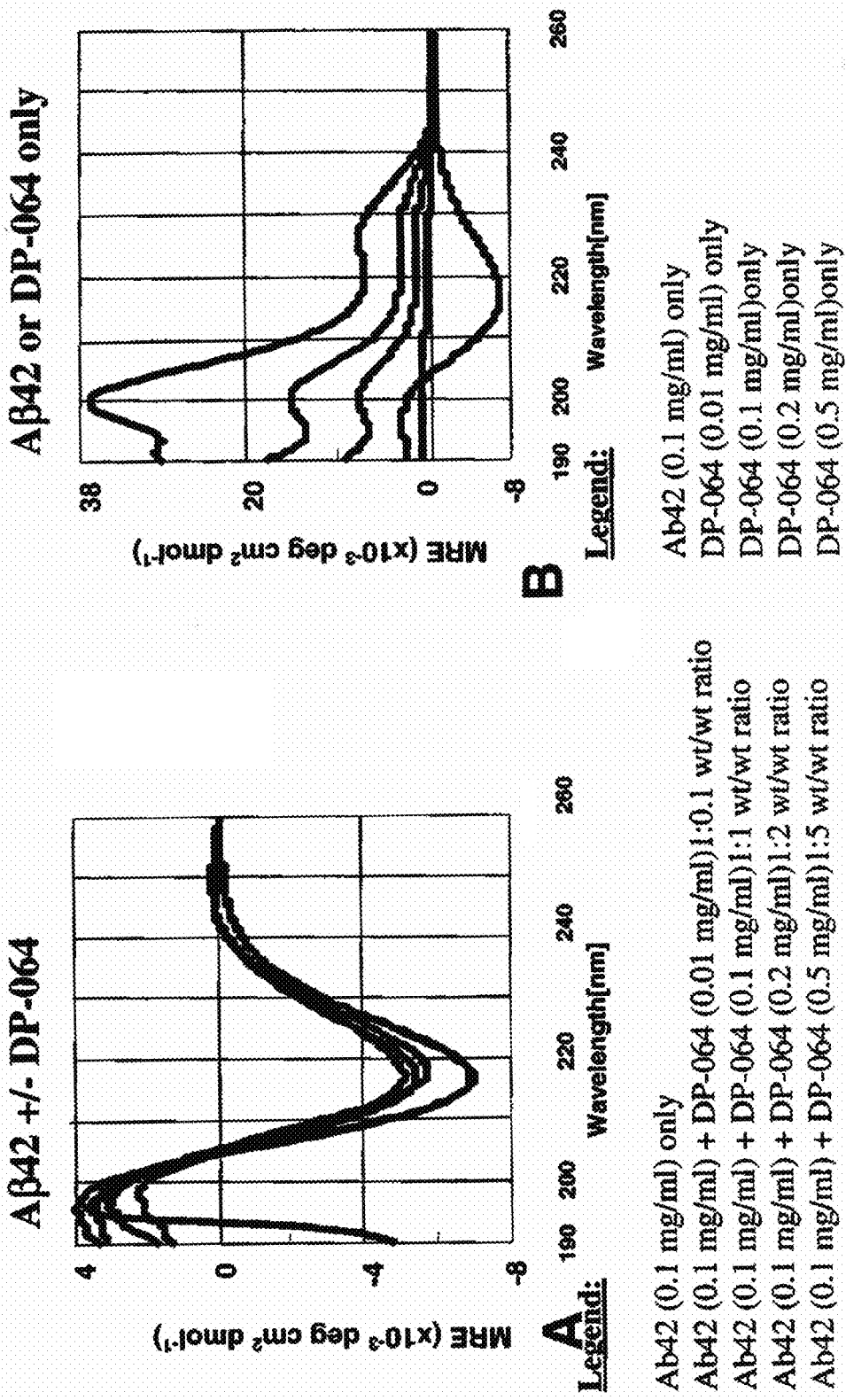

FIG. 5 is a summary of Ab42 binding for peptides LP-025 and DP-026-049.

FIGS. 6-20 are all CD spectra of Ab42 plus DP-50 through DP-064, respectively, at Ab42/peptide wt/wt concentration of 1:2), showing respective inhibition and disruption efficacies.

FIGS. 21-30 are CD spectra of Ab42 plus DP-50, 51, 52, 56-61 and DP-064, respectively, at 1:0.1, 1:1, 1:2, 1:5).

Figure 31:
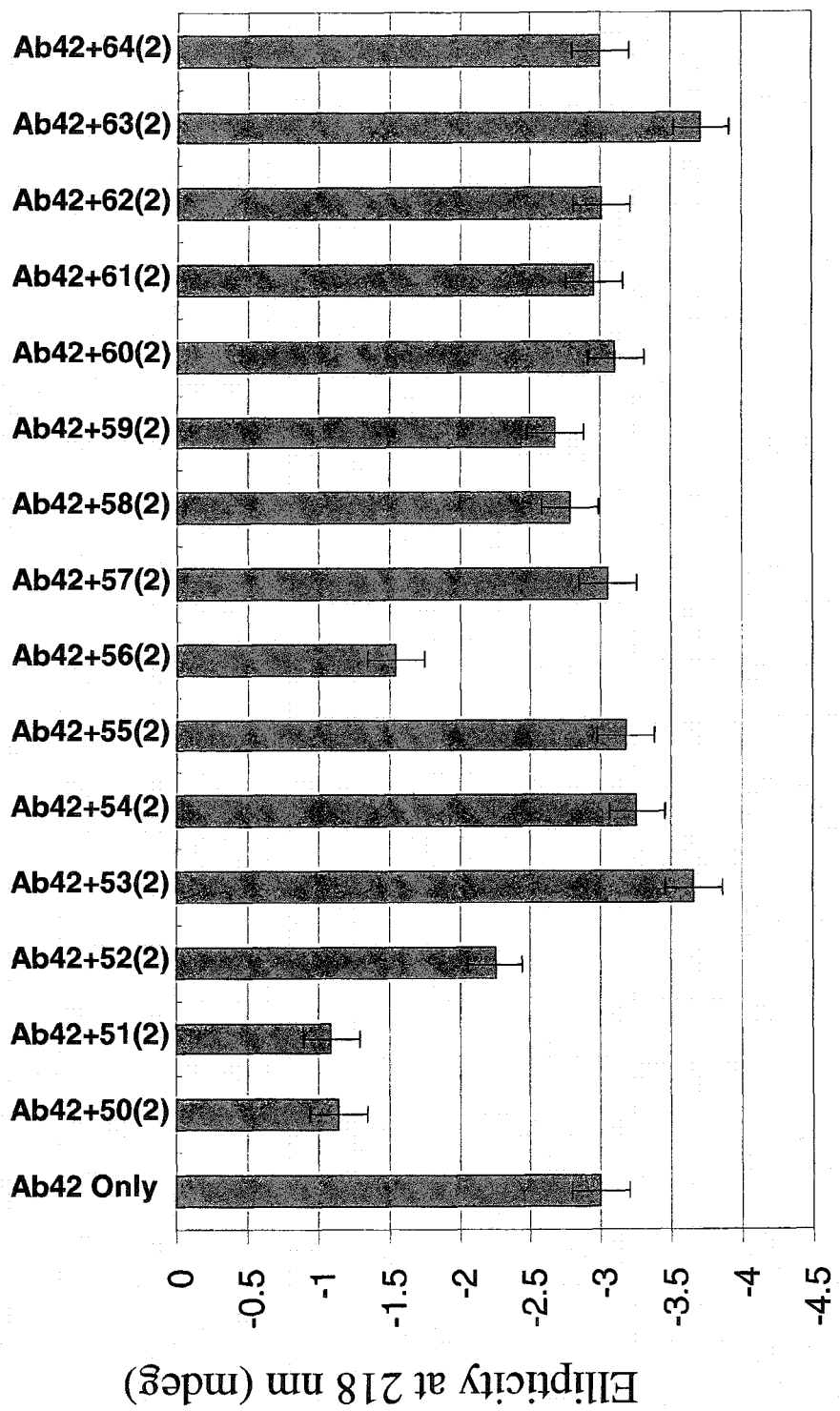
FIG. 31 is a summary of CD spectroscopy results for DP-50 through DP-064 at 1:2).
Figure 32:
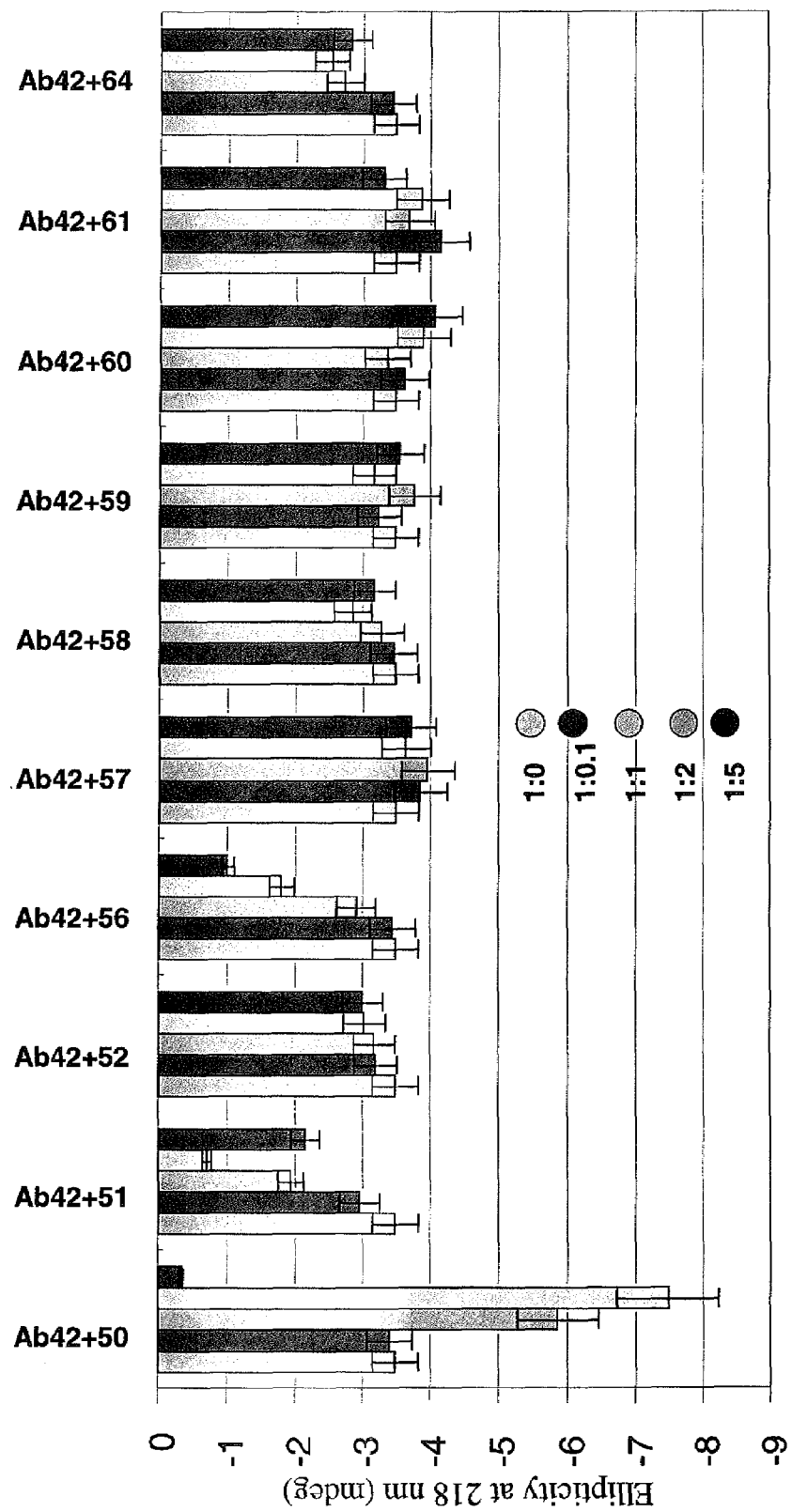
FIG. 32 is a summary of CD spectroscopy results for DP-50, 51, 52, 56-61 and DP-064 at 1:0.1, 1:1, 1:2, 1:5).

FIG. 31 is a summary of CD spectroscopy results for DP-50 through DP-064 at 1:2), while FIG. 32 is a summary of CD spectroscopy results for DP-50, 51, 52, 56-61 and DP-064 at 1:0.1, 1:1, 1:2, 1:5).

Figure 33:
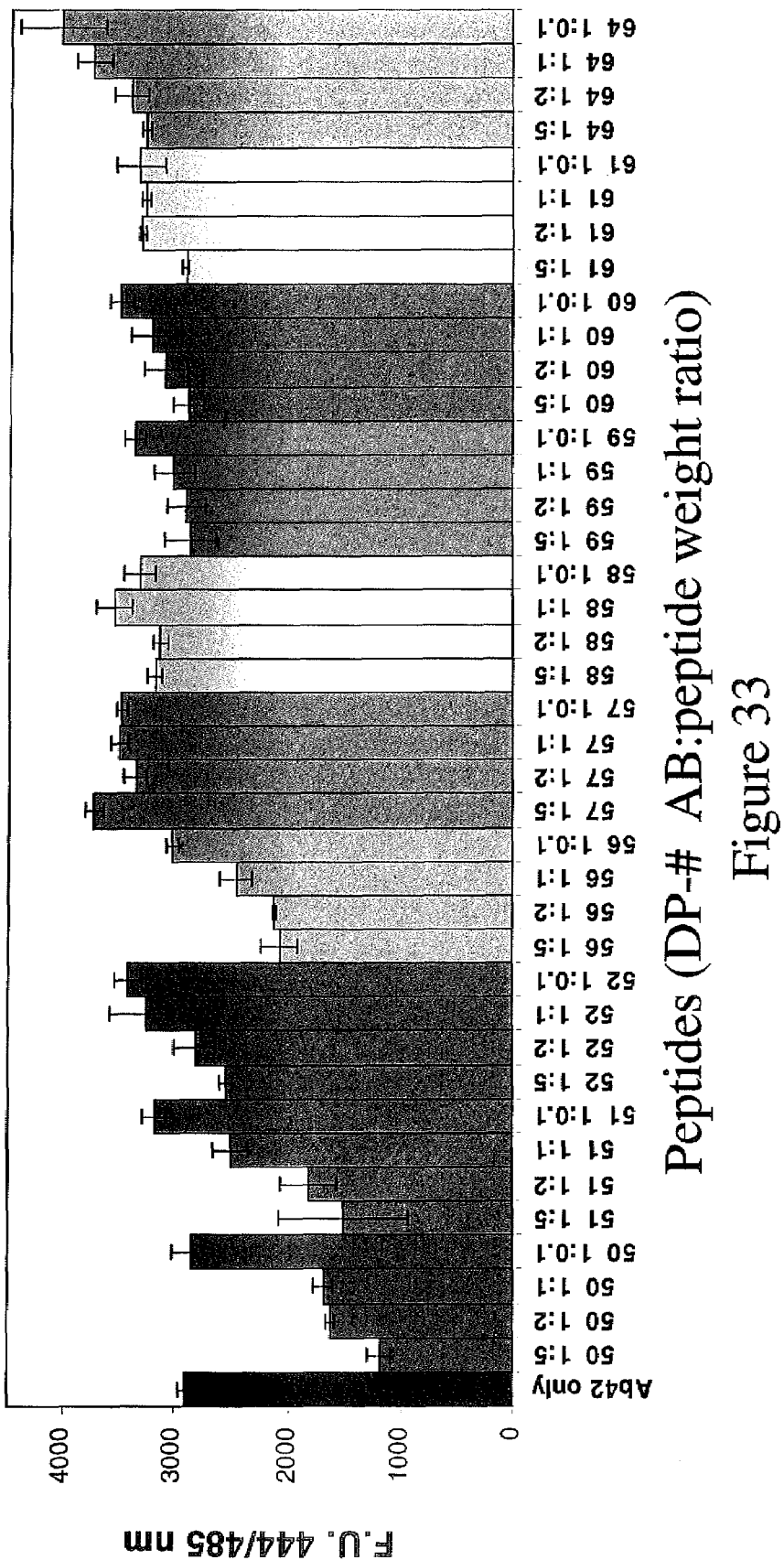
FIG. 33 is a Thio T summary of Aβ42+/−DP50-64 at 1:0.1, 1:1, 1:2, 1:5).
Figure 34:
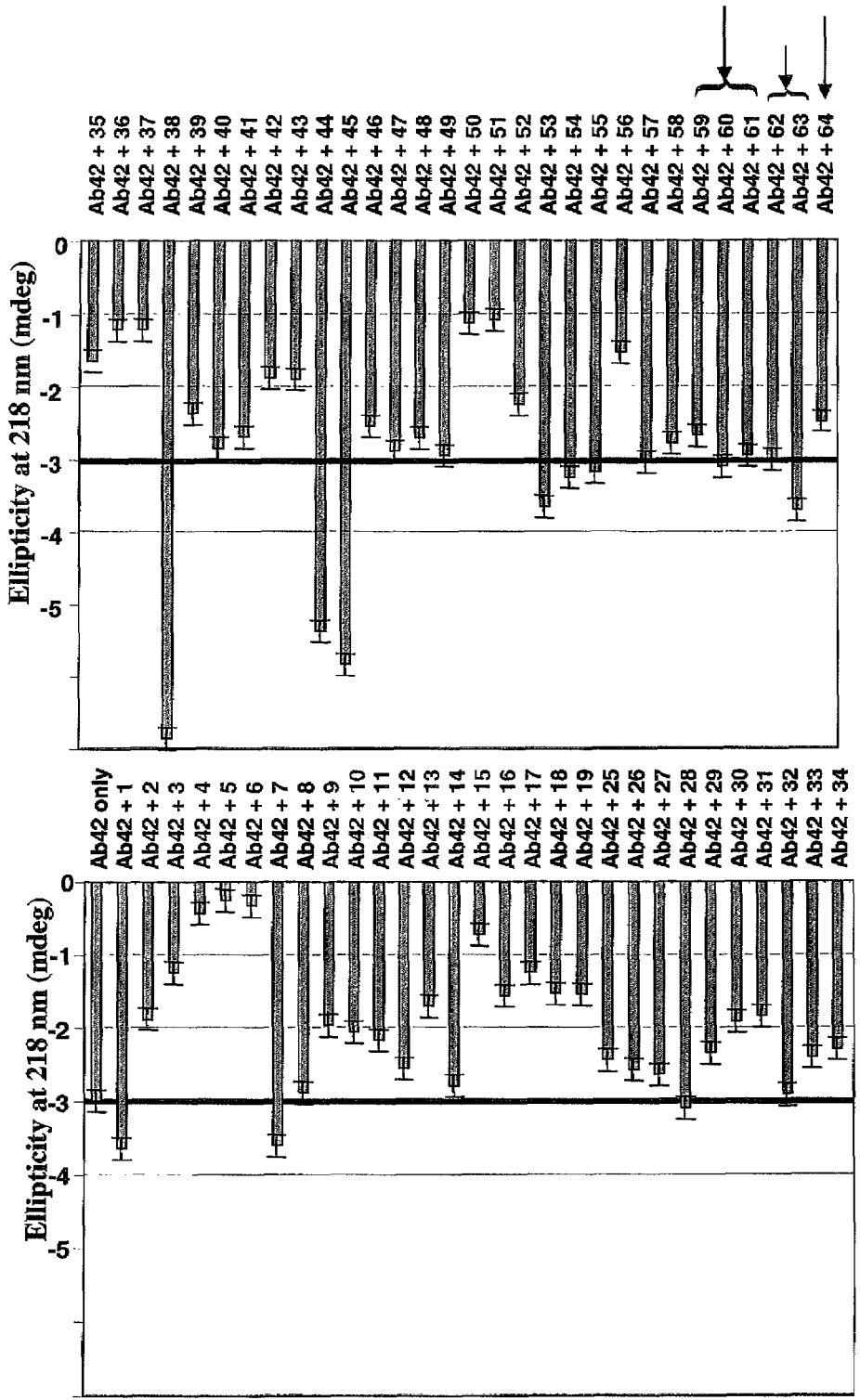
FIG. 34 is a CD summary from DP-01 to DP-064 1:2).
Figure 35:
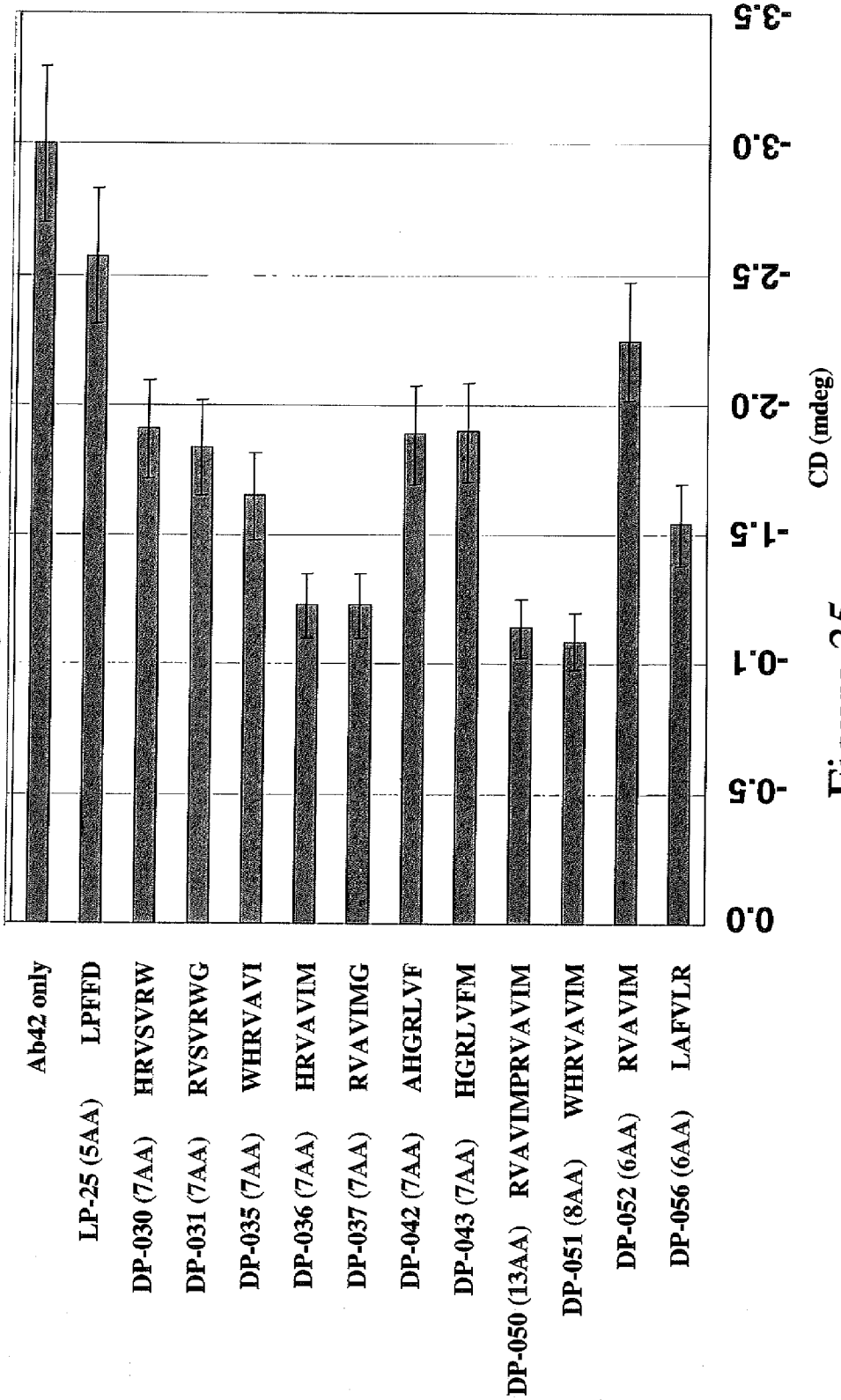
FIG. 35 is a CD summary of selected 11 peptides from DP1-64 compared to IAb5. LP-025) 1:2).
Figure 36:
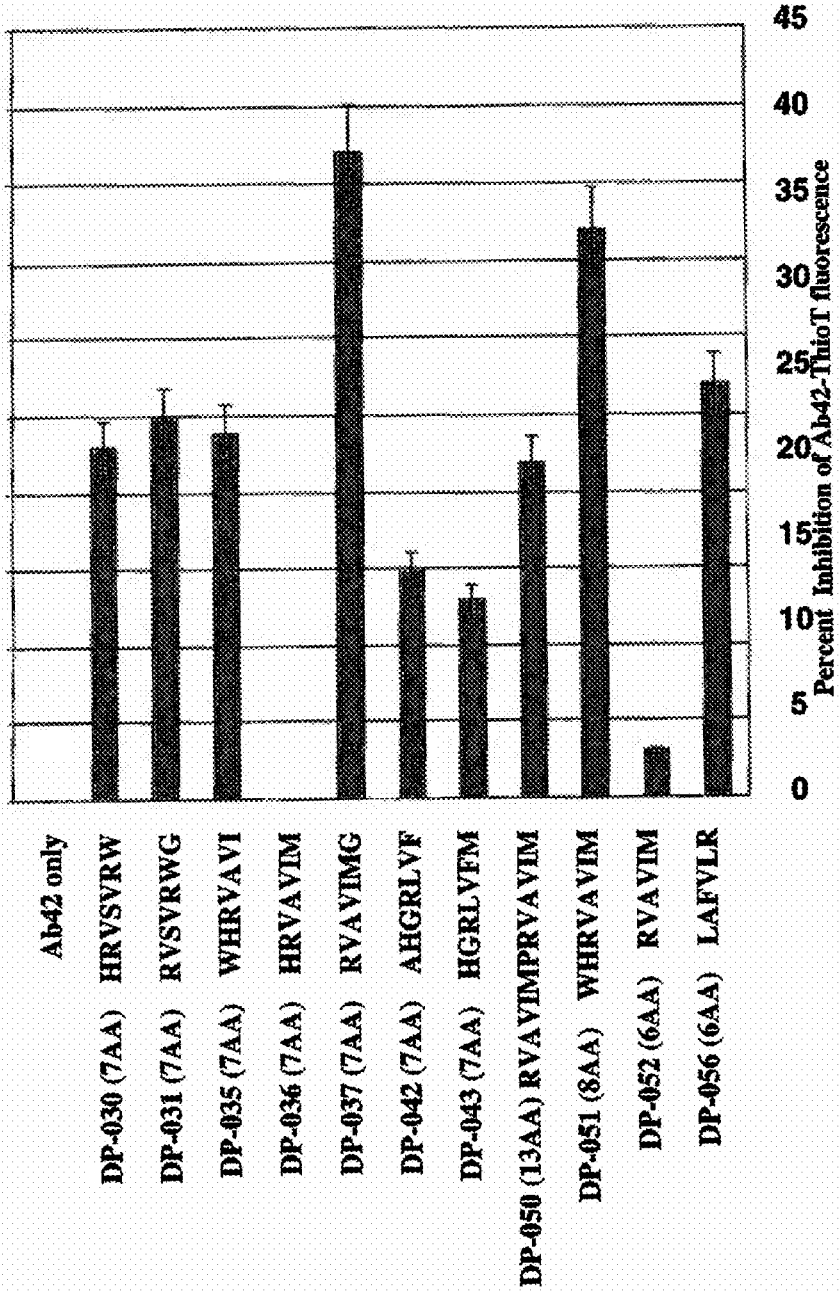
FIG. 36 is a ThioT summary of selected 11 peptides from DP1-64 1:2).
Figure 37:
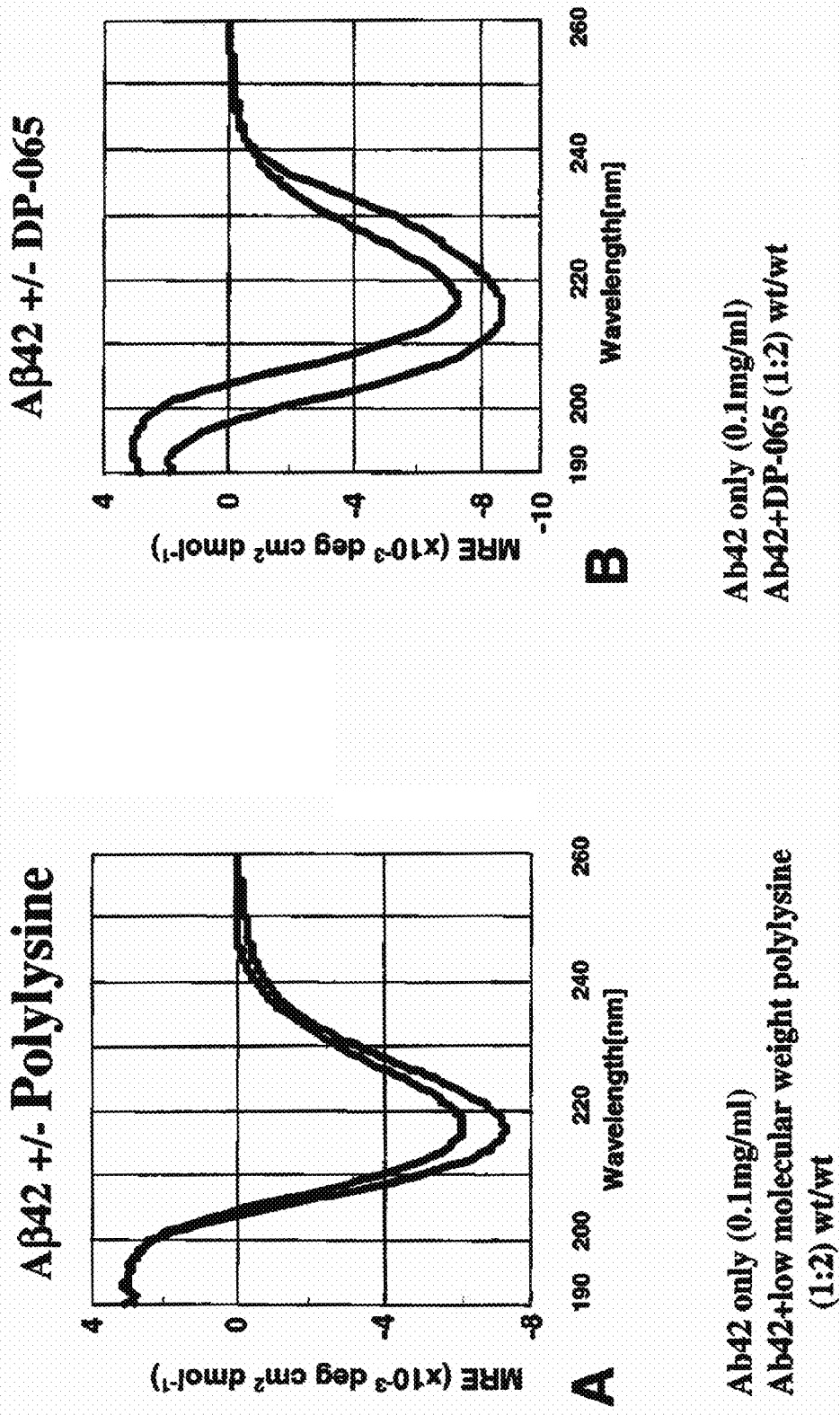
FIGS. 37-41 are CD spectra of Ab42 plus polylysine and DP-065 through DP-072 at 1:2).
Figure 38:
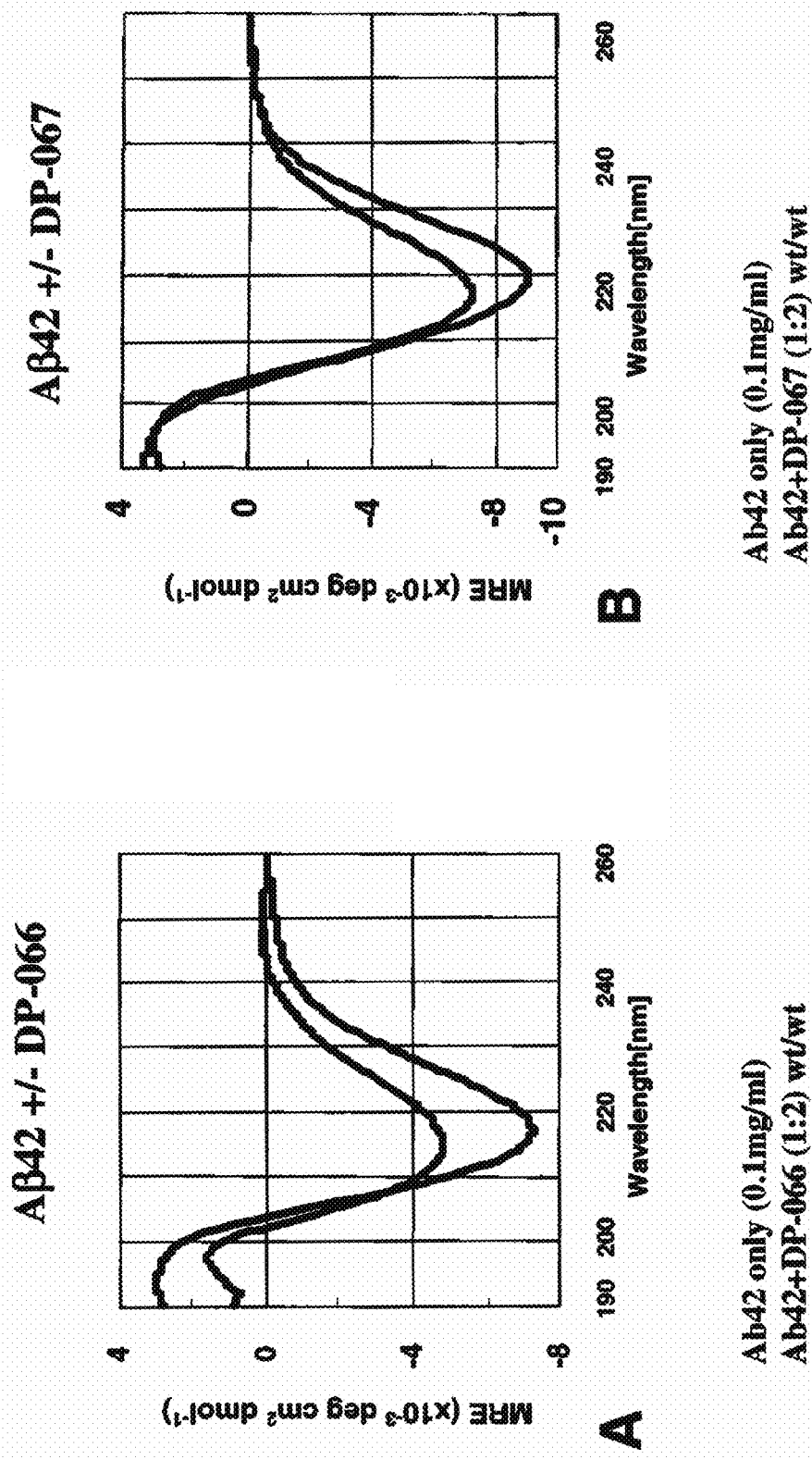
Figure 39:
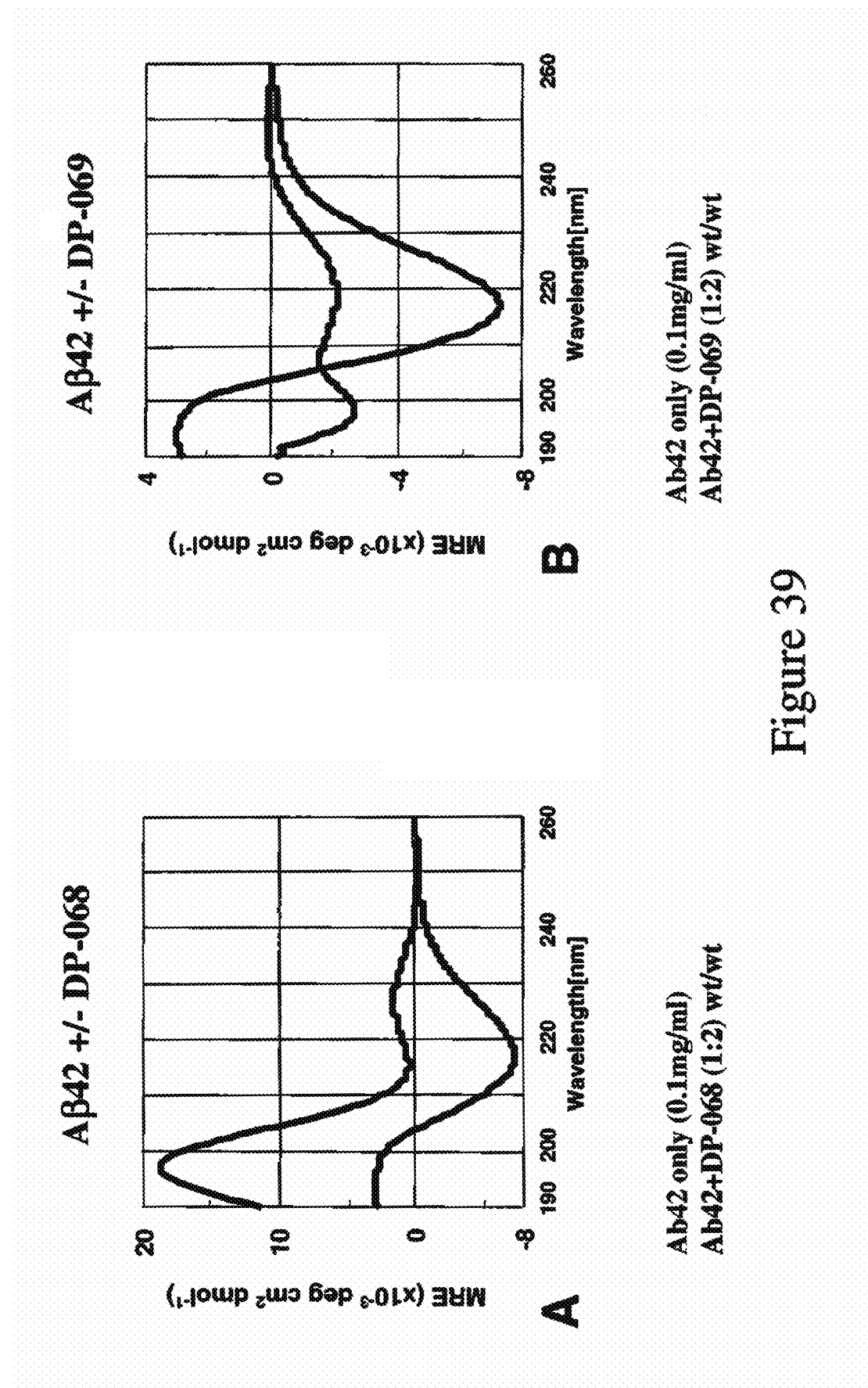
Figure 40:
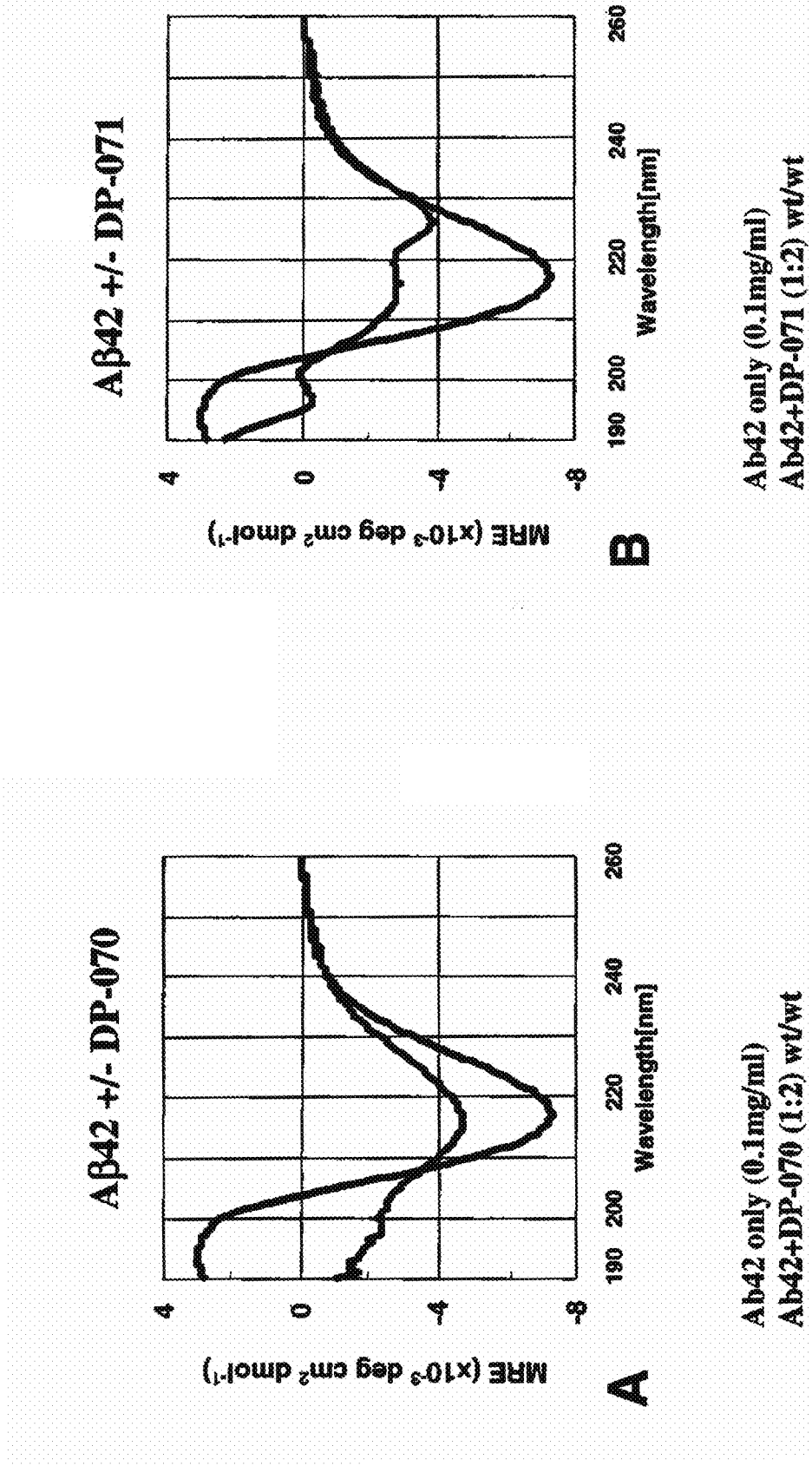
Figure 41:
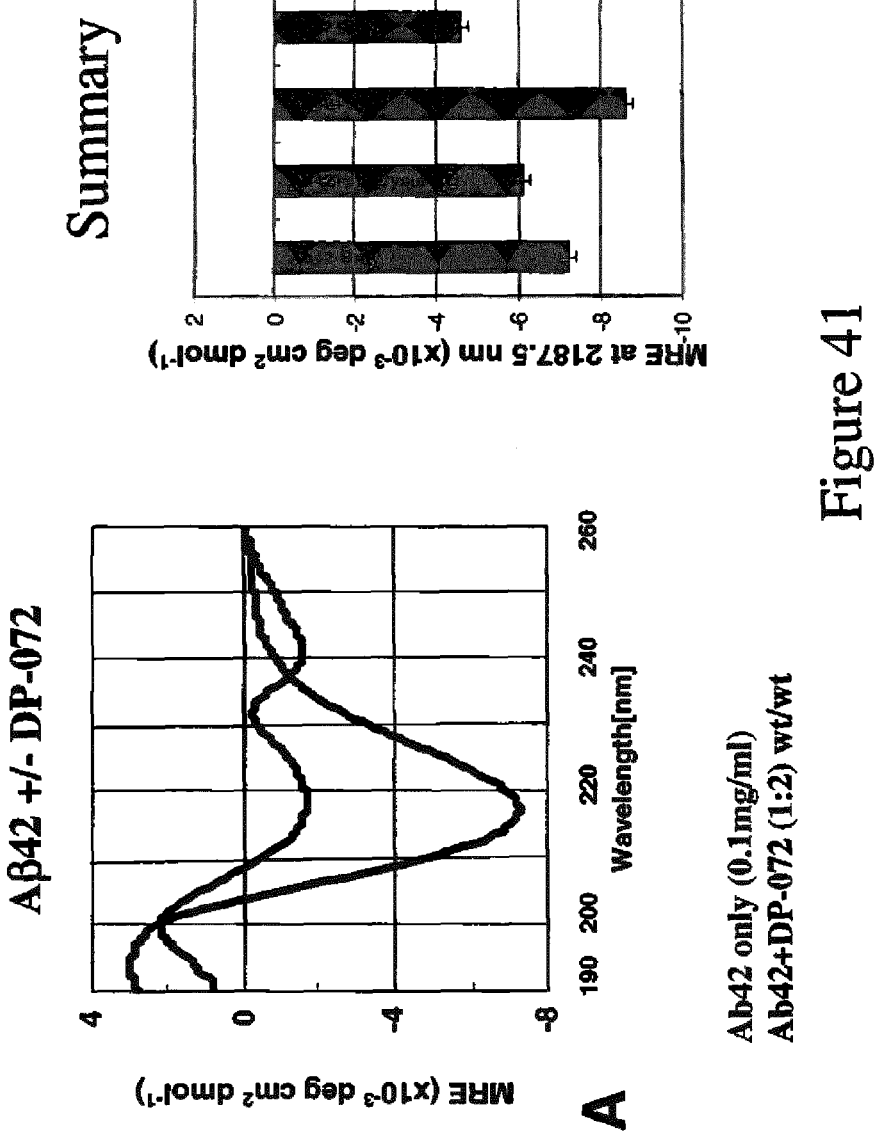
Figure 42:
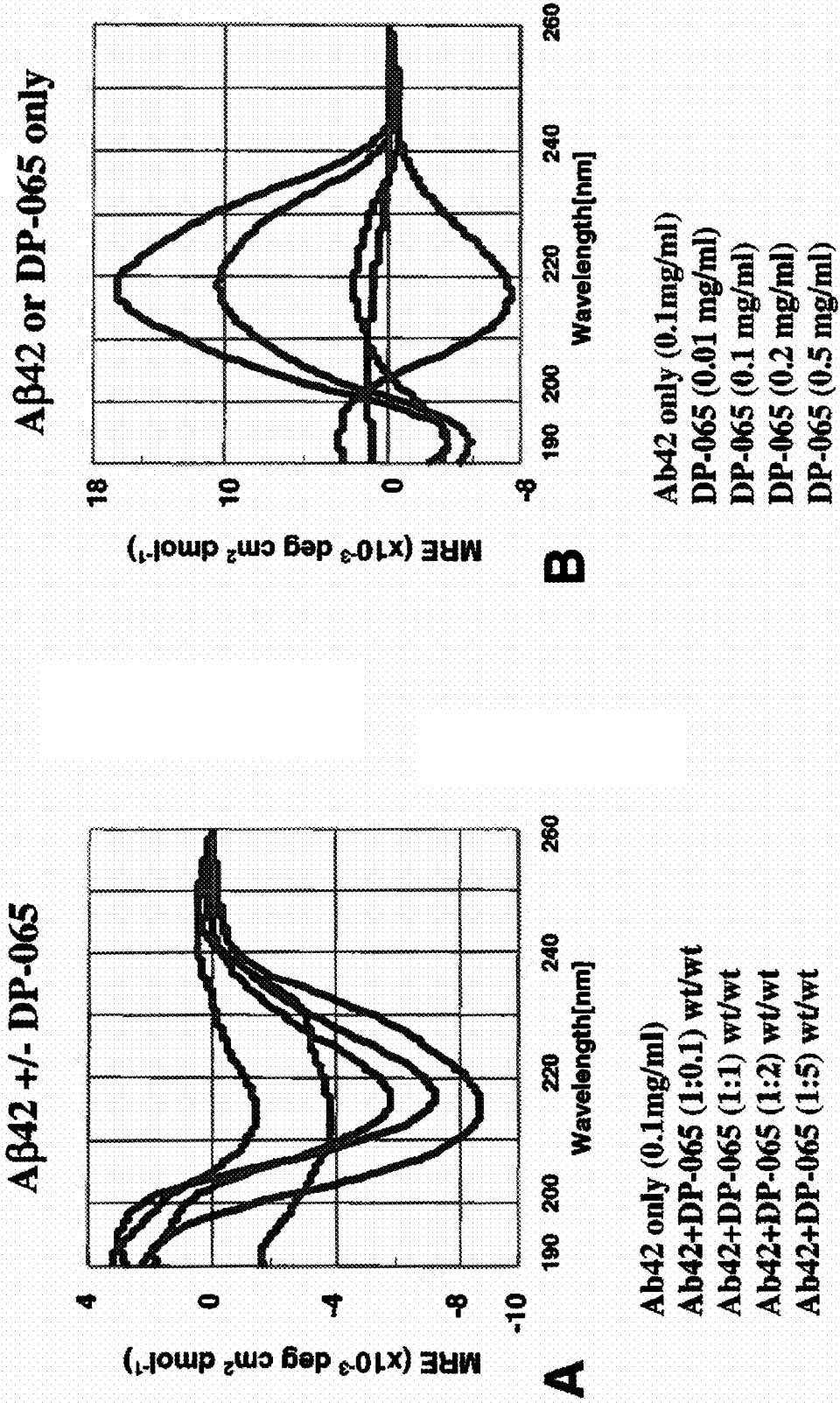
FIGS. 42-49 are CD spectra of Ab42 plus DP-065 through DP-072 at 1:0.1, 1:1, 1:2, 1:5).
Figure 43:
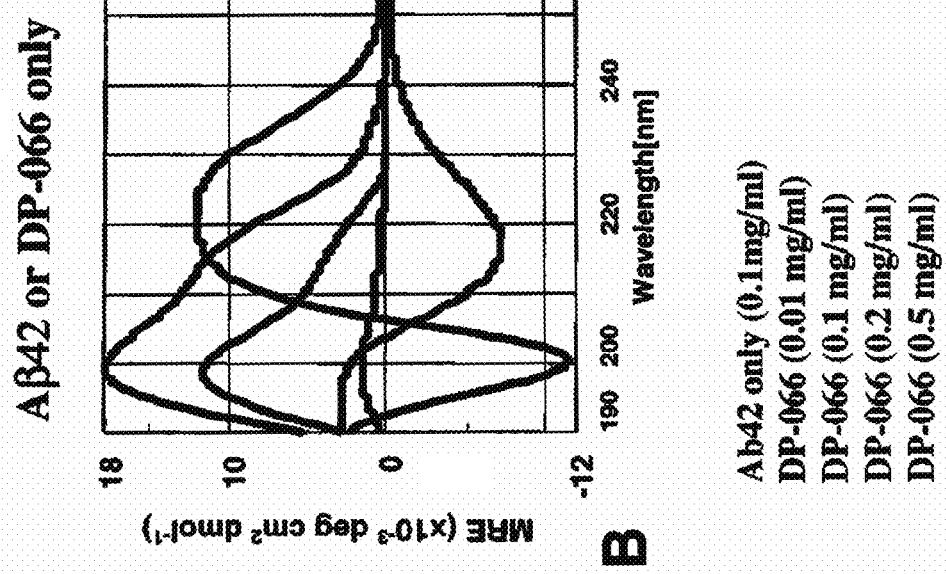
Figure 43:
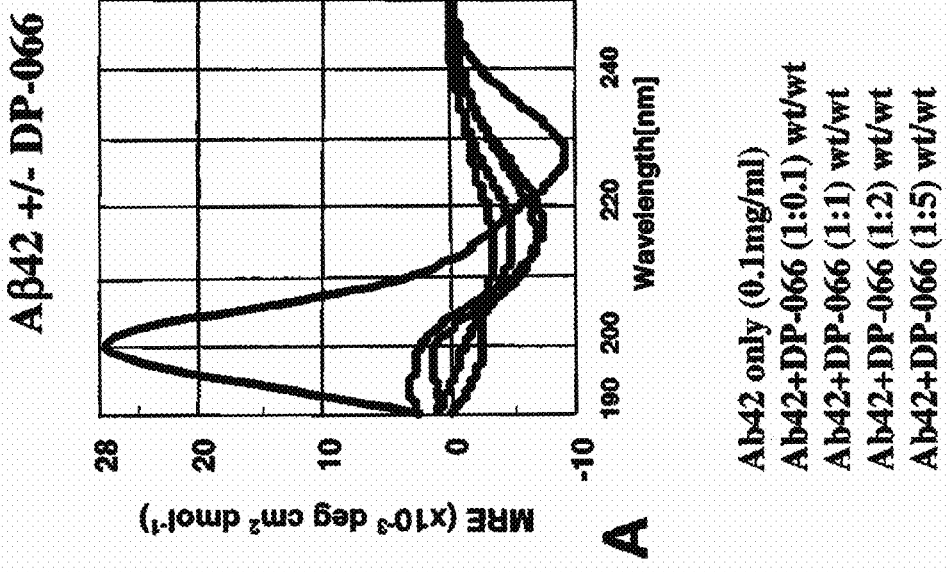
Figure 44:
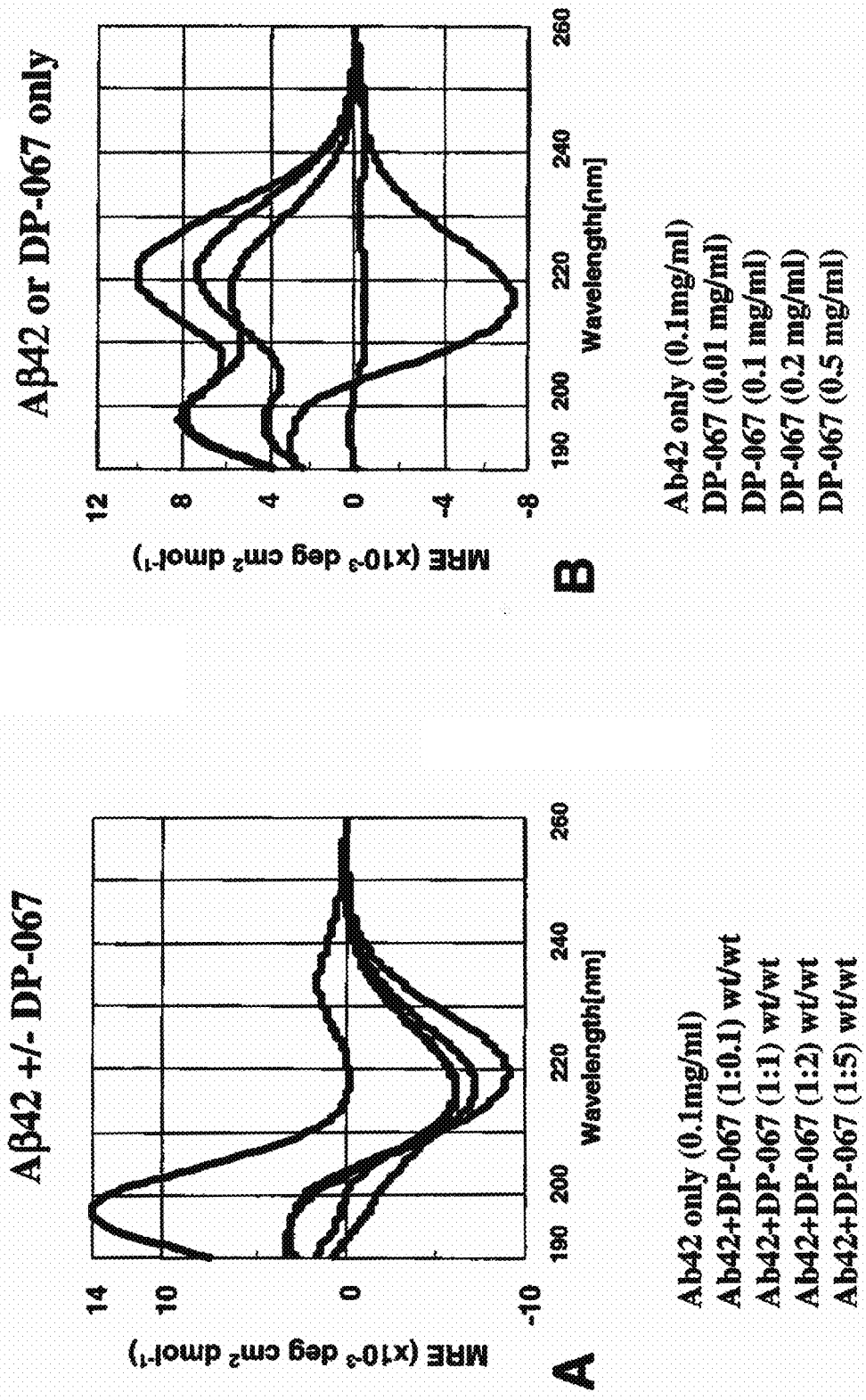
Figure 45:
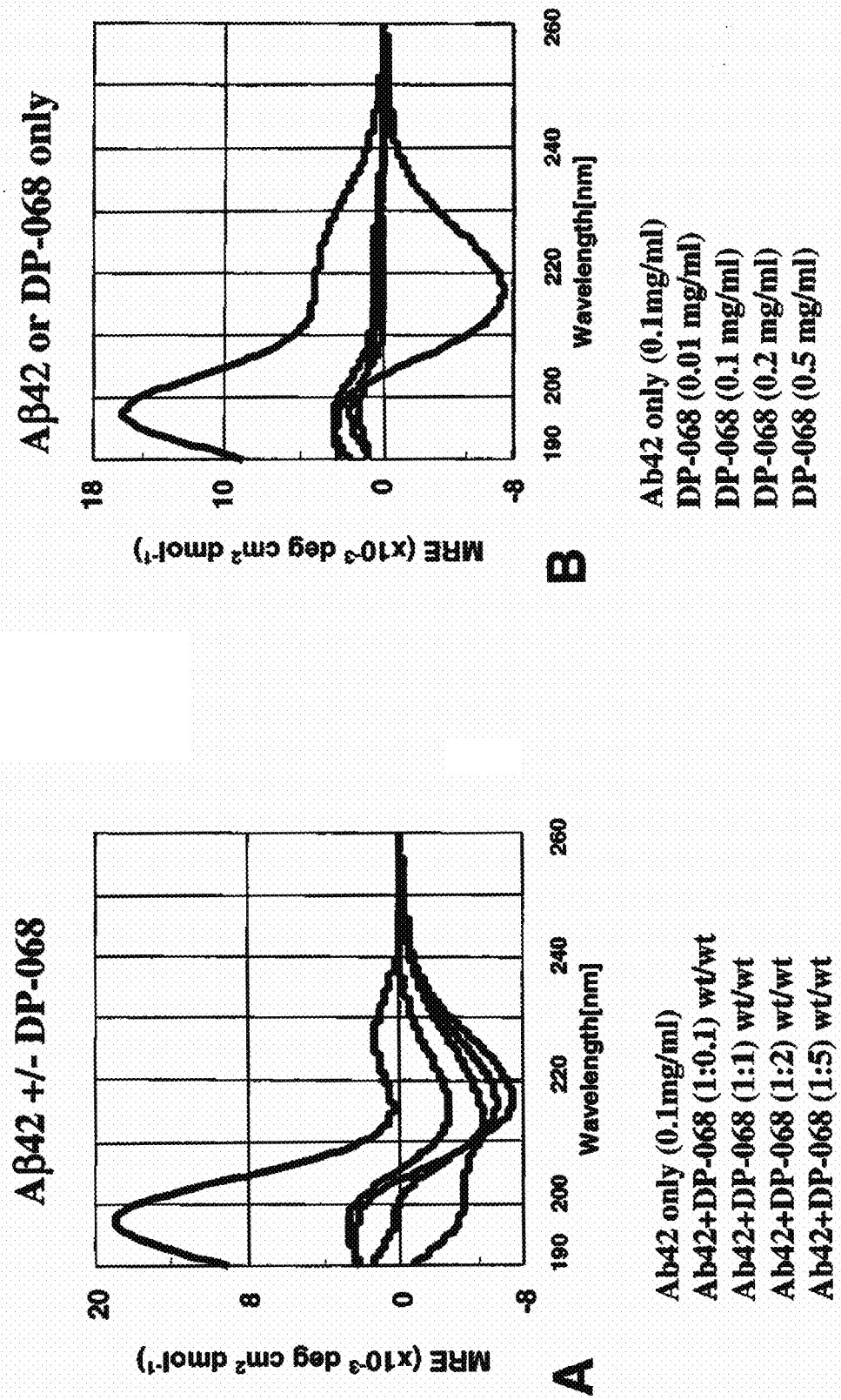
Figure 46:
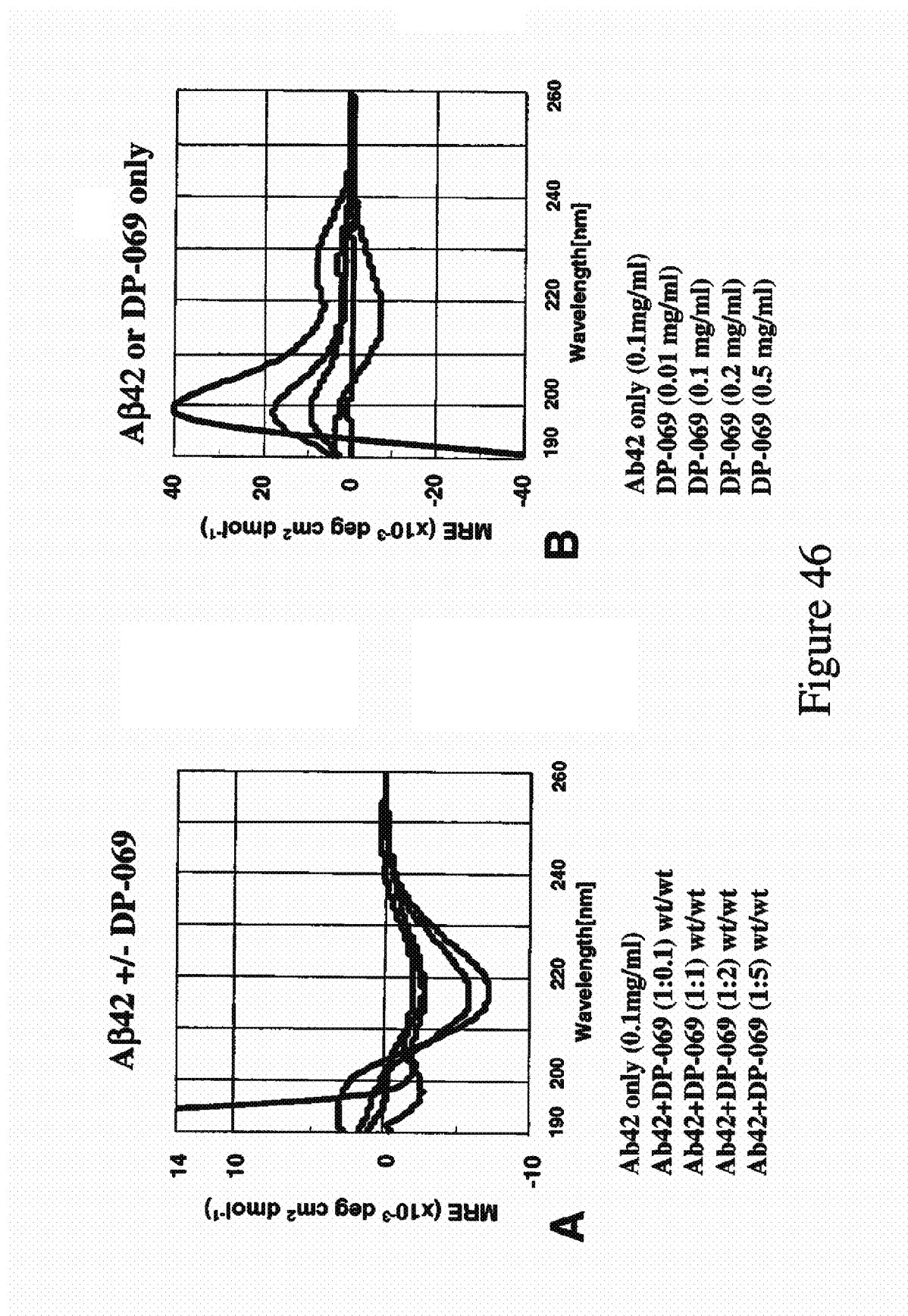
Figure 47:
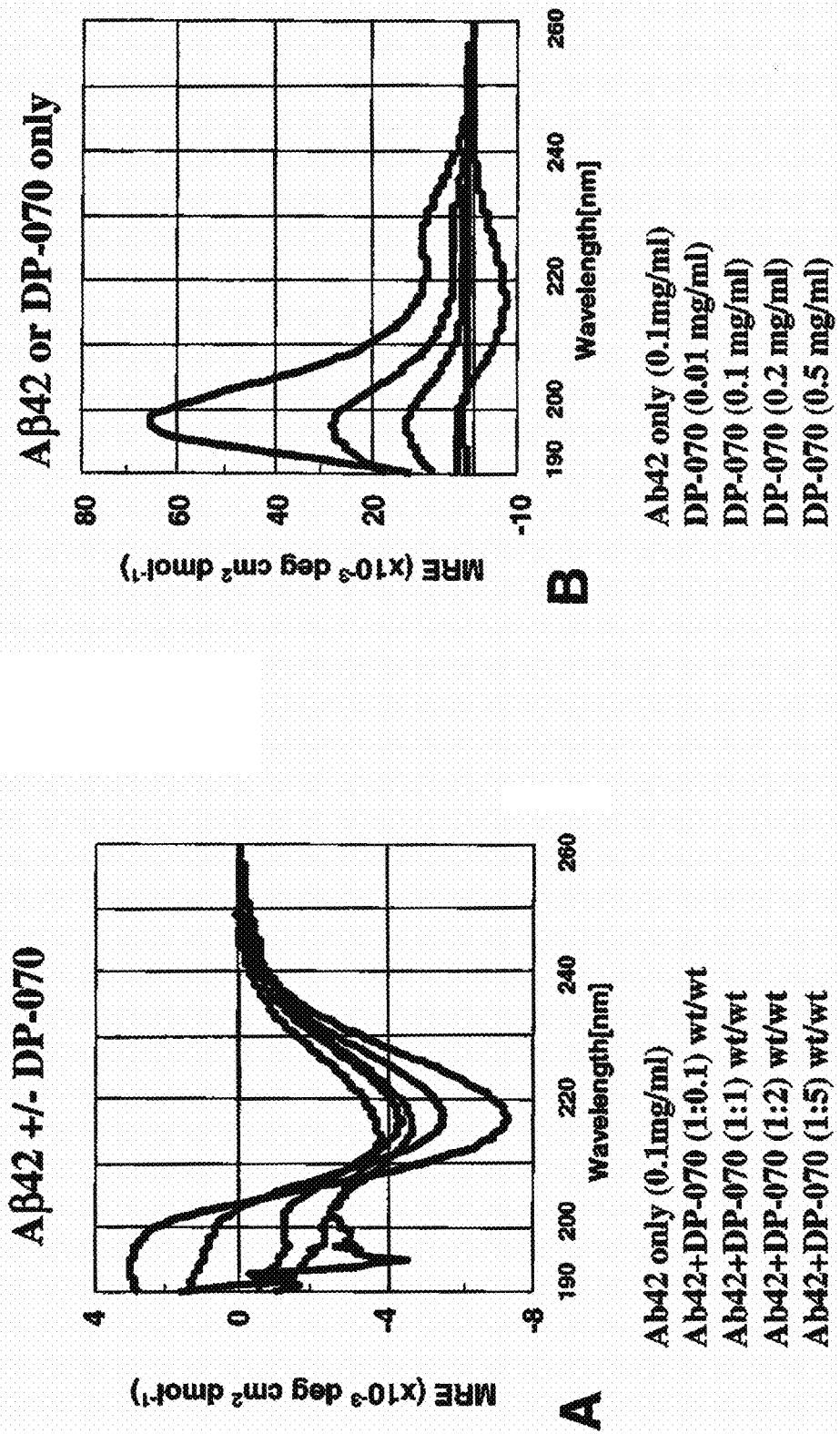
Figure 48:
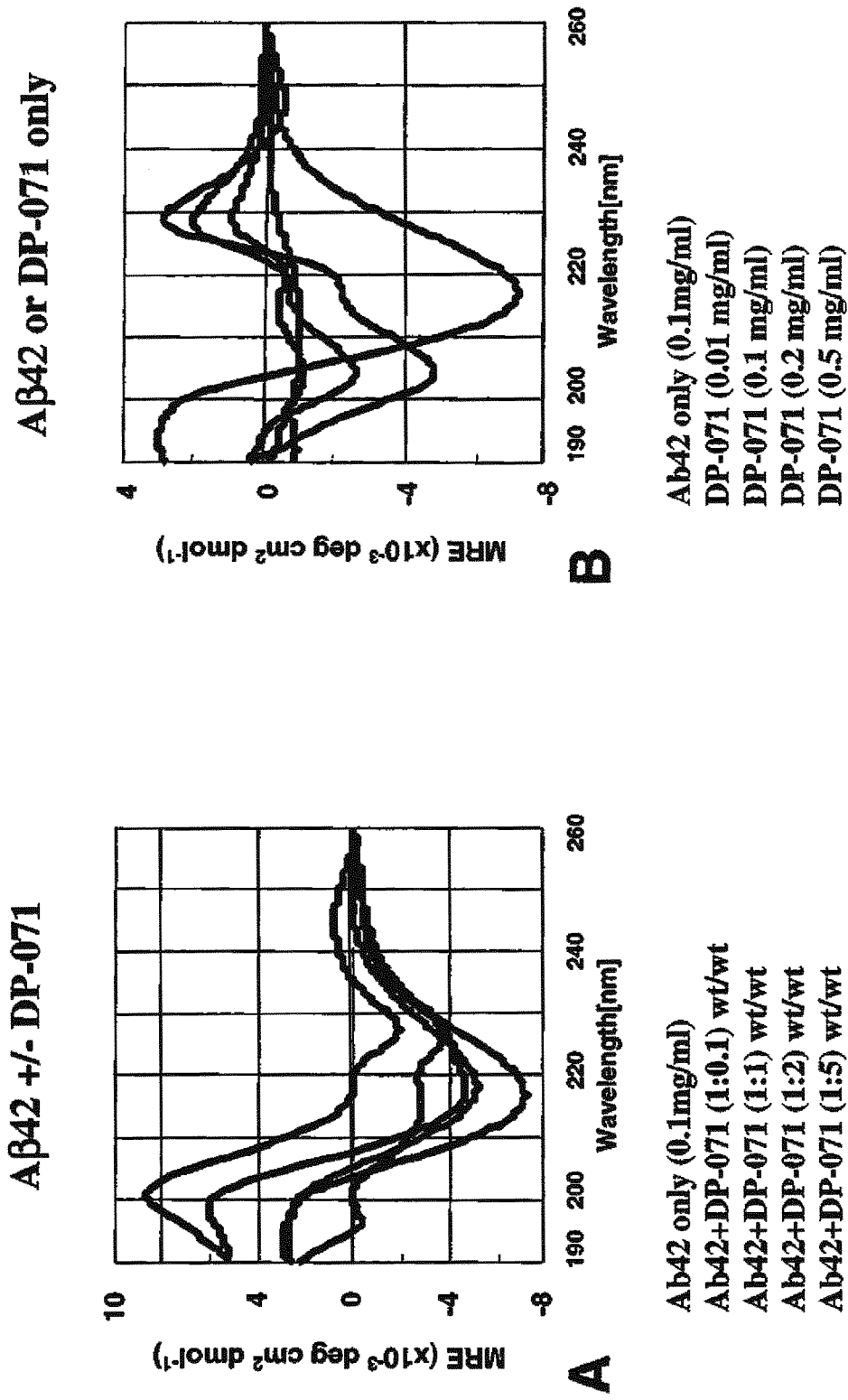
Figure 49:
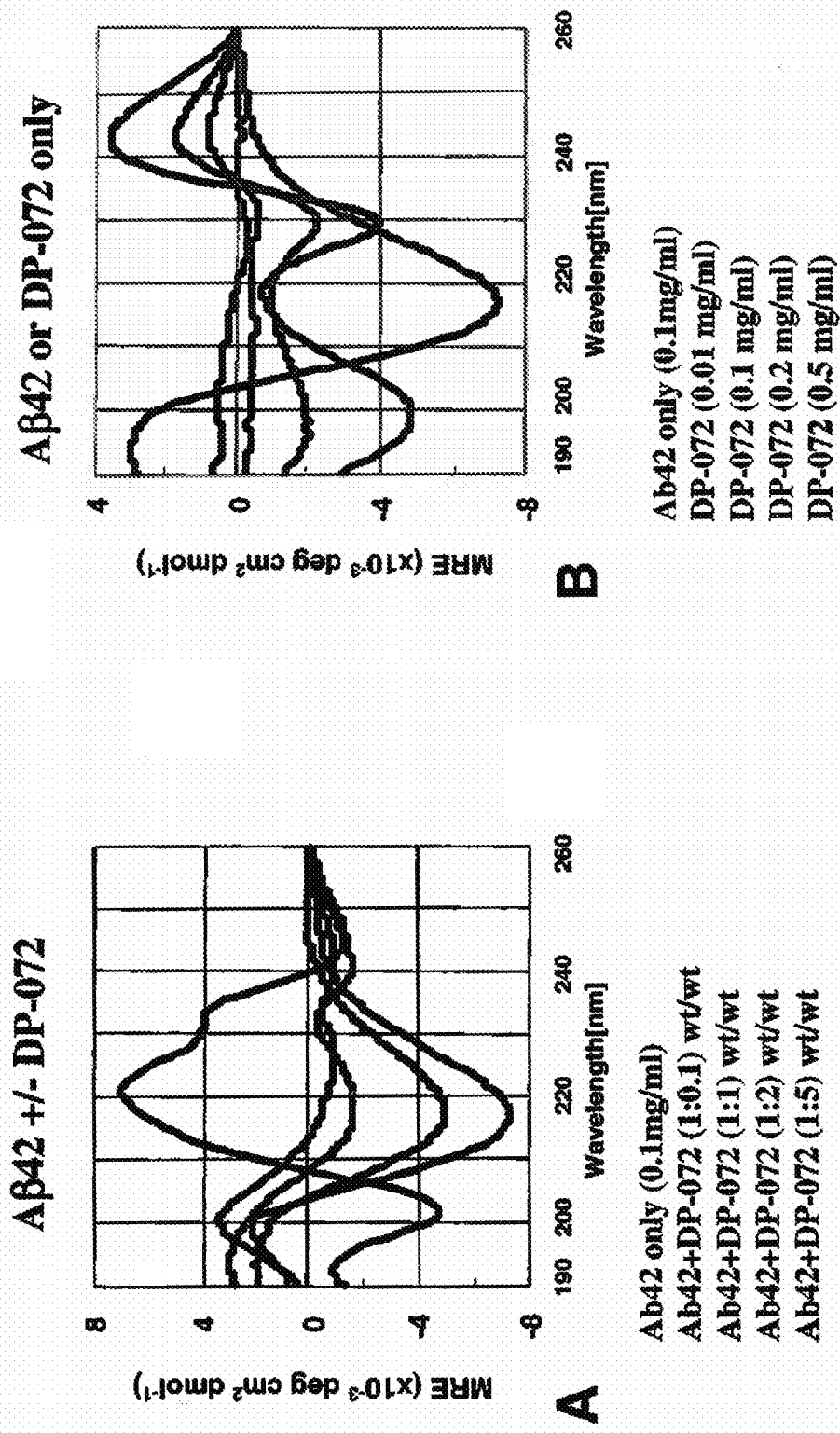

FIG. 33 is a Thio T summary of Ab42+/−DP50-64 at 1:0.1, 1:1, 1:2, 1:5); FIG. 34 is a CD summary from DP-01 to DP-064 1:2); FIG. 35 is a CD summary of selected 11 peptides from DP1-64 compared to IAb5. LP-025) at 1:2); FIG. 36 is a ThioT summary of selected 11 peptides from DP1-64 1:2).

Figure 50:
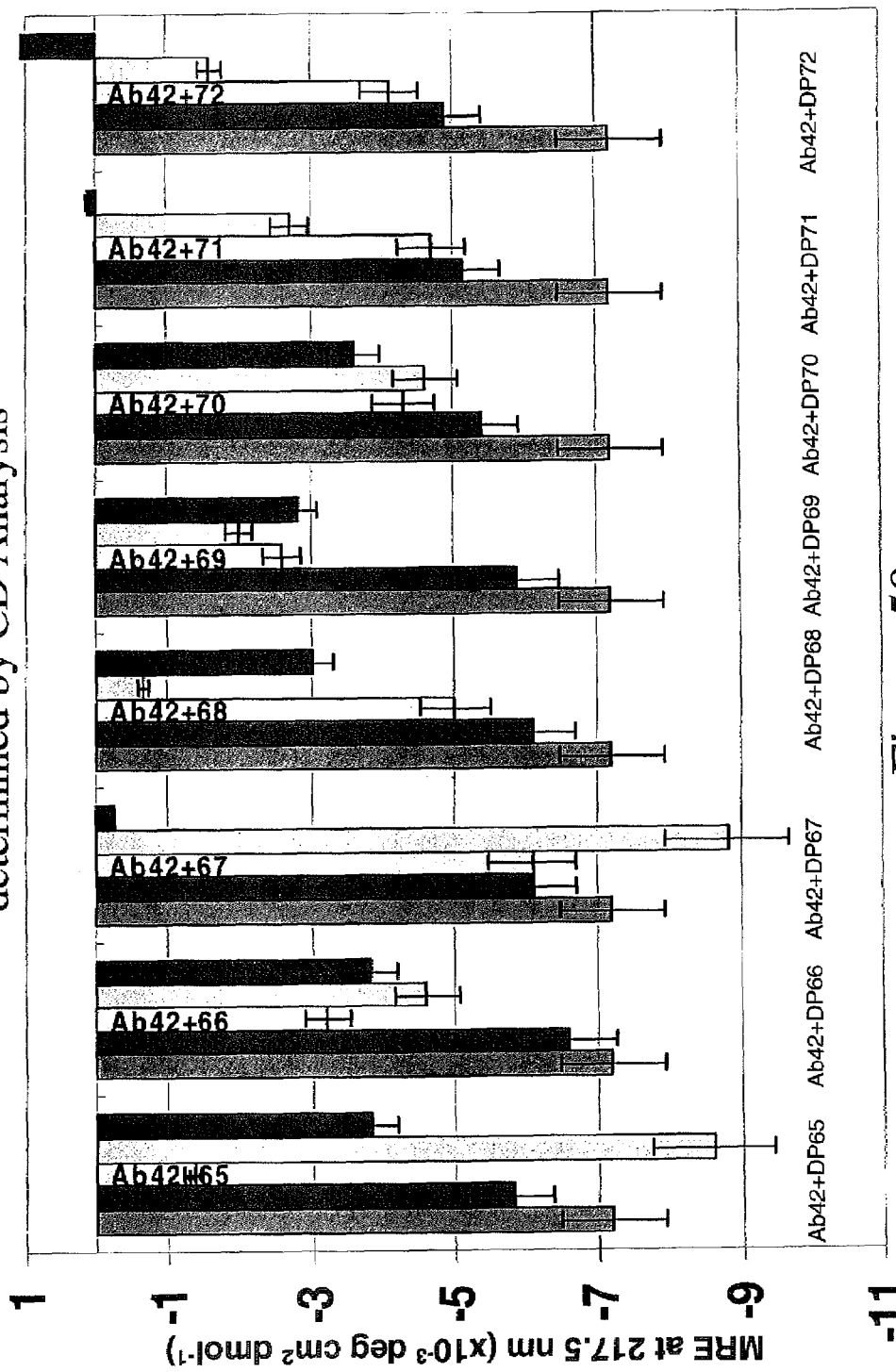
FIG. 50 is a summary of dose response CD of Ab42+/−DP-065 to DP-072.

FIGS. 37-41 are CD spectra of Ab42 plus polylysine and DP-065 through DP-072 at Ab42/peptide wt./wt. concentration of 1:2). FIGS. 42-49 are CD spectra of Ab42 plus DP-065 through DP-072 at 1:0.1, 1:1, 1:2, 1:5), with FIG. 50 as a summary of dose response CD of Ab42+/−DP-065 to DP-072.

Figure 51:
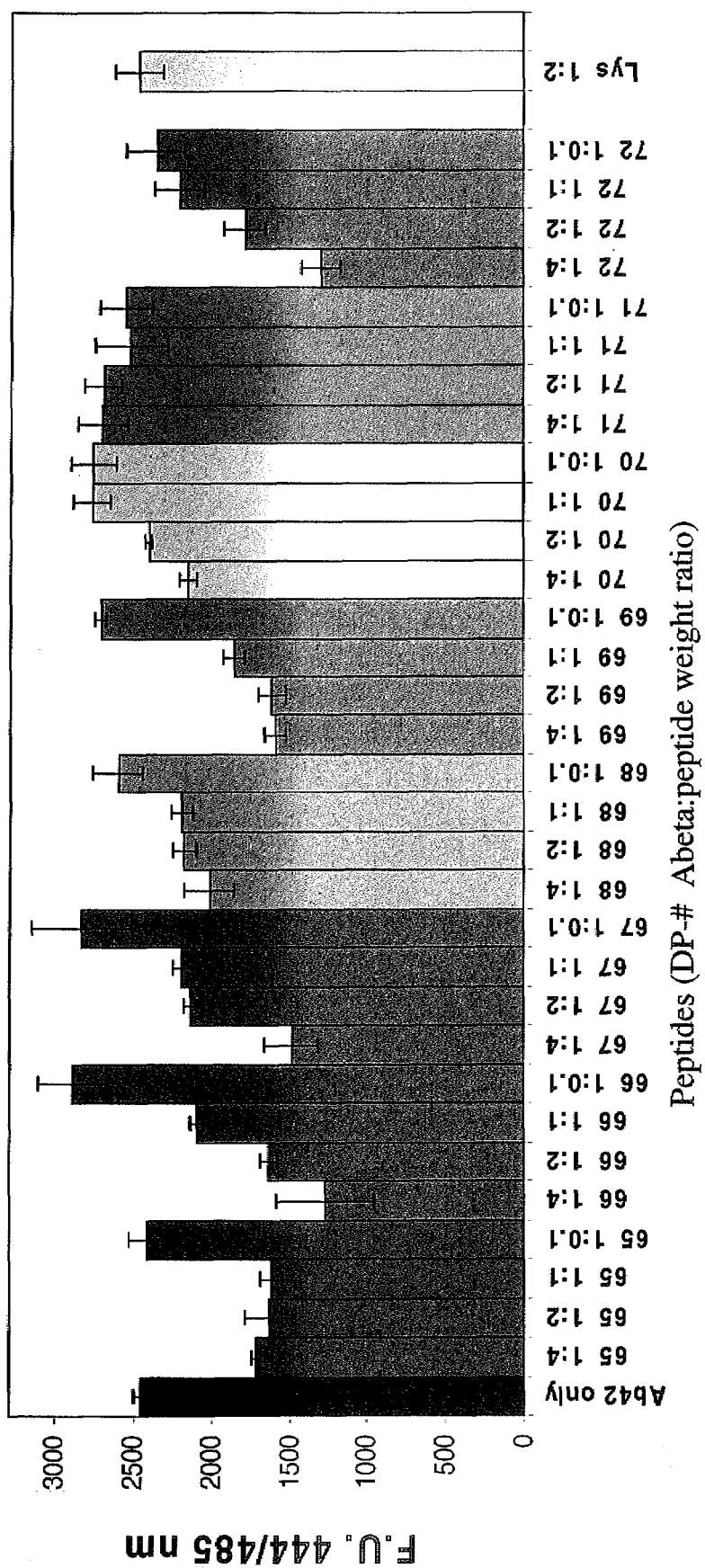
FIG. 51 is a summary of Thio T of Ab42+/−DP65-72 1:0.1, 1:1, 1:2, 1:5) and polylysine.
Figure 53:
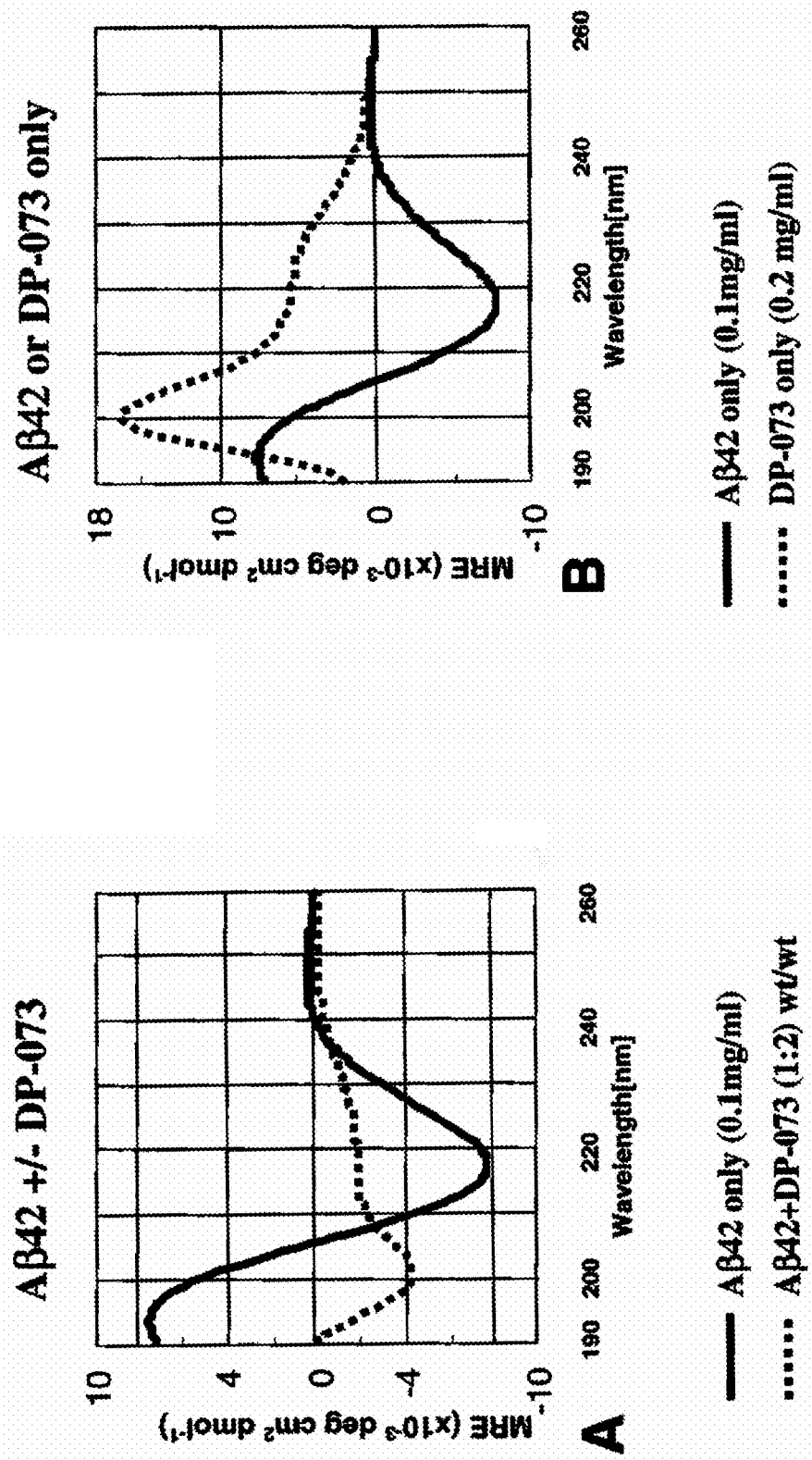
FIG. 53A are CD spectra showing the effects of 0.2 mg/ml of peptide DP-073 on beta-sheet secondary structure of Aβ42 amyloid fibrils i.e. Aβ 42+/−DP-073).
FIG. 53B shows the CD spectra of Aβ 42 or DP-073 only.
Figure 54:
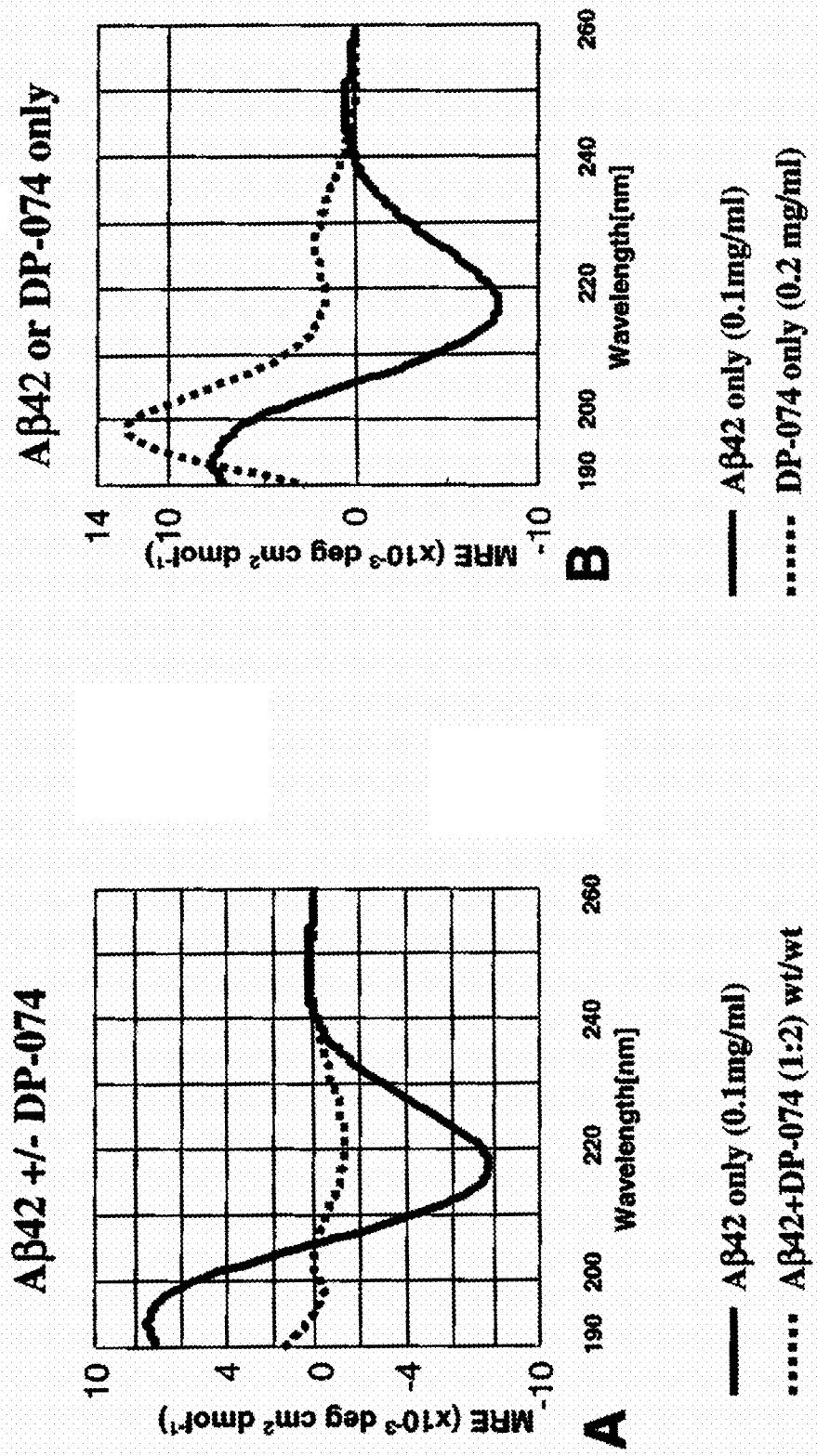
FIG. 54A are CD spectra showing the effects of 0.2 mg/ml of peptide DP-074 on beta-sheet secondary structure of Aβ42 amyloid fibrils i.e. Aβ 42+/−DP-074).
FIG. 54B shows the CD spectra of Aβ 42 or DP-074 only.
Figure 55:
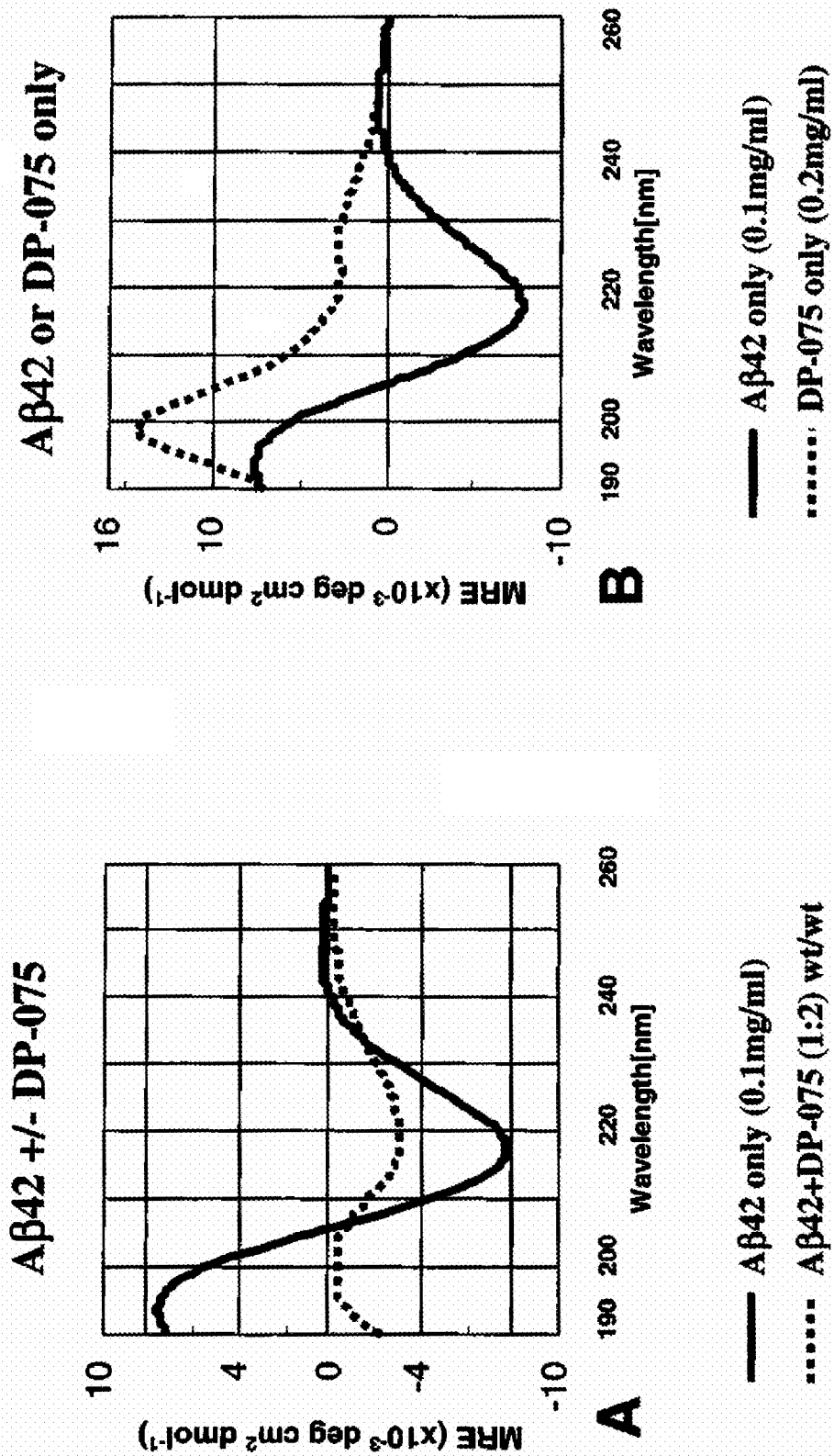
FIG. 55A are CD spectra showing the effects of 0.2 mg/ml of peptide DP-075 on beta-sheet secondary structure of Aβ42 amyloid fibrils i.e. Aβ 42+/−DP-075).
FIG. 55B shows the CD spectra of Aβ 42 or DP-075 only.
Figure 56:
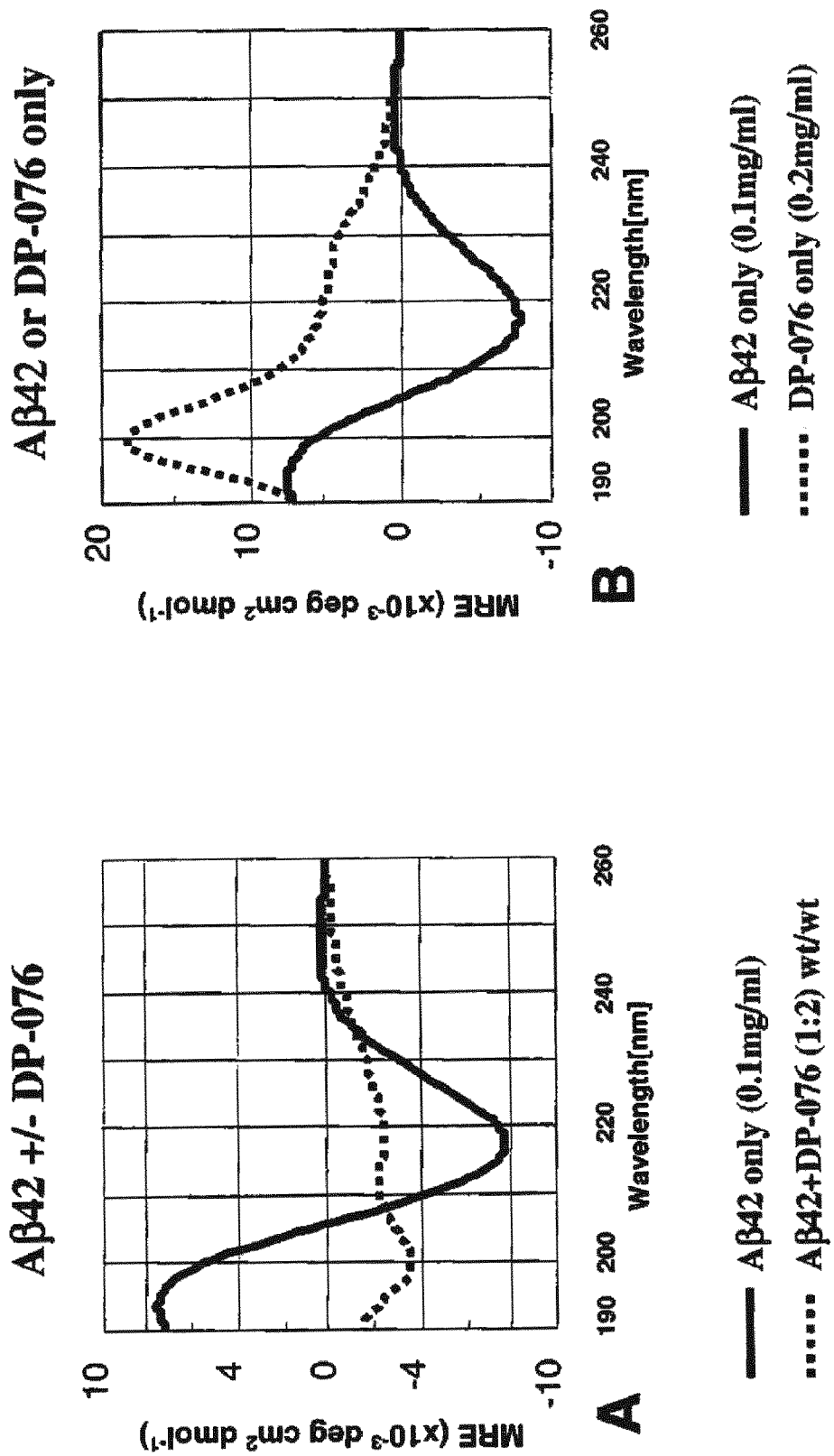
FIG. 56A are CD spectra showing the effects of 0.2 mg/ml of peptide DP-076 on beta-sheet secondary structure of Aβ42 amyloid fibrils i.e. Aβ 42+/−DP-076).
FIG. 56B shows the CD spectra of Aβ 42 or DP-076 only.
Figure 57:
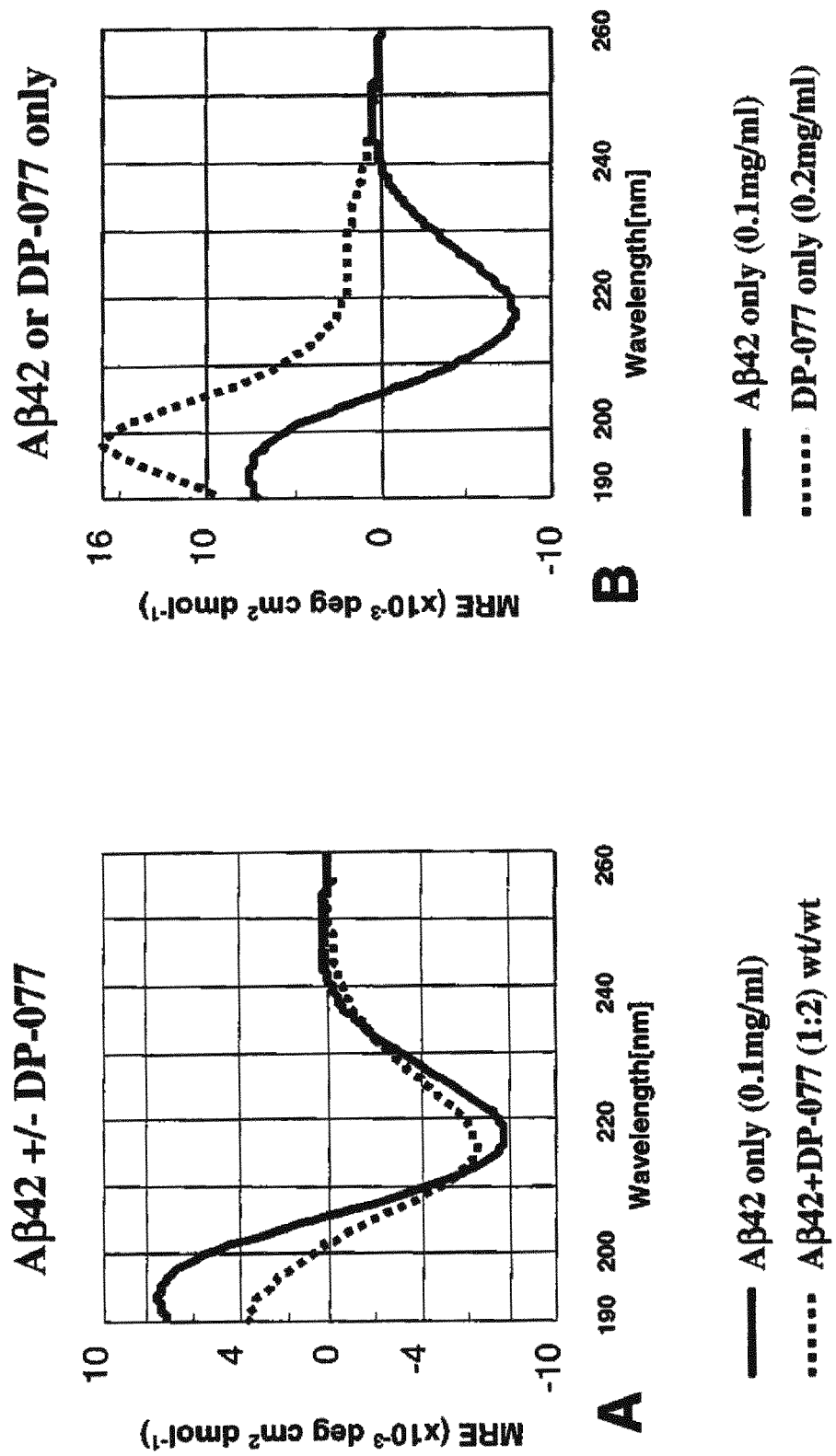
FIG. 57A are CD spectra showing the effects of 0.2 mg/ml of peptide DP-077 on beta-sheet secondary structure of Aβ42 amyloid fibrils i.e. Aβ 42+/−DP-077).
FIG. 57B shows the CD spectra of Aβ 42 or DP-077 only.
Figure 58:
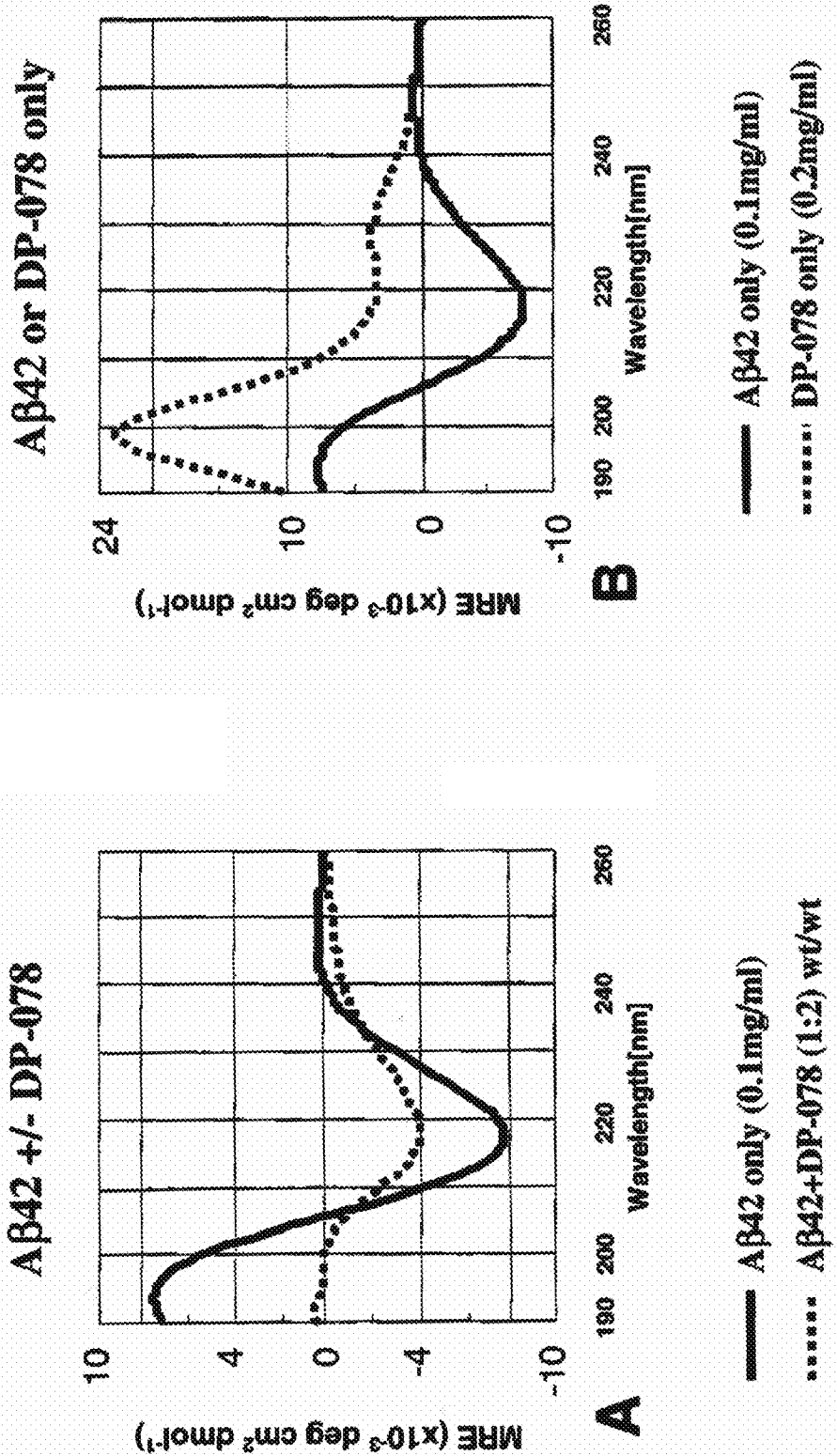
FIG. 58A are CD spectra showing the effects of 0.2 mg/ml of peptide DP-078 on beta-sheet secondary structure of Aβ42 amyloid fibrils i.e. Aβ 42+/−DP-078).
FIG. 58B shows the CD spectra of Aβ 42 or DP-078 only.
Figure 59:
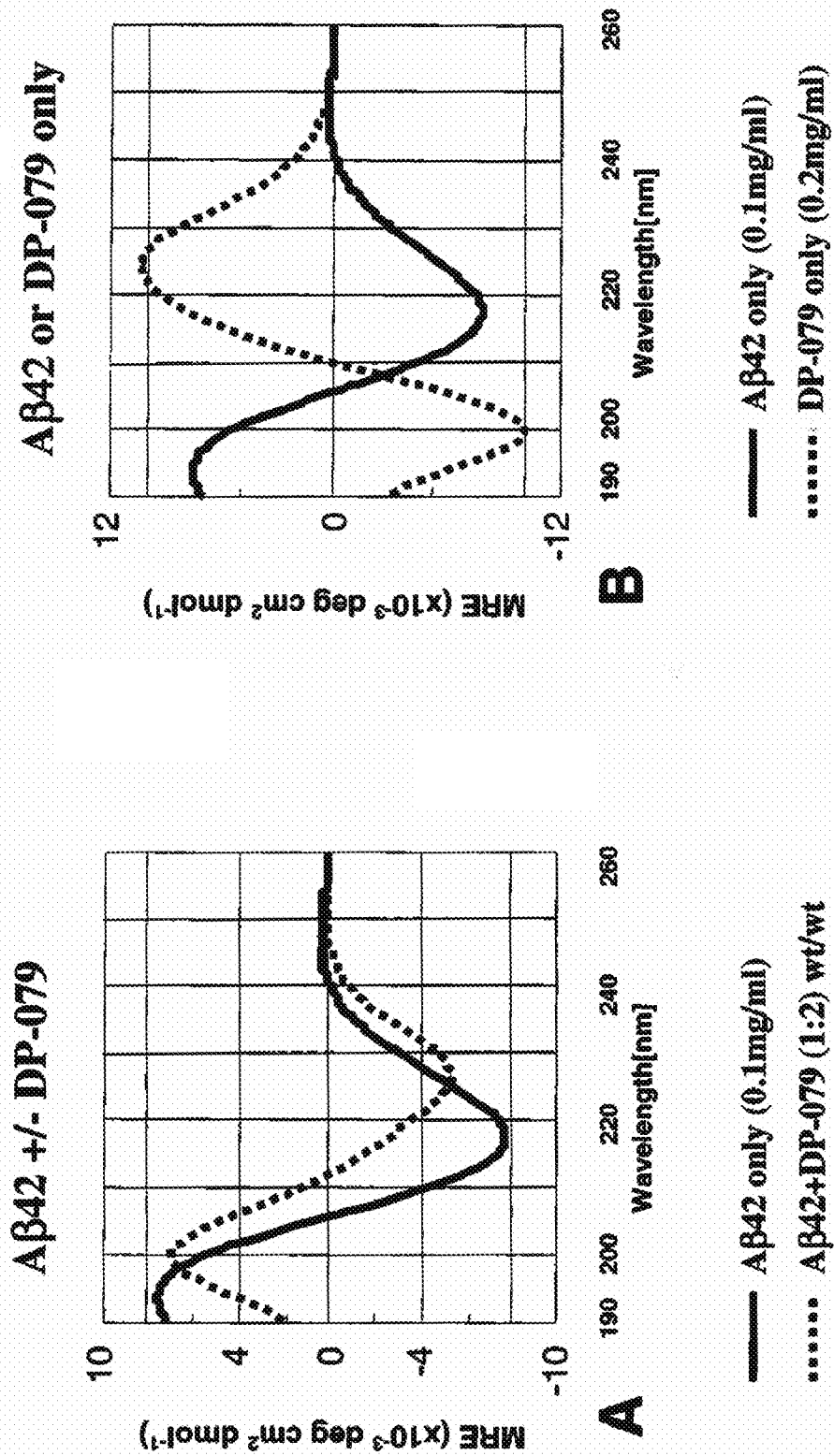
FIG. 59A are CD spectra showing the effects of 0.2 mg/ml of peptide DP-079 on beta-sheet secondary structure of Aβ42 amyloid fibrils i.e. Aβ 42+/−DP-079).
FIG. 59B shows the CD spectra of Aβ 42 or DP-079 only.
Figure 60:
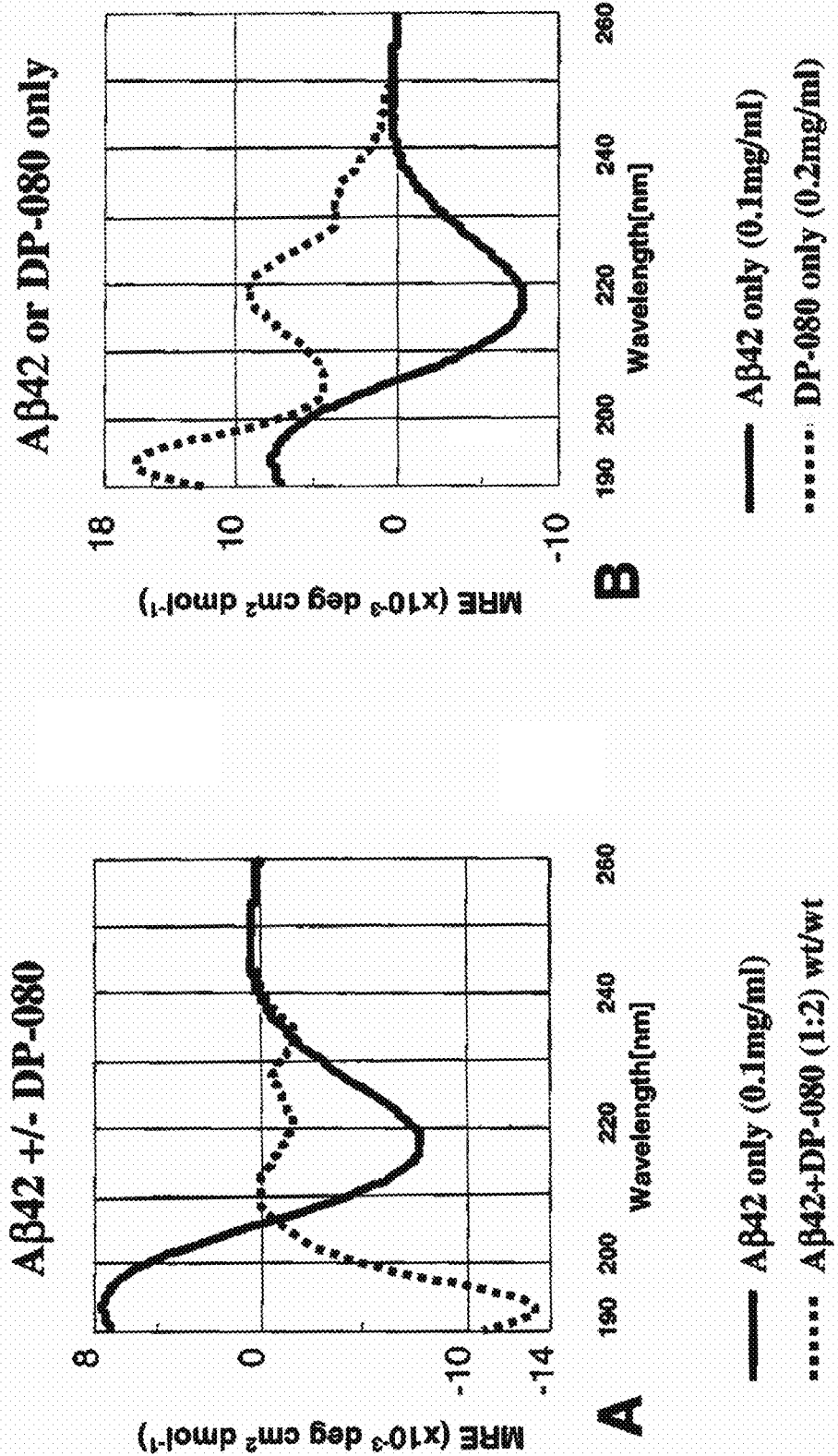
FIG. 60A are CD spectra showing the effects of 0.2 mg/ml of peptide DP-080 on beta-sheet secondary structure of Aβ42 amyloid fibrils i.e. Aβ 42+/−DP-080).
FIG. 60B shows the CD spectra of Aβ 42 or DP-080 only.
Figure 61:
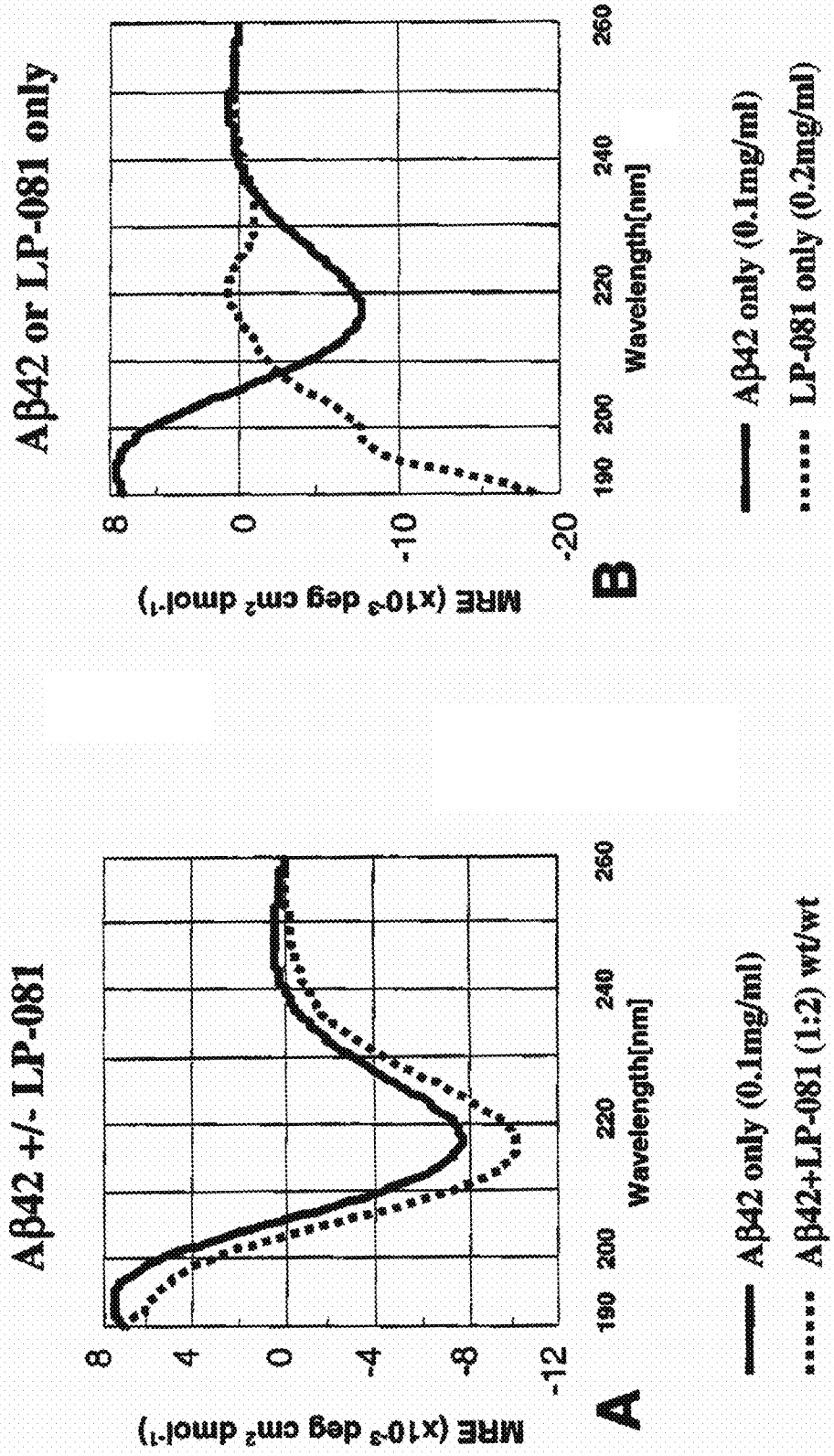
FIG. 61A are CD spectra showing the effects of 0.2 mg/ml of peptide LP-081 on beta-sheet secondary structure of Aβ42 amyloid fibrils i.e. Aβ 42+/−LP-081).
FIG. 61B shows the CD spectra of Aβ 42 or LP-081 only.

FIG. 51 is a summary of Thio T of Ab42+/−DP65-72 1:0.1, 1:1, 1:2, 1:5) and lysine, while FIG. 52 is a summary of Thio T ranking 65-72.

Example 10

Dose-Dependent Modulation of β and γ Cleavage of APP in Cell Cultures by 6-9 mer Peptides as Assessed by Immunoprecipitation and Western Analysis 1) cDNA Constructs, Cell Cultures and Stable Transfected Cell Lines Mammalian expression constructs, pCA-APP695 and pcDNA3.1-APP695-myc, have been described by Fukuchi et al. J. Neurochem. 58: 1863-1873 1992) and Yang et al. J. Biol. Chem. 2817):4207-4214 2006), respectively. pCA-APP695 contains the cDNA sequence coding for the human full-length APP695, and is driven by a chicken actin promoter. pcDNA3.1-APP695-myc was generated by subcloning of an APP695 cDNA fragment from pCA-APP695 into the BamHI and EcoRI sites of the pcDNA3.1-myc/His vector Invitrogen), which is driven by a cytomegalovirus immediate-early promoter.

Two cell lines stably transfected with pCA-APP695 and pcDNA3.1-APP695-myc were generated to assess APP processing and Aβ generation in cell culture. Human Embryonic Kidney HEK) 293 cells ATCC #CRL-1573), and human brain neuroblastoma cells, SK-N-SH ATCC #HTB-11), were employed to generate the APP stable cell lines. Cells were routinely cultured in a regular growth media RGM) that contained Dulbecco's Modified Eagle Medium DMEM) Invitrogen) supplemented with 10% fetal bovine serum at 37° C. in a cell culture incubator supplemented with 5% $CO_2$. HEK293 and SK-N-SH cells were grown to 70-80% confluence in 35 mm dishes, and transfected with 3 µg of pCA-APP695, and pcDNA3.1-APP695-myc, respectively. Transfection was mediated by polyethylenimines Polysciences, Inc.) as described by Hu et al. J. Biol. Chem. 28013):12548-12558 2005). Twenty-four hours after transfection, cells were plated at low density 400-2000 cells/plate), and grown in RGM containing 0.6-0.8 mg/ml G418 Invitrogen) to select stable colonies. After two weeks, stable colonies were picked, and sub-cultured. Stable expression of APP was confirmed by Western analysis of conditioned media for secreted APP using monoclonal antibody 6E10 Covance #SIG-39320), and of cell lysates for intracellular APP using an anti-APP C-terminal polyclonal antibody Sigma # A8717). The stable cell lines were maintained by periodic selection with G418-containing RGM. HEK293 cells stably transfected with pCA-APP695 are referred as HEK293-APP cells, while SK-N-SH cells stably transfected with pcDNA3.1-APP695-myc are referred as SKNSH-APP cells.

2) Treatment of Cultured Cells with 6-9 mer Peptides

Twenty-millimolar stock solutions of peptides DP-068 and DP-074 were prepared in PBS, aliquoted and stored at −80° C. before use. On the day before treatment, HEK293-APP and SKNSH-APP cells were plated in 6-well culture plates with low IgG growth media [DMEM+10% of low IgG fetal bovine serum Invitrogen #16250)]. The plating density allows cells to reach 80-95% of confluence on the next day. Upon treatment, cell culture media were replaced with 1.6 ml per well of low IgG growth media containing freshly-diluted peptides. Cells were incubated at 37° C. in a cell culture incubator for 20 hours. After incubation, conditioned media were collected, and centrifuged at 8000×g for 10 min at 4° C. to remove cell debris. Supernatants were saved and stored at −80° C. for analyses of secreted APPαsAPPα) secreted APPβsAPPβ), and secreted Aβ peptides. Cell lysates were collected for determining intracellular levels of APP, CTFs and β-actin. Briefly, the cell monolayer was washed once with PBS, and directly lysed in 200 µl of 2× Laemmli sample buffer 75 mM Tris-HCl, pH 8.4, 4% SDS, 20% glycerol, 50 mM DTT, 0.004% bromphenol blue) on ice for 15 min. Lysates were collected, boiled at 100° C. for 10 min without centrifugation, and stored at −80° C. for Western analysis.

3) Immunoprecipitation of Aβ Peptides in Conditioned Media

The immunoprecipitation methodology was employed to enrich secreted Aβ peptides from conditioned media. In the assay, all centrifugation steps were conducted at 5,000 rpm in a bench-top centrifuge for 1 min at room temperature unless otherwise indicated. Twenty microliters of 50% protein-A/G agarose slurry PIERCE, #53135) per sample was aliquoted, and washed twice with cold PBS containing 0.01% Triton X-100 PBS-T) by mixing and spinning to remove the residues from the bead storage buffer. The beads were then resuspended in 0.8 ml of cold PBS-T containing 1.2 µg of monoclonal antibody mAb) 4G8 Covance #SIG-39220) that specifically recognizes amino acids 17-24 of the Aβ region, and incubated on an orbital rotator for 2 h at 4° C. to allow the mAb to bind to the protein-A/G. The mAb-bound beads were then centrifuged and washed twice with 1 ml of cold PBS-T to remove unbound mAb 4G8. Equal amounts of conditioned media 0.5-0.9 ml per sample) collected from peptide-treated cell cultures were added into the 4G8-containing tubes, and incubated at 4° C. on an orbital rotator overnight. The beads were then centrifuged, and washed once with 1 ml of cold PBS-T, and once with 1 ml of cold PBS by mixing and spinning. Bound Aβ peptides were eluted with 20 μl of 2× Laemmli sample buffer eliminating dithiothreitol to minimize the co-elution of IgG), followed by 4-min boiling and 2-min centrifugation at 8000 rpm. The supernatant was carefully collected in a fresh tube that contained 1/20 volume of 1M dithiothreitol, and stored at −30° C. for Bicine/Tris/Urea/SDS polyacrylamide gel electrophoresis PAGE).

4) Electrophoresis of Aβ Peptides

Secreted Aβ peptides were analyzed by a Bicine/Tris/Urea/SDS PAGE system described by Klafki et al., Analytical Biochem. 237:24 1996). Bicine/Tris/Urea/SDS/polyacrylamide mini gels 6 cm×9 cm×0.75 mm) were prepared the day before electrophoresis, and stored at 4° C. The gel system consists of a separating gel [10% of acrylamide/bis19:1; Bio-Rad #161-0144), 8M of urea, and 0.1% SDS prepared in separating buffer 0.4 M Tris; 0.1 M $H_2SO_4$)], a stacking gel [6% of acrylamide/bis19:1) and 0.1% SDS prepared in a stacking buffer 0.4 M Bistris; 0.1 M $H_2SO_4$)] and a comb gel [9% of acrylamide/bis19:1) and 0.1% SDS prepared in a comb gel buffer 0.36 M bistris; 0.16 M bicine)]. Immunoprecipitation elutes 8-10 μl per sample) were resolved in gels at 200 volts constant) for about one hour. The gel running buffers consist of a cathodic buffer 0.2M bicine; 0.1 M NaOH; 0.25% SDS) and an anodic buffer 0.2 M Tris; 0.05 M $H_2SO_4$). Peptide bands in gels were transferred onto Immobilon-PSQ membrane Millipore) using a Trans-Blot Semi-Dry system Bio-Rad) at 0.04 A constant) per mini-gel for 50 min. The transfer buffers Klafki et al. 1996) were buffer A 0.3 M Tris; 30% methanol), buffer B 25 mM Tris; 30% methanol), and buffer C 25 mM Tris, pH 9.4; 0.025% SDS). The transfer sandwich was set up from bottom to top as an extra-thick filter paper Bio-Rad) soaked in buffer A, an extra-thick filter paper soaked in buffer B, two layers of Immobilon-PSQ membranes the bottom layer was used to block peptides going through, and discarded after transfer) soaked in buffer B, the gel briefly soaked in buffer C for 1 min, and an extra-thick filter paper soaked in buffer C. After transfer, the membrane next to the gel was boiled in PBS for 3 min using a microwave oven before blocking with 5% milk in PBS containing 0.05% Tween-20.

5) Western Blotting

Cellular APP and CTFs in lysates were separated in 16.5% Tris/Tricine Criterion peptide gels Bio-Rad), whereas sAPPα and sAPPβ in conditioned media were separated in 4-12% Bis/Tris Criterion XT gels Bio-Rad), with buffer systems recommended by the manufacturer. After electrophoresis, protein bands were transferred onto Immobilon-PSQ membranes using Bio-Rad Criterion™ Blotters, and a transfer buffer system Bio-Rad). The transfer was conducted at 0.4 A constant) for 90-120 min at 4° C. All transferred membranes were blocked with 5% milk in PBS+0.05% Tween-20 for 30-60 min at room temperature, and incubated with primary antibodies for overnight at 4° C., and with HRP-conjugated secondary antibody Vector) at 1:4000 at room temperature for 2 h. Aβ peptides were detected using mAb 6E10 Covance; 1:3000), intracellular CTFs with a rabbit polyclonal antibody specifically recognizing the C-terminus of APP695 amino acids 676-695) Sigma; 1:50,000), sAPPα with mAb 6E10 Covance; 1:20,000), sAPPβ with a polyclonal antibody specific for secreted APPβ Covance; 1:500), and β-actin with mAb C4 Sigma; 1:200,000). Protein bands were visualized with an ECL system GE Healthcare) by exposing to autoradiography films. For re-probing membranes with a different antibody, membranes were stripped and reprobed with the next primary antibody. Quantitation of relative intensities of protein bands on autoradiographic films was performed by image quantification with the Scion Image software http://www.scioncorp.com).

6) ELISA

To evaluate Aβ levels, conditioned media from cells were measured with commercial ELISA kits The Genetics Company, Zurich, Switzerland) according to the manufacturer's instructions. For Aβ40, samples were diluted 1:2 with kit sample diluent buffer. For Aβ42, samples were applied to ELISA plates without dilution. Standards were prepared in low IgG media in the same dilution as the samples. Media or standards containing known amounts of Aβ were applied to micro-titre plates coated with monoclonal antibodies specific to the C-terminus of Aβ40 or Aβ42 and incubated overnight. After a wash step, captured Aβ was bound to a monoclonal biotin-conjugated antibody recognizing the N-terminus of Aβ. The biotinylated-Aβ complex was then bound to streptavidin-HRP and detected in an enzymatic calorimetric reaction. Samples were quantified by comparing the optical density 450 nm) of the standards to that of the unknowns.

Figure 82:
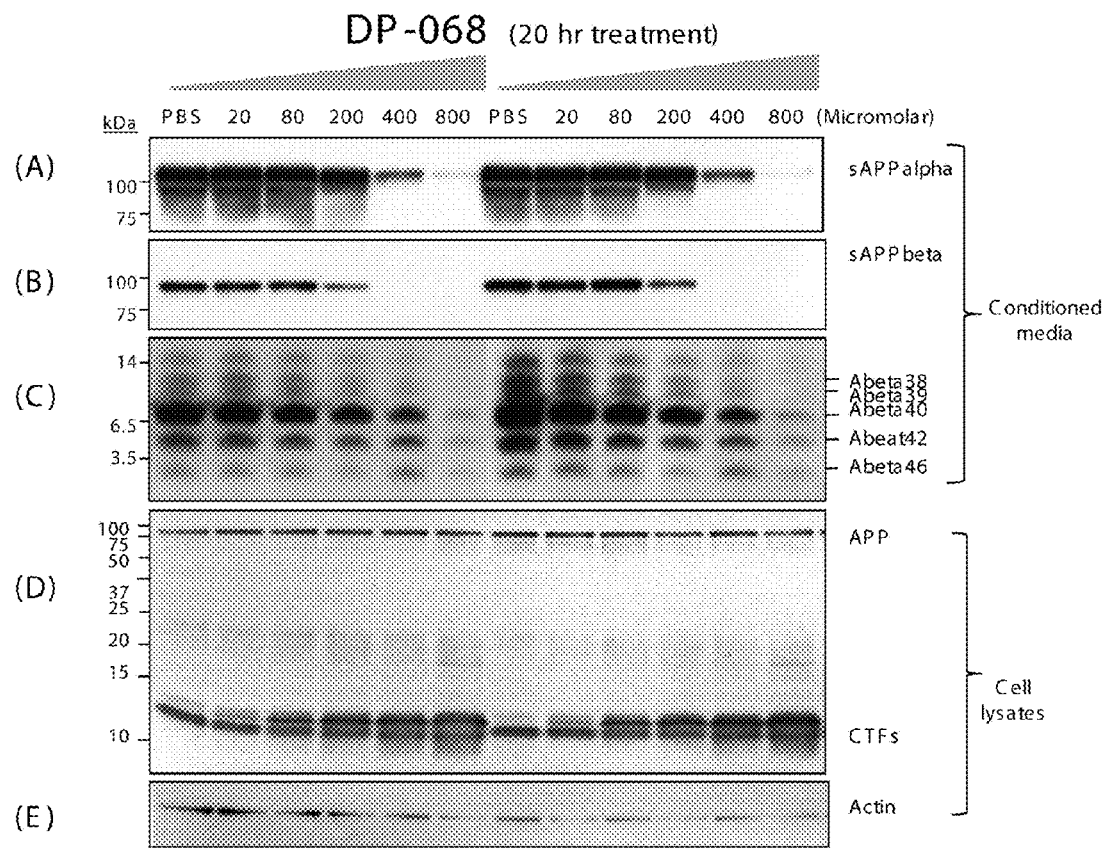
FIG. 82A-E are photos of Western blots showing effects of peptide DP-068 on APP processing and Aβ generation in cultured human embryonic kidney 293 cells that are stably transfected with the human wild type APP isoform 695 HEK293-APP cells) as assessed by Western analysis and immunoprecipitation.

7) Peptide DP-068 Modulates α, β, and γ Cleavage of APP and Reduces Aβ Peptide Generation in HEK293-APP Cells FIGS. 82A-B show that peptide DP-068 reduces levels of sAPPα and sAPPβ in conditioned media of HEK293-APP cell cultures as assessed by Western analysis. HEK293-APP cells were treated with 0 PBS vehicle control), 20, 80, 200, 400, and 800 μM of DP-068 in 6-well plates for 20 hrs. Each condition was in triplicate only duplicate was shown). After incubation, conditioned media were collected and analyzed by Western analysis for sAPPβ FIG. 82B), and then re-probed for sAPPα FIG. 82A). Reduced levels of both sAPPα and sAPPβ were found in cells treated with peptide DP-068, when compared to PBS vehicle control. The reductions were dose-dependent. The reduction became evident at 80 μM treatment for sAPPα reduced by 11%), and at 200 μM for sAPPβ by 75%). At 400 μM and 800 μM treatments, sAPPα levels were reduced by 89% and 99%, respectively, while sAPPβ levels were non-detectable. The results indicate that peptide DP-068 is a potent agent that can modulate both α and β cleavage of APP.

FIG. 82C shows that peptide DP-068 reduces generation of Aβ1-40 and Aβ1-42 peptides in HEK293-APP cells as assessed by immunoprecipitation followed by Western analysis. HEK293-APP cells were treated with DP-068 as described in FIGS. 82A-B. Secreted Aβ peptides in conditioned media were analyzed by immuneprecipitation with mAb 4G8 specific to residues 17-24 of the Aβ region, followed by Western analysis with mAb 6E10 specific to residues 1-16 of the Aβ. Reduced levels of Aβ 1-40 and Aβ 1-42 peptides, along with other Aβ species, were found in conditioned media of the cells treated with DP-068 when compared to PBS vehicle controls. The reduction appeared to be dose-dependent. Consistent with FIGS. 82B and 82D below), the results indicate that peptide DP-068 can modulate both β and γ cleavage of APP, leading to reduced generation of Aβ peptides in HEK293-APP cell cultures.

FIG. 82D shows that treatment with peptide DP-068 causes an increase in intracellular levels of CTFs in HEK293-APP cells as assessed by Western analysis. HEK293-APP cells were treated as described in FIGS. 82A-B. Cell lysates were analyzed by Western analysis for intracellular APP and CTFs.

An increase in 1.5-2.7 fold increase) intracellular CTF was found in the cells treated with 80-800 μM of peptide DP-068 when compared to PBS controls. The increase was dose-dependent. Importantly, peptide DP-068 did not affect intracellular levels of APP. These observations suggest that the DP-068 induced an increase of CTF which did not result from increased steady-state levels of APP. The membrane was re-probed for β-actin to assess protein loading and transfer efficiency FIG. 82E). Because CTFs are direct substrates for γ secretase, increases of CTFs with DP-068 treatment strongly suggests that the peptide can modulate γ cleavage of APP.

Figure 83:
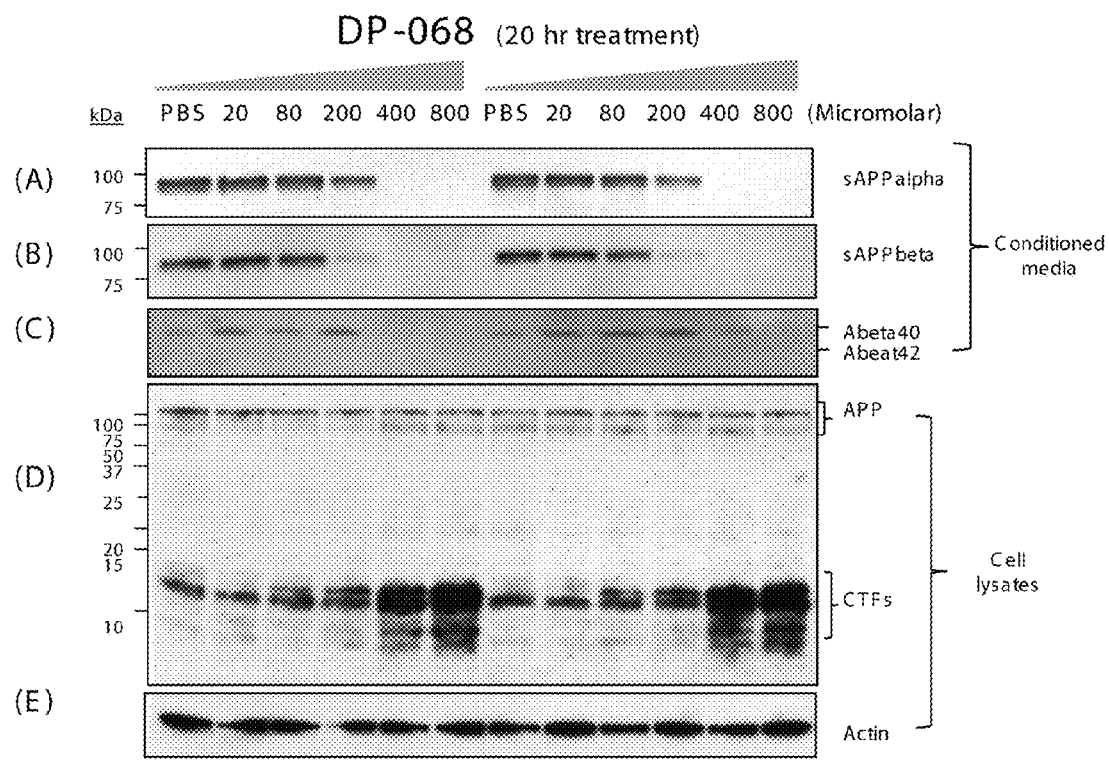
FIG. 83A-E are photos of Western blots showing effects of peptide DP-068 on APP processing and Aβ generation in cultured human brain neuroblastoma SK-N-SH cells that are stably transfected with the human wild type APP isoform 695 SK-N-SH-APP cells) as assessed by Western analysis and immunoprecipitation.

8) Peptide DP-068 Modulates α, β, and γ Cleavage of APP and Reduces Aβ Generation in SKNSH-APP Cells FIGS. 83A-B show that treatment with peptide DP-068 results in reduced levels of sAPPα and sAPPβ in SKNSH-APP cell cultures as assessed by Western analysis. SKNSH-APP cells were treated with 0 PBS vehicle control), 20, 80, 200, 400, and 800 μM of DP-068 in 6-well plates for 20 hrs. Each condition was in triplicate. After treatment, conditioned media were collected and analyzed by Western analysis for sAPPβ FIG. 83B), and then re-probed for sAPPα FIG. 83A). Similar to those observed in HEK293-APP cells, reduced levels of sAPPα and sAPPβ were found in cells treated with peptide DP-068, when compared to PBS vehicle control. The reductions were dose-dependent. Reduced levels of sAPPα down by 7-99%) and sAPPβ down by 17-100%) were observed in cells treated with 80-800 μM DP-068. The results confirm that peptide DP-068 can modulate α and β cleavage of APP in both HEK293-APP and SKNSH cell lines.

FIG. 83C shows that peptide DP-068 reduces generation of Aβ1-40 and Aβ1-42 peptides in conditioned media of SKNSH-APP cells as assessed by immunoprecipitation followed by Western analysis. The cells were treated with DP-068 as described in FIGS. 83A-B. Secreted Aβ peptides in conditioned media were analyzed by immuneprecipitation with mAb 4G8, followed by Western analysis using mAb 6E10. Reduced levels of Aβ1-40 and Aβ1-42 peptides down by 65-90%) were found in cells treated with 400-800 μM of DP-068 when compared to PBS vehicle controls.

FIGS. 83D-E show that treatment with peptide DP-068 causes an increase in intracellular levels of CTFs in SKNSH-APP cells as assessed by Western analysis. The cells were treated as described in FIGS. 83A-B. Cell lysates were analyzed by Western analysis for intracellular APP and CTFs. Increases in intracellular CTFs 1.2-6 fold increase) were found in the cells treated with 80-800 μM of peptide DP-068 when compared to PBS treated controls. The increases were dose-dependent. Once again, peptide DP-068 did not affect intracellular levels of APP, suggesting that the increased CTFs are not due to increased steady-state levels of APP. The membrane was re-probed for β-actin to assess protein loading and transfer efficiency FIG. 83E). These results suggest that peptide DP-068 can modulate γ cleavage of APP, leading to increased levels of direct γ secretase substrates CTFs.

9) Peptide DP-074 Selectively Modulates β and γ Cleavage of APP and Reduces Aβ Generation in HEK293-APP Cells.

Figure 84:
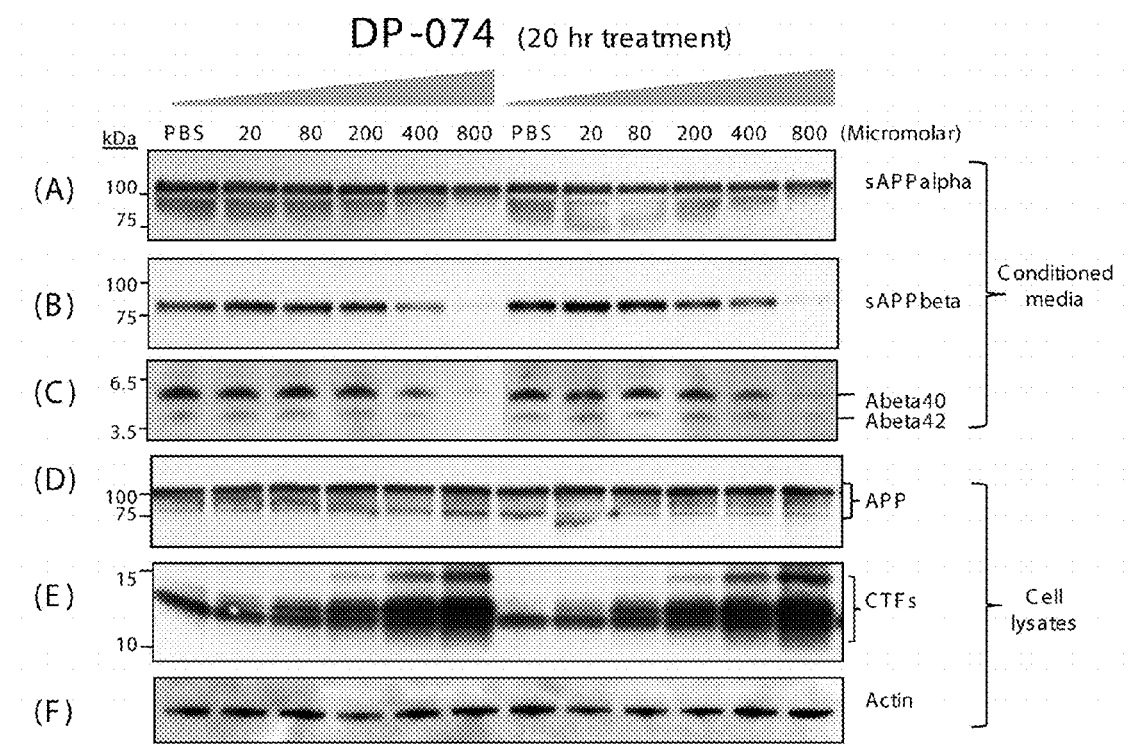
FIG. 84A-F are photos of Western blots showing effects of peptide DP-074 on APP processing and Aβ generation in HEK293-APP cell cultures as assessed by Western analysis and immunoprecipitation.

FIGS. 84A-B show that peptide DP-074 selectively modulates β cleavage of APP in HEK293-APP cell cultures as assessed by Western analysis. HEK293-APP cells were treated with 0 PBS vehicle control), 20, 80, 200, 400, and 800 μM of DP-074 in 6-well plates for 20 hrs. Each condition was in triplicate. After incubation, conditioned media were collected and analyzed by Western analysis for sAPPβ FIG. 84B), and then re-probed for sAPPα FIG. 84A). A reduction in levels of sAPPβ down by 6-97%) was observed in cells treated with 80-800 μM of peptide DP-074, compared to PBS vehicle control. The reduction was dose-dependent. In sharp contrast, peptide DP-074 did not significantly affect levels of sAPPα FIG. 84A). These results indicate that peptide DP-074 can selectively modulate β cleavage of APP without affecting α cleavage even at the highest concentrations tested.

FIGS. 84D-F show that peptide DP-074 causes an increase in intracellular CTFs, the substrates of γ secretase, in HEK293-APP cells as assessed by Western analysis. HEK293-APP cells were treated as described in FIGS. 84A-B. Cell lysates were analyzed by Western analysis for intracellular APP FIG. 84D) and CTFs FIG. 84E). Elevated amounts 1.6-7.8 fold increase) of intracellular CTFs were found in cells treated with 80-800 μM of peptide DP-074 when compared to PBS controls. The increase was dose-dependent. Importantly, peptide DP-074 did not affect intracellular levels of APP, which was detected with the same antibody on the same Western blot. This data suggests that the DP-074 caused an increase in CTFs which is not a result of increased steady-state levels of APP. The membrane was also re-probed for β-actin to assess protein loading and transfer efficiency FIG. 84F). As CTFs are direct substrates for γ secretase, increases in the levels of CTFs upon DP-074 treatment strongly suggests that the peptide can modulate γ cleavage of APP.

FIG. 84C shows that treatment with peptide DP-074 reduces the generation of Aβ peptides in conditioned media of HEK293-APP cells, as assessed by immuno-precipitation followed by Western analysis. HEK293-APP cells were treated with DP-074 as described above. Secreted Aβ peptides in conditioned media were analyzed by immuneprecipitation with mAb 4G8, followed by Western analysis with mAb 6E10. Cells treated with DP-074 showed significantly reduced levels of Aβ peptides in conditioned media when compared to those treated with PBS vehicle control. The reduction appeared to be dose-dependent. At 800 μM of DP-074, total Aβ levels in conditioned media were reduced by 94%. Consistent with the results shown in FIGS. 84B and 84E, the data indicates that peptide DP-074 can modulate both α, β and γ cleavage of APP, leading to reduced generation of Aβ peptides in HEK293-APP cell cultures.

Figure 85:
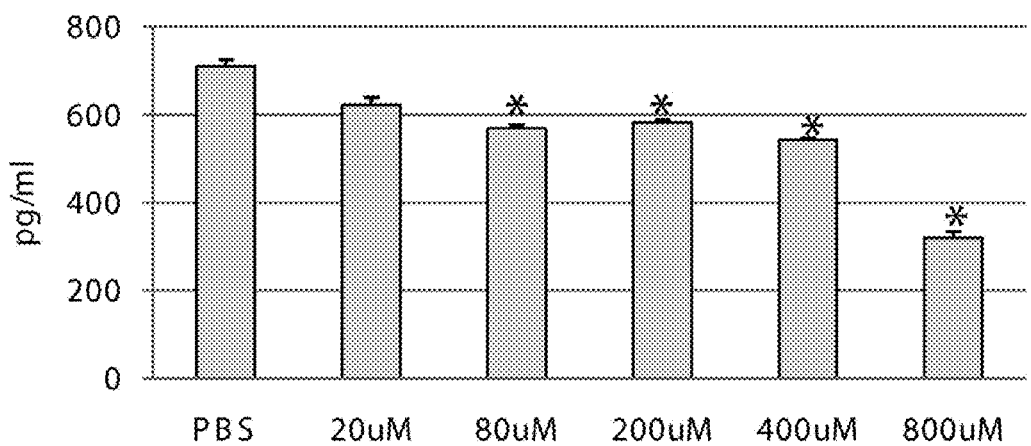
FIGS. 85A and B are graphs showing effects of peptide DP-074 on Aβ generation in HEK293-APP cell cultures as assessed by ELISA.
Figure 85:
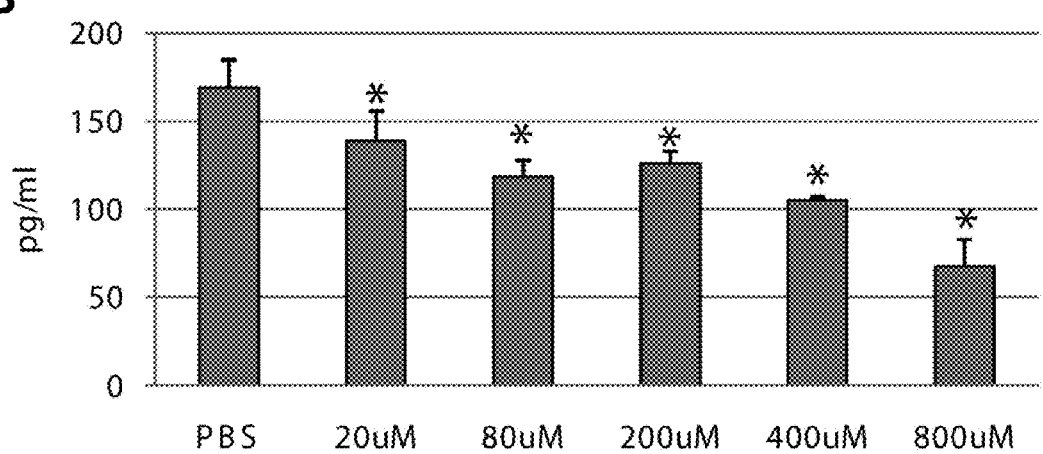

FIGS. 85A-B show that peptide DP-074 reduces generation of Aβ peptides in conditioned media of HEK293-APP cells as assessed by ELISA. A significant reduction t-test, $p<0.05$) in Aβ1-40 levels was found in HEK293-APP conditioned media from cells treated with 80 to 800 μM DP-074 compared to PBS vehicle control FIG. 85A). There appeared to be a dose dependent effect as there was a 12% reduction of Aβ1-40 with 20 μM DP-074 treatment, a significant ~20% reduction with 80 to 400 μM DP74 treatment, and a significant 55% reduction in Aβ1-40 levels with 800 μM DP-074 compared to the vehicle control. A significant reduction t-test, $p<0.05$) in Aβ42 was also found in HEK293-APP conditioned media from cells treated with 20 to 800 μM DP-074 FIG. 85B). There was a ~20% reduction of Aβ42 with 20 μM DP-074 treatment, a ~30% reduction with 80 to 200 μM DP-074 treatment, a ~40% reduction with 400 μM DP-074, and a ~60% reduction in Aβ1-42 levels with 800 μM DP-074 compared to vehicle control.

10) Peptide DP-074 Selectively Modulates β and γ Cleavage of APP and Reduces Aβ Generation in SKNSH-APP Cells.

Figure 86:
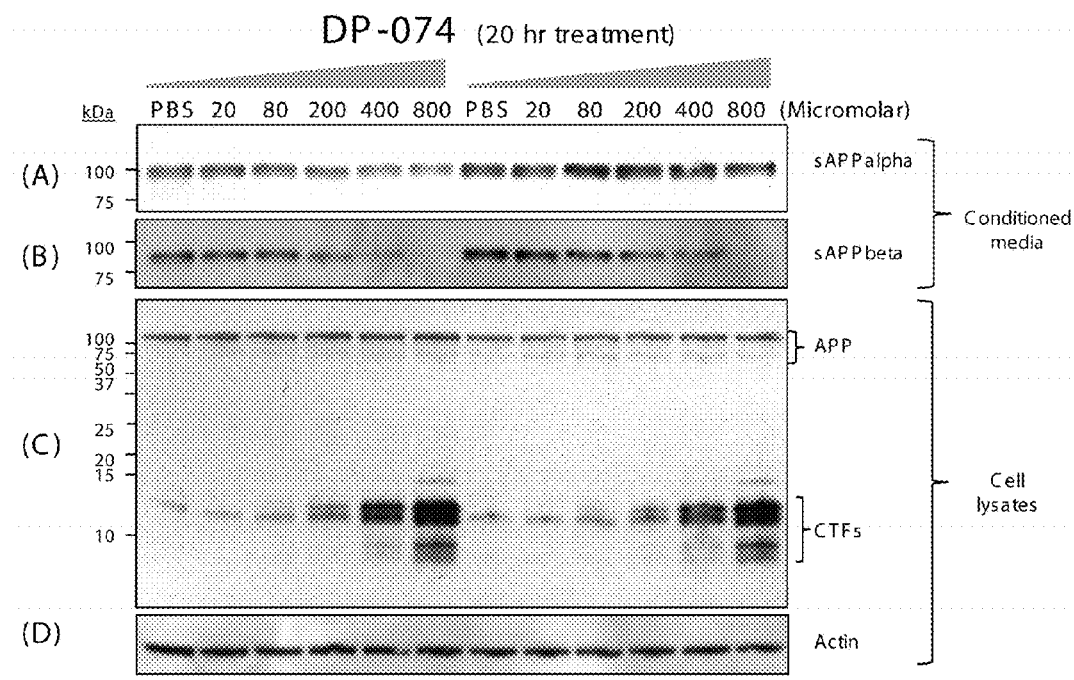
FIG. 86A-D are photos of Western blots showing effects of peptide DP-074 on APP processing in SKNSH-APP cell cultures as assessed by Western analysis.

FIGS. 86A-B show that peptide DP-074 selectively modulates β cleavage of APP in SKNSH-APP cells as assessed by Western analysis. SKNSH-APP cells were treated with 0 PBS vehicle control), 20, 80, 200, 400, and 800 μM of DP-074 in 6-well plates for 20 hrs. Each condition was in triplicate. After incubation, conditioned media were collected and analyzed by Western analysis for sAPPβ FIG. 86B), and then re-probed for sAPPα FIG. 86A). Reduced levels of sAPPβ down by 14-95%) were observed in cells treated with 20-800 μM of DP-074 treatment when compared to those treated with PBS controls. The reduction was dose-dependent. In sharp contrast, peptide DP-074 exerted no effect on levels of sAPPα. These results indicate that peptide DP-074 can selectively modulate α cleavage of APP without effect on a cleavage even at the highest dose tested.

FIGS. 86C-D show that peptide DP-074 can increase levels of intracellular CTFs in SKNSH-APP cells as assessed by Western analysis. SKNSH-APP cells were treated as described above. Cell lysates were analyzed by Western analysis for intracellular APP and CTFs. Cells treated with 20-800 μM of peptide DP-074 showed an increase in amounts of intracellular CTFs 1.2-33 fold increase) when compared to those treated with PBS. The increase was dose-dependent. In contrast, DP-074 did not affect levels of intracellular APP. The results indicate that an increase in CTFs is not a result of increased steady-state levels of APP. The membrane was also re-probed for β-actin to assess protein loading and transfer efficiency FIG. 86D). Increases in levels of CTFs upon DP-074 treatment strongly suggest that the peptide can modulate β cleavage of APP.

Figure 87:
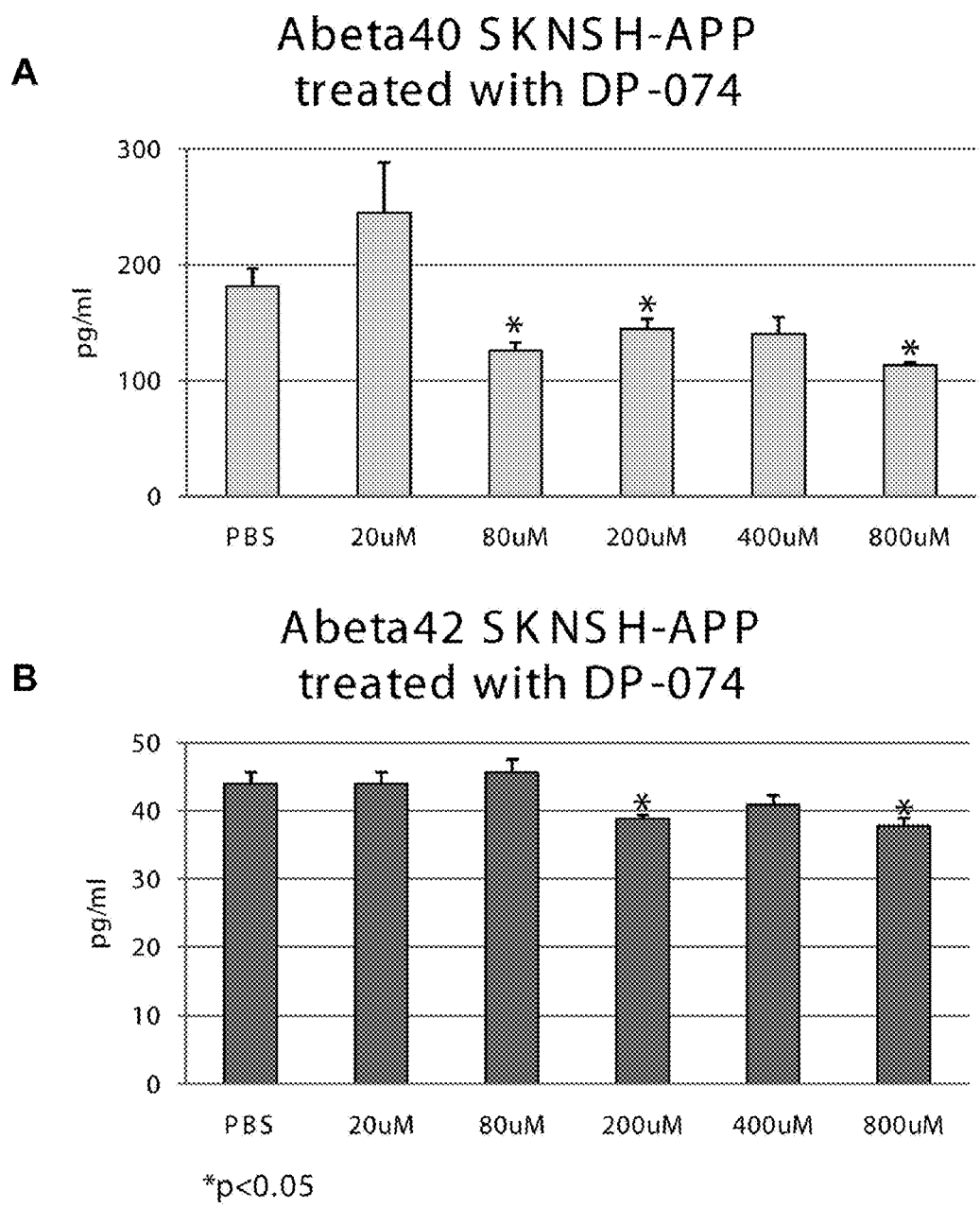
FIGS. 87A and B are graphs showing effects of peptide DP-074 on Aβ generation in SKNSH-APP cell cultures as assessed by ELISA.

FIGS. 87A-B show that peptide DP-074 reduces generation of A1-40 and Aβ1-42 peptides in HEK293-APP cells as assessed by ELISA. Conditioned media as described previously was analyzed by ELISA. A 20-40% reduction in Aβ40 levels was found in SKNSH-APP conditioned media from cells treated with 80 to 800 μM DP74 which was statistically significant for 80, 200 and 800 μM DP-074 treatment t-test, p<0.05) FIG. 87A). A small 12-14% decrease from vehicle control) but significant reduction t-test, p<0.05) in Aβ42 levels was found in SKNSH-APP conditioned media from cells treated with 200 and 800 μM DP-074 FIG. 87B).

Taken together, these results indicate that the 6-9 mer peptides modulate APP processing and reduce Aβ generation in cell culture. Our conclusions are based on endpoint measurements of direct APP cleavage products, including sAPPα, sAPPβ, CTFs, and Aβ peptides in two cell lines stably expressing the human wild type APP as measured by Western analysis, immunoprecipitation, and ELISA. DP-068 acts as a modulator that reduces the products of APP cleaved by all major secretases, including α, β and γ cleavage. This modulation also leads to reduced generation of Aβ peptides in conditioned media. In contrast, peptide DP-074 acts as a selective modulator that mainly reduces the products of the β and γ cleavage of APP, the two events that are essential for generating pathological Aβ species in Alzheimer disease. More importantly, peptide DP-074 exerts no affect on a cleavage of APP, leaving the physiological pathway intact Postina, Curr Alzheimer Res. 52):179-86 2008)).

Other secretase modulators, specifically those which modulate gamma secretase GSM) have been reported to interact with residues 28-36 of the Aβ region of APP Kukar et al., Nature 4537197):925-9 2008). This is also a likely mechanism of action for peptides DP-068 and DP-074 which alter Aβ generation, disrupt Aβ aggregation and, consequently may reduce plaque formation and deposition in Alzheimer disease.

Further Aspects and Utilizations

One therapeutic application is to use peptides of Sequence Group A, B, or C as binders or sequesters of Aβ, inhibitors of Aβ amyloid fibril formation, inhibitors of Aβ amyloid fibril deposition, inhibitors of Aβ amyloid fibril accumulation and/or persistence, in Alzheimer's disease, Down's syndrome and other amyloid disorders involving Aβ fibrillogenesis.

"Peptide" refers to two or more amino acids linked together by peptide bonds as known to those skilled in the art. Preferred peptides are those disclosed herein, but may also advantageously include peptides which have at least a 70%, and more preferably an 80-90% identity to a disclosed peptide. "% Identity" as used herein for peptides means the same amino acids in the same place. Thus, two 10 amino acid peptides are 90% identical if juxtaposition to each other showed that the placement and identity of each amino acid is identical, except for one amino acid. If a ten amino acid peptide is juxtaposed to another ten amino acid peptide and the placement and identity of amino acids is identical, except for two amino acids, then the two 10 amino acid peptides have an 80% identity with each other.

Disclosed peptides are produced by chemical synthetic procedures. Chemical peptide synthesis is a rapidly evolving area in the art, and methods of solid phase peptide synthesis are well-described in the following references, hereby entirely incorporated by reference Merrifield, J. Amer. Chem. Soc. 85:2149-2154, 1963; Merrifield, Science 232:341-347, 1986; Fields, Int. J. Polypeptide Prot. Res. 35, 161, 1990). Disclosed peptides may also be utilized as research reagents and materials for discovery of treatments and diagnostics for human diseases.

The route of administration includes oral, intravenous, intra-peritoneal, intra-muscular, subcutaneous, intra-articular, intra-nasal, intra-thecal, intra-dermal, transdermal or by inhalation. An effective dose of each of the peptides disclosed herein as potential therapeutics for use in treating Aβ amyloidosis in Alzheimer's disease and other disorders is from about 1 μg to 500 mg/kg body weight, per single administration, which may readily be determined by one skilled in the art. The dosage depends upon the age, sex, health, and weight of the recipient, kind of concurrent therapy, if any, and frequency of treatment. Other effective dosage range upper limits are 100 mg/kg body weight, 50 mg/kg body weight, 25 mg/kg body weight, and 10 mg/kg body weight.

As used herein polypeptides may consist of -L amino acids, -D amino acids or a mixture of both forms. Amino acids in nature usually consist of -L amino acids. However, substitution with -D amino acids generally demonstrates enhanced bioavailability due to less degradation in biological fluids such as plasma), and enhanced penetration across the blood-brain-barrier. Polypeptides having an identical amino acid sequence to that found within a disclosed peptide, but in which all or part of the L-amino acids have been substituted with D-amino acids, is a part of the disclosed development of therapeutics to treat Alzheimer's disease and other Aβ amyloidoses.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration into the central nervous system e.g. intraspinally or intracerebrally). Alternatively, the carrier can be suitable for intravenous, intraperitoneal or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is compatible with the active compound, use thereof in the pharmaceutical compositions is contemplated. Supplementary active compounds can also be incorporated into the compositions.

As used here in "Aβ amyloidoses" refers to amyloid diseases which involve the formation, deposition, accumulation and/or persistence of Aβ i.e. beta-amyloid protein), including but not limited to Aβ containing 39-43 amino acids in length, but more preferably, Aβ 1-40, or Aβ 1-42, and mixtures or fragments thereof.

"Aβ amyloidoses" and "Aβ fibrillogenesis diseases" include, but are not limited to Alzheimer's disease, Down's syndrome, forms of familial amyloidosis, cerebrovascular amyloidosis and cerebral hemorrhage, cystatin C amyloid angiopathy, hereditary cerebral hemorrhage with amyloidosis Dutch type), hereditary cerebral hemorrhage with amyloidosis Icelandic type), and inclusion body myositis.

Therapeutic Applications

In preferred embodiments, Sequence Group A, B, and C peptides, fragments, analogs, and derivatives thereof are used as amyloid inhibitory therapeutic agents. The Sequence Group A, B, and C peptides, fragments, analogs and derivatives thereof can be synthesized utilizing standard techniques i.e. using an automated synthesizer). In a preferred embodiment, specific Sequence Group A, B, or C peptides, fragments, analogs or derivatives thereof may be used to bind or sequester Aβ amyloid, inhibit Aβ amyloid formation, deposition, accumulation, and/or persistence in a given patient. Likewise, in another preferred embodiment anti-idiotypic antibodies made against Sequence Group A, B, or C peptides, fragments, analogs or derivatives thereof as described above) may be given to a human patient as potential Aβ binding or sequestering antibodies, that may disrupt or inhibit Aβ amyloid formation, deposition, accumulation and/or persistence in the given patient.

A formulation for use in the treatment of Aβ amyloidoses comprises a pharmaceutically effective amount of a peptide in Sequence Group A, B, or C, fragment, analog or derivative thereof, anti-idiotypic antibody, or anti-idiotypic antibody fragment which includes a pharmaceutically acceptable carrier. The formulations may additionally include other antibodies or conjugates. For parenteral administration, preferred formulations include sterile aqueous or non-aqueous solutions, suspensions, and emulsions, which may contain axillary agents or excipients that are known in the art. The anti-idiotypic antibody formulations can be administered using conventional modes of administration including, but not limited to, topical, intravenous, intra-arterial, intraperitoneal, oral, intralymphatic, intramuscular or intralumbar. Intravenous administration is preferred. Pharmaceutical formulations such as tablets, pills, caplets, soft and hard gelatin capsules, lozenges, sachets, cachets, vegicaps, liquid drops, elixers, suspensions, emulsions, solutions, syrups, tea bags, aerosols as a solid or in a liquid medium), suppositories, sterile injectable solutions, sterile packaged powders, can be prepared according to routine methods and are known in the art. The administration of such a composition may be by oral or various parenteral routes such as subcutaneous, intravenous, intradermal, intramuscular, intraperitoneal, intranasal, transdermal, anal or buccal routes. Parenteral administration can be by bolus injection or by gradual perfusion over time. Preferred modes of administration of the formulations of Sequence Group A, B, or C, fragments, analogs or derivatives thereof is by oral administration, intravenous, or intranasal application.

Compounds of Sequence Group A, B, or C, fragments, analogs and derivatives thereof, may be administered in the form of a pharmaceutical formulation by any means that achieve their intended purpose, for example, to treat pathologies, such as Alzheimer's disease and other Aβ amyloid diseases, or other related pathologies. The therapeutic formulations can be a variety of dosage forms, with the preferred form depending upon the mode of administration and the therapeutic application. Optimal dosage, frequency, length and modes of administration for an individual patient can readily be determined by conventional protocols, known to those skilled in the art.

It is understood that the dosage of the compound in Sequence Group A, B, or C, fragment, analog and derivative thereof administered in vivo or in vitro will be dependent upon the age, sex, health, and weight of the recipient, type of concurrent treatment if any), frequency of treatment, and the nature of the effect desired. The most preferred dosage will be tailored to the individual subject, as is understood and determinable by one of skill in the art, without undue experimentation.

A typical regimen for preventing, suppressing or treating pathologies, such as Alzheimer's disease amyloidosis, comprises administration of an effective amount of compound in Sequence Group A, B, or C, fragment, analog or derivative thereof, administered over a period of one to several days, up to and including between one week and about 72 months.

The total dose required for each treatment may be administered in multiple doses or in a single dose. A compound in Sequence Group A, B, or C, fragment, analog and derivative thereof may be administered alone or in conjunction with other therapeutics directed to pathologies, such as Alzheimer's disease or other Aβ amyloid diseases, as described herein.

Effective amounts of a compound in Sequence Group A, B, or C, fragment, analog and derivative thereof, are about 0.01 μg to about 100 mg/kg body weight, and preferably from about 10 μg to about 50 mg/kg body weight, such as 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg.

Pharmaceutical compositions comprising at least one Sequence Group A, B, or C compound or anti-idiotypic antibody may also include suitable solutions for administration intravenously, subcutaneously, dermally, nasally, orally, mucosally, rectally or may by injection or orally, and contain from about 0.01 to 99 percent, preferably about 20 to 75 percent of active component i.e. peptide or antibody) together with the excipient. Pharmaceutical compositions for oral administration include pills, tablets, caplets, soft and hard gelatin capsules, lozenges, sachets, cachets, vegicaps, liquid drops, elixers, suspensions, emulsions, solutions, and syrups.

The Sequence Group A, B, or C compound, fragment, analog and derivative thereof for the treatment of Alzheimer's disease and other central nervous system Aβ amyloidoses may be modified to cross the blood-brain barrier. Various modifications known in the art for increasing transport across the blood-brain-barrier for reviews of such modifications, see e.g. Pardridge W. M. 1994) Trends in Biotechnol. 12:239-245; Van Bree, J. et al 1993) Pharm World Sci. 15:2-9; and Pardridge W. M. 1992) Pharmacol. Toxicol. 71:3-10). One approach is to increase the lipophilicity log P) of the peptide by covalent linking of the amino or carboxyl terminal to a fatty acid or acyl group such as acetyl) as was done in some of Sequence Group A, B, or C peptides. Another approach is to conjugate the peptide to a protein that normally undergoes absorptive mediated transcytosis or receptor mediated transcytosis through the blood-brain-barrier. These proteins include ligands for brain capillary endothelial receptors such as a monoclonal antibody to the transferrin receptor, histones, biotin, folate, niacin, panthothenic acid, or glycopeptides. Another approach is to link the peptide to a highly positively charged compound as were done in some of the Sequence Group A, B, and C peptides) such as lysine, polylysine, arginine, polyarginine, lysine-arginine peptide, putrescine, spermidine, spermine, etc, all of which are known to facilitate crossing through the blood-brain-barrier presumably by binding to a receptor.

Another approach to enhance blood-brain-barrier transport of peptides is by encapsulation into a carrier vector such as liposome or polymeric microspheres, preferably positively charged for the same reason as described above. The carrier vector can also be modified to target blood-brain-barrier transport receptors, such as the transferrin receptor, by linking the peptide, for example, to an antibody against the transferrin receptor.

Another approach is to co-administer the peptide with agents that permeabilize the blood-brain-barrier, such as bradykinin or a bradykinin agonist.

The blood-brain-barrier permeable drug is a desirable characteristic of central nervous system drugs in general. However, the disclosed embodiments do not necessarily have to fulfill blood-brain-barrier permeability requirements in order to fulfill intended purposes i.e., effective treatment of Alzheimer's disease and other amyloidosis). Peripheral sequestration of Aβ by Sequence Group A, B, or C compounds, fragments, analogs, derivatives thereof, and anti-idiotypic antibodies will result in movement of Aβ from the brain to the peripheral circulation, depleting brain Aβ, inhibiting brain Aβ amyloid fibril formation, and/or causing dissolution of pre-formed brain Aβ amyloid fibrils. This is due to the fact as demonstrated in the previous studies that Aβ freely crosses the blood-brain-barrier Poduslo et al., Neurobiol. Dis. 4:27-34, 1997; Ghilardi et al., Neuroreport 17:2607-11, 1996; Pluta et al., Neuroreport. 7:1261-51996, 1996; Zlokovic, Neurobiol Dis. 4:23-6, 1996).

The Sequence Group A, B, or C compound, fragment, analog and derivative thereof for the treatment of Alzheimer's disease and other central nervous system Aβ amyloidoses may be administered in various ways. Methods of administration include but are not limited to systemic administration, parenteral administration i.e., via an intraperitoneal, intravenous, perioral, subcutaneous, intramuscular, intraarterial, intradermal, intramuscular, intranasal, epidural or oral routes. In a preferred embodiment, Sequence Group A, B, or C compound, fragment, analog and derivative thereof may be directly administered to the cerebrospinal fluid by intraventricular injection. In a specific embodiment, it may be desirable to administer Sequence Group A, B, or C compound, fragment, analog and derivative thereof locally to the area or tissue in need of treatment; this may be achieved by, for example, and not by way of limitation, local infusion during surgery, topical application, by injection, by infusion using a cannulae with an osmotic pump, by means of a catheter, by means of a suppository, or by means of an implant.

In yet another embodiment Sequence Group A, B, or C compound, fragment, analog and derivative thereof may be administered in a controlled release system, such as a well-calibrated osmotic pump. In yet another embodiment, a controlled release system can be placed in proximity to the therapeutic target, i.e. the brain, thus requiring only a fraction of the systemic dose.

In yet another aspect, peptidomimetic compounds modeled from Sequence Group A, B, or C peptides identified as binding Aβ or other amyloid proteins, serve as potent inhibitors of amyloid formation, deposition, accumulation and/or persistence in Alzheimer's disease and other Aβ amyloidoses. Peptidomimetic modeling is implemented by standard procedures known to those skilled in the art. These peptidomimetic compounds may be administered with formulations, dosages, frequencies, lengths, and routes as outlined above, for the therapeutic purpose of treating Aβ amyloidosis.

Diagnostic Applications

In disclosed methods, Aβ amyloid can be contacted with a disclosed peptide either in vitro or in vivo. Thus the term "contacted with" is intended to encompass both incubation of the peptide and anti-idiotypic antibodies with Aβ amyloid preparation in vitro and delivery of the peptide and anti-idiotypic antibodies to a site in vivo where Aβ amyloid is present. Since the peptides and anti-idiotypic antibodies interact with Aβ amyloid, they can be used to detect Aβ amyloid, either in vitro or in vivo. Accordingly, the compounds can also be used as diagnostic agents to detect the presence or absence of Aβ amyloid in a biological sample or in vivo in a subject. Furthermore, detection of Aβ amyloid using the compounds can be used to diagnose Aβ amyloidosis in a subject.

In one embodiment, a compound is used in vitro to detect and quntitate Aβ amyloid in sample such as cerebrospinal fluid from AD patient, suspected AD patient, a person with a family history of AD, or a normal adult). To aid in detection, the compound can be modified with a detectable substance. The Aβ amyloid in the sample can be immobilized and the compound with the detectable substance is contacted with the immobilized Aβ amyloid or sample, such as in tissue sections. The remaining unbound compound is removed and the compound bound to Aβ can be detected. Alternatively, the unbound compound which is inversely proportional to the bound compound and hence amount of Aβ in the sample can be detected by various means, such as mass spectrometry and other spectrometric determinations including fluorescence, phosphorescence, and, absorbance of various wavelengths of light from UV to infrared, all the way down to radiowaves such as that for NMR. For example, the detectable substance can be biotin i.e. an amino-terminally biotinylated Sequence Group A, B, or C peptide) that can be detected using enzyme labeled avidin. The enzyme, in turn, when later exposed to an appropriate substrate, will react with the substrate in such a manner as to produce a chemical moiety which can be detected, for example, by spectrophotometric, fluorometric, or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colometric methods which employ a chromogenic substrate for the enzyme. Detection can be accomplished by colometric methods which employ a chromogenic substrate for the enzyme. Detection can also be accomplished by visual comparison of the extent of enzymatic reaction of a substrate with similarly prepared standards see Harlow and Lane, Antibodies: A Laboratory Manual, Cold Spring Harbor Laboratory 1988; Ausubel et al, eds., Current Protocols in Molecular Biology, Wiley Interscience, N.Y. 1987, 1992).

Selected disclosed compounds may also be used to quantitatively or qualitatively detect Aβ amyloid in a biological sample. This can be accomplished by immunofluorescence techniques employing a fluorescently labeled disclosed compound coupled with light microscopic, flow cytometric or fluorometric detection.

Detection may be accomplished using any of a variety of other immunoassays. For example, by radiolabeling of the compound. A good description of this assay may be found in Laboratory Techniques and Biochemistry in Molecular Biology, by Work et al, North Holland Publishing Company, NY 1978) with particular reference to the chapter entitled "An Introduction to Radioimmune Assay and Related Techniques" by Chard, incorporated entirely by reference herein. The radioactive isotope can be detected by such means as the use of a gamma-counter, a scintillation counter or by autoradiography.

It is also contemplated to label the compound with a fluorescent compound. When the fluorescently labeled compound is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine, that are commercially available, e.g., from Molecular Probes, Inc. Eugene, Oreg., U.S.A.).

Compounds can also be detectably labeled by coupling it to a chemiluminescent compound. The presence of the chemiluminescent-tagged compound is then determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Likewise, a bioluminescent compound may be used to label the compound. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, lucifers and aequorin.

Compounds may also be used histologically, as in immunofluorescence or immunoelectron microscopy, for in situ detection of Aβ amyloid. Removing a histological specimen from a patient, and providing the labeled compound to such a specimen may accomplish in situ detection. The compound is preferably provided by applying or by overlaying the labeled compound or fragment) to a biological sample. Through the use of such a procedure, it is possible to determine not only the presence of Aβ amyloid but also its distribution in the examined tissue. Thus, those of ordinary skill will readily perceive that any of a wide variety of histological methods such as staining procedures) can be modified in order to achieve such in situ detection.

Compounds which interact with Aβ, or derivatives thereof are also disclosed herein. The compounds can be used for a number of important diagnostic and/or therapeutic applications as described herein. In one aspect, peptides which bind Aβ may be utilized for ligand blot analysis using standard ligand blotting techniques known to those skilled in the art) to detect the presence of Aβ amyloid protein fragments in human tissues and in tissues of other species. Ligand blot analysis can also be used to determine the apparent size of each amyloid protein fragment. In addition, ligand blotting followed by scanning densitometry known to those skilled in the art) can be used to quantitate and compare levels of each of the peptides in tissue samples, biological fluids or biopsies obtained from individuals with specific diseases such as the amyloid diseases) in comparison to tissue samples, biological fluids or biopsies obtained from normal individuals or controls. Biological fluids, include, but are not limited to, blood, plasma, serum, cerebrospinal fluid, sputum, saliva, urine and stool.

In another embodiment, a compound is used in vivo to detect, and if desired, quantitate, Aβ amyloid deposition in a subject, for example, to aid in the diagnosis of Aβ amyloidosis in the subject. To aid in detection, the compound can be modified with a detectable substance, preferably $^{99m}$Tc or radioactive iodine. Methods for labeling peptide compounds with technetium are known in the art. A modifying group can be chosen that provides a site at which a chelation group for $^{99m}$Tc can be introduced, such as a derivative of cholic acid, which has a free amino group. Also provided are Sequence Group A, B, or C peptides labeled with radioactive iodine through their aromatic amino acid, either already present or incorporated, for the purpose of labeling. Any of the various isotopes of radioactive iodine can be incorporated to create a diagnostic agent. Preferably, $^{123}$I half-life=13.2 hrs) can be used for whole body scintigraphy, $^{124}$I half-life=4 days) or $^{13}$F for positron emission tomography PET), $^{125}$I half-life=60 days) for metabolic turnover studies, and $^{131}$I half-life=8 days) for whole body counting and delayed low resolution imaging studies.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

---

We claim:

1. A method of reducing beta-amyloid protein Aβ) in vivo comprising administration of a peptide Leu-Ala-Phe-Val-Leu-Arg-Lys-amide having at least one D amino acid to a mammal suffering from accumulation of beta-amyloid protein.

2. A method of treating a beta-amyloid protein disease comprising administration of a peptide Leu-Ala-Phe-Val-Leu-Arg-Lys-amide having at least one D amino acid to a mammal suffering from a beta-amyloid protein disease.

3. The method of claim 2 where the beta-amyloid protein disease is selected from the group of diseases consisting of; Alzheimer's disease, Down's syndrome, congophilic angiopathy, hereditary cerebral hemorrhage of the Dutch type, inclusion body myositosis, dementia pugilistica, cerebral β-amyloid angiopathy, dementia associated with progressive supranuclear palsy, dementia associated with cortical basal degeneration and mild cognitive impairment.

4. The method of claim 2 where the beta-amyloid protein disease is Alzheimer's disease.

5. A method of reducing beta-amyloid protein Aβ) in vivo comprising administration of a pharmaceutical composition to a mammal suffering from accumulation of beta-amyloid protein, wherein the pharmaceutical composition comprises a peptide Leu-Ala-Phe-Val-Leu-Arg-Lys-amide having at least one D amino acid.

6. A method of treating a beta-amyloid protein disease comprising administration of a pharmaceutical composition to a mammal suffering from a beta-amyloid protein disease wherein the pharmaceutical composition comprises peptide Leu-Ala-Phe-Val-Leu-Arg-Lys-amide having at least one D amino acid.

7. The method of claim 6 where the beta-amyloid protein disease is selected from the group of diseases consisting of; Alzheimer's disease, Down's syndrome, congophilic angiopathy, hereditary cerebral hemorrhage of the Dutch type, inclusion body myositosis, dementia pugilistica, cerebral β-amyloid angiopathy, dementia associated with progressive supranuclear palsy, dementia associated with cortical basal degeneration and mild cognitive impairment.

8. The method of claim 6 where the beta-amyloid protein disease is Alzheimer's disease.

9. The method of claim 6 wherein the pharmaceutical composition further comprises a pharmaceutically acceptable carrier, diluent or excipient.

10. A method of modulating APP processing comprising administration of a peptide Leu-Ala-Phe-Val-Leu-Arg-Lys-amide having at least one D amino acid to a mammal in need of APP modulation.

11. A method of modulating APP secretase comprising administration of a peptide Leu-Ala-Phe-Val-Leu-Arg-Lys-amide having at least one D amino acid to a mammal in need of APP secretase modulation.

12. The method according to claim 11 wherein the secretase is gamma secretase.

13. The method according to claim 11 wherein the secretase is beta secretase.

14. The method of claim 6 wherein one or more of the amino acids in the peptide are N-methylated.

15. The method claim 6 wherein the amount of peptide comprises a dosage in the range of from about 10 μg to about 100 mg/kg body weight/day.

16. The method claim 6 wherein the amount of peptide comprises a dosage in the range of from about 100 μg to about 50 mg/kg body weight/day.

17. The method claim 6 wherein the pharmaceutical composition is administered in a subcutaneous, interperitoneal, intramuscular, parenteral injectable form, or in infusible form.

18. The method claim 6 wherein the pharmaceutical composition is administered orally.

19. The method claim 6 wherein the pharmaceutical composition is administered by nasal spray.

* * * * *